US012714506B2

(12) United States Patent
Mosnier et al.

(10) Patent No.: US 12,714,506 B2
(45) Date of Patent: *Aug. 25, 2026

(54) SYSTEMS, METHODS, AND DEVICES FOR DEVELOPING PATIENT-SPECIFIC SPINAL IMPLANTS, TREATMENTS, OPERATIONS, AND/OR PROCEDURES

(71) Applicant: Medicrea International, Rillieux-la-Pape (FR)

(72) Inventors: Thomas Mosnier, Rochetaillée sur Saône (FR); Denys Sournac, Reyrieux (FR); Christophe X. Javelot, Porte des Pierres Dorees (FR)

(73) Assignee: MEDICREA INTERNATIONAL (FR)

( * ) Notice: Subject to any disclaimer, the term of this patent is extended or adjusted under 35 U.S.C. 154(b) by 0 days.

This patent is subject to a terminal disclaimer.

(21) Appl. No.: 19/023,942

(22) Filed: Jan. 16, 2025

(65) Prior Publication Data

US 2025/0152249 A1 May 15, 2025

Related U.S. Application Data

(63) Continuation of application No. 18/601,891, filed on Mar. 11, 2024, now Pat. No. 12,251,165, which is a (Continued)

(51) Int. Cl.

*A61B 34/10* (2016.01)
*A61B 17/70* (2006.01)
*A61B 17/56* (2006.01)

(52) U.S. Cl.

CPC .......... *A61B 34/10* (2016.02); *A61B 17/7013* (2013.01); *A61B 2017/568* (2013.01); *A61B 2034/104* (2016.02)

(58) Field of Classification Search

CPC .............. A61B 34/10; A61B 2034/104; A61B 17/7013; A61B 2017/568

See application file for complete search history.

(56) References Cited

U.S. PATENT DOCUMENTS

| | | | |
|---|---|---|---|
| 4,382,438 | A | 5/1983 | Jacobs |
| 5,006,984 | A | 4/1991 | Steele |

(Continued)

FOREIGN PATENT DOCUMENTS

| | | | |
|---|---|---|---|
| AU | 2015258176 | A1 | 12/2015 |
| AU | 2015202416 | B2 | 3/2017 |

(Continued)

OTHER PUBLICATIONS

Abe et al. "Scoliosis corrective force estimation from the implanted rod deformation using 3 D FEM analysis", 2015, Scoliosis 10(Suppl 2):52, 6 pages.

(Continued)

*Primary Examiner* — Chao Sheng
(74) *Attorney, Agent, or Firm* — FOX ROTHSCHILD LLP

(57) ABSTRACT

A surgical planning and assessment system is disclosed. The system may include a computing system having a processor, a data store, and a patient specific planning and analysis module. The system may be configured to store a patient specific target plan including a digital representation of a spinal rod having a target geometry and transform the digital representation into a curved line. The system may generate a spline data set comprising a plurality of spline segments that are sequentially linked to one another. The system may adjust, iteratively, each spline segment until the plurality of spline segments approximate the curved line. The system may generate a digital file comprising drawings for manufacturing a spinal rod based on the plurality of spline segments. In various embodiments, each spline segment (Continued)

may be defined by a corresponding arc or a corresponding line extending between a corresponding starting point and a corresponding ending point.

20 Claims, 67 Drawing Sheets

Related U.S. Application Data continuation of application No. 17/130,492, filed on Dec. 22, 2020, now Pat. No. 11,925,417, which is a continuation-in-part of application No. 16/837,461, filed on Apr. 1, 2020, now Pat. No. 11,877,801.

(60) Provisional application No. 62/953,690, filed on Dec. 26, 2019, provisional application No. 62/952,647, filed on Dec. 23, 2019, provisional application No. 62/939,144, filed on Nov. 22, 2019, provisional application No. 62/932,701, filed on Nov. 8, 2019, provisional application No. 62/932,727, filed on Nov. 8, 2019, provisional application No. 62/932,743, filed on Nov. 8, 2019, provisional application No. 62/828,741, filed on Apr. 3, 2019, provisional application No. 62/828,337, filed on Apr. 2, 2019, provisional application No. 62/828,326, filed on Apr. 2, 2019.

(56) References Cited

U.S. PATENT DOCUMENTS 5,163,440 A 11/1992 DeLuca et al.
5,209,752 A 5/1993 Ashman et al.
5,224,035 A 6/1993 Yamashita et al.
5,251,127 A 10/1993 Raab
5,291,901 A 3/1994 Graf
5,305,203 A 4/1994 Raab
5,312,405 A 5/1994 Korotko et al.
5,413,116 A 5/1995 Radke et al.
5,514,180 A 5/1996 Heggeness et al.
5,667,506 A 9/1997 Sutterlin
5,748,767 A 5/1998 Raab
5,785,663 A 7/1998 Sarvazyan
6,015,409 A 1/2000 Jackson
6,213,958 B1 4/2001 Winder
6,282,437 B1 8/2001 Franck et al.
6,302,888 B1 10/2001 Mellinger et al.
6,364,849 B1 4/2002 Wilcox
6,385,475 B1 5/2002 Cinquin et al.
6,409,684 B1 6/2002 Wilk
6,443,953 B1 9/2002 Perra et al.
6,499,488 B1 12/2002 Hunter et al.
6,565,519 B2 5/2003 Benesh
6,585,666 B2 7/2003 Suh et al.
6,711,432 B1 3/2004 Krause et al.
6,715,213 B2 4/2004 Richter
6,716,213 B2 4/2004 Shitoto
6,746,449 B2 6/2004 Jones et al.
6,786,930 B2 9/2004 Biscup
7,066,938 B2 6/2006 Slivka et al.
7,338,526 B2 3/2008 Steinberg
7,509,183 B2 3/2009 Lin et al.
7,534,263 B2 5/2009 Burdulis, Jr. et al.
7,542,791 B2 6/2009 Mire et al.
7,570,791 B2 8/2009 Frank et al.
7,606,613 B2 10/2009 Simon et al.
7,611,522 B2 11/2009 Gorek
7,618,451 B2 11/2009 Berez et al.
7,634,119 B2 12/2009 Tsougarakis et al.
7,635,367 B2 12/2009 Groiso
7,639,866 B2 12/2009 Pomero et al.
7,660,623 B2 2/2010 Hunter et al.
7,674,293 B2 3/2010 Kuiper et al.
7,715,602 B2 5/2010 Richard
7,763,054 B2 7/2010 Clement et al.
7,824,413 B2 11/2010 Varieur et al.
7,835,778 B2 11/2010 Foley et al.
7,840,253 B2 11/2010 Tremblay et al.
7,862,593 B2 1/2011 Clement et al.
7,918,887 B2 4/2011 Roche
7,953,471 B2 5/2011 Clayton et al.
7,974,677 B2 7/2011 Mire et al.
7,981,158 B2 7/2011 Fitz et al.
7,996,061 B2 8/2011 Mollard et al.
7,996,064 B2 8/2011 Simon et al.
8,000,926 B2 8/2011 Roche et al.
8,036,441 B2 10/2011 Frank et al.
8,038,716 B2 10/2011 Duggal et al.
8,046,050 B2 10/2011 Govari et al.
8,066,708 B2 11/2011 Lang et al.
8,077,950 B2 12/2011 Tsougarakis et al.
8,083,778 B2 12/2011 Clement et al.
8,105,330 B2 1/2012 Fitz et al.
8,142,842 B2 3/2012 Sugita et al.
8,196,825 B2 6/2012 Turner et al.
8,211,109 B2 7/2012 Groiso
8,211,153 B2 7/2012 Shaolian et al.
8,234,097 B2 7/2012 Steines et al.
8,241,296 B2 8/2012 Wasielewski
8,246,680 B2 8/2012 Betz et al.
8,265,790 B2 9/2012 Amiot et al.
8,270,253 B1 9/2012 Roche et al.
8,275,594 B2 9/2012 Lin et al.
8,308,772 B2 11/2012 Clement et al.
8,308,775 B2 11/2012 Clement et al.
8,337,501 B2 12/2012 Fitz et al.
8,357,111 B2 1/2013 Caillouette et al.
8,357,166 B2 1/2013 Aram et al.
8,372,075 B2 2/2013 Groiso
8,377,073 B2 2/2013 Wasielewski
8,394,142 B2 3/2013 Bertagnoli et al.
8,398,681 B2 3/2013 Augostino et al.
8,400,312 B2 3/2013 Hotokebuchi et al.
8,414,592 B2 4/2013 Quirno
8,442,621 B2 5/2013 Gorek et al.
8,457,930 B2 6/2013 Schroeder
8,465,527 B2 6/2013 Clement
8,494,805 B2 7/2013 Roche et al.
8,506,632 B2 8/2013 Ganem et al.
8,532,806 B1 9/2013 Masson
8,535,337 B2 9/2013 Chang et al.
8,549,888 B2 10/2013 Isaacs
8,556,983 B2 10/2013 Bojarski et al.
8,588,892 B2 11/2013 Hladio et al.
8,636,776 B2 1/2014 Rosenberg et al.
8,672,948 B2 3/2014 Lemaitre
8,685,093 B2 4/2014 Anderson et al.
8,690,888 B2 4/2014 Stein et al.
8,705,829 B2 4/2014 Frank et al.
8,718,820 B2 5/2014 Amiot et al.
8,758,357 B2 6/2014 Frey
8,775,133 B2 7/2014 Schroeder
8,777,877 B2 7/2014 Stein et al.
8,784,339 B2 7/2014 Stein et al.
8,801,786 B2 8/2014 Bernard et al.
8,814,877 B2 8/2014 Wasielewski
8,814,915 B2 8/2014 Hess et al.
8,852,237 B2 10/2014 Kalfas et al.
8,855,389 B1 10/2014 Hoffmann et al.
8,864,764 B2 10/2014 Groiso
8,870,889 B2 10/2014 Frey
8,900,316 B2 12/2014 Lenz et al.
8,911,448 B2 12/2014 Stein
8,926,673 B2 1/2015 Clement et al.
8,945,133 B2 2/2015 Stein et al.
8,956,416 B2 2/2015 McCarthy
8,974,467 B2 3/2015 Stone
8,983,813 B2 3/2015 Miles et al.
8,998,962 B2 4/2015 Birch
9,011,448 B2 4/2015 Roche et al.
9,034,037 B2 5/2015 Fiere et al.
9,039,772 B2 5/2015 Park et al.

(56) References Cited

U.S. PATENT DOCUMENTS 9,056,017 B2 6/2015 Kotlus
9,066,701 B1 6/2015 Finley et al.
9,066,734 B2 6/2015 Schoenefeld et al.
9,078,755 B2 7/2015 Mahfouz
9,101,492 B2 8/2015 Mangione et al.
9,115,998 B2 8/2015 Proulx et al.
9,119,572 B2 9/2015 Gorek et al.
9,119,671 B2 9/2015 Kast
9,125,680 B2 9/2015 Kostrzewski et al.
9,144,440 B2 9/2015 Aminian
9,144,470 B2 9/2015 Proulx et al.
9,168,153 B2 10/2015 Bettenga
9,173,661 B2 11/2015 Metzger et al.
9,180,015 B2 11/2015 Fitz et al.
9,192,412 B2 11/2015 Meyrat et al.
9,198,678 B2 12/2015 Frey et al.
9,232,955 B2 1/2016 Bonin, Jr. et al.
9,233,001 B2 1/2016 Miles et al.
9,237,952 B2 1/2016 Kurtz
9,248,023 B2 2/2016 Ries et al.
9,250,620 B2 2/2016 Kotlus
9,278,010 B2 3/2016 Gibson et al.
9,283,048 B2 3/2016 Kostrzewski et al.
9,289,221 B2 3/2016 Gelaude et al.
9,289,270 B2 3/2016 Gielen et al.
9,295,482 B2 3/2016 Fitz et al.
9,295,497 B2 3/2016 Schoenefeld et al.
9,295,561 B2 3/2016 Ball et al.
9,301,768 B2 4/2016 Buza et al.
9,308,050 B2 4/2016 Kostrzewski et al.
9,308,091 B2 4/2016 Lang
9,314,275 B2 4/2016 Clement et al.
9,314,343 B2 4/2016 Parisi et al.
9,320,547 B2 4/2016 Augostino
9,320,604 B2 4/2016 Miles et al.
9,326,780 B2 5/2016 Wong et al.
9,339,277 B2 5/2016 Jansen et al.
9,345,492 B2 5/2016 Stein et al.
9,358,051 B2 6/2016 Sournac et al.
9,358,130 B2 6/2016 Livorsi et al.
9,358,136 B2 6/2016 Stein et al.
9,364,370 B2 6/2016 Kuhnel
9,381,085 B2 7/2016 Axelson, Jr. et al.
9,387,015 B2 7/2016 Taylor
9,392,953 B1 7/2016 Gharib
9,393,052 B2 7/2016 Berg et al.
9,398,962 B2 7/2016 Steinberg
9,402,726 B2 8/2016 Linderman et al.
9,408,615 B2 8/2016 Fitz et al.
9,408,642 B2 8/2016 Wong et al.
9,408,698 B2 8/2016 Miles et al.
9,414,940 B2 8/2016 Stein et al.
9,433,443 B2 9/2016 Montello et al.
9,439,659 B2 9/2016 Schoenefeld et al.
9,439,767 B2 9/2016 Bojarski et al.
9,439,781 B2 9/2016 Gibson
9,445,913 B2 9/2016 Donner et al.
9,452,022 B2 9/2016 McIntosh et al.
9,452,023 B2 9/2016 Boillot et al.
9,452,050 B2 9/2016 Miles et al.
9,452,064 B2 9/2016 Trautwein et al.
9,468,436 B2 10/2016 Groiso
9,468,502 B2 10/2016 Wiebe, III et al.
9,491,415 B2 11/2016 Deitz et al.
9,492,183 B2 11/2016 Wilkinson et al.
9,495,483 B2 11/2016 Steines et al.
9,495,509 B2 11/2016 Amiot et al.
9,498,260 B2 11/2016 Funk et al.
9,504,502 B2 11/2016 Kuiper et al.
9,510,771 B1 12/2016 Finley et al.
9,510,864 B2 12/2016 Devito
9,517,134 B2 12/2016 Lang
9,517,143 B2 12/2016 Prevost et al.
9,526,514 B2 12/2016 Kelley et al.
9,532,730 B2 1/2017 Wasielewski
9,539,031 B2 1/2017 Fauth
9,539,116 B2 1/2017 Claypool et al.
9,539,760 B2 1/2017 Stahl et al.
9,547,897 B2 1/2017 Parent et al.
9,549,782 B2 1/2017 Park et al.
9,554,411 B1 1/2017 Hall et al.
9,554,910 B2 1/2017 Vanasse et al.
9,561,115 B2 2/2017 Elahinia et al.
9,566,075 B2 2/2017 Carroll et al.
9,579,043 B2 2/2017 Chien et al.
9,585,597 B2 3/2017 McCaulley et al.
9,597,096 B2 3/2017 Aghazadeh
9,597,156 B2 3/2017 Amiot et al.
9,603,613 B2 3/2017 Schoenefeld et al.
9,603,623 B2 3/2017 Brooks et al.
9,603,711 B2 3/2017 Bojarski et al.
9,610,086 B2 4/2017 Park et al.
9,615,834 B2 4/2017 Agnihotri et al.
9,622,712 B2 4/2017 Munro et al.
9,629,723 B2 4/2017 Parisi et al.
9,636,181 B2 5/2017 Isaacs
9,642,633 B2 5/2017 Frey et al.
9,649,170 B2 5/2017 Park et al.
9,655,729 B2 5/2017 Parisi et al.
9,662,214 B2 5/2017 Li et al.
9,668,748 B2 6/2017 McKinnon et al.
9,668,873 B2 6/2017 Winslow et al.
9,675,471 B2 6/2017 Bojarski et al.
9,693,831 B2 7/2017 Mosnier et al.
9,715,563 B1 7/2017 Schroeder
9,757,072 B1 9/2017 Urbalejo
9,782,228 B2 10/2017 Mosnier et al.
9,788,966 B2 10/2017 Steinberg
9,827,109 B2 11/2017 Steinberg
9,848,922 B2 12/2017 Tohmeh et al.
9,968,408 B1 5/2018 Casey et al.
9,987,048 B2 6/2018 Mosnier et al.
9,993,177 B2 6/2018 Chien et al.
10,010,426 B2 7/2018 Kuiper et al.
10,045,824 B2 8/2018 Mosnier et al.
10,052,135 B2 8/2018 Berg et al.
10,064,743 B2 9/2018 Funk et al.
10,098,671 B2 10/2018 Augostino
10,188,480 B2 1/2019 Scholl et al.
10,201,320 B2 2/2019 Saget et al.
10,219,865 B2 3/2019 Jansen et al.
10,292,770 B2 5/2019 Ryan et al.
10,314,657 B2 6/2019 Mosnier et al.
10,318,655 B2 6/2019 Mosnier et al.
10,413,365 B1 9/2019 Mosnier et al.
10,420,615 B1 9/2019 Mosnier et al.
10,433,893 B1 10/2019 Scholl et al.
10,433,912 B1 10/2019 Mosnier et al.
10,433,913 B2 10/2019 Mosnier et al.
10,441,363 B1 10/2019 Mosnier et al.
10,456,211 B2 10/2019 McAfee
10,463,433 B2 11/2019 Turner et al.
2002/0035321 A1 3/2002 Bucholz et al.
2002/0038118 A1 3/2002 Shoham
2002/0045812 A1 4/2002 Ben-Haim et al.
2002/0103432 A1 8/2002 Kawchuk
2003/0191383 A1 10/2003 Ben-Haim et al.
2003/0204189 A1 10/2003 Cragg
2004/0120781 A1 6/2004 Luca et al.
2004/0143243 A1 7/2004 Wahrburg
2004/0152972 A1 8/2004 Hunter
2004/0167637 A1 8/2004 Biscup
2004/0171924 A1 9/2004 Mire et al.
2004/0172020 A1 9/2004 Beaurain et al.
2004/0215190 A1 10/2004 Nguyen et al.
2004/0243148 A1 12/2004 Wasielewski
2004/0267279 A1 12/2004 Casutt et al.
2005/0149050 A1 7/2005 Stifter et al.
2005/0177239 A1 8/2005 Steinberg
2005/0182320 A1 8/2005 Stifter et al.
2005/0182454 A1 8/2005 Gharib et al.
2005/0203531 A1 9/2005 Lakin et al.
2005/0203532 A1 9/2005 Ferguson
2005/0262911 A1 12/2005 Dankowicz et al.

(56) References Cited

U.S. PATENT DOCUMENTS

| | | | |
|---|---|---|---|
| 2006/0015018 | A1 | 1/2006 | Jutras et al. |
| 2006/0015030 | A1 | 1/2006 | Poulin et al. |
| 2006/0036259 | A1 | 2/2006 | Carl et al. |
| 2006/0069324 | A1 | 3/2006 | Block et al. |
| 2006/0074431 | A1 | 4/2006 | Sutton et al. |
| 2006/0136058 | A1 | 6/2006 | Pietrzak |
| 2006/0142657 | A1 | 6/2006 | Quaid et al. |
| 2006/0285991 | A1 | 12/2006 | McKinley |
| 2006/0287627 | A1 | 12/2006 | Johnson |
| 2007/0021682 | A1 | 1/2007 | Gharib et al. |
| 2007/0118243 | A1 | 5/2007 | Schroeder et al. |
| 2007/0225731 | A1 | 9/2007 | Couture et al. |
| 2008/0058945 | A1 | 3/2008 | Hajaj et al. |
| 2008/0108991 | A1 | 5/2008 | von Jako |
| 2008/0177203 | A1 | 7/2008 | von Jako |
| 2008/0255575 | A1 | 10/2008 | Justis et al. |
| 2008/0281332 | A1 | 11/2008 | Taylor |
| 2009/0024164 | A1 | 1/2009 | Neubardt |
| 2009/0076615 | A1 | 3/2009 | Duggal et al. |
| 2009/0157083 | A1 | 6/2009 | Park et al. |
| 2009/0194206 | A1 | 8/2009 | Jeon et al. |
| 2009/0204159 | A1 | 8/2009 | Justis et al. |
| 2009/0248080 | A1 | 10/2009 | Wilcox et al. |
| 2009/0249851 | A1 | 10/2009 | Isaacs |
| 2009/0254326 | A1 | 10/2009 | Isaacs |
| 2010/0042157 | A1 | 2/2010 | Trieu |
| 2010/0100011 | A1 | 4/2010 | Roche |
| 2010/0191071 | A1 | 7/2010 | Anderson et al. |
| 2010/0191088 | A1 | 7/2010 | Anderson et al. |
| 2010/0217270 | A1 | 8/2010 | Polinski et al. |
| 2010/0217336 | A1 | 8/2010 | Crawford et al. |
| 2011/0004309 | A9 | 1/2011 | Holm |
| 2011/0071802 | A1 | 3/2011 | Bojarski et al. |
| 2011/0118740 | A1 | 5/2011 | Rabiner et al. |
| 2011/0172566 | A1 | 7/2011 | Kawchuk |
| 2011/0214279 | A1 | 9/2011 | Park et al. |
| 2011/0224796 | A1 | 9/2011 | Weiland et al. |
| 2011/0257653 | A1 | 10/2011 | Hughes et al. |
| 2011/0257657 | A1 | 10/2011 | Turner et al. |
| 2011/0295159 | A1 | 12/2011 | Shachar et al. |
| 2011/0306873 | A1 | 12/2011 | Shenai et al. |
| 2012/0022357 | A1 | 1/2012 | Chang et al. |
| 2012/0027261 | A1 | 2/2012 | Frank et al. |
| 2012/0035611 | A1 | 2/2012 | Kave |
| 2012/0123301 | A1 | 5/2012 | Connor et al. |
| 2012/0143090 | A1 | 6/2012 | Hay et al. |
| 2012/0150243 | A9 | 6/2012 | Crawford et al. |
| 2012/0172884 | A1 | 7/2012 | Zheng et al. |
| 2012/0203289 | A1 | 8/2012 | Beerens et al. |
| 2013/0079678 | A1 | 3/2013 | Stein et al. |
| 2013/0079679 | A1 | 3/2013 | Roche et al. |
| 2013/0079790 | A1 | 3/2013 | Stein et al. |
| 2013/0131486 | A1 | 5/2013 | Copf et al. |
| 2013/0211531 | A1 | 8/2013 | Steines et al. |
| 2013/0245631 | A1 | 9/2013 | Bettenga |
| 2013/0253599 | A1 | 9/2013 | Gorek et al. |
| 2013/0268007 | A1 | 10/2013 | Rezach et al. |
| 2013/0303883 | A1 | 11/2013 | Zehavi et al. |
| 2013/0345718 | A1 | 12/2013 | Crawford et al. |
| 2014/0058407 | A1 | 2/2014 | Tsekos et al. |
| 2014/0100579 | A1 | 4/2014 | Kelman et al. |
| 2014/0135658 | A1 | 5/2014 | Hladio et al. |
| 2014/0180415 | A1 | 6/2014 | Koss |
| 2014/0194889 | A1 | 7/2014 | Chang et al. |
| 2014/0228670 | A1 | 8/2014 | Justis et al. |
| 2014/0228860 | A1 | 8/2014 | Steines et al. |
| 2014/0244220 | A1 | 8/2014 | McKinnon et al. |
| 2014/0257402 | A1 | 9/2014 | Barsoum |
| 2014/0272881 | A1 | 9/2014 | Barsoum |
| 2014/0277149 | A1 | 9/2014 | Rooney et al. |
| 2014/0296860 | A1 | 10/2014 | Stein et al. |
| 2014/0303672 | A1 | 10/2014 | Tran et al. |
| 2014/0316468 | A1 | 10/2014 | Keiser et al. |
| 2015/0057756 | A1 | 2/2015 | Lang et al. |
| 2015/0066145 | A1 | 3/2015 | Rogers et al. |
| 2015/0080901 | A1 | 3/2015 | Stein |
| 2015/0081029 | A1 | 3/2015 | Bojarski et al. |
| 2015/0088030 | A1 | 3/2015 | Taylor |
| 2015/0100066 | A1 | 4/2015 | Kostrzewski et al. |
| 2015/0100091 | A1 | 4/2015 | Tohmeh et al. |
| 2015/0105782 | A1 | 4/2015 | D'Lima et al. |
| 2015/0127055 | A1 | 5/2015 | Dvorak et al. |
| 2015/0150646 | A1 | 6/2015 | Pryor et al. |
| 2015/0164657 | A1 | 6/2015 | Miles et al. |
| 2015/0182292 | A1 | 7/2015 | Hladio et al. |
| 2015/0223900 | A1 | 8/2015 | Wiebe, III et al. |
| 2015/0245844 | A1 | 9/2015 | Kennedy et al. |
| 2015/0250597 | A1 | 9/2015 | Lang et al. |
| 2015/0265291 | A1 | 9/2015 | Wilkinson |
| 2015/0305878 | A1 | 10/2015 | O'Neil et al. |
| 2015/0305891 | A1 | 10/2015 | Bergin et al. |
| 2015/0313723 | A1 | 11/2015 | Jansen et al. |
| 2015/0328004 | A1 | 11/2015 | Mafhouz |
| 2015/0366630 | A1 | 12/2015 | Gorek et al. |
| 2016/0000571 | A1 | 1/2016 | Mahfouz |
| 2016/0007983 | A1 | 1/2016 | Frey et al. |
| 2016/0015465 | A1 | 1/2016 | Steines et al. |
| 2016/0022176 | A1 | 1/2016 | Le Huec et al. |
| 2016/0022370 | A1 | 1/2016 | Pavlovskaia et al. |
| 2016/0038161 | A1 | 2/2016 | Gibson |
| 2016/0038238 | A1 | 2/2016 | Kostrzewski et al. |
| 2016/0038242 | A1 | 2/2016 | Lo Iacono et al. |
| 2016/0038293 | A1 | 2/2016 | Slamin et al. |
| 2016/0038307 | A1 | 2/2016 | Bettenga |
| 2016/0045230 | A1 | 2/2016 | Lowery et al. |
| 2016/0045317 | A1 | 2/2016 | Lang et al. |
| 2016/0045326 | A1 | 2/2016 | Hansen et al. |
| 2016/0058320 | A1 | 3/2016 | Chien et al. |
| 2016/0058523 | A1 | 3/2016 | Chien et al. |
| 2016/0074052 | A1 | 3/2016 | Keppler et al. |
| 2016/0074202 | A1 | 3/2016 | Reed et al. |
| 2016/0081754 | A1 | 3/2016 | Kostrzewski et al. |
| 2016/0095710 | A1 | 4/2016 | Juszczyk et al. |
| 2016/0100907 | A1 | 4/2016 | Gomes |
| 2016/0106483 | A1 | 4/2016 | Mayer et al. |
| 2016/0128847 | A1 | 5/2016 | Kurtaliaj et al. |
| 2016/0143744 | A1 | 5/2016 | Bojarski et al. |
| 2016/0157751 | A1 | 6/2016 | Mahfouz |
| 2016/0199101 | A1 | 7/2016 | Sharifi-Mehr et al. |
| 2016/0210374 | A1* | 7/2016 | Mosnier ............. A61B 17/7011 |
| 2016/0228192 | A1 | 8/2016 | Jansen et al. |
| 2016/0235480 | A1 | 8/2016 | Scholl et al. |
| 2016/0235493 | A1 | 8/2016 | LeBoeuf, II et al. |
| 2016/0242819 | A1 | 8/2016 | Simpson et al. |
| 2016/0242857 | A1 | 8/2016 | Scholl |
| 2016/0242934 | A1 | 8/2016 | van der Walt et al. |
| 2016/0256279 | A1 | 9/2016 | Sanders et al. |
| 2016/0256285 | A1 | 9/2016 | Jansen |
| 2016/0262800 | A1 | 9/2016 | Scholl et al. |
| 2016/0262895 | A1 | 9/2016 | Shea et al. |
| 2016/0270802 | A1 | 9/2016 | Fang et al. |
| 2016/0270931 | A1 | 9/2016 | Trieu |
| 2016/0274571 | A1 | 9/2016 | Lavallee et al. |
| 2016/0283676 | A1 | 9/2016 | Lyon et al. |
| 2016/0287395 | A1 | 10/2016 | Khalili et al. |
| 2016/0296285 | A1 | 10/2016 | Chaoui et al. |
| 2016/0310221 | A1 | 10/2016 | Bar et al. |
| 2016/0331417 | A1 | 11/2016 | Trautwein et al. |
| 2016/0354009 | A1 | 12/2016 | Schroeder |
| 2016/0354161 | A1 | 12/2016 | Deitz |
| 2016/0360997 | A1 | 12/2016 | Yadav et al. |
| 2017/0000568 | A1 | 1/2017 | O'Neil et al. |
| 2017/0007145 | A1 | 1/2017 | Gharib et al. |
| 2017/0007328 | A1 | 1/2017 | Cattin et al. |
| 2017/0007408 | A1 | 1/2017 | Fitz et al. |
| 2017/0027590 | A1 | 2/2017 | Amiot et al. |
| 2017/0027617 | A1 | 2/2017 | Strnad |
| 2017/0035580 | A1 | 2/2017 | Murphy |
| 2017/0056179 | A1 | 3/2017 | Lorio |
| 2017/0056196 | A1 | 3/2017 | Kuiper et al. |
| 2017/0071503 | A1 | 3/2017 | Wasielewski |
| 2017/0119472 | A1 | 5/2017 | Herrmann et al. |
| 2017/0132389 | A1 | 5/2017 | Mccaulley et al. |
| 2017/0135706 | A1 | 5/2017 | Frey et al. |

(56) References Cited

U.S. PATENT DOCUMENTS

| | | | |
|---|---|---|---|
| 2017/0135707 | A9 | 5/2017 | Frey et al. |
| 2017/0135770 | A1 | 5/2017 | Scholl et al. |
| 2017/0143426 | A1 | 5/2017 | Isaacs et al. |
| 2017/0143494 | A1 | 5/2017 | Mahfouz |
| 2017/0143502 | A1 | 5/2017 | Yadin et al. |
| 2017/0156798 | A1 | 6/2017 | Wasielewski |
| 2017/0189121 | A1 | 7/2017 | Frasier et al. |
| 2017/0231709 | A1 | 8/2017 | Gupta et al. |
| 2017/0252107 | A1 | 9/2017 | Turner et al. |
| 2017/0273718 | A1 | 9/2017 | Metzger et al. |
| 2017/0323037 | A1 | 11/2017 | Schroeder |
| 2017/0360493 | A1 | 12/2017 | Zucker et al. |
| 2018/0178148 | A1 | 6/2018 | Mazor et al. |
| 2018/0256067 | A1 | 9/2018 | Chien et al. |
| 2018/0289396 | A1 | 10/2018 | McGahan et al. |
| 2018/0295584 | A1 | 10/2018 | Gliner et al. |
| 2018/0301213 | A1 | 10/2018 | Zehavi et al. |
| 2018/0303552 | A1 | 10/2018 | Ryan et al. |
| 2018/0310993 | A1 | 11/2018 | Hobeika et al. |
| 2018/0349519 | A1 | 12/2018 | Schroeder |
| 2019/0015136 | A1 | 1/2019 | Kraemer |
| 2019/0046269 | A1 | 2/2019 | Hedblom et al. |
| 2019/0046287 | A1 | 2/2019 | Fallin et al. |
| 2019/0059951 | A1 | 2/2019 | Barrus |
| 2019/0060086 | A1 | 2/2019 | Krause et al. |
| 2019/0069956 | A1 | 3/2019 | Ryan et al. |
| 2019/0083144 | A1 | 3/2019 | Sharifi-Mehr et al. |
| 2019/0103190 | A1 | 4/2019 | Schmidt et al. |
| 2019/0110819 | A1 | 4/2019 | Triplett et al. |
| 2019/0117278 | A1 | 4/2019 | Chin |
| 2019/0122364 | A1 | 4/2019 | Zhang et al. |
| 2019/0142599 | A1 | 5/2019 | Thibodeau |
| 2019/0167314 | A1 | 6/2019 | Mosnier et al. |
| 2019/0201013 | A1 | 7/2019 | Siccardi et al. |
| 2019/0201155 | A1 | 7/2019 | Gupta et al. |
| 2019/0209212 | A1 | 7/2019 | Scholl et al. |
| 2019/0223916 | A1 | 7/2019 | Barrus et al. |
| 2019/0231443 | A1 | 8/2019 | McGinley et al. |
| 2019/0231557 | A1 | 8/2019 | Sutterlin, III et al. |
| 2019/0239935 | A1 | 8/2019 | Willis et al. |
| 2019/0247100 | A1 | 8/2019 | Mundis, Jr. et al. |
| 2019/0254769 | A1 | 8/2019 | Scholl et al. |
| 2019/0262015 | A1 | 8/2019 | Siccardi et al. |
| 2019/0269463 | A1 | 9/2019 | Mosnier et al. |
| 2019/0343587 | A1 | 11/2019 | Mosnier et al. |
| 2019/0362028 | A1 | 11/2019 | Mosnier et al. |
| 2019/0380782 | A1 | 12/2019 | McAfee et al. |
| 2020/0060768 | A1 | 2/2020 | Mosnier et al. |
| 2020/0121394 | A1 | 4/2020 | Mosnier et al. |

FOREIGN PATENT DOCUMENTS

| | | | |
|---|---|---|---|
| AU | 2019200740 | A1 | 2/2019 |
| AU | 2019200888 | A1 | 2/2019 |
| AU | 2019203557 | A1 | 6/2019 |
| CA | 2872845 | A1 | 11/2013 |
| CA | 2927955 | A1 | 4/2014 |
| CN | 1816134 | A | 8/2006 |
| CN | 102805677 | A | 12/2012 |
| CN | 104127229 | A | 11/2014 |
| CN | 205073000 | U | 3/2016 |
| CN | 103892953 | B | 5/2016 |
| CN | 104323843 | B | 1/2017 |
| CN | 104434287 | B | 1/2017 |
| CN | 105078555 | B | 9/2018 |
| EP | 1 570 781 | A1 | 9/2005 |
| EP | 2 053 580 | A1 | 4/2009 |
| EP | 2 749 235 | A1 | 7/2014 |
| EP | 2 754 419 | A2 | 7/2014 |
| EP | 2 496 183 | B1 | 9/2015 |
| EP | 3 000 443 | A2 | 3/2016 |
| EP | 2 608 749 | B1 | 8/2016 |
| EP | 2 403 434 | B1 | 4/2017 |
| EP | 3 431 032 | A1 | 1/2019 |
| FR | 1358988 | A | 4/1964 |
| FR | 1360208 | A | 5/1964 |
| JP | 2016-537036 | A | 12/2016 |
| JP | 2016-540610 | A | 12/2016 |
| SU | 1497721 | A1 | 7/1989 |
| SU | 1704102 | A1 | 1/1992 |
| WO | 9855038 | A1 | 12/1998 |
| WO | 00/53077 | A2 | 9/2000 |
| WO | 04/017836 | A2 | 3/2004 |
| WO | 04/030559 | A1 | 4/2004 |
| WO | 04/089224 | A2 | 10/2004 |
| WO | 04/111948 | A2 | 12/2004 |
| WO | 05/074368 | A2 | 8/2005 |
| WO | 06/075331 | A2 | 7/2006 |
| WO | 06/084193 | A2 | 8/2006 |
| WO | 07/035925 | A2 | 3/2007 |
| WO | 07/038290 | A2 | 4/2007 |
| WO | 08/002588 | A2 | 1/2008 |
| WO | 08/079546 | A2 | 7/2008 |
| WO | 08/124079 | A1 | 10/2008 |
| WO | 09/119181 | A1 | 10/2009 |
| WO | 09/124245 | A1 | 10/2009 |
| WO | 10/044880 | A1 | 4/2010 |
| WO | 10/064234 | A2 | 6/2010 |
| WO | 10/121147 | A1 | 10/2010 |
| WO | 10/147972 | A1 | 12/2010 |
| WO | 11/021192 | A1 | 2/2011 |
| WO | 12/012863 | A1 | 2/2012 |
| WO | 12/113030 | A1 | 8/2012 |
| WO | 12/131660 | A1 | 10/2012 |
| WO | 13/003435 | A1 | 1/2013 |
| WO | 14/191790 | A1 | 12/2014 |
| WO | 15/040552 | A1 | 3/2015 |
| WO | 15/054543 | A1 | 4/2015 |
| WO | 15/056131 | A1 | 4/2015 |
| WO | 15/079011 | A1 | 6/2015 |
| WO | 15/089118 | A1 | 6/2015 |
| WO | 15/185219 | A1 | 12/2015 |
| WO | 15/195843 | A2 | 12/2015 |
| WO | 2015200720 | A2 | 12/2015 |
| WO | 16/012726 | A1 | 1/2016 |
| WO | 16/019424 | A1 | 2/2016 |
| WO | 16/019425 | A1 | 2/2016 |
| WO | 16/019426 | A1 | 2/2016 |
| WO | 16/026053 | A1 | 2/2016 |
| WO | 16/032875 | A1 | 3/2016 |
| WO | 16/044352 | A1 | 3/2016 |
| WO | 16/048800 | A1 | 3/2016 |
| WO | 16/088130 | A1 | 6/2016 |
| WO | 16/094826 | A1 | 6/2016 |
| WO | 16/102026 | A1 | 6/2016 |
| WO | 16/137347 | A1 | 9/2016 |
| WO | 16/148675 | A1 | 9/2016 |
| WO | 16/165030 | A1 | 10/2016 |
| WO | 17/001851 | A1 | 1/2017 |
| WO | 17/039596 | A1 | 3/2017 |
| WO | 17/064719 | A1 | 4/2017 |
| WO | 17/066518 | A1 | 4/2017 |
| WO | 17/077356 | A1 | 5/2017 |
| WO | 17/079655 | A2 | 5/2017 |
| WO | 17/127838 | A1 | 7/2017 |
| WO | 17/151949 | A1 | 9/2017 |
| WO | 2017176802 | A1 | 10/2017 |
| WO | 17/221257 | A1 | 12/2017 |
| WO | 18/045086 | A1 | 3/2018 |
| WO | 18/055494 | A1 | 3/2018 |
| WO | 18/055518 | A1 | 3/2018 |
| WO | 18/078636 | A1 | 5/2018 |
| WO | 18/087758 | A1 | 5/2018 |
| WO | 18/131044 | A1 | 7/2018 |
| WO | 18/131045 | A1 | 7/2018 |
| WO | 18/183314 | A1 | 10/2018 |
| WO | 18/185755 | A1 | 10/2018 |
| WO | 18/193316 | A2 | 10/2018 |
| WO | 18/193317 | A1 | 10/2018 |
| WO | 18/203100 | A1 | 11/2018 |
| WO | 18/203101 | A1 | 11/2018 |
| WO | 19/014452 | A1 | 1/2019 |
| WO | 2019036039 | A2 | 2/2019 |
| WO | 2019043426 | A1 | 3/2019 |

(56) References Cited

FOREIGN PATENT DOCUMENTS

| | | | |
|---|---|---|---|
| WO | 2019068085 | A1 | 4/2019 |
| WO | 2019070729 | A1 | 4/2019 |
| WO | 2019118844 | A1 | 6/2019 |
| WO | 2019140240 | A1 | 7/2019 |

OTHER PUBLICATIONS

Aubin et al. "Preoperative Planning Simulator for Spinal Deformity Surgeries", Spine 2008, 33(20):2143-2152.
Barton et al., Mar./Apr. 2016, Early experience and initial outcomes with patient-specific spine rods for adult spinal deformity, Trending in Orthopedics, 39(2):79-86.
Fiere et al., Jul. 2016, 40. Preoperative planning and patient-specific rods for surgical treatment of thoracolumbar sagittal imbalance, in Surgery of the Spine and Spinal Cord. A Neurosurgical Approach, Van de Kalft ed., Springer International Publishing, Switzerland, pp. 645-662.
Foroozandeh et al., Summer 2012, 3D reconstruction using cubic Bezier spline curves and active contours (case study), Iranian Journal of Medical Physics, 9(3):169-176.
Galbusera et al., Feb. 2019, Artificial intelligence and machine learning in spine research, JOR Spine, 2:E1044, 20 pp.
Grove, 2011, Heterogeneous modeling of medical image data using B-spline functions, doctoral dissertation, Department of Computer Science and Engineering, University of South Florida, 212 pp.
Lazarus, Jun. 21, 2013, an introduction to splines, 29 pp.
Li et al., 2009, Modeling and measurement of 3D deformation of scoliotic spine using 2D x-ray images, Lecture Notes in Computer Science, 8 pp.
Lin, Sep. 17-21, 2003, the simplified spine modeling by 3-D Bezier curve based on the orthogonal spinal radiographic images, Proceedings of the 25th Annual International Conference of the IEEE EMBS, Cancun, Mexico, pp. 944-946.
Pasha et al., 2018, Data-driven classification of the 3D spinal curve in adolescent idiopathic scoliosis with an applications in surgical outcome prediction, Scientific Reports, 8:16296, 10 pp.
Poredos et al., 2015, Determination of the human spine curve based on laser triangulation, BMC Medical Imaging 15(2):1-11.
Prautzsch et al., Mar. 26, 2001, Bezier-and B-spline techniques, 58 pp.
Ratnakar et al. 2011, Predicting thoracic spinal postures in finite element model with Bezier technique, Ircobe Conference 2011, IRC-11-57, 4 pp.
Reinshagen et al. "A novel minimally invasive technique for lumbar decompression, realignment, and navigated interbody fusion", J Clin Neurosci. 2015, 22(9):1484-1490: XP055503028.
Rickert et al., "Posterior lumbar interbody fusion implants", Orthopaede. Springer Verlag, Berlin, DE vol. 44, No. 2 dated Jan. 28, 2015 pp. 162-169.
Solla et al., Mar. 2019, Patient-specific rods for surgical correction of sagittal imbalance in adults: Technical aspects and preliminary results: Clin Spine Surg, 32(2): 7 pp.
Spontech Medical AG Vertaplan—die Software fur Wirbelsaulenchirurgen, Aug. 29, 2013 Retrieved from the Internet: URL: https://www.youtube.com/watch?v=q0qhW1T1cp8 in 1 page.
Office Action in Chinese Application No. 202080027765.8 dated Aug. 20, 2024.

* cited by examiner

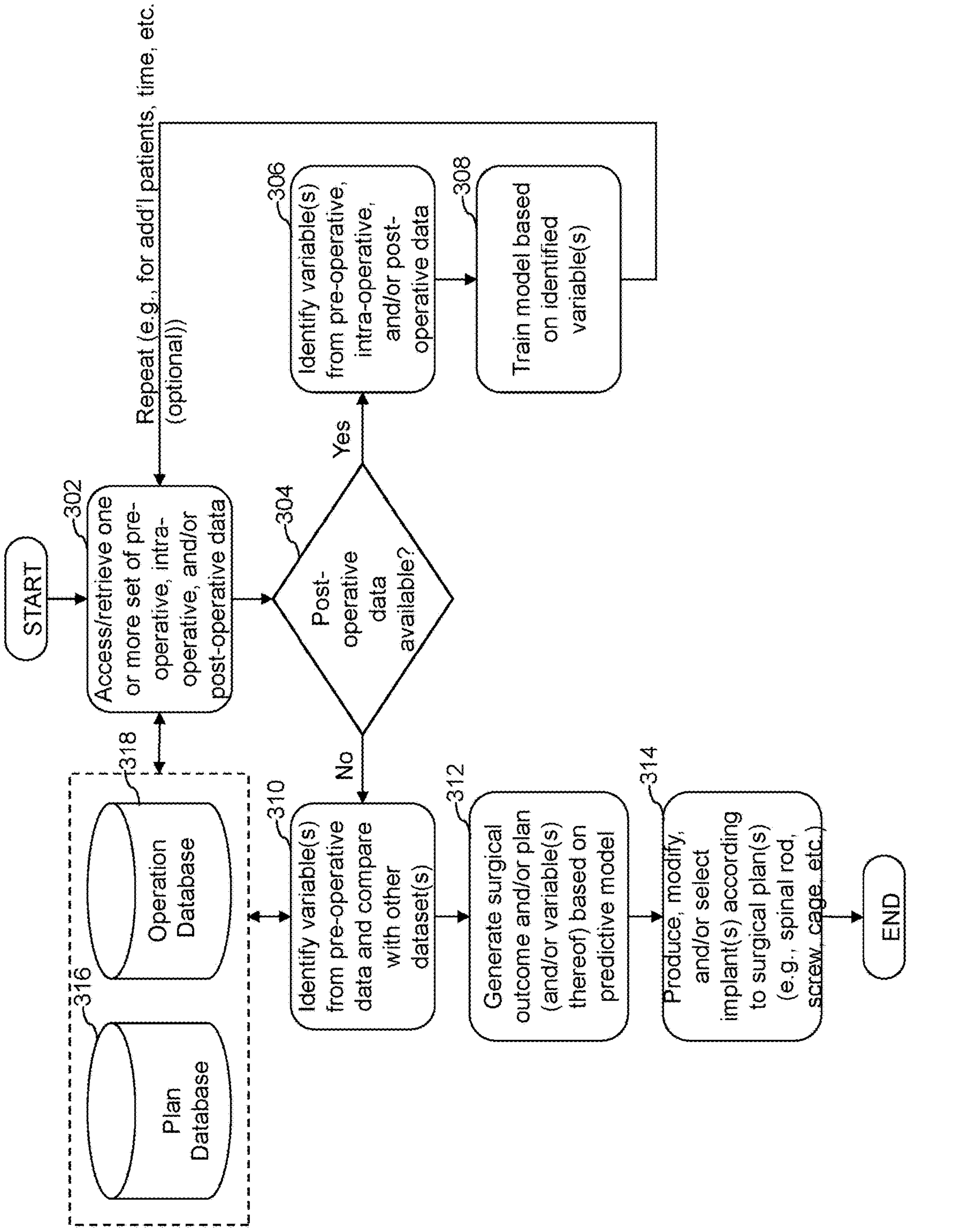

FIG. 3
START
302
Access/retrieve one or more set of pre-operative, intra-operative, and/or post-operative data
304
Post-operative data available?
Yes
No
306
Identify variable(s) from pre-operative, intra-operative, and/or post-operative data
308
Train model based on identified variable(s)
Repeat (e.g., for add'l patients, time, etc.
(optional))
310
Identify variable(s) from pre-operative data and compare with other dataset(s)
312
Generate surgical outcome and/or plan (and/or variable(s) thereof) based on predictive model
314
Produce, modify, and/or select implant(s) according to surgical plan(s) (e.g., spinal rod, screw, cage, etc.)
END
316
Plan Database
318
Operation Database

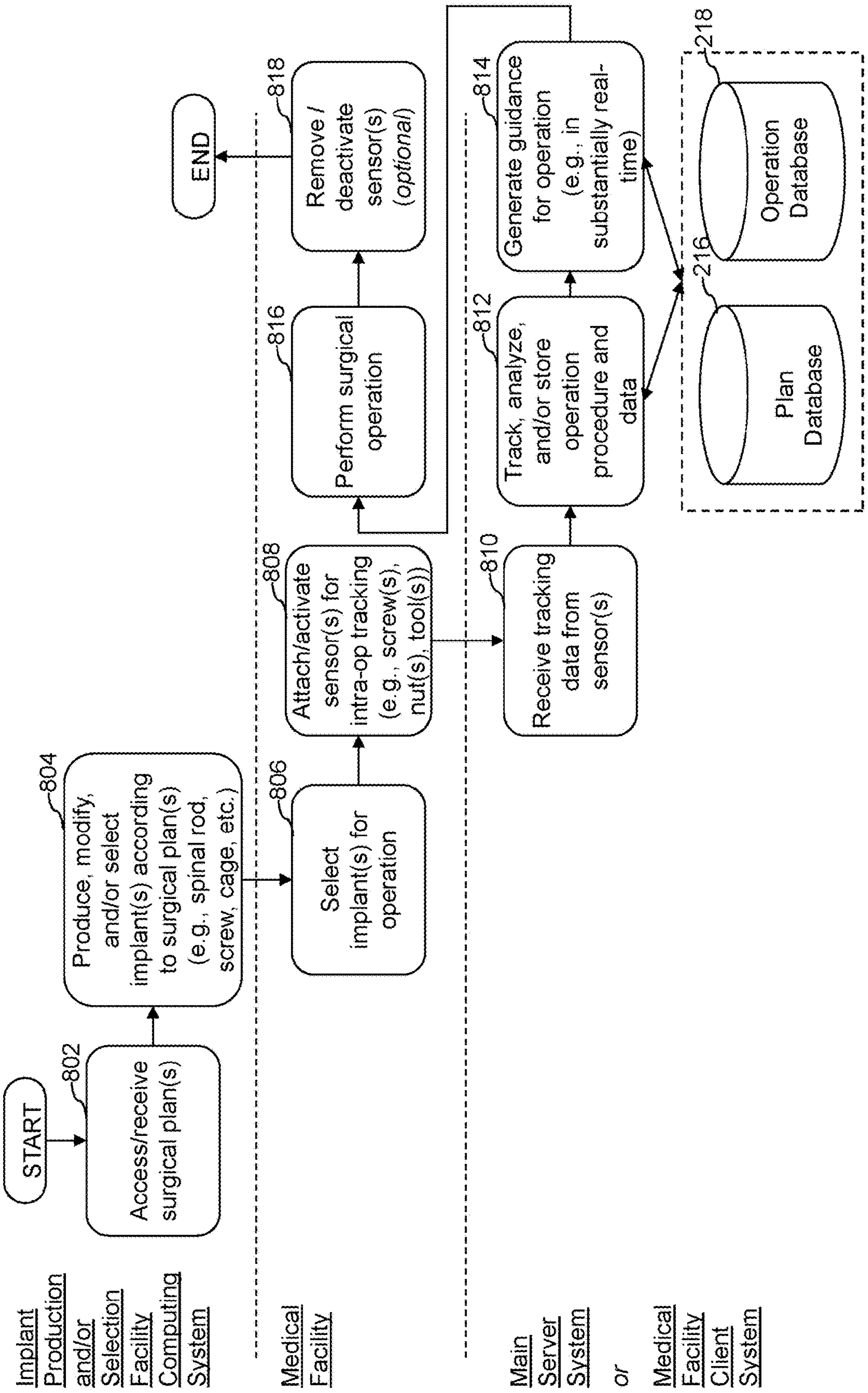

FIG. 8
Implant Production and/or Selection Facility Computing System
Medical Facility
Main Server System
or
Medical Facility Client System
START
802
Access/receive surgical plan(s)
804
Produce, modify, and/or select implant(s) according to surgical plan(s) (e.g., spinal rod, screw, cage, etc.)
806
Select implant(s) for operation
808
Attach/activate sensor(s) for intra-op tracking (e.g., screw(s), nut(s), tool(s))
816
Perform surgical operation
818
Remove / deactivate sensor(s) (optional)
END
810
Receive tracking data from sensor(s)
812
Track, analyze, and/or store operation procedure and data
814
Generate guidance for operation (e.g., in substantially real-time)
216
Plan Database
218
Operation Database

1804

1810

| SURGERY DATE | CASE ID | PATIENT INITIALS |
|---|---|---|
| 10/24/2018 | 12345678 | CB |
| ROD MATERIAL | ROD DIAMETER | LEVELS |
| Titanium | Ø5,5mm | L1-L5 |

L2

| L2 | LEFT | RIGHT | VALIDATION / COMMENT |
|---|---|---|---|
| Diameter | 4,5mm | 4,5mm | |
| Length | 35mm | 35mm | |

SURGERY DATE
10/24/2018

CASE ID
12345678

PATIENT INITIALS
CB

ROD MATERIAL
Titanium

ROD DIAMETER
Ø5,5mm

LEVELS
L1-L5

L3

| L3 | LEFT | RIGHT | VALIDATION / COMMENT |
|---|---|---|---|
| Diameter | 4,5mm | 4,5mm | |
| Length | 40mm | 40mm | |

| L4 | LEFT | RIGHT | VALIDATION / COMMENT |
|---|---|---|---|
| Diameter | 6,5mm | 5,5mm | |
| Length | 35mm | 35mm | |

FIG. 32F
| SURGERY DATE | CASE ID | PATIENT INITIALS |
|---|---|---|
| 10/24/2018 | 12345678 | CB |
| ROD MATERIAL | ROD DIAMETER | LEVELS |
| Titanium | Ø5.5mm | L1-L5 |
L5
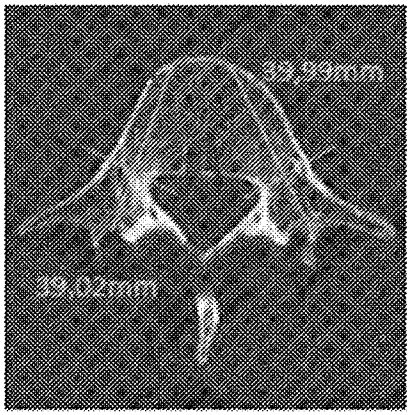
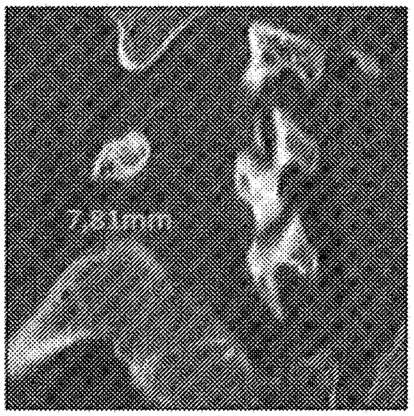
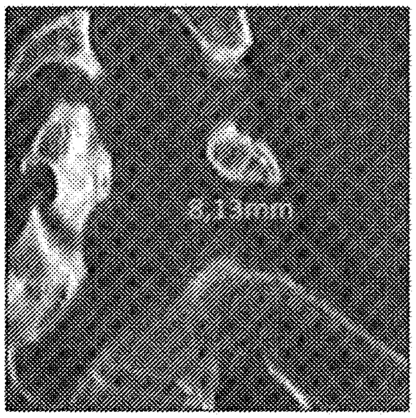
| L5 | LEFT | RIGHT | VALIDATION / COMMENT |
|---|---|---|---|
| Diameter | 6,5mm | 7,5mm | |
| Length | 35mm | 35mm | |

FIG. 33B
SURGERY DATE
06/24/2019
CASE ID
0VNjY25R
PATIENT INITIALS
LL
ROD MATERIAL
Ti
ROD DIAMETER
Ø6.0mm
LEVELS
T10 ~ Iliac
T10
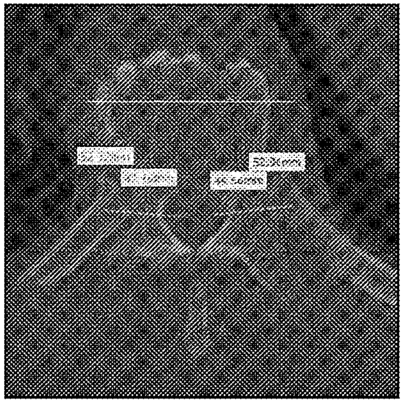
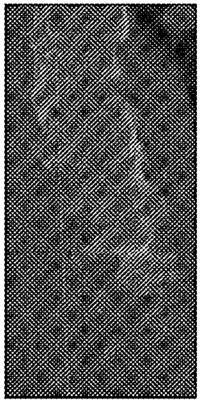
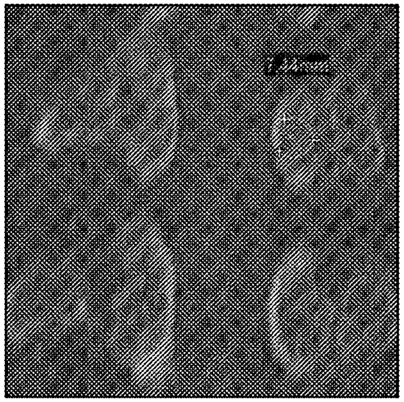
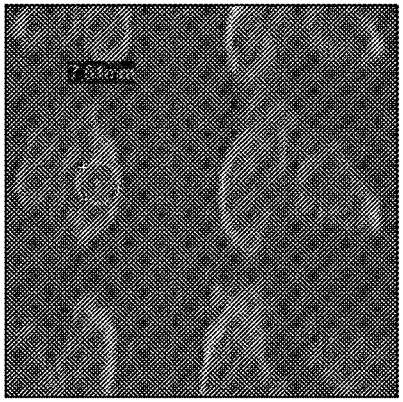
| T10 | LEFT | RIGHT | VALIDATION / COMMENT |
|---|---|---|---|
| Diameter | 6.5mm | 6.5mm | |
| Length | 40mm | 45mm | |

| SURGERY DATE | CASE ID | PATIENT INITIALS |
|---|---|---|
| 06/24/2019 | 0VNJY25R | LL |
| ROD MATERIAL | ROD DIAMETER | LEVELS |
| Ti | Ø6.0mm | T10 - Iliac |

T11

| T11 | LEFT | RIGHT | VALIDATION / COMMENT |
|---|---|---|---|
| Diameter | 6.5 | 6.5 | |
| Length | 45mm | 45mm | |

SURGERY DATE
06/24/2019

CASE ID
0VNJY25R

PATIENT INITIALS
LL

ROD MATERIAL
Ti

ROD DIAMETER
Ø6.0mm

LEVELS
T10 - Iliac

T12

| T12 | LEFT | RIGHT | VALIDATION / COMMENT |
|---|---|---|---|
| Diameter | 6.5 | 6.5 | |
| Length | 50mm | 45mm | |

FIG. 33E
| SURGERY DATE | CASE ID | PATIENT INITIALS |
|---|---|---|
| 06/24/2019 | 0VNJY25R | LL |
| ROD MATERIAL | ROD DIAMETER | LEVELS |
| Ti | Ø6.0mm | T10 – Iliac |
L1
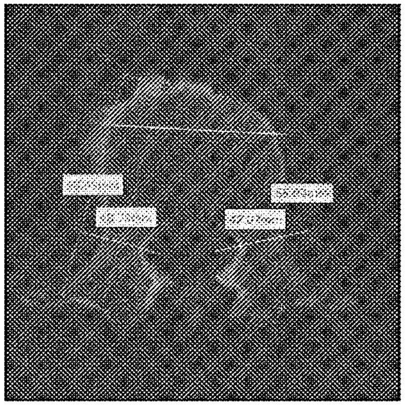
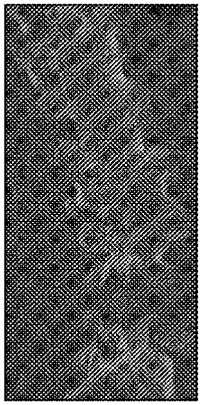
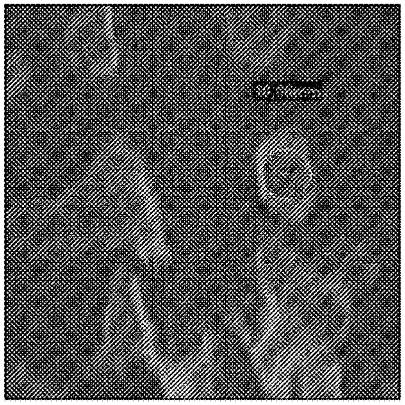
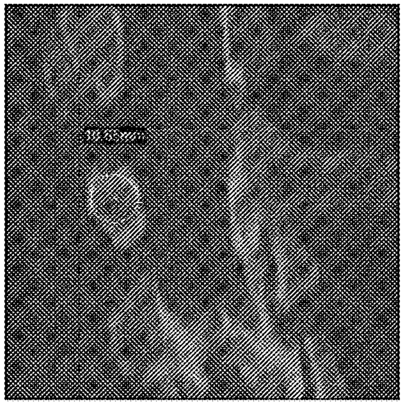
| L1 | LEFT | RIGHT | VALIDATION / COMMENT |
|---|---|---|---|
| Diameter | 6.5 | 6.5 | |
| Length | 45mm | 50mm | |

SURGERY DATE
06/24/2019

CASE ID
0VNJY25R

PATIENT INITIALS
LL

ROD MATERIAL
Ti

ROD DIAMETER
Ø6.0mm

LEVELS
T10 ~ Iliac

L3

| L3 | LEFT | RIGHT | VALIDATION / COMMENT |
|---|---|---|---|
| Diameter | 6.5 | 6.5 | |
| Length | 45mm | 45mm | |

SURGERY DATE
05/24/2019

CASE ID

PATIENT INITIALS
LL

ROD MATERIAL
Ti

ROD DIAMETER
Ø6.0mm

LEVELS
T10 - Iliac

L4

| L4 | LEFT | RIGHT | VALIDATION / COMMENT |
|---|---|---|---|
| Diameter | 6.5 | 6.5 | |
| Length | 40mm | 40mm | |

FIG. 33J
| SURGERY DATE | CASE ID | PATIENT INITIALS |
|---|---|---|
| 06/24/2019 | 0VNJY25R | LL |
| ROD MATERIAL | ROD DIAMETER | LEVELS |
| Ti | Ø6.0mm | T10 - Iliac |
S1
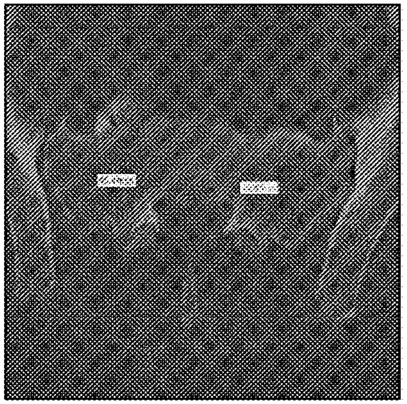
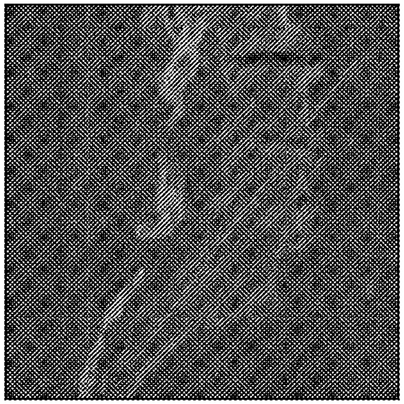
| S1 | LEFT | RIGHT | VALIDATION / COMMENT |
|---|---|---|---|
| Diameter | 6.5 | 6.5 | |
| Length | 45mm | 45mm | |

3800A

3900

SYSTEMS, METHODS, AND DEVICES FOR DEVELOPING PATIENT-SPECIFIC SPINAL IMPLANTS, TREATMENTS, OPERATIONS, AND/OR PROCEDURES

CROSS-REFERENCE TO RELATED APPLICATIONS

This application is a continuation of U.S. patent application Ser. No. 18/601,891, filed Mar. 11, 2024, which is a continuation of U.S. patent application Ser. No. 17/130,492, filed Dec. 22, 2022, now U.S. Pat. No. 11,925,417, which is a continuation in part of U.S. patent application Ser. No. 16/837,461, filed Apr. 1, 2020, now U.S. Pat. No. 11,877, 801, which claims the benefit under 35 U.S.C. § 119(c) of U.S. Provisional Patent Application No. 62/828,337, filed Apr. 2, 2019, U.S. Provisional Patent Application No. 62/932,727, filed Nov. 8, 2019, U.S. Provisional Patent Application No. 62/828,741, filed Apr. 3, 2019, U.S. Provisional Patent Application No. 62/932,743, filed Nov. 8, 2019, U.S. Provisional Patent Application No. 62/828,326, filed Apr. 2, 2019, U.S. Provisional Patent Application No. 62/932,701, filed Nov. 8, 2019, U.S. Provisional Patent Application No. 62/939,144, filed Nov. 22, 2019, and U.S. Provisional Patent Application No. 62/952,647, filed Dec. 23, 2019, each of which is incorporated herein by reference in its entirety under 37 C.F.R. § 1.57. U.S. patent application Ser. No. 17/130,492 also claims priority to and the benefit of U.S. Provisional Patent Application Ser. No. 62/953,690, entitled "SYSTEMS, DEVICES, AND METHODS FOR DEVELOPING PATIENT-SPECIFIC SPINAL IMPLANTS, TREATMENTS, OPERATIONS, AND/OR PROCEDURES," filed Dec. 26, 2019, which is incorporated herein by reference in its entirety. Any and all applications for which a foreign or domestic priority claim is identified in the Application Data Sheet as filed with the present application are hereby incorporated by reference under 37 C.F.R. § 1.57.

BACKGROUND

Field

The present application relates to developing patient-specific spinal implants, surgical plans, treatments, operations, and/or procedures.

Description

Spinal surgery is one of the most frequently performed surgical procedures worldwide. Spinal surgery may involve implantation of one or more spinal implants, such as a spinal rod, to correct the curvature of the spine of a patient and to prevent further deterioration. As such, the particular curvature of the spinal rod can be a key factor in obtaining successful results from surgery.

SUMMARY

Various embodiments described herein relate to systems, methods, and devices for developing patient-specific spinal implants, treatments, operations, and/or procedures. In particular, some embodiments described herein are directed to the design and/or manufacture of patient-specific spinal rods. In some embodiments, the systems, methods, and devices described herein are configured to design and/or produce a patient-specific spinal rod based at least in part on a mathematical curve. In some embodiments, the systems, methods, and devices described herein are configured to design and/or produce a patient-specific spinal rod based at least in part on using an Initial Graphics Exchange Specification (IGES) file format.

Various embodiments described herein relate to systems, methods, and devices for developing patient-specific spinal implants, surgical plans, treatments, operations, and/or procedures. In some embodiments, systems, methods, and devices described herein for developing patient-specific spinal implants, surgical plans, treatments, operations, and/or procedures can comprise an iterative virtuous cycle. In some embodiments, the iterative virtuous cycle can further comprise preoperative, intraoperative, and postoperative techniques or processes. For example, the iterative virtuous cycle can comprise imaging analysis, case planning/simulation, implant production, case support, data collection, machine learning, and/or predictive modeling. One or more techniques or processes of the iterative virtuous cycle can be repeated. Further, in some embodiments, systems, methods, and devices described herein can comprise using artificial intelligence, machine learning, and/or predictive modeling to predict the outcome of a spinal surgery, one or more parameters of a spine of a patient after spinal surgery, for example after implantation of a spinal rod which can be patient-specific, and/or one or more parameters of one or more recommended patient-specific spinal rods. Furthermore, in some embodiments, systems, methods, and devices described herein can comprise intraoperative tracking for tracking and/or suggesting improvements during spinal surgery based on a pre-operatively determined surgical plan, for example in real-time or substantially real-time. In addition, in some embodiments, systems, methods, and devices described herein can comprise preoperatively determining and/or planning one or more implants and/or screws prior to spinal surgery, which can comprise screw and/or other spinal implant planning/selection.

In particular, in some embodiments, a computer-implemented method for generating and assisting patient-specific spinal treatment comprises: analyzing, using a computer system, one or more preoperative medical images of a spine of a patient to determine one or more preoperative spinopelvic parameters, wherein the one or more spinopelvic parameters comprise one or more of lumbar lordosis (LL), preoperative thoracic kyphosis (TK), pelvic incidence (PI), pelvic tilt (PT), or sagittal vertical axis (SVA) for one or more vertebrae; transforming, using the computer system, the determined one or more preoperative spinopelvic parameters to obtain one or more preoperative spinopelvic parameters in a frequency domain, wherein the transforming comprises applying a Fourier transformation to the determined one or more preoperative spinopelvic parameters; filtering, using the computer system, the one or more preoperative spinopelvic parameters in the frequency domain, wherein the filtering comprises filtering out one or more of the one or more preoperative spinopelvic parameters in the frequency domain comprising a frequency level above a predetermined threshold; applying, using the computer system, one or more predictive models to generate a predicted surgical outcome in the frequency domain based at least in part on the filtered one or more preoperative spinopelvic parameters in the frequency domain and the one or more preoperative non-imaging data of the subject, wherein the one or more predictive models comprises one or more of a generative adversarial network (GAN) algorithm, convolutional neural network (CNN) algorithm, or recurrent neural network (RNN) algorithm; and transforming, using the computer system, the generated predicted surgical outcome in the frequency domain to obtain a generated predictive surgical outcome in a spatial domain, wherein the transforming the generated predicted surgical outcome in the frequency domain comprises applying an inverse Fourier transformation to the generated predicted surgical outcome in the frequency domain, generating, using the computer system, a patient-specific spinal treatment based at least in part on the generated predictive surgical outcome in the spatial domain, wherein the generated patient-specific spinal treatment comprises one or more patient-specific spinal surgical procedures; attaching one or more intraoperative tracking modules to one or more vertebral implants for implanting to one or more vertebrae of interest during spinal surgery of the patient, wherein the one or more intraoperative tracking modules comprise a strip for blocking a power circuit within the one or more intraoperative tracking modules; removing the strip from one or more intraoperative tracking modules to initiate tracking of one or more angles between the one or more vertebrae to which the one or more intraoperative tracking modules are attached to; and generating, by the computer system, intraoperative tracking data in real-time and comparing the generated tracking data in real-time to the generated one or more patient-specific spinal surgical procedures to assist the generated patient-specific spinal treatment, wherein the computer system comprises a computer processor and an electronic storage medium.

In some embodiments of a computer-implemented method for generating and assisting patient-specific spinal treatment, the one or more vertebral implants comprise one or more vertebral screws. In some embodiments, the one or more vertebral screws comprise one or more tulip screws. In some embodiments, the one or more intraoperative tracking modules comprises one or more notches configured to attach or remove the one or more intraoperative tracking modules to the one or more vertebral screws. In some embodiments, the one or more intraoperative tracking modules comprises a first conduit adapted to allow insertion of a surgical tool, and wherein the one or more intraoperative tracking modules comprises a second conduit adapted to allow insertion of a spinal rod. In some embodiments, a longitudinal axis of the first conduit is substantially perpendicular to a longitudinal axis of the second conduit. In some embodiments, the second conduit comprises a top section and a bottom section, wherein a width of the top section is larger than a width of the bottom section. In some embodiments, the second conduit is formed by two notches of the one or more intraoperative tracking modules, wherein the two notches are adapted to attach to a horizontal notch of the one or more vertebral screws.

In some embodiments of a computer-implemented method for generating and assisting patient-specific spinal treatment, the one or more spinopelvic parameters are determined automatically by the computer system. In some embodiments, the one or more preoperative medical images of the spine of the patient comprise one or more sagittal x-ray images and one or more frontal x-ray images. In some embodiments, the generated predictive surgical outcome in the spatial domain comprises one or more postoperative spinopelvic parameters. In some embodiments, the generated patient-specific spinal treatment further comprises one or more specifications of a spinal rod to be implanted to the spine of the patient.

In some embodiments, a computer-implemented method of predicting a surgical outcome a spinal surgery of a subject comprises: inputting, into a computer system, one or more preoperative inputs relating to the subject, wherein the one or more preoperative inputs comprise one or more preoperative medical images of a spine of the subject and one or more preoperative non-imaging data of the subject; determining, using the computer system, one or more measurements from the inputted one or more preoperative medical images of the spine of the subject, wherein the one or more measurements comprise a position of one or more vertebrae of the spine of the subject; determining, using the computer system, one or more preoperative spinopelvic parameters based at least in part on the one or more determined measurements, wherein the one or more preoperative spinopelvic parameters comprise one or more of lumbar lordosis (LL), preoperative thoracic kyphosis (TK), pelvic incidence (PI), pelvic tilt (PT), or sagittal vertical axis (SVA) for one or more vertebrae; transforming, using the computer system, the determined one or more preoperative spinopelvic parameters to obtain one or more preoperative spinopelvic parameters in a frequency domain, wherein the transforming comprises applying a Fourier transformation to the determined one or more preoperative spinopelvic parameters; filtering, using the computer system, the one or more preoperative spinopelvic parameters in the frequency domain, wherein the filtering comprises filtering out one or more of the one or more preoperative spinopelvic parameters in the frequency domain comprising a frequency level above a predetermined threshold; applying, using the computer system, one or more predictive models to generate a predicted surgical outcome in the frequency domain based at least in part on the filtered one or more preoperative spinopelvic parameters in the frequency domain and the one or more preoperative non-imaging data of the subject; and transforming, using the computer system, the generated predicted surgical outcome in the frequency domain to obtain a generated predictive surgical outcome in a spatial domain, wherein the transforming the generated predicted surgical outcome in the frequency domain comprises applying an inverse Fourier transformation to the generated predicted surgical outcome in the frequency domain, wherein the computer system comprises a computer processor and an electronic storage medium.

In some embodiments of a computer-implemented method of predicting a surgical outcome a spinal surgery of a subject, the one or more predictive models comprises one or more of a generative adversarial network (GAN) algorithm, convolutional neural network (CNN) algorithm, or recurrent neural network (RNN) algorithm. In some embodiments, a computer-implemented method of predicting a surgical outcome a spinal surgery of a subject further comprises generating, by the computer system, a preoperatively determined spinal surgical plan for the subject based at least in part on the generated predictive surgical outcome in the spatial domain. In some embodiments, the generated preoperatively determined spinal surgical plan comprises one or more specifications of a spinal rod for implantation during the spinal surgery of the subject.

In some embodiments of a computer-implemented method of predicting a surgical outcome a spinal surgery of a subject, the one or more measurements from the inputted one or more preoperative medical images of the spine of the subject are determined automatically by the computer system. In some embodiments, the inputted one or more preoperative medical images of the spine of the subject comprises one or more sagittal x-ray images and one or more frontal x-ray images. In some embodiments, the generated predictive surgical outcome in the spatial domain comprises one or more of one or more postoperative spinopelvic parameters or one or more specifications of a spinal rod to be implanted to the spine of the subject. In some embodiments, the one or more preoperative inputs further comprise one or more specifications of a spinal rod proposed to be implanted to the spine of the subject.

In some embodiments, a computer-implemented method of training a predictive model for predicting a surgical outcome a spinal surgery of a subject comprises: inputting, into a computer system, one or more preoperative inputs and one or more postoperative inputs relating to one or more previous subjects, wherein each of the one or more preoperative inputs and the one or more postoperative inputs relating to one or more previous subjects comprise one or more preoperative medical images and one or more postoperative medical images of a spine of the one or more previous subjects and one or more preoperative non-imaging data and one or more postoperative non-imaging of the one or more previous subjects; determining, using the computer system, one or more measurements from the inputted one or more preoperative medical images and one or more postoperative medical images of the spine of the one or more previous subjects, wherein the one or more measurements comprise a position of one or more vertebrae of the spine of the one or more previous subjects; determining, using the computer system, one or more preoperative spinopelvic parameters and one or more postoperative spinopelvic parameters of the spine of the one or more previous subjects based at least in part on the one or more determined measurements, wherein the one or more preoperative spinopelvic parameters and the one or more postoperative spinopelvic parameters of the one or more previous subjects comprise one or more of lumbar lordosis (LL), preoperative thoracic kyphosis (TK), pelvic incidence (PI), pelvic tilt (PT), or sagittal vertical axis (SVA) for one or more vertebrae; applying, using the computer system, a data compression technique to the determined one or more preoperative spinopelvic parameters and the one or more postoperative spinopelvic parameters of the one or more previous subjects to obtain compressed one or more preoperative spinopelvic parameters and one or more postoperative spinopelvic parameters of the one or more previous subjects; filtering, using the computer system, the compressed one or more preoperative spinopelvic parameters and the one or more postoperative spinopelvic parameters of the one or more previous subjects, wherein the filtering comprises filtering out one or more compressed preoperative spinopelvic parameters and one or more postoperative spinopelvic parameters of the one or more previous subjects comprising a noise level above a predetermined threshold; training, using the computer system, one or more predictive models based at least in part on the filtered compressed one or more preoperative spinopelvic parameters and one or more postoperative spinopelvic parameters of the one or more previous subjects, the one or more preoperative non-imaging data of the one or more previous subjects, and the one or more postoperative non-imaging of the one or more previous subjects; and testing, using the computer system, the trained one or more predicted models on one or more test preoperative inputs and one or more test postoperative inputs relating to one or more test subjects, wherein each of the one or more test preoperative inputs and the one or more test postoperative inputs relating to one or more test subjects comprise one or more test preoperative medical images and one or more test postoperative medical images of a spine of the one or more test subjects, wherein the one or more test subjects are separate from the one or more previous subjects, wherein the trained and tested one or more predictive models are configured to predict the surgical outcome of the spinal surgery of the subject based at least in part on one or more spinopelvic parameters derived from one or more preoperative medical images of a spine of the subject, wherein the computer system comprises a computer processor and an electronic storage medium.

In some embodiments of a computer-implemented method of training a predictive model for predicting a surgical outcome a spinal surgery of a subject, the data compression technique comprises a Fourier transformation. In some embodiments, the data compression technique comprises a polynomial function. In some embodiments, the training of the one or more predictive models is based at least in part on one or more of a generative adversarial network (GAN) algorithm, convolutional neural network (CNN) algorithm, or recurrent neural network (RNN) algorithm.

In some embodiments, a computer-implemented method of training a predictive model for predicting a surgical outcome a spinal surgery of a subject further comprises generating, using the computer system, one or more augmented measurements by applying a Gaussian process to the determined one or more measurements from the inputted one or more preoperative medical images of the spine of the previous subjects, wherein the generated one or more augmented measurements are configured to be used to train the one or more predictive models.

In some embodiments, a computer-implemented method of training a predictive model for predicting a surgical outcome a spinal surgery of a subject further comprises generating, using the computer system, one or more augmented measurements from rotating the one or more preoperative medical images and the one or more postoperative medical images of the spine of the one or more previous subjects along a vertical axis, wherein the generated one or more augmented measurements are configured to be used to train the one or more predictive models. In some embodiments, the one or more preoperative medical images and the one or more postoperative medical images of the spine of the one or more previous subjects are rotated along the vertical axis in 180 degrees.

In some embodiments of a computer-implemented method of training a predictive model for predicting a surgical outcome a spinal surgery of a subject, the one or more postoperative inputs relating to one or more previous subjects further comprise one or more specifications of a spinal rod implanted to the spine of the one or more previous subjects.

In various embodiments, a computer-implemented method for generating a drawing of a spinal rod having a plurality of spline segments is disclosed. The method may include providing a computing system having a processor, a data store, and a patient specific planning and analysis module. The method may include inputting a patient specific target plan comprising a digital representation of a spinal rod having a target geometry. The method may include transforming the digital representation of the spinal rod into a curved line corresponding to the target geometry, and generating a spline data set comprising a plurality of spline segments, each spline segment being sequentially linked to an adjacent spline segment. The method may include adjusting, iteratively, each spline segment until the plurality of spline segments approximate the curved line, and generating, after the adjusting step is completed, a digital file comprising drawings for manufacturing a spinal rod based on the plurality of spline segments.

In various embodiments, a surgical planning and assessment system is disclosed. The system may include a computing system comprising a processor, a data store, and a patient specific planning and analysis module. The computing system may include computer executable code that, when executed by the processor, is configured to perform a number of operations. The system may store a patient specific target plan in the data store, the patient specific target plan comprising a digital representation of a spinal rod having a target geometry. The system may transform the digital representation of the spinal rod into a curved line corresponding to the target geometry. The system may generate a spline data set comprising a plurality of spline segments, each spline segment being sequentially linked to an adjacent spline segment. The system may adjust, iteratively, each spline segment until the plurality of spline segments approximate the curved line. The system may generate a digital file comprising drawings for manufacturing a spinal rod based on the plurality of spline segments.

For purposes of this summary, certain aspects, advantages, and novel features of the disclosure are described herein. It is to be understood that not necessarily all such advantages may be achieved in accordance with any particular embodiment of the disclosure. Thus, for example, those skilled in the art will recognize that the disclosure may be embodied or carried out in a manner that achieves one advantage or group of advantages as taught herein without necessarily achieving other advantages as may be taught or suggested herein.

All of these embodiments are intended to be within the scope of the disclosure herein disclosed. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

A better understanding of the devices and methods described herein will be appreciated upon reference to the following description in conjunction with the accompanying drawings, wherein:

FIG. 3 is a flowchart illustrating an example embodiment(s) of predictive modeling that can be used for developing patient-specific implants, treatments, operations, and/or procedures;

FIG. 8 is a flowchart illustrating an example embodiment(s) of implant production, case support, data collection, and/or intraoperative tracking during spinal surgery for developing patient-specific spinal implants, treatments, operations, and/or procedures;

FIGS. 32A-32G illustrate an example embodiment(s) of a screw planning memo(s);

FIGS. 33A-33K illustrate an example embodiment(s) of a screw planning memo(s);

DETAILED DESCRIPTION

Figure 1:
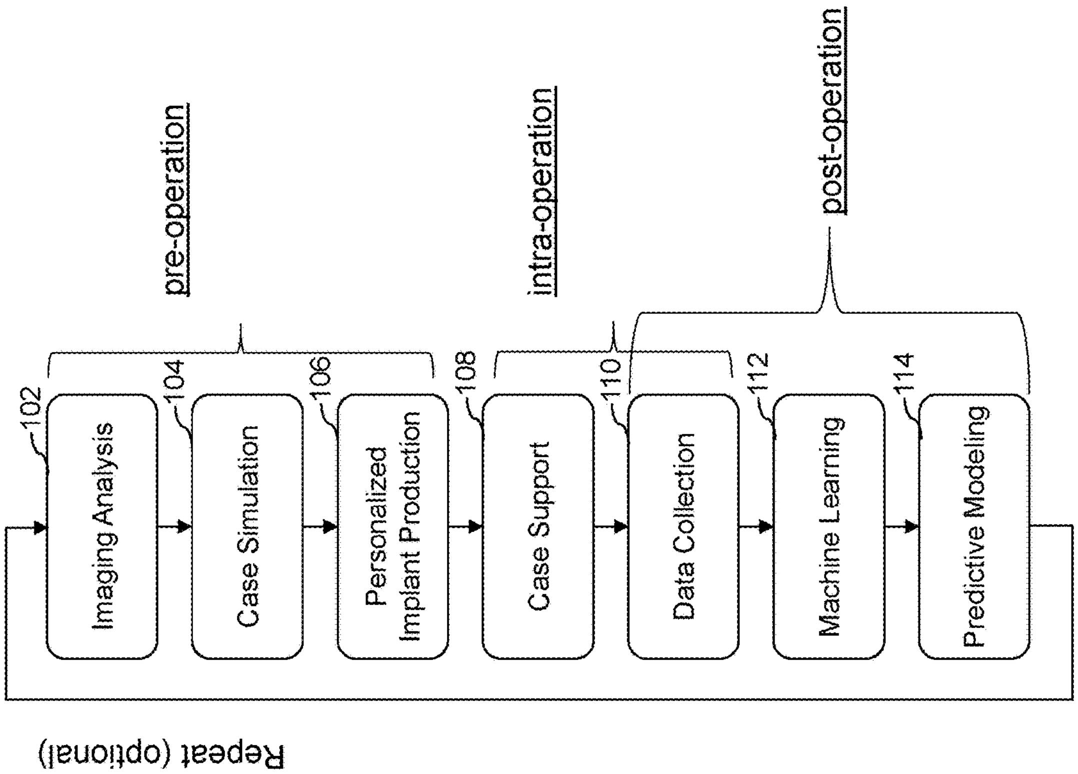
FIG. 1 is a flowchart illustrating an overview of an example embodiment(s) of an iterative virtuous cycle for developing patient-specific spinal implants, treatments, operations, and/or procedures.

Although several embodiments, examples, and illustrations are disclosed below, it will be understood by those of ordinary skill in the art that the disclosures described herein extend beyond the specifically disclosed embodiments, examples, and illustrations and includes other uses of the disclosures and obvious modifications and equivalents thereof. Embodiments of the disclosures are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the disclosures. In addition, embodiments of the disclosures can comprise several novel features and no single feature is solely responsible for its desirable attributes or is essential to practicing the disclosures herein described.

Spinal surgery is one of the most frequently performed surgical procedures worldwide. Generally speaking, spinal surgery may involve implantation of one or more implants, such as a spinal rod(s), cage(s), and/or one or more screw(s) to correct the curvature of the spine of a patient and to prevent further deterioration. As such, correspondence between one or more spinal implants and patient anatomy can be a key factor in obtaining successful results from surgery. In particular, the particular curvature, dimensions, shape and/or size of one or more spinal rods, cages, and/or screws can be crucial to obtain successful surgical results.

Various embodiments described herein relate to systems, methods, and devices for developing patient-specific spinal implants, treatments, operations, and/or procedures. In some embodiments, systems, methods, and devices described herein for developing patient-specific spinal implants, surgical plans, treatments, operations, and/or procedures can comprise an iterative virtuous cycle. The iterative virtuous cycle can further comprise one or more preoperative, intraoperative, and postoperative techniques or processes. For example, the iterative virtuous cycle can comprise one or more of imaging analysis, case simulation, implant production, case support, data collection, machine learning, and/or predictive modeling. One or more techniques or processes of the iterative virtuous cycle can be repeated.

In particular, there can be a desired surgical outcome that is particular to each patient. For example, based on the current state of a spine of a patient, it can be known from past data, experience, and/or literature, that a particular patient's spine should be corrected in a certain way and/or degree. In turn, in order to obtain such corrective results, it can be advantageous to design, generate, and/or other formulate specific dimensions and/or other variables pertaining to one or more implants that are specific to the particular patient. For example, there can be one or more desirable variables and/or parameters for one or more spinal rods, cages, and/or screws for implantation for a specific patient. As such, some systems, devices, and methods described herein are configured to utilize one or more medical images of a spine of a patient and/or one or more parameters of the spine of the patient and analyze the same to determine one or more desired parameters and/or variables of one or more spinal rods, cages, and/or screws for implantation. Based on the determined one or more desired parameters and/or variables, some systems, devices, and methods described herein can be further configured to manufacture, produce, modify, select, provide guidance for selection of, and/or generate instructions to manufacture, produce, modify, and/or select one or more spinal rods, cages, and/or screws that are specifically customized for a particular patient. In particular, in some embodiments, the systems, methods, and devices described herein can utilize predictive modeling, machine learning, and/or artificial intelligence as part of developing patient-specific spinal implants, surgical plans, treatments, operations, and/or procedures In addition to designing, producing, and/or otherwise obtaining an ideal or desired patient-specific spinal implant, it can be equally, if not more, important that such implant is correctly implanted according to a desired and/or predetermined surgical plan. In other words, even if one or more spinal rods, cages, and/or screws are produced, selected, or otherwise obtained for a specific patient, its effects can be limited if the implantation or other surgical procedure is not conducted according to a desired or predetermined plan. As such, it can be advantageous to be able to ensure or at least increase the chances that surgery or a procedure thereof is performed as desired. To such effect, some systems, devices, and methods described herein provide intraoperative tracking to provide guidance and/or performance evaluation during spinal surgery, for example in real-time or in substantially real-time.

Further, it can be advantageous to be able to analyze data relating to specific patient spinal conditions pre-operation and/or post-operation and utilize the same in order to predict the outcome of spinal surgery for a new patient. In some embodiments, predictive analysis can also be used in generating a patient-specific surgical plan, which can comprise one or more parameters and/or variables for one or more spinal rods, cages, and/or screws. Accordingly, some systems, methods, and devices disclosed herein are configured to utilize predictive modeling to generate predictive surgical outcome(s) and/or patient-specific surgical plan(s).

Iterative Virtuous Cycle

FIG. 1 is a flowchart illustrating an overview of an example embodiment(s) of an iterative virtuous cycle for developing patient-specific spinal implants, treatments, operations, and/or procedures. As illustrated in FIG. 1, some embodiments of the systems, methods, and devices described herein comprise one or more processes that can form an iterative virtuous cycle. For example, an iterative virtuous cycle can comprise one or more of the following: (1) imaging analysis 102; (2) case simulation 104; (3) personalized or patient-specific implant production 106; (4) case support 108; (5) data collection 110; (6) machine learning 112; and/or (7) predictive modeling 114. Certain embodiments may comprise any subset of the aforementioned processes. Further, one or more processes or techniques of a virtuous iterative cycle can be repeated.

Some processes or techniques of the virtuous iterative cycle can be performed at different points in time. For example, in some embodiments, imaging analysis, case simulation, and/or implant production can be performed pre-operation or prior to surgery. In some embodiments, case support and/or data collection may be performed during operation or intra-operation or during surgery. Lastly, in some embodiments, some data collection, machine learning, and/or predictive modeling can be performed post-operation or after surgery. In some embodiments, the whole virtuous iterative cycle and/or portions thereof can be repeated for the same and/or different patient in certain embodiments. U.S. Pat. No. 10,292,770 in its entirety is hereby incorporated by reference under 37 C.F.R. § 1.57.

Figure 2:
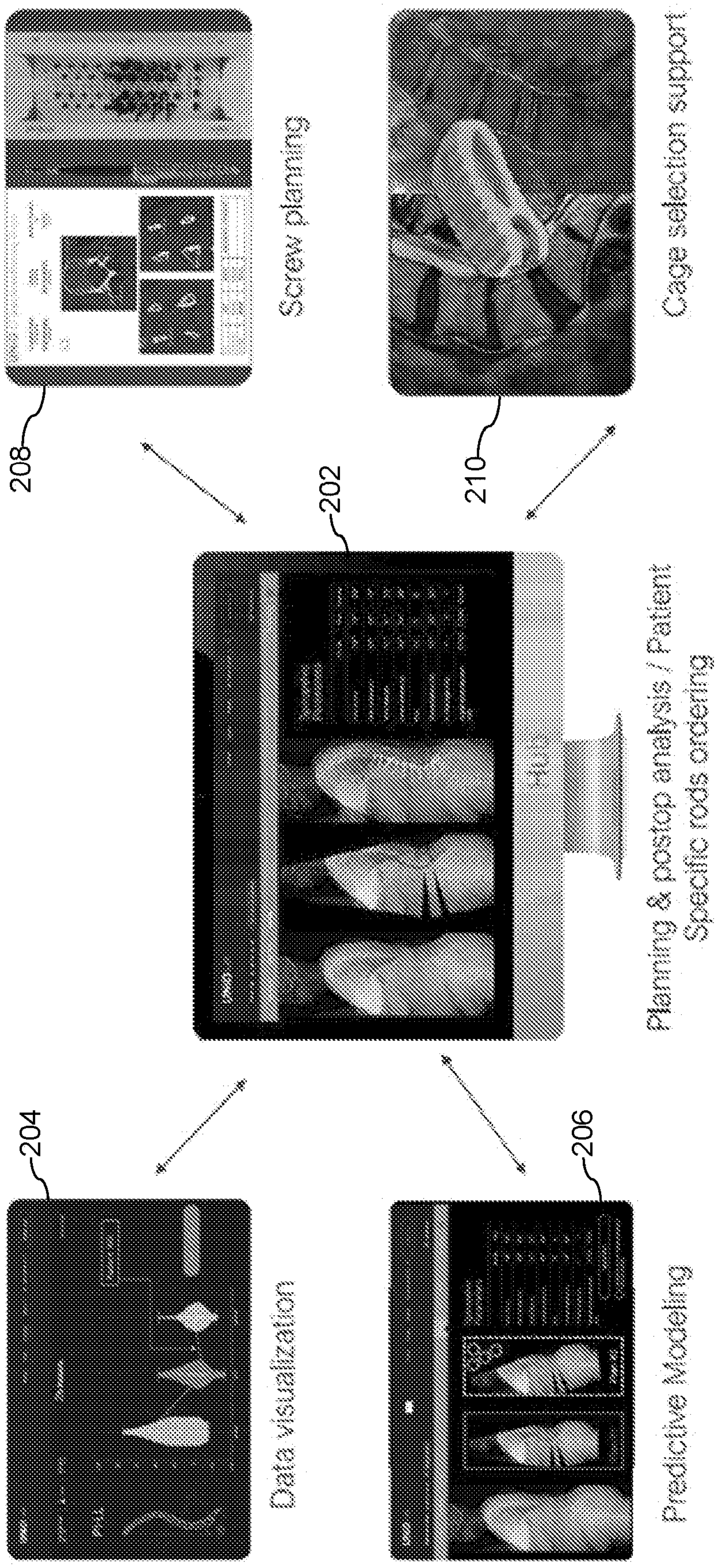
FIG. 2 illustrates an example embodiment(s) for developing spinal implants, treatments, operations, and/or procedures that comprises a software platform.

FIG. 2 illustrates an example embodiment(s) for developing spinal implants, treatments, operations, and/or procedures using a software platform. As illustrated in FIG. 2, in some embodiments, the systems, devices, and methods described herein can comprise and/or utilize a software platform. In some embodiments, the software platform can comprise a user interface 202 that allows users, such as a surgeon and/or other medical personnel, to access the system. In some embodiments, the user interface 202 can allow a user to access and/or conduct preoperative analysis and/or preoperative planning of a spinal surgery, which can comprise specifying a patient-specific spinal rod and/or developing a patient-specific plan for implantation of a rod. In some embodiments, the user interface 202 can allow a user to access and/or conduct postoperative analysis of a spinal surgery, which can comprise analyzing the results of surgery according to a preoperatively defined plan. In some embodiments, the user interface 202 can also comprise and/or facilitate ordering of one or more patient-specific spinal implants, such as for example spinal rods, cages, screws, and/or the like.

In some embodiments, the user interface 202 can comprise and/or be configured to provide data visualization 204 to a user of the case at hand during preoperative planning and/or postoperative analysis. For example, in some embodiments, such data visualization 204 can include one or more representations of one or more parameters of the spine of the patient prior to and/or after surgery.

In some embodiments, the user interface 202 can comprise and/or be configured to provide one or more predictive modeling aspects or features 206 to a user. As discussed herein, predictive modeling can be used in some embodiments to predict the outcome of spinal surgery based on one or more of patient characteristics, preoperative spinal parameters, proposed spinal rod specifications, and/or the like.

In some embodiments, the user interface 202 can comprise and/or be configured to provide screw planning aspects or features 208 to a user. For example, in some embodiments, the system can provide preoperative screw planning features to allow a surgeon or other medical personnel to reduce and/or predict the types of screws that will be used during surgery, thereby decreasing the size of the screw kit that needs to be prepared and shipped prior to surgery.

In some embodiments, the user interface 202 can comprise and/or be configured to provide cage selection support aspects or features 210 to a user. For example, in some embodiments, the system can provide cage selection support features to facilitate selection of a particular type or range of cages that are desirable for a patient prior to surgery.

Predictive Modeling

In some embodiments, the system is configured to generate and/or utilize one or more predictive models, machine learning algorithms, and/or artificial intelligence for developing patient-specific implants, surgical plans, treatments, operations, and/or procedures.

In particular, in some embodiments, the system can be configured to predict the surgical outcome and/or the results of a compensatory mechanism(s) and/or spinal curvature or parameters post-surgery based at least in part on one or more inputs, such as for example one or more preoperative medical images of a spine of a patient, one or more spinal parameters of the patient prior to surgery, one or more proposed surgical steps, and/or specifications of a proposed spinal rod for implantation.

In some embodiments, the system can be configured to predict the surgical outcome, results of a compensatory mechanism(s) and/or spinal curvature or parameters post-surgery, and/or specifications of a proposed spinal rod for implantation based at least in part on one or more inputs, such as for example one or more preoperative medical images of a spine of a patient, one or more spinal parameters of the patient prior to surgery, and/or one or more proposed surgical steps.

Further, in some embodiments, the system can be configured to predict the surgical outcome, results of a compensatory mechanism(s) and/or spinal curvature or parameters post-surgery, specifications of a proposed spinal rod for implantation, and/or one or more proposed surgical steps based at least in part on one or more inputs, such as for example one or more preoperative medical images of a spine of a patient and/or one or more spinal parameters of the patient prior to surgery.

In some embodiments, the one or more predictive models and/or algorithms can be configured to predict one or more surgical parameters and/or variables that may result from a surgical procedure, for example, of the spine of a patient. In some embodiments, the one or more predictive models and/or algorithms can be configured to generate a surgical plan for achieving desired surgical outcome. For example, in some embodiments, the systems, devices, and methods described herein can be configured to access preoperative patient input data and generate a surgical plan for implanting a spinal rod into the patient where the generated surgical plan that is personalized for the patient is configured to generate an optimized post-surgical spine curvature for the particular patient.

When a patient undergoes surgery by a doctor, the surgical outcomes can be generally determined based on the surgeon's estimations and/or prior surgical experience. For example, when a spinal rod is implanted into a patient, the surgeon can analyze the patient's body and other characteristics. Based on these observations, the surgeon can provide a general estimate and/or select certain surgical parameters that the surgeon believes will result in a better spinal curvature for the patient post-surgery. However, in reality, the surgeon's estimations and selected surgical parameters may not result in the most desired or optimal surgical outcomes.

For example, when performing a spinal surgery for improving a patient's spinal curvature, the doctor can select a curvature for the spinal rod to be implanted into a patient. The rod curvature selection can be determined and/or estimated by the surgeon based on the doctor's observations of the patient, and such determinations and estimations may result in the patient having a spinal curvature that is less than optimal after the surgery. Accordingly, it can be beneficial to have a system that can predict surgical parameters post-surgery based on pre-operative patient characteristics. For example, it can be helpful to determine, before performing spinal surgery, one or more optimal surgical parameters that should be utilized in a surgical plan in order to achieve the optimal spinal curvature post-surgery for a particular patient with certain characteristics. In some embodiments described herein, systems, methods, and devices are configured to address the foregoing issues.

In particular, in some embodiments, the system can be configured to access pre-operative patient characteristics and input one or more variables therefrom into a predictive algorithm. In certain embodiments, the system can be configured to utilize the predictive algorithm to generate one or more surgical plans having one or more specific surgical parameters that are predicted to generate an optimal or optimized post-surgical outcome for the patient. For example, the system can be configured to receive one or more patient characteristics, such as preoperative spinal curvatures and angles, patient age, genetic mapping or genetic conditions, and/or other variables. In particular, the existence of certain genes or genetic conditions may have a correlation with a particular condition, such as scoliosis, and/or surgical outcome. In some embodiments, the system can be configured to utilize such patient characteristics and/or variables for inputting into a predictive algorithm. In some embodiments, the system can be configured to output based on the predictive algorithm specific surgical parameters, such as the optimal or optimized spinal rod curvature and/or instrumentation positions and/or other variables for achieving the optimal spinal curvature post-surgery for the patient.

In some embodiments, the system is configured to utilize the one or more predictive algorithms to generate a predictive post-surgical outcome. For example, the system can be configured to access one or more patient characteristics and/or surgical parameters that a surgeon intends to use in a surgical plan. In some embodiments, the system can be configured to utilize the predictive algorithm to determine the post-surgical outcome that is predicted to result from the surgical parameters associated with the surgical plan. For example, the system can be configured to access patient characteristics, such as preoperative spinal curvature and/or angles, patient age, genetic conditions, and/or any other variable. The system can also be configured to access the curvature of the spinal rod that the surgeon intends to implant into the patient. In some embodiments, the system can be configured to generate a predictive post-surgical spinal curvature for the patient based on the inputted of variables, in this example, the patient characteristics and the curvature of the spine rod to be implanted into the patient.

As one of ordinary skill will appreciate, the systems, devices, and methods disclosed herein can be applied to a myriad of surgical procedures and is not intended to be limited to spinal surgeries. For example, the systems, devices, and methods disclosed herein can be applied to any kind of surgery, including but not limited orthopedic surgeries, such as, for a patient's neck, head, hand, foot, leg, and arm surgeries.

In some embodiments, the system can be configured to generate a predictive model for predicting one or more post-surgical parameters. In some embodiments, the system can be configured to generate the predictive model by selecting a dataset comprising one or more preoperative and/or postoperative data for one or more patients. As a non-limiting example, in some embodiments, the system can be configured to identify all cases with proximal junctional kyphosis (PJK) and remove such cases from the dataset. In some embodiments, the system can be configured to remove all pediatric cases from the dataset. In some embodiments, removal of the pediatric cases can be based on prior knowledge of the cases in the dataset.

In some embodiments, the system can be configured to split data based on instrumented levels into different groups. For example, the system can be configured to split the dataset into a first group wherein there is instrumentation at L1-L5 and at S1-Iliac, and into a second group wherein there is instrumentation at T10-T12 and at S1-Iliac. For each group, in some embodiments, the system can be configured to split data into a training set and a testing set (for example,—75% of the data for the training set and—25% of the data for the testing set).

In some embodiments, the system can be configured to select one or more input parameters, for example, age, PI pre-op value, PT pre-op value, LL pre-op value, TK pre-op value, SVA pre-op value, lower instrumented level, upper instrumented level, LL post-op target value, surgeon, weight, shape of the preoperative spline, preoperative x-ray, or the like. In some embodiments, the system can be configured to standardize the range of input parameters and/or utilize a scaling methodology.

In some embodiments, the system can be configured to standardize the data based on the training set. In some embodiments, the system can be configured to select a first model type from a plurality of model types, such as for example a linear model, neural network, deep learning, Support Vector Machine-Regression (SVR), or the like. In some embodiments, the system can be configured to select the best model using cross validation. In some embodiments, the system can be configured to perform cross validation by splitting the data set into a new training set and a new testing set. In some embodiments, the system can be configured to train the model with the new training set and evaluate the results with the new testing set.

In some embodiments, the system can be configured to repeat the training process until each data has been once and only once in a testing set. In some embodiments, the system can be configured to train the model selected with the training set. In some embodiments, the system can be configured to utilize a linear model named least-angle regression (LARS) with regularization and variable selection algorithm least absolute shrinkage and selection operator (LASSO). In some embodiments, the system can be configured to test the trained model with the testing set to determine whether the trained model satisfies an accuracy threshold level. In some embodiments, the system can be configured to utilize the trained model to compare with a proposed surgical plan to determine whether the surgical plan is optimal for the patient and/or will produce optimal post-operative surgical results for the patient having certain patient characteristics.

[FIG. 3 is a flowchart illustrating an example embodiment(s) of predictive modeling. In the illustrated example embodiment, the system can be configured to access and/or retrieve one or more preoperative, intraoperative, and/or postoperative data sets at block 302. The one or more datasets can be accessed and/or retrieved from one or more databases, such as a plan database 316 and/or operation database 318 among others.

In some embodiments, the system can be configured to determine whether the retrieved or accessed dataset comprises postoperative data at block 304. If a dataset comprises postoperative data, the system can be configured to identify one or more variables of interest, such as those described herein, from the postoperative data and/or related preoperative and/or intraoperative datasets at block 306. In some embodiments, based in part on the identified one or more variables, the system can be configured to train a predictive modeling algorithm at block 308 according to one or more processes or techniques described herein. In some embodiments, this training process and/or technique and/or portion thereof can be repeated as necessary. For example, in certain embodiments, the system can be configured to repeat the training algorithm and/or a portion thereof as additional data becomes available, such as data from an additional patient and/or additional postoperative data from a known patient or the like.

In some embodiments, if the retrieved or accessed dataset is for a new case, and as such does not comprise postoperative data the system can be configured to apply one or more predictive modeling algorithms to such input preoperative data. In particular, in some embodiments, the system can be configured to identify one or more variables from the input preoperative data and/or compare the same with one or more other datasets at block 310. In some embodiments, based on the comparison and/or other data analysis, the system can be configured to apply one or more predictive modeling algorithms to the input preoperative data. Subsequently, in some embodiments, the system can be configured to generate one or more predicted surgical outcomes and/or plan and/or one or more variables thereof based on the predictive model at block 312. In some embodiments, based at least in part on the resulting surgical plan and/or one or more variables thereof, the system can be configured to produce, modify, select, and/or provide guidance for selection of one or more spinal implants at block 314, such as spinal rods, cages, and/or screws.

Additional Features of Predictive Modeling

In some embodiments, the system is configured to perform a computer-implemented method that is configured to generate a predictive model for determining post-operative parameters, such as for example thoracic kyphosis and/or pelvic tilt, wherein the computer-implemented method can comprise accessing a dataset from an electronic database, the dataset comprising data about the patient (for example, an X-ray images or clinical information) and the surgery strategy (for example, upper instrumented vertebra, lower instrumented vertebra, or the like). In some embodiments, the computer-implemented method is configured to define in the dataset which parameters should be inputs of the model and which parameters should be outputs of the model. For example, outputs of the model can comprise the parameters that the system is configured to be predicted.

In some embodiments, the system is configured to optionally divide the dataset into a plurality of categories based on the spinal surgery domain knowledge. For example, the dataset can be configured to separate adult cases and pediatric cases. In some embodiments, the system can be configured to generate a predictive model for each category. In some embodiments, the system is configured to separate the data into a first subcategory and a second subcategory, wherein the first subcategory is used for training and the second subcategory is for testing the predictive model. In some embodiments, the system is configured to standardize the data using the first category.

In some embodiments, the system is configured to select a model algorithm, for example, neural network, support vector regression, linear models, or the like. In some embodiments, the system is configured to select the model based on using a cross validation strategy. In some embodiments, the system is configured to input one or more input values into the model based on the first subcategory to train the statistical models based on the output values of the first subcategory. In some embodiments, the system is configured to input one or more input data values in the generated trained model and compare the outputs generated by the model with the output values of the first subcategory. In some embodiments, based on the foregoing comparison, a model is generated and the performance of the model is known. In some embodiments, the system is configured to store the first trained statistical model in a data repository. In some embodiments, the system comprises a computer processor and electronic memory. In certain embodiments, one or more of the above-identified processes or techniques are repeated for each of the categories defined by when dividing the dataset based on a spinal surgery domain knowledge block as described above.

In some embodiments, the system is configured to perform a computer-implemented method for generating a predictive model for estimating post-operative parameters, wherein the computer-implemented method comprises accessing a dataset from an electronic database, the dataset comprising data collected from one or more patients and spinal surgical strategy employed for the one or more patients. In some embodiments, the system is configured to divide the dataset into one or more categories based on spinal surgery domain knowledge. In some embodiments, the system is configured to separate the data, for each category, into a first subcategory and a second subcategory, wherein the first subcategory is used for training and the second subcategory is for testing the predictive model.

In some embodiments, the system is configured to standardize the data in the first subcategory. In some embodiments, the system is configured to select a model algorithm to the data in the first subcategory. In some embodiments, the system is configured to input a first set of input values from the first subcategory into the model algorithm to train the predictive model based on a first set of output values from the first subcategory. In some embodiments, the system is configured to input a second set of input values from the second subcategory into the trained predictive model and compare results generated by the trained predictive model with a second set of output values from the second subcategory. In some embodiments, the system is configured to store in a data repository the trained predictive model for implementation or future use. In some embodiments, the post-operative parameters comprise one or more of thoracic kyphosis or pelvic tilt. In some embodiments, the system comprises a computer processor and electronic memory.

In some embodiments, the data collected from one or more patients comprises one or more of an x-ray or clinical information. In some embodiments, the surgical strategy employed for the one or more patients comprises data relating to one or more of upper instrumented vertebra or lower instrumented vertebra. In some embodiments, the spinal surgery domain knowledge comprises one or more of adult cases or pediatric cases. In some embodiments, the model algorithm comprises one or more of a neural network, support vector regression, linear model, and/or the like. In some embodiments, the model algorithm is selected using a cross-validation strategy.

In some embodiments, the system is configured to perform a computer-implemented method for generating a predictive model for estimating post-operative thoracic kyphosis and/or pelvic tilt parameters, wherein the computer-implemented method comprises accessing a dataset from an electronic database, the dataset comprising data from spinal surgeries, wherein the spinal surgeries involve at least an upper instrumented vertebra and a lower instrumented vertebra. In some embodiments, the system is configured to analyze the dataset to divide the dataset into a plurality of categories, the plurality of categories comprising a first category comprising data from surgeries, wherein the upper instrumented vertebra is positioned between L1 and L5 vertebrae and the lower instrumented vertebra is positioned between S1—and Iliac.

In some embodiments, the system is configured to select the first category, and access the data from the surgeries, the data comprising one or more of patient ages, pelvic incidence pre-operative values, pelvic tilt pre-operative values, lumbar lordosis pre-operative values, thoracic kyphosis pre-operative values, sagittal vertical axis pre-operative values, lower instrumented vertebra values, upper instrumented vertebra values, and/or lumbar lordosis post-operative target values for each of the surgeries in the first category. In some embodiments, the system is configured to standardize the data in the first category.

In some embodiments, the system is configured to separate the data into a first subcategory and a second subcategory, wherein the first subcategory is used for training and the second subcategory is for testing the predictive model for determining the post-operative thoracic kyphosis and pelvic tilt parameters. In some embodiments, the system is configured to input pre-operative data values in the first subcategory into a plurality of statistical models to train the statistical models based on the post-operative data values. In some embodiments, the system is configured to input pre-operative data values in the second subcategory into the plurality of trained statistical models and compare one or more output values from the plurality of trained statistical models with post-operative data values in the second subcategory.

In some embodiments, the system is configured to select a first trained statistical model from the plurality of trained statistical models, wherein the first trained statistical model generated one or more output values nearest to the post-operative data values based on the comparing. In some embodiments, the system is configured to store in electronic memory the first trained statistical model. In some embodiments, the system comprises a computer processor and electronic memory.

In some embodiments, the system is configured to perform a computer-implemented method for generating a surgical plan based on a predictive model for estimating post-operative parameters, the computer-implemented method comprising accessing one or more medical images of a portion of a spine of a patient. In some embodiments, the system is further configured to analyze the one or more medical images to determine one or more pre-operative variables relating to the spine of the patient, wherein the one or more pre-operative variables comprise at least one of upper instrument (vertebrae) level ("UIL"), lower instrument (vertebrae) level ("LIL"), age of the patient, pelvic incidence pre-operative values, pelvic tilt pre-operative values, lumbar lordosis pre-operative values, thoracic kyphosis pre-operative values, and/or sagittal vertical axis pre-operative values. In some embodiments, the system is configured to generate a prediction of one or more post-operative variables based at least in part on applying a predictive model, wherein the predictive model is generated by one or more of the following processes.

In some embodiments, the predictive model is configured to access a dataset from an electronic database, the dataset comprising data collected from one or more previous patients and spinal surgical strategy employed for the one or more previous patients. In some embodiments, the predictive model is configured to divide the dataset into one or more categories based on spinal surgery domain knowledge. In some embodiments, the predictive model is configured to standardize the data in the first subcategory.

In some embodiments, the predictive model is configured to select a model algorithm to the data in the first subcategory. In some embodiments, the predictive model is configured to input a first set of input values from the first subcategory into the model algorithm to train the predictive model based on a first set of output values from the first subcategory. In some embodiments, the predictive model is configured to input a second set of input values from the second subcategory into the trained predictive model and compare results generated by the trained predictive model with a second set of output values from the second subcategory.

In some embodiments, the post-operative parameters of the predictive model comprise one or more of thoracic kyphosis and/or pelvic tilt. In some embodiments, the system is configured to generate a surgical plan based at least in part on the predicted one or more post-operative variables generated by the predictive model. In some embodiments, the surgical plan comprises at least one of a number of cages for implantation, location of implantation of cages, length of a spinal rod for implantation, or curvature of the spinal rod. In some embodiments, the system comprises a computer processor and electronic memory.

In some embodiments, the system is configured to perform a computer-implemented method for generating a surgical plan based on a predictive model for estimating post-operative thoracic kyphosis and pelvic tilt parameters, the computer-implemented method comprising accessing one or more medical images of a portion of a spine of a patient. In some embodiments, the system is further configured to analyze the one or more medical images to determine one or more pre-operative variables relating to the spine of the patient, wherein the one or more pre-operative variables comprise at least one of UIL, LIL, age of the patient, pelvic incidence pre-operative values, pelvic tilt pre-operative values, lumbar lordosis pre-operative values, thoracic kyphosis pre-operative values, and/or sagittal vertical axis pre-operative values. In some embodiments, the system is configured to generate a prediction of one or more post-operative variables based at least in part on applying a predictive model, wherein the predictive model is generated by one or more of the following processes.

In some embodiments, the predictive model is configured to access a dataset from an electronic database, the dataset comprising data from spinal surgeries, wherein the spinal surgeries involve at least an upper instrumented vertebra and a lower instrumented vertebra. In some embodiments, the predictive model is configured to analyze the dataset to divide the dataset into a plurality of categories, the plurality of categories comprising a first category comprising data from surgeries, wherein the upper instrumented vertebra is positioned between L1 and L5 vertebrae and the lower instrumented vertebra is positioned between Si and iliac.

In some embodiments, the predictive model is configured to select the first category, and access the data from the surgeries, the data comprising one or more of patient ages, pelvic incidence pre-operative values, pelvic tilt pre-operative values, lumbar lordosis pre-operative values, thoracic kyphosis pre-operative values, sagittal vertical axis pre-operative values, lower instrumented vertebra values, upper instrumented vertebra values, and/or lumbar lordosis post-operative target values for each of the surgeries in the first category. In some embodiments, the predictive model is configured to standardize the data in the first category.

In some embodiments, the predictive model is configured to separate the data into a first subcategory and a second subcategory, wherein the first subcategory is used for training and the second subcategory is for testing the predictive model for determining the post-operative thoracic kyphosis and pelvic tilt parameters. In some embodiments, the predictive model is configured to input pre-operative data values in the first subcategory into a plurality of statistical models to train the statistical models based on the post-operative data values. In some embodiments, the predictive model is configured to input pre-operative data values in the second subcategory into the plurality of trained statistical models and compare one or more output values from the plurality of trained statistical models with post-operative data values in the second subcategory.

In some embodiments, the predictive model is configured to select a first trained statistical model from the plurality of trained statistical models, wherein the first trained statistical model generated one or more output values nearest to the post-operative data values based on the comparing. In some embodiments, the predicted one or more post-operative variables comprises at least one of lumbar lordosis post-operative target values, thoracic kyphosis post-operative values, or sagittal vertical axis post-operative values. In some embodiments, the system is configured to generate a surgical plan based at least in part on the predicted one or more post-operative variables. In some embodiments, the surgical plan comprises at least one of a number of cages for implantation, location of implantation of cages, length of a spinal rod for implantation, and/or curvature of the spinal rod. In some embodiments, the system comprises a computer processor and electronic memory.

Sample Data Elements/Parameters for Predictive Modeling

In some embodiments, in order to perform one or more processes or techniques relating to predictive modeling, the system can be configured to receive, access, and/or obtain one or more of the following data elements or parameters that can be collected from one or more patients.

In particular, in some embodiments, the system can be configured to receive, access, and/or obtain one or more demographic characteristics, such as for example, age at surgery, gender, height, weight, activity level, date of narcotics, disability, education, home care requirements, insurance coverage, job, race, date of return to work/school/sport, socioeconomic status, and/or the like.

In some embodiments, the system can be configured to receive, access, and/or obtain one or more patient-reported outcomes, such as for example, Oswestry Disability Index (ODI), Neck Disability Index (NDI), Scoliosis Research Society (SRS-22), Nurick, and/or the like.

In certain embodiments, the system can be configured to receive, access, and/or obtain one or more radiographic parameters, such as for example, preoperative and/or post-operative data such as T4-T12 Thoracic Kyphosis (TK), L1-S1 Lumbar Lordosis (LL), Sagittal Vertical Axis (SVA), Pelvic Tilt (PT), Pelvic Incidence (PI), Lordosis, and/or the like.

In some embodiments, the system can be configured to receive, access, and/or obtain one or more other radiographic parameters as well, such as Central Sacral Vertical Line (CSVL), C2T1 Pelvic Angle (CTPA, °), C2C7 SVA (mm) (Sagittal Vertical Axis), Cervical Lordosis, Lenke Classification, Proximal Junctional Kyphosis (PJK), Rod Tracing, SS, Ti Slope (TIS, °) Ti Tilt Angle and Direction, T10-L2 angle, T12-S1 Lumbar Lordosis (LL), T1-T12, T2-T12, T2-T5, T5-T12 Thoracic Kyphosis, Th Apex, Th Bending films parameters, Th Curves/Cobb angles, Th Curve Levels, (Th/L Lumbar Apex, Th/L Lumbar Curve, Th/L Lumbar Curve Direction of curve, Th/L Lumbar Curve Levels), T1 Pelvic Angle (TPA), Anatomical Kyphosis, Anatomical Lordosis, Cobb Angles, Coordinates of all vertebra corners in the sagittal and/or coronal planes and the femoral heads, any other pre-operative and/or post-operative data like, Computerized tomography Performed, Tri-Radiate Cartilage, External Auditory Meadus, Pelvic Obliquity, Acetabular Index, and/or the like.

In some embodiments, the systems disclosed herein can be configured to generate spinal surgical strategies comprising one or more surgical data parameters, such as Instrumentation Material, Instrumentation Size, Instrumentation Type, Minimal Invasive Surgery (MIS) options, Number of instrumented Levels, Osteotomies Performed, Rod Bending shapes and/or Angles, Rod Cutting Parameters, Uppermost Instrumented Parameters, Upper Instrumented Vertebrae (UIV), Lower Instrumented Vertebrae (LIV), Surgeon, surgical techniques (in some embodiments, using one or more machine learning algorithms to analyze surgeon's surgical techniques to be able to simulate the surgery and the rod that will match surgeon's expectations), radiography as an image, scanner, MRI (image or set of images), and/or the like.

In some embodiments, a first set of input values for preoperative and/or postoperative data can include one or more of the following: T4-T12 TK, L1-S1 LL, SVA, Lowermost Instrumented Vertebrae (LIV), Uppermost Instrumented Vertebrae (UIV), Pelvic Tilt, Age at the time of surgery, and/or Pelvic Incidence (PI).

In some embodiments, a first set of output values for preoperative and/or postoperative data can include the following: T4-T12 TK, L1-S1 LL, and Pelvic Tilt.

Additional Features of Predictive Modeling

As discussed herein, various embodiments described herein relate to systems, methods, and devices for developing spinal implants, treatments, operations, and/or procedures. In some embodiments, the systems, devices, and methods described herein can be configured to utilize machine learning, predictive modeling, and/or artificial intelligence based on previous surgical outcomes and/or one or more parameters of previously implanted spinal rods or other implants to predict, design, develop, and/or plan patient-specific spinal rods and/or other implants prior to surgery. Further, in some embodiments, the systems, devices, and methods described herein can be configured to utilize patient-specific and/or surgeon-specific parameters in its analysis to develop a surgical plan prior to spinal surgery. In some embodiments, the generated surgical plan can be surgeon-dependent.

In some embodiments, the systems, devices, and methods described herein can be configured to design a spinal rod and/or other implant to match or substantially match a surgical plan desired by the surgeon in the instrumentation.

In some embodiments, the systems, methods, and devices described herein can be configured to build a predictive model taking into account the patient and/or the surgeon. In some embodiments, the systems, methods, and devices described herein can be configured to generate or develop or utilize a patient-specific and/or surgeon-specific predictive model. In some embodiments, the systems, devices, and methods described herein can be able to anticipate what the position of the rod and/or the shape of the spine and/or the position of the vertebra for each vertebra will be in the instrumentation. In some embodiments, based on a predictive model utilized, generated, and/or developed, the systems, methods, and devices described herein can be configured to design, produce, and/or cause to produce a physical spinal rod that could reach the plan.

In some embodiments, the systems, methods, and devices described herein can be configured to utilize one or more inputs and/or outputs for training or developing a predictive model, artificial intelligence model, and/or machine learning model.

In some embodiments, the one or more inputs can comprise one or more past spinal surgery cases performed by a surgeon and one or more parameters thereof, such as the rod designed, the position of the vertebrae and/or the position of some specific endplates (which can be preoperative, planned, and/or post-operative), the spinopelvic parameters (which can be preoperative, planned, and/or post-operative), age, weight, and/or height of the patient, and/or material and/or diameter of the rod. In some embodiments, the spinopelvic parameters can comprise lumbar lordosis (LL), pelvic tilt (PT), pelvic incidence (PI), T1 pelvic angle (TPA), sagittal vertical axis (SVA), thoracic kyphosis (TK), and/or any other parameter, including those described herein.

In some embodiments, the one or more outputs can comprise the shape of the rod, one or more specifications or parameters thereof, and/or its position to match the plan, the shape of the spine depending of the shape of the rod, the position of the rod (such as, for example, distance with the spine and/or angles with some specific endplates and/or other lines), and/or guidelines to anticipate the position of the rod.

In some embodiments, in order to build the predictive model, the systems, devices, and methods can be configured to utilize a generative adversarial network (GAN). In some embodiments, in order to build or develop the predictive model, the systems, devices, and methods can be configured to utilize one or more GAN-type artificial intelligence (AI) algorithms and/or predictive modeling algorithms. For example, in some embodiments, one or more GAN algorithms can be used to predict the position of the rod for a specific surgeon. In some embodiments, the input to the predictive model can comprise the shape of the manufactured rod and/or the preoperative spine.

In some embodiments, the systems, devices, and methods can be configured to utilize data augmentation, for example in addition to GAN-type AI algorithms, predictive modeling algorithms, and/or others. In particular, in some embodiments, the systems, devices, and methods can be configured to use data augmentation to make false columns using a Gaussian process. In some embodiments, the data augmentation is used for machine learning training or training the predictive model, but not for testing.

In some embodiments, one or more algorithms developed or built by the systems, methods, and devices can be configured to predict the position of the post-operative rod. In some embodiments, the model built or developed by the systems, methods, and devices can be configured to predict one or more parameters and/or specifications of a spinal rod that is predicted to result in a desired or actual post-operative spine based on the preoperative spine.

In some embodiments, one or more algorithms, such a GAN algorithm, can be used to analyze one or more medical images of a patient for other tasks, such as automatic detection of the vertebra.

In some embodiments, the systems, devices, and methods described herein can be configured to convert a prior rod used by a surgeon into a mathematical object. For example, in some embodiments, if the rod were a segment, the system can be configured to convert the rod into a mathematical object as follows: [A;B], with A coordinates of the first point of the segment and B the last point of the segment. As such, in some embodiments, the system can identify and/or analyze a rod as a set of numbers that can be used by one or more algorithms and/or predictive models of the system without losing any information. In some embodiments, the systems, methods, and devices described herein can be configured to convert the rods into one or more Bezier curves, b-splines, sequences of segments and/or arc, and/or the like. In some embodiments, the one or more parameters used by the one or more algorithms and/or predictive models as inputs and/or outputs can depend on the mathematical object chosen to convert the rod into a model. In some embodiments, the systems, methods, and devices described herein can be configured to consider the whole shape of the rod.

In some embodiments, the systems, methods, and devices described herein can be configured to analyze, identify, and/or determine the position of the vertebrae and/or specific endplates (preoperative, planned, and/or post-operative), such as by using coordinates. In some embodiments, the systems, methods, and devices can be configured to use one or more coordinates of the vertebrae as input and/or output parameter(s) for a model and/or algorithm.

In some embodiments, the systems, methods, and devices can not only identify similar previous surgical cases from a database but also build one or more predictive models and/or algorithms based on the same.

As discussed herein, in some embodiments, predictive modeling, artificial intelligence, and/or machine learning can play an important role in preoperative surgical planning for patient-specific spinal surgery, treatments, implant manufacturing or selection, and/or the like.

Figure 4:
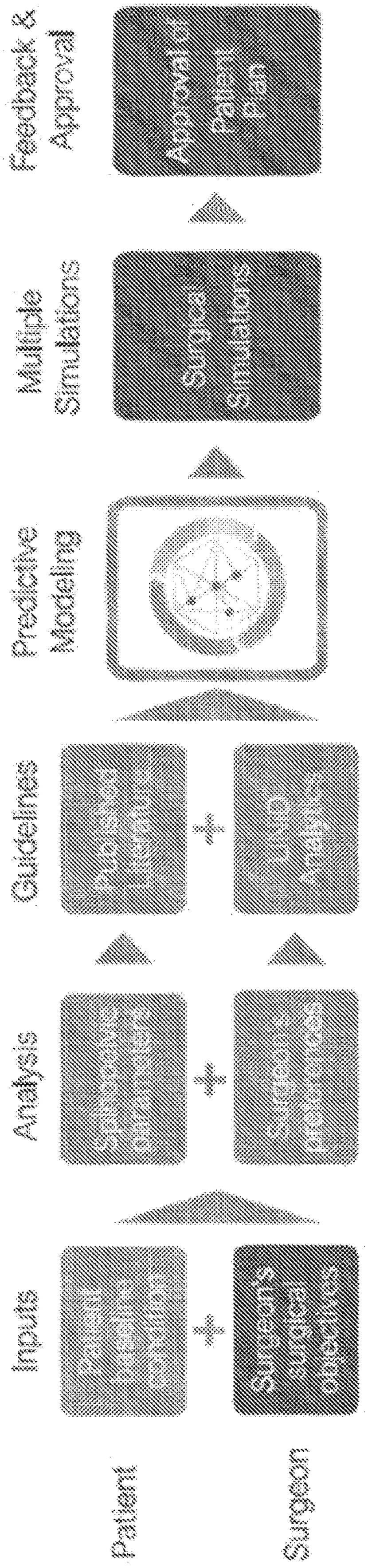
FIG. 4 is a flowchart illustrating an example embodiment(s) of predictive modeling and its role in developing patient-specific implants, treatments, operations, and/or procedures.

FIG. 4 is a flowchart illustrating an example embodiment (s) of predictive modeling and its role in developing patient-specific implants, treatments, operations, and/or procedures. As illustrated in FIG. 4, in some embodiments, input for a predictive model of the system can comprise one or more patient inputs and/or surgeon inputs. For example, in some embodiments, a patient input can include one or more patient baseline conditions. In some embodiments, a surgeon input can include one or more surgical objectives of the surgeon. In some embodiments, the system and/or predictive model thereof can be configured to facilitate collection of one or more inputs that can be critical, such as the patient's condition and/or the surgeon's objectives.

In some embodiments, the system and/or a predictive model thereof can be configured to analyze the input to determine and/or identify, for example, one or more spinopelvic parameters and/or surgeon preferences. In some embodiments, one or more spinopelvic parameters and/or surgeon preferences can be additional inputs for the system and/or predictive model thereof. In some embodiments, inputs for the system and/or predictive model thereof can include one or more published literature and/or analytics from previous cases from the system database.

In some embodiments, the system and/or predictive model thereof can be configured to take into account one or more of the aforementioned inputs to generate one or more surgical simulations. In some embodiments, the system and/or predictive model thereof can generate one or multiple surgical simulations based on different assumptions and/or inputs. In some embodiments, the system can transmit or otherwise provide the one or more surgical simulations generated by the system or predictive model thereof to a medical personnel or surgeon, who can review, approve and/or provide other feedback to the system.

Figure 5:
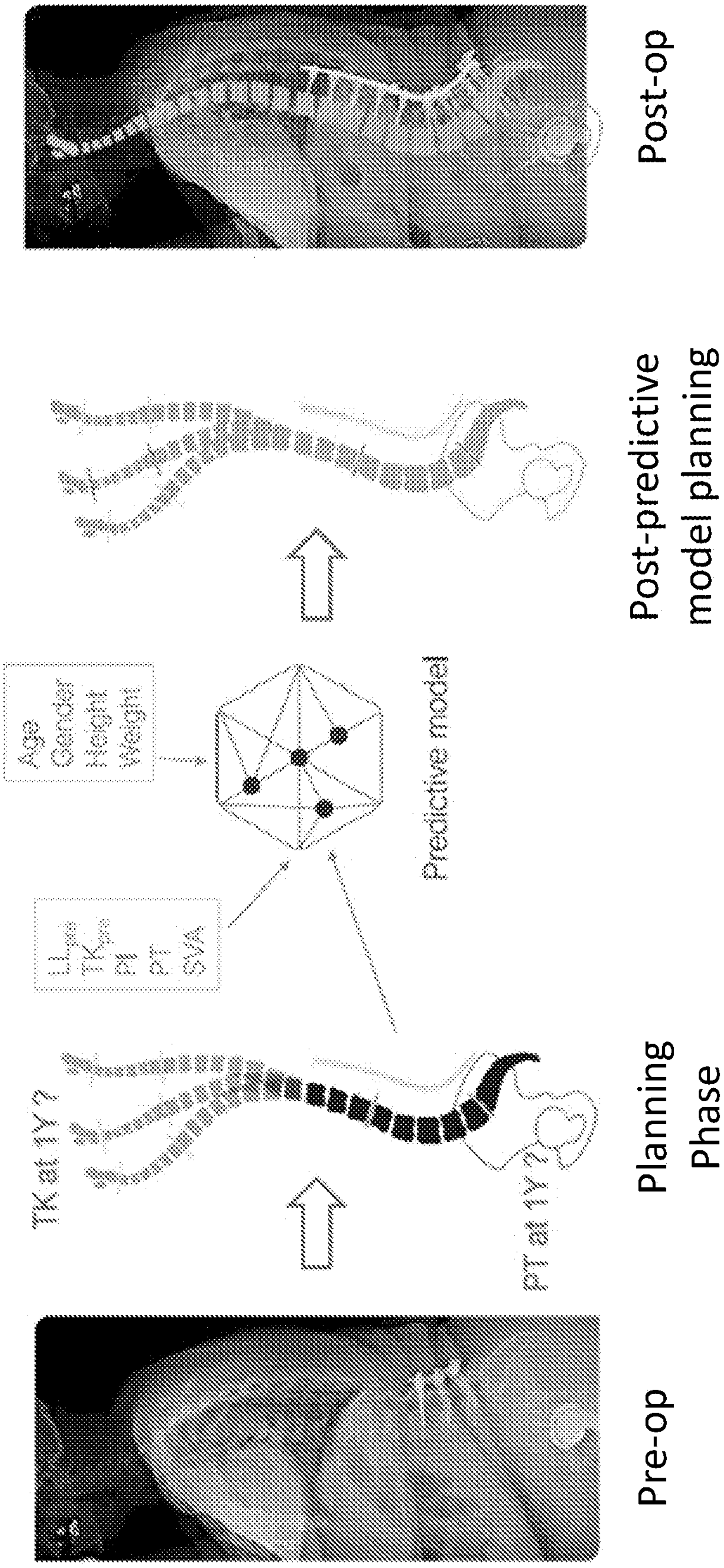
FIG. 5 is a flowchart illustrating an example embodiment(s) of predictive modeling and its role in developing patient-specific implants, treatments, operations, and/or procedures.

FIG. 5 is a flowchart illustrating an example embodiment(s) of predictive modeling and its role in developing patient-specific implants, treatments, operations, and/or procedures. As illustrated in FIG. 5, in some embodiments, the system and/or predictive model thereof can be configured to determine and/or predict a surgical outcome of what is likely to occur above and/or below the instrumentation or spinal rod implant. For example, in some embodiments, the system or predictive model thereof can be configured to analyze one or more preoperative images of a spine of a patient, such as for example a sagittal and/or frontal x-ray image. In some embodiments, the system or predictive model thereof can be configured to analyze the one or more inputted images and plan what parameters to predict, which can be time-dependent parameters or variables. For example, such parameters for prediction can include predicted thoracic kyphosis (TK) at 1 year from spinal surgery and/or pelvic tilt (PT) at 1 year from spinal surgery.

In some embodiments, the system and/or predictive model thereof can generate one or more predictions, such as of surgical outcome and/or others, based on one or more inputs, such as preoperative lumbar lordosis (LL), preoperative thoracic kyphosis (TK), pelvic incidence (PI), pelvic tilt (PT), sagittal vertical axis (SVA), patient age, gender, height, weight, and/or the like. In some embodiments, the system, based on the predicted outcome or result, can be configured to generate a surgical plan. In some embodiments, after surgery, the system can be configured to analyze one or more postoperative images of a spine of a patient, such as for example a sagittal and/or frontal x-ray image, which can be used to compare to the preoperative prediction to further train the algorithm.

In some embodiments, the system can be configured to analyze one or more preoperative and/or postoperative medical images of a spine, such as for example x-ray images, CT images, MR images, and/or the like, and/or measurements therefrom. In some embodiments, the system or predictive model thereof can be configured to simulate one or more surgical gestures and/or implants, such as spinal rods and/or cages.

In some embodiments, the system or predictive model thereof can be configured to query one or more of patient demographics, measurements, and/or instrumentation data, such as upper instrumented vertebrae (UIV) and/or lower instrumented vertebrae (LIV) to determine one or more compensatory mechanism. In some embodiments, after the predictive model has updated the surgical plan, the plan can then be considered ready for submission to the surgeon or medical personnel. In some embodiments, the system provides, facilitates, and/or generates multiple planning options, data-driven decision support, and/or planning approval.

Figure 6:
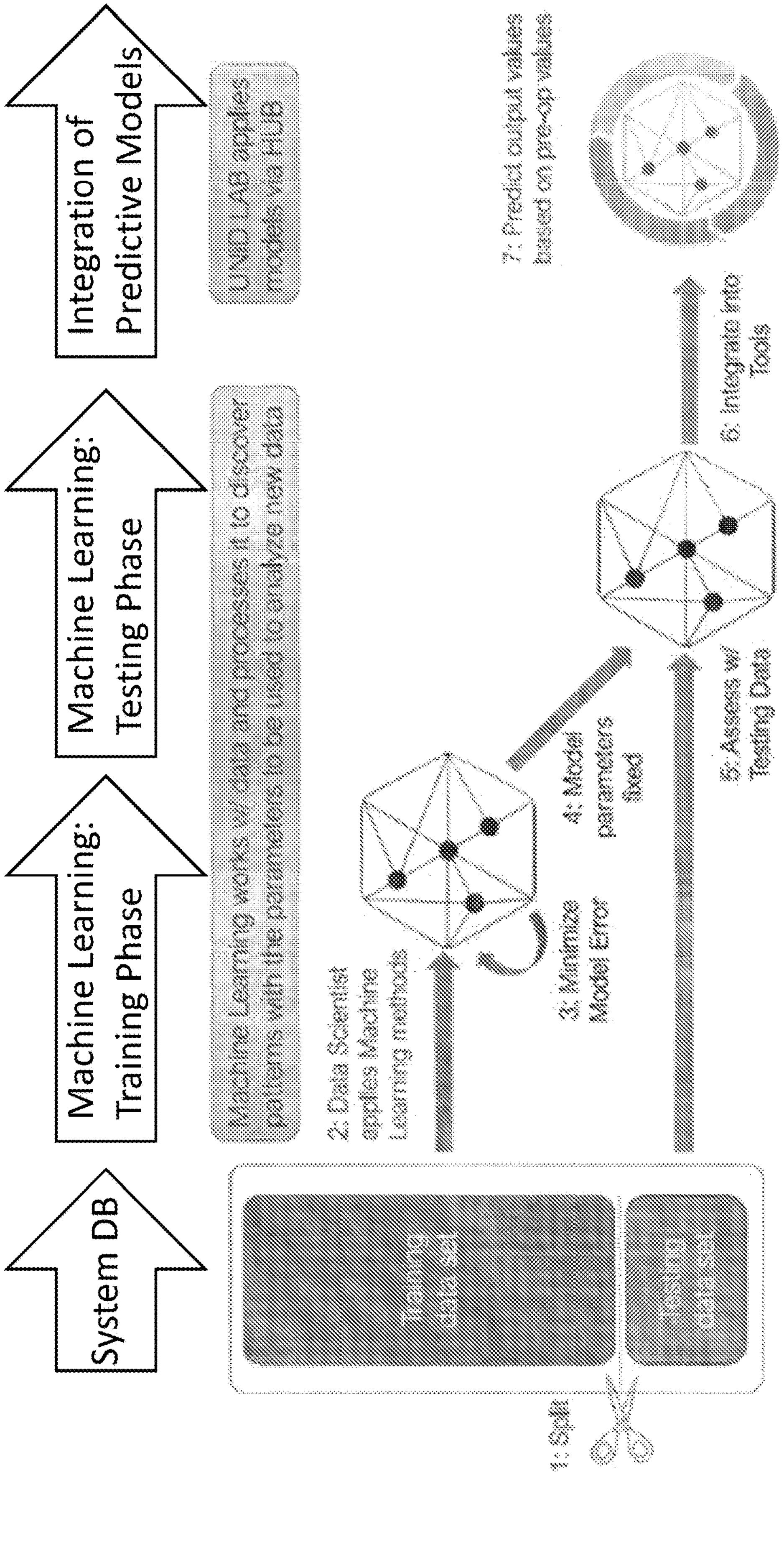
FIG. 6 is a flowchart illustrating an example embodiment(s) and/or overview of machine learning in developing patient-specific implants, treatments, operations, and/or procedures.

FIG. 6 is a flowchart illustrating an example embodiment(s) and/or overview of machine learning in developing patient-specific implants, treatments, operations, and/or procedures. As illustrated in FIG. 6, in some embodiments, the system is configured to utilize machine learning and/or a training algorithm(s) to generate the predictive model. In particular, in some embodiments, the system is configured to utilize a system database comprising a plurality of previous spinal surgery cases, results thereof, and/or one or more spinal parameters derived therefrom. In some embodiments, the system can utilize such data in a training phase and/or testing phase of the machine learning process. In some embodiments, after training and/or testing, the predictive model can be integrated in the system.

In particular, in some embodiments, the data from the system database or any other database can be split into a training data set and a testing data set. Splitting the data into a training set and a testing set can be advantageous, in some embodiments, because testing an algorithm on the same data it was trained on may not provide accurate testing results. In some embodiments, machine learning can work with the data and process it to discover one or more patterns with the parameters to be used to analyze new data.

In some embodiments, during the training phase, a data scientist or other user can apply one or more machine learning methods to the training data. In some embodiments, the system can re-train and/or re-analyze the data to minimize model error. In some embodiments, once the model parameters are fixed, the trained predictive model can then be tested.

As discussed herein, in some embodiments, the trained predictive model is tested or assessed with testing data, which can be separate from the training data. In some embodiments, after testing is finalized, the predictive model can be integrated into system tools and then be used to predict one or more output values of the spine of a patient post-surgery based on one or more preoperative values.

Additional Features of Predictive Modeling

In some embodiments, systems, devices, and methods discussed herein can be configured to generate and/or utilize one or more predictive models to predict the postoperative shape or curvature of a spine of a patient. In some embodiments, this can be advantageous in several aspects. For example, in some embodiments, the systems, devices, and methods described herein can provide information of the length of a spinal rod to be implanted, help anticipate one or more compensatory mechanisms, and/or inform the patient and/or surgeon on one or more results that can be expected from spinal surgery. As such, in some embodiments, the systems, devices, and methods described herein can be configured to generate, build, and/or apply an algorithm that is configured to predict one or more characteristics and/or parameters of a postoperative spine based on one or more characteristics and/or parameters of a preoperative spine.

In some embodiments, one or more input data and/or collected data for a predictive model can comprise one or more characteristics and/or parameters from a preoperative spine of a subject. In some embodiments, the inputted spine data can comprise coupled data, (Coronalcurve, Sagittalcurve). In some embodiments, each curve or spline can comprise several mathematical curves linking one or more identified anatomical landmarks from one or more medical images measurements. In some embodiments, the one or more identified anatomical landmarks can be identified automatically, semi-automatically, and/or manually, such as for example using one or more techniques described herein.

In some embodiments, the system can be configured to apply one or more data transformation techniques to one or more collected data. For example, in some embodiments, the system can be configured to apply an analog to discrete conversion. In some embodiments, the system can be configured to work only with mathematical curves. In some embodiments, the system can be configured to make one or more splines discrete. In particular, in some embodiments, for each coronal and/or sagittal spline, the system can be configured to obtain N number of points uniformly distributed along the vertical axis between the inferior and superior points of the spline.

In some embodiments, the system can be configured to transform the collected or inputted data from two dimensions to three dimensions, for example to prepare the data for machine learning. In particular, in some embodiments, the system can be configured to create or generate a single three-dimensional object that represents the spine of a subject based on two or more two-dimensional representations of the spine. In some embodiments, in order to do so, the system can be configured to assume that the coronal and sagittal x-ray images are perpendicular, that both calibration ratios of the two x-ray images are perfectly accurate, and/or that both x-ray images were taken simultaneously in time.

In some embodiments, the system can be configured to assume that the x-axis extends from the back of the patient to the chest, that the y-axis extends from the right side of the patient to the left side, and/or that the z-axis is vertical and ascending. In some embodiments, such assumptions can define a direct landmark. In some embodiments, the system can be configured to utilize a polar representation of the three-dimensional spine instead of a Cartesian representation. In some embodiments, the system can be configured to utilize a Cartesian representation of the spine.

In some embodiments, the system can be configured to utilize one or more data compression techniques and/or algorithms. For example, in some embodiments, the system can be configured to utilize a low-pass filter for data compression, which can be advantageous for machine learning purposes, while preserving most of the relevant information.

In some embodiments, based at least in part on the transformed input or collected data, the system can be configured to apply one or more machine learning techniques and/or algorithms. In some embodiments, the system can be configured to utilize one or more machine learning, artificial intelligence, and/or predictive modeling algorithms to predict one or more postoperative parameters, such as a spinal curvature for example, knowing only one or more preoperative and/or potentially planned parameters. In particular, in some embodiments, the system can be configured to utilize one or more linear models and/or neural networks.

In some embodiments, the system can be configured to utilize one or more machine learning, artificial intelligence, and/or predictive modeling algorithms to simulate the outcome of spinal surgery. In particular, in some embodiments, depending on the data transformation done through input data preparation, if any, the system can be configured to convert the direct output of the model through a reversed process of the data transformation or data compression algorithm employed to obtain predicted one or more postoperative parameters. As such, in some embodiments, the system can be configured to utilize one or more machine learning, artificial intelligence, and/or predictive modeling algorithms to predict one or more postoperative spinal parameters, such as a spinal curvature.

Figure 7:
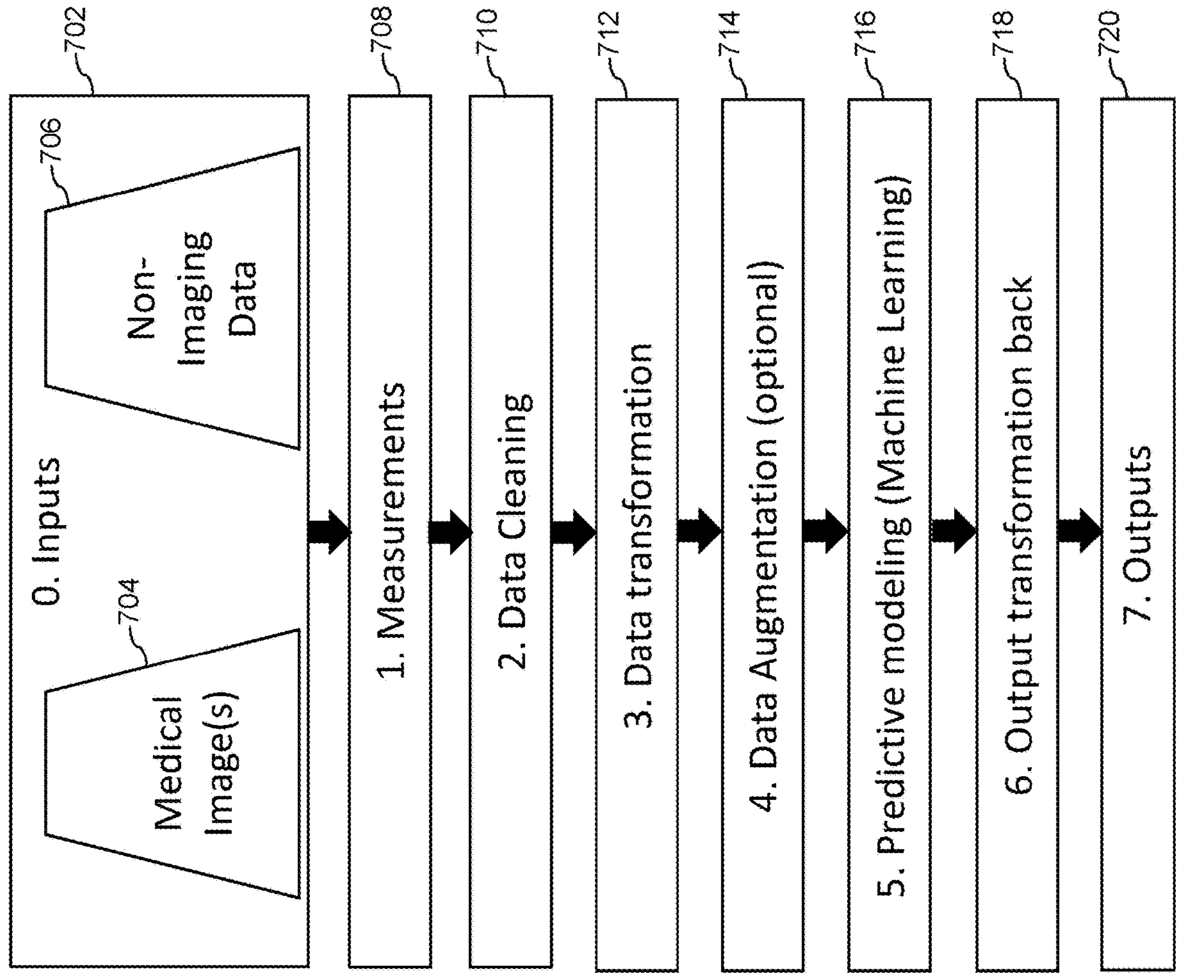
FIG. 7 is a flowchart illustrating an example embodiment(s) of predictive modeling in developing patient-specific implants, treatments, operations, and/or procedures.

FIG. 7 is a flowchart illustrating an example embodiment(s) of predictive modeling in developing patient-specific implants, treatments, operations, and/or procedures. As illustrated in FIG. 7, in some embodiments, the systems, devices, and methods described herein are configured to utilize predictive modeling, artificial intelligence, and/or machine learning in predicting the surgical outcome of spinal surgery based in part on one or more of one or more medical images of the patient's spine, parameters of the patient's spine, specifications of a proposed implant, such as a spinal rod or cage, demographic information about the patient, and/or the like.

In some embodiments, as illustrated in FIG. 7, one or more inputs are inputted into the system and/or predictive model thereof for predicting the surgical outcome and/or building the predictive model at block 702. In some embodiments, one or more medical images can be inputted into the system as shown in block 704. The one or more medical images can be one or more x-ray images of the spine, such as sagittal and/or frontal x-ray images, CT images, MR images, and/or the like. In some embodiments, the one or more inputs can include one or more other information, such as non-imaging data or inputs, as shown in block 706. The one or more other information can include the surgeon's name, one or more preferences of the surgeon, one or more demographic information of the patient, such as height, weight, age, medical condition(s), and/or the like. Further, in some embodiments, the one or more inputs at block 702, whether medical images (as in block 704) or non-imaging data (as in block 706), can comprise one or more preoperative and/or postoperative data, for example to train and/or build the predictive model. As an example, in some embodiments, the preoperative data can comprise one or more spinal parameters prior to surgery and the postoperative data can comprise one or more spinal parameters and/or specifications of one or more spinal implants, such as a rod, cage, screw, and/or the like.

In some embodiments, as illustrated in FIG. 7, the system can be configured to determine one or more measurements from the one or more inputs at block 708. In particular, in some embodiments, the system can be configured to measure one or more specific points and/or parameters on one or more medical images. For example, in some embodiments, the system can be configured to determine and/or identify, automatically or semi-automatically or manually, one or more points on each endplate and/or vertebrae and/or a position and/or one or more angles of each endplate and/or vertebrae. As an example, in some embodiments, the system can generate a user interface that allows a user to pinpoint one or more points on the edge of one or more endplates and/or vertebrae and/or one or more positions and/or angles of one or more endplates and/or vertebrae using a mouse, touch, or other computer input method. As another example, in some embodiments, the system can be configured to automatically determine the boundary of each endplate, for example using edge detection techniques, and/or automatically determine one or more angles of each vertebrae. Some examples of measurements can include preoperative lumbar lordosis (LL), preoperative thoracic kyphosis (TK), pelvic incidence (PI), pelvic tilt (PT), sagittal vertical axis (SVA), position, boundary, position of femoral head, and/or any other spinopelvic parameters of one or more endplates and/or vertebrae.

In some embodiments, the system can be configured to take one or more measurements of one or more spinopelvic parameters directly from a CT image, MM image, or other three-dimensional medical image of the spine of a patient. In some embodiments, the system can be configured to analyze one or more x-ray images of the spine of a patient to first determine or extract the position of one or more vertebrae and then determine one or more spinopelvic parameters based on the extracted position of one or more vertebrae. For x-ray image based analysis, in some embodiments, it can be advantageous to extract the position of one or more vertebrae first before taking measurements of one or more spinopelvic parameters, because some information can be lost if measurements are taken directly from x-ray images due to transformation of the data in the measurement step. This can be different from embodiments that use CT or Mill images, because for CT or Mill images, no information can be lost by taking direct measurements of spinopelvic parameters. As such, in some embodiments that utilize one or more x-ray images, the system can be configured to first extract the position of one or more or every vertebrae on the image to obtain a larger fundamental set of data that can be used later to further extract one or more angles and/or other spinopelvic parameters. That way, in some embodiments, once the system has determined the position of one or more or each vertebrae, the system can then be configured to further determine any angle and/or any spinopelvic parameter as necessary without losing information.

In some embodiments, as illustrated in FIG. 7, the system is configured to clean some of the collected data or measurements at block 710. In some cases, one or more measurements taken from the one or more medical images may not be reliable or clean. If unreliable or unclean data is inputted into a predictive modeling or machine learning algorithm, the output or prediction of the post-surgical outcome may not be reliable as well. As such, in some embodiments, the system can be configured to discard or remove one or more measurements if the quality does not meet a predetermined or preset threshold.

In some embodiments, as illustrated in FIG. 7, the system can be configured to transform the data or measurements or perform a data transformation at block 712. In some embodiments, there can be a trade-off between the number of parameters and the complexity of the predictive model. In other words, in some embodiments, it can be advantageous to limit the number of parameters inputted into the predictive model and/or used to build the predictive model in order to maintain the complexity of the predictive model at a manageable level. Also, if a large number of parameters are used, a large dataset may also be required to train the predictive model to an acceptable accuracy level. At the same time, however, in some embodiments, it can be advantageous to have a large dataset or large number of cases in training the predictive model. As such, for training purposes, in some embodiments, the system can be configured to train a predictive model based on a large dataset or large number of cases but with a limited or restricted number of parameters. In some embodiments, the system can be configured not to directly use all of the measurements or the input data, such as measurements taken from an x-ray image(s), MRI image, or CT image for example, but rather use a subset of parameters thereof. In some embodiments, both preoperative and/or postoperative parameters or data can be transformed using one or more data transformation techniques as discussed herein. In some embodiments, the preoperative and postoperative parameters can be transformed using the same or different technique. Further, in some embodiments, the preoperative and postoperative parameters being transformed can the same or different. For example, the preoperative and postoperative parameters can be of a spine, compensation mechanism, spinal rod, whether before or after implantation, cage, screw, and/or any other spinal implant or parameter.

In some embodiments, data transformation can comprise mathematical modeling, such as manipulating one or more mathematical objects. In some embodiments, data transformation can comprise data compression, for example to reduce the number of input parameters as discussed here. In some embodiments, data transformation can comprise data compression to obtain the minimum pertinent parameters, which can refer to a subset of parameters with the most information. In other words, in some embodiments, the system can be configured to only use those parameters with the most information as possible.

In some embodiments, the system can be configured to utilize one or more data compression techniques, such as Fourier transformation and/or a polynomial function. In particular, in some embodiments, from the inputs, the system can obtain a measurement of the shape of a spine, which can comprise a plurality of short straight segments. In some embodiments, the system can determine and save the angle between each short straight segment and a vertical line, which can be modeled through a Fourier transformation to have less parameters than before. In some embodiments, after a Fourier transformation, only a portion of the parameters with more information or more accurate information can be kept for use in training and/or applying the predictive model.

In some embodiments, after applying a Fourier transformation to the data, the system can be configured to keep only low frequency data or parameters and discard high frequency data or parameters for purposes of training and/or applying the predictive model. As will be discussed herein, in some embodiments, the data transformation can later be reversed to obtain data for each parameter or segment in the real world or spatial domain, as opposed to the Fourier transformation world or frequency domain. In other words, in some embodiments, the system can be configured to apply a Fourier transformation to the measured dataset and then filter out high frequency data such that only low frequency data remains, because high frequency data can comprise a large number of noise or unclear data, thereby reducing the quality of data to use to build a mathematical model of the spine. Further, in some embodiments, the system can be configured to reverse or inverse the Fourier transformation afterwards to convert the data and/or angles back to the real world or spatial domain. In other words, in some embodiments, the system can be configured to utilize Fourier transformation and then apply a low frequency filter with a predetermined frequency threshold as a technique for filtering out noise or high frequency data or parameters in the frequency domain to improve the quality of the predictive model and/or output from the predictive model. That way, in some embodiments, the system can generate a model of a preoperative and/or postoperative spine based only on low frequency data in the Fourier world, which can be converted back to the real world or spatial domain.

In addition, by utilizing a mathematical model and/or data transformation rather than working directly from the input, in some embodiments, a predictive model built on one modality of medical imaging, such as for example x-ray, can be applied to medical imaging input from another modality, such as for example CT or MRI, as long as it is converted to 3D or 2D as necessary. For example, in some embodiments, by building or training a predictive model by utilizing a mathematical model and/or data transformation to x-ray image(s), such predictive model can also be applied to CT and/or Mill images after converting to three-dimensional space.

In some embodiments, as illustrated in FIG. 7, the system is configured to augment the data at block 714, which can be optional in certain embodiments. In order to augment the data, in some embodiments, the system can be configured to create artificial data based on the actual or real dataset, for example to improve the training of the predictive model and/or obtain a more complex model. In some embodiments, the augmented and/or artificial data generated by the system can be based on preoperative data and/or curvature of a spine and/or postoperative data and/or curvature of a spine and/or rod or other spinal implant, for example for purposes of training the predictive model.

As discussed herein, in some embodiments, it can be advantageous to train a predictive model using a large dataset with a large number of cases. In addition, in some embodiments, having a larger set of data can allow the system to utilize a more complex algorithm for predictive modeling. For example, in some embodiments, by using a larger set of data, whether it is by augmented the data or by initially starting with a large set of data, the system can utilize a Convolutional Neural Network (CNN) algorithm to train the predictive model. In addition, in some embodiments, as the system can obtain a larger dataset through data augmentation, it can be possible to utilize more parameters for training the predictive model. Further, in some embodiments, as the system can obtain a larger dataset through data augmentation, it can be possible to identify even better parameters for training the predictive model. Furthermore, in some embodiments, as the system can obtain a larger dataset through data augmentation, it can be possible to obtain a larger set of clean data for training the predictive model As such, in some embodiments, the system augments the dataset for training the model by creating artificial data, but not for testing the predictive model. In other words, in some embodiments, the system can be configured to use augmented data to increase the learning dataset for training the predictive model, but not for testing the predictive model. In some embodiments, augmented or artificial data is never used for testing a predictive model.

In some embodiments, the system can be configured to augment the dataset by applying a Gaussian process or another statistical and/or mathematical technique to the actual data. As an example, in some embodiments, the system can be configured to consider a spine of a patient to comprise one or more vectors, in which case the system can be configured to utilize the sampling function of a Gaussian process on each vector to generate one or more artificial inputs or spinal curvatures. As another example, in some embodiments, augmented data can comprise one or more parameters that are different or off from the actual or real data by some statistically and/or predetermined acceptable threshold, for example within about 1%, about 2%, about 3%, about 4%, about 5%, about 10%, about 0.5 standard deviation, about 1 standard deviation, about 1.5 standard deviation, about 2 standard deviations, and/or within a range defined by two of the aforementioned values. As such, in some embodiments, the system can be configured to build artificial data points or cases from the actual dataset based on statistics, which can then be used to train the model.

In some embodiments, the system can be configured to generate augmented or artificial data by a non-statistical process or technique. For example, in some embodiments, the system can be configured to generate augmented or artificial data by flipping or rotating in 180 degrees or mirroring a particular curvature of a spine, whether from the frontal view or sagittal view. In particular, in some embodiments, the system can be configured to flip the left-right orientation of a curve of a spine as depicted on a medical image, whether from a sagittal or frontal view, which can be the basis for generating augmented or artificial data. In addition, in some embodiments, the system can be configured to rotate the orientation of a curve of a spine as depicted on a medical image, whether from a sagittal or frontal view, along a vertical axis, which can be the basis for generating augmented or artificial data. In some embodiments, the degree of rotation of the spine along the vertical axis, either left or right, for generating the augmented or artificial data can be about 10 degrees, about 20 degrees, about 30 degrees, about 40 degrees, about 50 degrees, about 60 degrees, about 70 degrees, about 80 degrees, about 90 degrees, about 100 degrees, about 110 degrees, about 120 degrees, about 130 degrees, about 140 degrees, about 150 degrees, about 160 degrees, about 170 degrees, about 180 degrees, and/or within a range defined by two of the aforementioned values.

In some embodiments, the system can be configured to generate augmented and/or artificial data by combining one or more techniques discussed herein, such as for example using a Gaussian process and/or rotation of a spine from actual data. In some embodiments, data can be augmented by the system based on either before or after data transformation according to one or more data transformation techniques discussed herein, such as a Fourier transformation.

In some embodiments, as illustrated in FIG. 7, the system is configured to train a predictive model and/or generate one or more postoperative predictions, for example using one or more machine learning techniques or neural networks, at block 716. In some embodiments, the system can be configured to utilize one or more of a Generative Adversarial Network (GAN) algorithm, a Convolutional Neural Network (CNN) algorithm, and/or a Recurrent Neural Network (RNN) algorithm, linear regression, Support Vector Machine (SVM) algorithm, Support Vector Machine-Regression (SVR) algorithm, and/or any combination thereof. For example, in some embodiments, the system can be configured to utilize a combination of a CNN algorithm with an SVM algorithm.

In some embodiments, the system can be configured to utilize one or more machine learning algorithms and/or any combination thereof to train a predictive model and/or generate one or more postoperative predictions on varying numbers of inputs. For example, in some embodiments, the system can be configured to take as an input data one or more parameters of one vertebra, two vertebrae, three vertebrae, four vertebrae, five vertebrae, and/or the like, and/or any combination thereof in training the predictive model and/or generating one or more postoperative predictions.

In some embodiments, the system can be configured to utilize a GAN algorithm to train a predictive model and/or generate one or more postoperative predictions. In some embodiments, a GAN algorithm can be used to predict a postoperative spine, a part thereof, and/or one or more parameters thereof. Further, in some embodiments, a GAN algorithm can be used to predict a rod shape and/or position post-surgery.

In some embodiments, the system can be configured to utilize a CNN algorithm to train a predictive model and/or generate one or more postoperative predictions. In some embodiments, the system can be configured to utilize data augmentation to help to be able to use a CNN algorithm. In some embodiments, the system can be configured to utilize a CNN algorithm to predict compensatory mechanism, rod position, rod shape, output(s) of surgery, proximal junctional kyphosis (PJK) risks, and/or the like.

In some embodiments, the system can be configured to utilize an RNN algorithm to train a predictive model and/or generate one or more postoperative predictions. In some embodiments, the system can be configured to utilize an RNN algorithm to deal with variable input sizes. For example, in some embodiments, the system can be configured to use the targeted position of the endplate instrumented as input, in which case the size of the input can depend on the number of instrumented vertebrae. As such, in such embodiments, an RNN algorithm can be useful to deal with the size of the input increasing with the number of vertebrae.

In some embodiments, as illustrated in FIG. 7, the system is configured to output data that has been transformed back at block 718. In particular, in some embodiments, as discussed herein, the system can be configured to train a predictive model and/or generate one or more postoperative predictions in the realm of transformed data, such as for example after applying a Fourier transformation. As such, in order to obtain usable output data in the real world, in some embodiments, the system can be configured transform the data in a frequency domain back into a spatial domain to make one or more postoperative predictions. For example, in some embodiments, the system can be configured to apply an inverse Fourier transformation to output data that was outputted by a predictive model that is in a Fourier transform.

In some embodiments, as illustrated in FIG. 7, the transformed output data can then be utilized at block 720. In particular, in some embodiments, the output can comprise one or more of a predicted surgical outcome, results of a compensatory mechanism and/or spinal curvature or other spinopelvic parameters, specifications of a proposed spinal rod or other spinal implant, one or more proposed surgical steps, and/or the like. In some embodiments, the output data can comprise one or more of one or more spinopelvic parameters, shape of the coronal and/or sagittal spine, position of one or more endplates, shape of a spinal rod to be implanted, and/or the like and/or any combination thereof.

Intraoperative Tracking

FIG. 8 is a flowchart illustrating an example embodiment(s) of implant production, case support, data collection, and/or intraoperative tracking during spinal surgery for developing patient-specific spinal implants, treatments, operations, and/or procedures.

In some embodiments, a computing system at an implant production and/or selection facility can be configured to access and/or receive a final surgical plan or a plurality thereof at block 802, for example via the Internet, wireless communication, and/or a portable electronic storage medium. In some embodiments, the implant production facility can be configured to produce, modify, and/or select one or more parts for the surgical procedure at block 804. For example, the implant production facility can be configured to produce a spinal rod(s), cage(s), and/or screw(s) based on one or more specifications and/or materials specified in the surgical plan(s). Similarly, the implant production facility can be configured to select and/or modify one or more pre-produced spinal rods, cages, and/or screws based on specifications and/or materials specified in the one or more surgical plans.

In some embodiments, a spinal rod, cage, and/or screw can be produced from one or more different materials. The particular material to be used for a particular patient-specific rod(s), screw(s), and/or cage(s) can depend on data and/or can be selected by a surgeon, other medical personnel, and/or other user. The particular material can also depend on the particular patient's height, weight, age, bone density, and/or bone strength, among others. In some embodiments, the system can be configured to design, select, and/or produce one or more of thoraco lumbar rods, cervico thoracic rods, MIS rods, and/or 3D bent rods. In certain embodiments, a spinal rod can be made of titanium, cobalt-chrome alloy, and/or any other material.

As discussed above, in some embodiments, the system can be configured to produce, select, and/or modify a rod that is bent in one or more directions. Generally, it can be difficult, if not impossible, for a surgeon to bend a rod in even one direction, let alone more than one direction, using tools prior to or during surgery. In contrast, by utilizing a composite of two-dimensional x-ray images and/or three-dimensional medical images, the system can be configured to produce, and/or select from pre-existing inventory, a rod that is bent or curved in more than one direction, for example sideways and also in a sagittal direction.

Referring back to FIG. 8, in some embodiments, one or more medical personnel can select one or more implants, such as spinal rod(s), cage(s), and/or screw(s) for implantation at block 806 that was produced, modified, and/or selected by the implant production facility based on the surgical plan at block 804.

In some embodiments, one or more medical personnel can attach and/or activate one or more intraoperative tracking sensors and/or modules for intraoperative tracking at block 808. For example, in some embodiments, one or more intraoperative tracking sensors and/or modules can be attached to one or more implants, such as a spinal screw and/or the like. In some embodiments, the one or more sensors and/or modules can be located in one or more screws and/or nuts for attaching to a patient's vertebrae and/or tools for attaching the same. One or more sensors and/or modules that can be used in certain embodiments are discussed in more detail below. In some embodiments, for spinal surgeries, a sensor and/or module can be placed in and/or attached to every vertebra. This can be advantageous for providing accurate data. However, this may not be desirable in some situations due to the size of data. For example, a large amount of unnecessary data can be collected, when the angle of the vertebrae can be one of the most important parameters. As such, in some embodiments, a sensor and/or module may be attached to only a subset of vertebrae that can provide valuable position and/or angular data of the spine.

In some embodiments, the system can be configured to utilize data collected from one or more sensors and/or modules inside and/or attached to one or more screws implanted into the vertebrae instead of and/or in addition to relying on imaging techniques, for example assuming that an implanted screw will be parallel to an endplate, in order to provide intraoperative tracking. In other words, in some embodiments, angulation of a screw in a sagittal plane can be assumed to be equal or substantially equal to the vertebra angulation. In some embodiments, a top portion of a screw can comprise an active or passive sensor. The top portion can be broken off later during surgery, in some embodiments, such that the sensors can be re-used. The one or more screws comprising one or more sensors can be inserted into every vertebra or a subset thereof. For example, in some embodiments, sensors and/or modules can be attached to all 20 vertebrae. In some embodiments, sensors and/or modules can be attached to only a subset thereof, for example two or more sensors and/or modules attached to the upper lumbar and/or two or more attached to one or more lower vertebrae. In some embodiments, the sensors and/or modules can then be utilized for providing data relating to the position and/or angle or orientation of one or more vertebrae in six degrees of freedom (or nine degrees of freedom) in translation and rotation in real-time, near real-time, and/or substantially real-time. In some embodiments, the raw data collected by the one or more sensors and/or modules can be transmitted to a computer system to translate the raw data into tracking the position and/or orientation of one or more vertebrae, for example to assist in determining a spinal curvature and/or surgical correction.

In some embodiments, based on real-time, near real-time, and/or substantially real-time intraoperative tracking or monitoring, the system can be configured to track the position and/or orientation or angulation of the vertebrae and/or screw(s). In other words, in some embodiments, correction of the spine during surgery can be monitored in real-time, near real-time, and/or substantially real-time. Referring again to FIG. 8, in some embodiments, tracking data corresponding to the position and/or angulation of each vertebra can be transmitted to the main server system and/or a client system at the medical facility at block 810.

In certain embodiments, after one or more medical personnel inserts one, two, or more screws into the spine of a patient, the main server system and/or medical facility client system can be configured to track, analyze, and/or store movement of the different vertebrae during the correction and other operating procedure data at block 812. In some embodiments, one or more medical personnel can thus visualize or otherwise track the position, orientation, correction and/or angulation of the vertebrae in real-time, near real-time, and/or substantially real-time and determine when desirable conditions, for example matching a pre-determined surgical plan, have been obtained. Such live-tracking can provide substantial assistance to the medical personnel. For example, without intraoperative tracking, a surgeon may believe that a 30 degree correction can be obtained when PSS is performed; however, in reality, a performed PSS may only result in a 10 degree correction. By providing intraoperative tracking or monitoring, in such situations in some embodiments, the surgeon can make further corrections as necessary before closing up the operation.

In some embodiments, the system can be configured to conduct analysis of the tracked data by comparing the same to a pre-determined surgical plan. To do so, in some embodiments, the system can retrieve data from a plan database 216 and/or operation database 218. Based on such comparison and/or analysis, in some embodiments, the system can be configured dynamically generate and/or provide guidance to the surgeon during the operation in real-time and/or near real-time in block 814. For example, based on the tracked data, in some embodiments, the system can be configured to instruct or guide the surgeon to change the angle of one or more vertebra based on the tracked data to obtain a curvature of the spine closer to the pre-determined plan.

In some embodiments, the system can further be configured to provide an audible and/or visible alert and/or guidance to the surgeon. In some embodiments, the audible and/or visible alert and/or guidance can comprise instructions to the surgeon to perform the surgery in a particular way or degree and/or alert the surgeon when the position and/or angulation of one or more vertebrae is within a predetermined threshold. For example, the system can be configured to provide an alert when the position and/or angulation of one or more screws and/or vertebrae is within about 1%, about 2%, about 3%, about 4%, about 5%, about 10%, about 15%, about 20%, about 25% of the predetermined plan and/or when within a range defined by two of the aforementioned values. In some embodiments, the system can be configured to provide a visual depiction of the position, location, orientation, and/or angulation of each vertebra on a display based on the tracked data to guide the surgeon during surgery.

In some embodiments, once an acceptable level of angulation of the vertebrae if obtained, the surgeon can insert a spinal rod and/or tighten the screws to the rod and lock all parts for example to complete the positioning of a spinal rod at block 816. In some embodiments, the surgeon can then remove and/or deactivate the one or more sensors at block 818.

The system can further be configured to collect and/or utilize postoperative data in some embodiments, for example to provide predictive modeling and/or other post-operation features or services. Moreover, in some embodiments, the system can be configured to take into account a level of sophistication and/or preferences of a surgeon to provide surgeon-specific recommendations for future cases. In some embodiments, comparison and/or analysis of preoperative, intraoperative, and/or postoperative data and/or surgeon input can be used to determine a skill level and/or strategic preferences of a surgeon. In some embodiments, the particular skill level of the surgeon and/or strategic preferences can be used to develop subsequent surgical planning for that surgeon. In addition, in some embodiments, data relating to growth of the spine and/or other subsequent developments, such as relating to curvature, can also be obtained from one or more postoperative x-ray images. In some embodiments, such long-term effects can also be utilized in preparing subsequent planning.

In some embodiments, as part of predictive modeling and/or machine learning as discussed herein, the system can be configured to analyze one or more different plans that were developed for a particular case. For example, in some embodiments, a first generated plan can be based on the strategy and/or objectives of a surgeon. In some embodiments, a second generated plan for the same case can be based on data from scientific literature. In some embodiments, a third generated plan for the same case can be based on historical data collected by the system through performance of surgical procedures. In some embodiments, as more data is collected, and as more feedback and input are given and received from surgeons, and/or as more scientific research is conducted, the one or more generated plans and/or particular features thereof for a single case may converge. In some embodiments, certain parameters that converge more so than others can be utilized more heavily by the system in planning stages for subsequent cases. Further, in some embodiments, the system can be configured to compare a given case to previous cases in the planning stage. For example, in some embodiments, the system can be configured to parse one or more databases to find one or more spines that match a given case and/or certain features thereof to make certain recommendations and/or predictions for planning.

Intraoperative Tracking Module(s)

Generally speaking, certain intraoperative imaging such as fluoroscopy and/or CT scans can be used for intraoperative assessment of spinal curvatures and/or correction thereof. However, such processes generally only provide instantaneous vision/assessment of spinal curvatures. As such, it can be advantageous to allow live or near-live tracking of spinal curvatures/angulations to provide substantial assistance to the surgeon, thereby further allowing the surgeon to make further corrections to the spine as may be necessary under live control. At the same time, certain live-tracking devices, such as those that may be based on optoelectronic passive sensors, may disturb the surgeon's workflow as many additional steps may be required compared to usual surgery.

Accordingly, in some embodiments described herein, systems, devices, and methods are provided that allow for intraoperative monitoring, for example during spinal surgery. In particular, in some embodiments, the system can be configured to track a surgeon's performance in real-time, near real-time, and/or in substantially real-time and further compare the same to the preoperative planning, while adding only a minor footprint on surgery workflow.

In some embodiments, the system can allow a surgeon to manipulate a patient's spine and follow one or more positions and/or one or more orientations or angles of one or more sensors and/or modules that are attached to one or more vertebrae. In some embodiments, one or more sensors and/or modules attached to one or more vertebrae can be configured to provide tracking data relating to one or more positions and/or orientations of the vertebra the sensor is attached to. As such, in some embodiments, based on such tracking data and/or guidance data derived therefrom, the surgeon can then manipulate the patient's spine until one or more sensor and/or module readings show that the positioning of the spine is optimal, desirable, and/or matches or substantially matches those of a predetermined plan.

In some embodiments, intraoperative imaging processes or techniques, such as fluoroscopy and/or CT scans can be used for intraoperative imaging. For example, in some embodiments, intraoperative fluoroscopy can be used to assess the position of screws regarding anatomy structures to provide intraoperative tracking. In some embodiments, one or more sensors and/or modules can be used in conjunction with one or more infrared cameras and/or electromagnetic detection. In some embodiments, the position(s) and/or orientation(s) of the one or more sensors and/or modules and/or bones can be identified by use of active sensors and/or modules. In certain embodiments, one or more passive sensors and/or modules can be used.

In some embodiments, the system can be configured to identify the position(s) and/or orientation(s) of one or more pedicle screws, and in turn one or more bones and/or vertebrae to which the one or more pedicle screws are attached thereto, by use of one or more active and/or passive sensors and/or modules. In some embodiments, the system is configured to utilize one or more active sensors and/or modules, without the need for any receivers to interpret the position, orientation, and/or angulation of one or more sensors and/or modules on a common axis system. In other words, in some embodiments, the whole intraoperative tracking system and/or device may be configured to operate using only one or more sensors and one or more computer devices or systems treating the signal of the one or more sensors and displaying one or more measurements obtained therefrom.

In some embodiments, an intraoperative tracking sensor and/or module, as the term is used herein, can comprise a power source, such as a battery, a wireless transmitter, and one or more active and/or passive sensors for real-time tracking. In some embodiments, the one or more sensors can comprise one or more accelerometers and/or one or more gyroscopes to provide one or more inertial measurement units, such as in 6 degrees of freedom (DOF) and/or 9 DOF. In some embodiments, the system can comprise one or more active sensors, which can be configured to be an inertial measurement unit in 6 DOF and/or 9 DOF. In some embodiments in which the system is configured to utilize one or more passive sensors and/or modules, visual tracking can be utilized to provide intraoperative tracking in real-time, near real-time, and/or in substantially real-time. In some embodiments in which only active sensors and/or modules are used, the system can be configured not to rely on visual tracking. Rather, in some embodiments, the system can utilize wireless transmission of motion data for intraoperative tracking in real-time, near real-time, and/or in substantially real-time.

In some embodiments, the system can be configured to determine relative orientation and/or position of two or more sensors and/or modules attached to a patient's spine to measure and/or calculate spinal curvature, for example by interpreting independent sensor data. In particular, in some embodiments, the system can be configured to interpret independent sensor data obtained from two or more sensors and/or modules, using the gravity force vector as a common reference axis. In some embodiments, two of the three axes of each central unit can be assumed or considered to be on a plane parallel or substantially parallel with a determinate angle to the sagittal plane of the patient lying on the operating table. In other words, in some embodiments, the position and/or orientation of two or more sensors and/or modules can be configured such that two of the three axes of position data to be collected by each sensor or module are on or assumed to be on a plane parallel or substantially parallel to the sagittal plane of a patient lying on the operating table. As such, in some embodiments, the right positioning of the inertial unit can be mechanically obtained through a sensor/implant interface.

In some embodiments, one or more sensors and/or modules can be attached to every vertebra, for example through one or more interfaces provided via one or more implants/screws and/or directly to bone structures. In some embodiments, one or more sensors and/or modules can be attached to only a portion or subset of the vertebrae. As such, in some embodiments, one or more sensors and/or modules may be attached to only a subset of vertebra that can provide valuable position and/or angular data of the spine.

Figure 9:
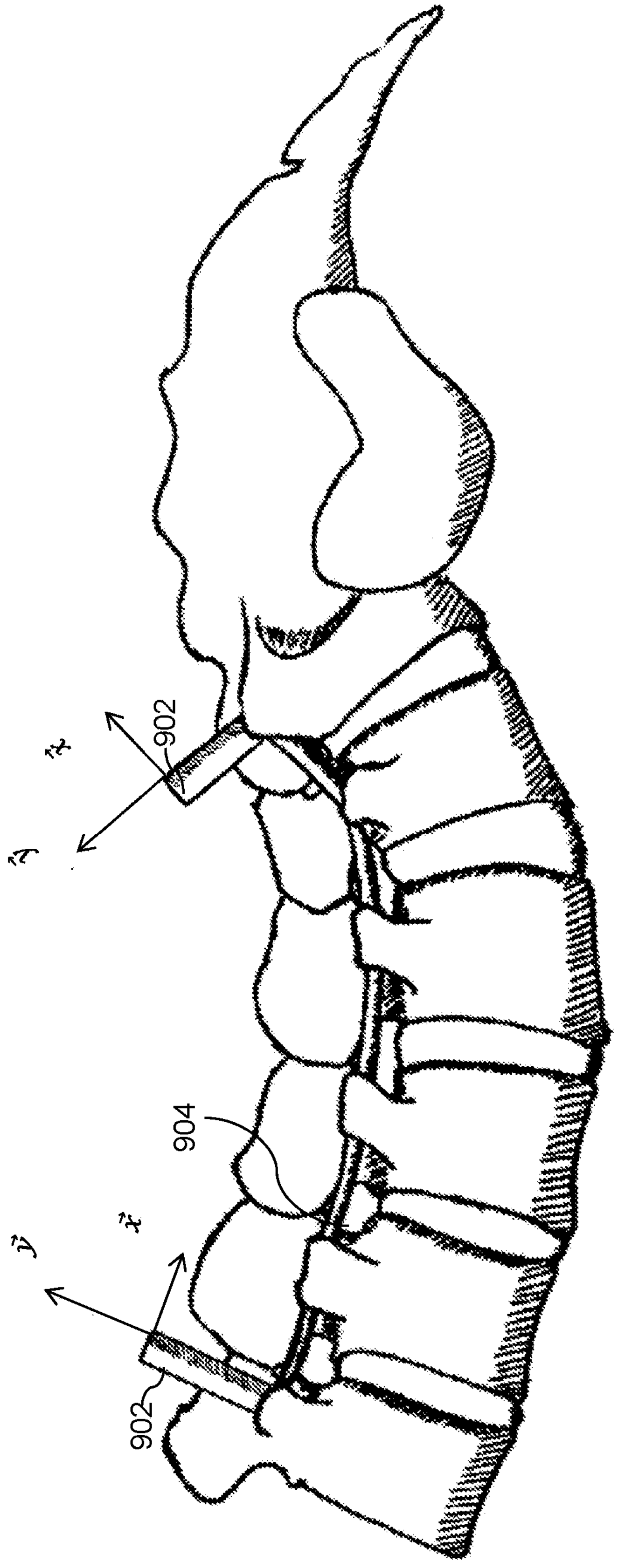
FIG. 9 is a schematic diagram illustrating an example embodiment(s) of intraoperative tracking.

FIG. 9 is a schematic illustrating an example embodiment (s) of intraoperative tracking. As illustrated in FIG. 9, in some embodiments, one or more intraoperative tracking sensors and/or modules 902 may be attached only to certain vertebrae, for example to which a spinal rod 904 is implanted. For example, in some embodiments, one or more intraoperative sensors and/or modules may be attached to Si, L1 and T4 vertebrae to assess L1-Si lordosis and/or T4-T12 kyphosis.

In some embodiments in which one or more intraoperative sensors and/or modules are directly linked and/or attached to one or more screws, the system can be configured to assume that angulation of a screw in a sagittal plane is substantially equal to the vertebra (or superior endplate) angulation. Optionally, in some embodiments, one or more intraoperative fluoroscopic images can be used to assess the position of screws regarding anatomic structures, such as vertebral endplates, in the sagittal plane, as well as other planes in some embodiments.

In some embodiments, one or more screws and/or other implants that comprise and/or to which one or more intraoperative tracking sensors and/or modules are attached to can be mono-axial, uniplanar, and/or poly-axial. In some embodiments where one or more mono-axial screws are used, the system can be configured to follow the position and/or angle of every implanted screw, thereby following the position of a vertebrae based on the screw position. A mono-axial screw may comprise only one intraoperative sensor and/or module, based on the assumption that every movement of the screw is due to rigid movement of the vertebrae. In certain embodiments, a mono-axial screw may comprise one or more intraoperative tracking sensors and/or modules.

In some embodiments, a poly-axial screw can comprise one or more intraoperative tracking sensors and/or modules and/or two or more intraoperative tracking sensors and/or modules, for example to be able to determine if a particular motion or movement is due to rigid movement of the vertebrae itself or at least partially or wholly because of motion between the different portions of the screws, such as in and outside the vertebra, or non-rigid movement. In some embodiments, the system can be configured to determine that a particular movement is rigid movement if there is correlation between the two or more sensor and/or module readings.

In some embodiments, a top portion of a screw and/or other implant can comprise one or more active and/or passive sensors and/or modules. In some embodiments, the top portion of a screw and/or other implant can also comprise a power source, such as a battery, and/or wireless transmitter, as well as one or active and/or passive sensors and/or modules. In some embodiments, the top portion can be broken off and removed later during surgery prior to completion of surgery. In some embodiments, the intraoperative tracking sensor and/or module, or at least one or more portions thereof, can then be reused, thrown away, and/or repurposed for future use.

In some embodiments, an intraoperative tracking system or device can require at least two or more screws to be attached to the vertebrae, wherein each of the two or more screws comprises at least one intraoperative tracking sensor and/or module. In certain embodiments, an intraoperative tracking system or device can require at least one, two, three, four, five, six, seven, eight, nine, and/or ten screws comprising and/or attached to one or more sensors and/or modules to be attached to the vertebrae. In some embodiments, an intraoperative tracking system or device can require a certain range of numbers of screws comprising at least one sensor and/or module, wherein the range is defined by two of the aforementioned values.

In some embodiments, once one, two, three, four, and/or more screws comprising and/or attached to at least one sensor and/or module are attached to the vertebrae, the system can be configured to obtain one or more sensor and/or module readings of the current position(s), orientation(s), and/or angle(s) of one or more screws and vertebrae. Based on the reading(s) from the one or more sensors and/or guidance generated therefrom, in some embodiments, a surgeon can further manipulate the patient's spine as desired. For example, in some embodiments, the intraoperative tracking system and/or device can be configured to continuously and/or periodically provide updated tracking data and/or analysis therefrom, such that the surgeon can manipulate the patient's spine until one or more sensor readings show that one or more positioning and/or orientation of the spine are optimal and/or matches or substantially matches a pre-determined plan.

In some embodiments, the system can also be configured to provide tips, guidance, and/or suggestions to the surgeon to manipulate the spine in a certain manner and/or direction, for example to reach and/or more closely follow the predetermined plan. In some embodiments, a surgeon can implant the spinal rod through one, two, three, four, and/or more screws once an optimal or desired configuration of the spine is obtained. In some embodiments, after rod implantation, the top portion of screw that comprises the one or more sensors can be broken off and removed.

In some embodiments, the one or more intraoperative tracking sensors and/or modules are not provided as part of screws or configured to be attached to screws. Rather, in some embodiments, one or more intraoperative tracking sensors and/or modules can provided as part of and/or be configured to be attached to one or more surgical tools, which can eventually be used to attach screws to the vertebrae. For example, in some embodiments, a screwdriver, nut driver, or other specific or usual surgical tool configured to attach a pedicle screw, anchorage, and/or other implant can comprise and/or be attached to one or more active and/or passive sensors and/or modules for intraoperative tracking purposes. In some embodiments, an intraoperative tracking system can require at least one, two, three, four, five, six, seven, eight, nine, and/or ten surgical tools to comprise and/or be attached to one or more sensors and/or modules. In certain embodiments, an intraoperative tracking system or device can require a certain range of numbers of tools to comprise at least one sensor and/or module, wherein the range is defined by two of the aforementioned values.

In some embodiments, a surgical tool comprising one or more sensors and/or modules for intraoperative tracking purposes can comprise a button or other signaling mechanism that measures and/or stores the current position and/or orientation data of the surgical tool, for example in 6 DOF and/or 9 DOF. As such, in some embodiments, once a screw, anchorage, or other implant is put in place, such as attached to a vertebra, using such surgical tool, the surgeon or other medical personnel can activate the sensor in the tool, thereby detecting and/or providing orientation and/or position data at that time. As such, in some embodiments, the intraoperative tracking system can be configured to provide data frozen in time rather than providing real-time tracking data.

Additional Features of Intraoperative Tracking

As discussed herein, various embodiments described herein relate to systems, methods, and devices for intraoperative tracking during spinal surgery. In particular, some embodiments described herein comprise an intraoperative tracking device and/or module that can be attached to a pedicle screw that has or is configured to be attached to vertebrae of a patient. In some embodiments, the intraoperative tracking device and/or module can comprise one or more accelerometers, gyroscopes, and/or other sensors to detect an orientation and/or position of the device and/or module. In some embodiments, when the intraoperative tracking device and/or module is attached to one or more screws, data relating to the position and/or orientation of the device and/or module can be detected and transmitted to a computer system using one or more transmitters, such as a wireless transmitter, that is part of the device and/or module. As such, in some embodiments, a surgeon and/or computer system can monitor the position and/or orientation of one or more screws attached to the vertebrae in real-time or in near real-time during spinal surgery. By utilizing such data, in some embodiments, the system can be configured to track progress of the surgery, for example as compared to a preoperatively determined surgical plan. For example, in some embodiments, the system can be configured to determine how closely a surgeon is performing surgery according to a preoperatively determined surgical plan.

In some embodiments, as discussed herein, an intraoperative tracking module and/or device can comprise one or more inertial sensors. In some embodiments, the an intraoperative tracking module and/or device can be configured to be coupled to, attached to, and/or otherwise associated to a vertebral screw. In some embodiments, an intraoperative tracking module and/or device and/or sensor therein can be configured to measure an orientation of a screw to which the module and/or device and/or sensor is attached to. In some embodiments, an intraoperative tracking module and/or device can be for single use purposes. In some embodiments, an intraoperative tracking device and/or module can be assembled in a sterilized environment.

In some embodiments, as discussed herein, an intraoperative tracking module and/or device and/or sensor thereof can be configured to ensure and/or facilitate application of required or preplanned spinal correction during surgery, for example as compared to a predetermined surgical plan. In some embodiments, an intraoperative tracking module and/or device can comprise one or more wireless transmitters for transmitting the tracked data to a computer system. For example, in some embodiments, an intraoperative tracking module and/or device can be configured to transmit the tracked data via Bluetooth and/or Bluetooth Low Energy (BLE) to a computer system.

In some embodiments, a computer system can be configured to receive the tracked data during surgery from one or more intraoperative tracking devices and/or modules and display the same in some format on a display or user interface. In some embodiments, the computer system and/or user interface and/or software operating thereon can provide real-time, near real-time, or substantially real-time display to a user or surgeon of the intraoperative tracking data. In particular, in some embodiments, the system can be configured to generate and/or provide an visual angle display and/or access to one or more patient sagittal parameters or other spinopelvic parameters.

As discussed herein, in some embodiments, a surgeon can attach a spinal rod to one or more screws attached to vertebrae of a patient during surgery. As some embodiments herein provide intraoperative tracking capabilities, in some embodiments, it can be possible to ensure that the spinal rod is correctly attached to the vertebrae of the patient according to a preoperatively determined surgical plan. In some embodiments, once the position of the spinal rod is finalized, the tracking device(s) and/or module(s) attached to the screw(s) can be detached prior to conclusion of the surgery. In some embodiments, an intraoperative tracking device and/or module can be pre-mounted to each screw or be provided separately for attachment to a screw during or prior to surgery.

Compatibility of Some Embodiments of Intraoperative Tracking Modules

In some embodiments, an intraoperative tracking device and/or module can be placed inside a head of a screw, which can either be selectively attached to a screw during surgery and/or be pre-mounted to a screw prior to surgery. In some embodiments, the head of the screw and/or sensor can be designed to fit, be compatible with, and/or be part of the same system of other medical devices and/or surgical tools provided by the same provider and/or different provider. For example, in some embodiments, the head of the screw and/or sensor can be part of the same system as one or more patient-specific spinal rods, patient-specific screws, surgical planning process, iterative surgical planning, spinal surgery predictive modeling, and/or the like.

Figure 10B:
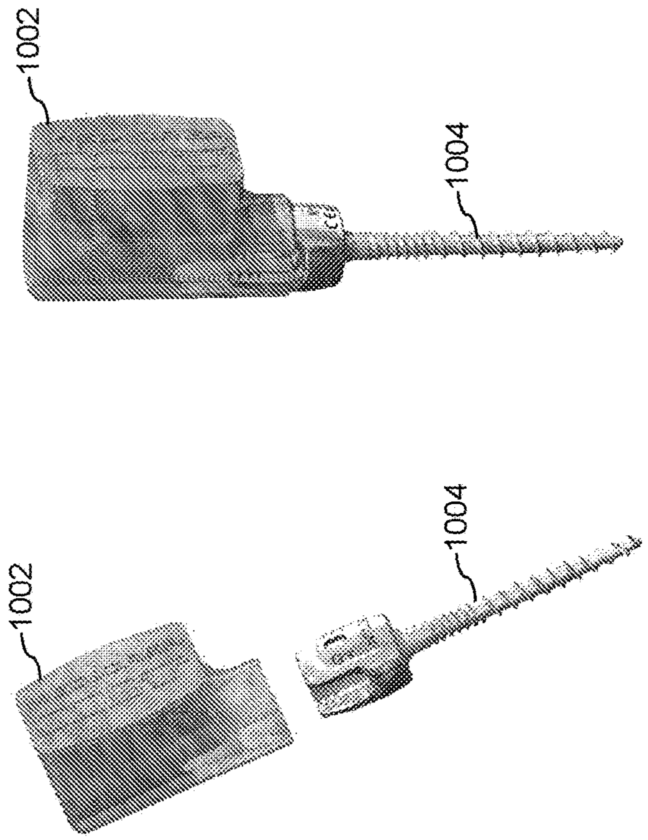
FIGS. 10A-10D are schematic diagrams illustrating an example embodiment(s) of an intraoperative tracking module and compatibility thereof.
Figure 10A:
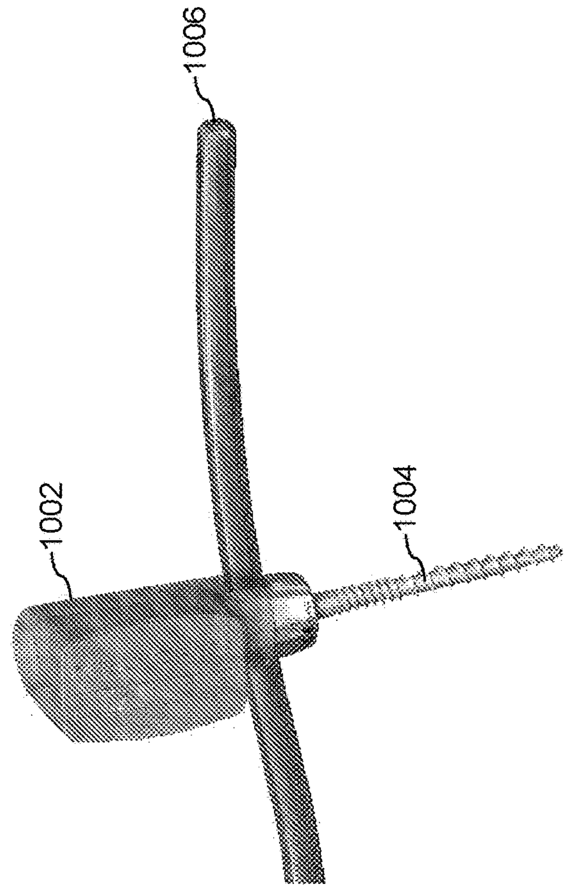

FIGS. 10A-10D are schematic diagrams illustrating an example embodiment(s) of an intraoperative tracking module and compatibility thereof. In particular, as illustrated in FIGS. 10A and 10B, in some embodiments, an intraoperative tracking module and/or device 1002 can be compatible with one or more spinal implants, such as a spinal rod 1006 and/or vertebral screw 1004. For example, as discussed in more detail below, in some embodiments, an intraoperative tracking module and/or device 1002 can comprise a hole or opening along a latitudinal axis of the tracking module and/or device that allows for insertion of a spinal rod 1006 therethrough.

In some embodiments, as illustrated in FIG. 10B, an intraoperative tracking device and/or module 1002 can be compatible with a tulip screw 1004. In some embodiments, an intraoperative tracking device and/or module 1002 can be delivered separately from a vertebral screw 1004, such as a tulip screw 1004, or be delivered directly attached to or associated to a vertebral screw 1004, such as a tulip screw 1004. In some embodiments, an intraoperative tracking device and/or module 1002 is delivered or otherwise provided sterile to the operating room. In some embodiments, an intraoperative tracking device and/or module 1002 comprises one or more latches or attachment mechanisms that allow the tracking module and/or device 1002 to attach to one or more protrusions of a tulip screw 1004. For example, as illustrated in FIG. 10B, in some embodiments, an intraoperative tracking module and/or device 1002 comprises two latches or attachment mechanisms or protrusions that attach to two extensions or protrusions of a tulip screw 1004. In some embodiments, as illustrated in FIG. 10B, the two latches or attachment mechanisms or protrusions of an intraoperative tracking device or module 1002 are separated from each other by a distance substantially equal to a distance of separation between two protrusions of a tulip screw 1004 to allow for insertion of a spinal rod 1006 therethrough.

Figure 10D:
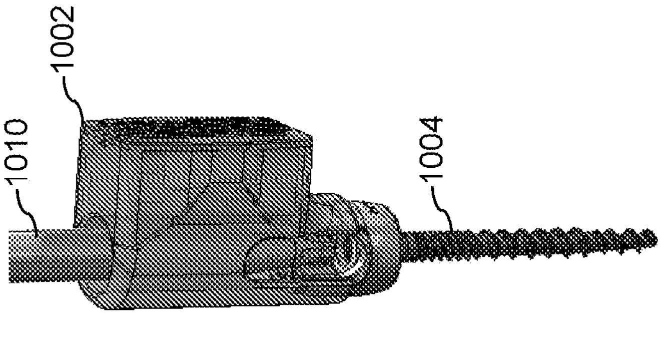
Figure 10C:
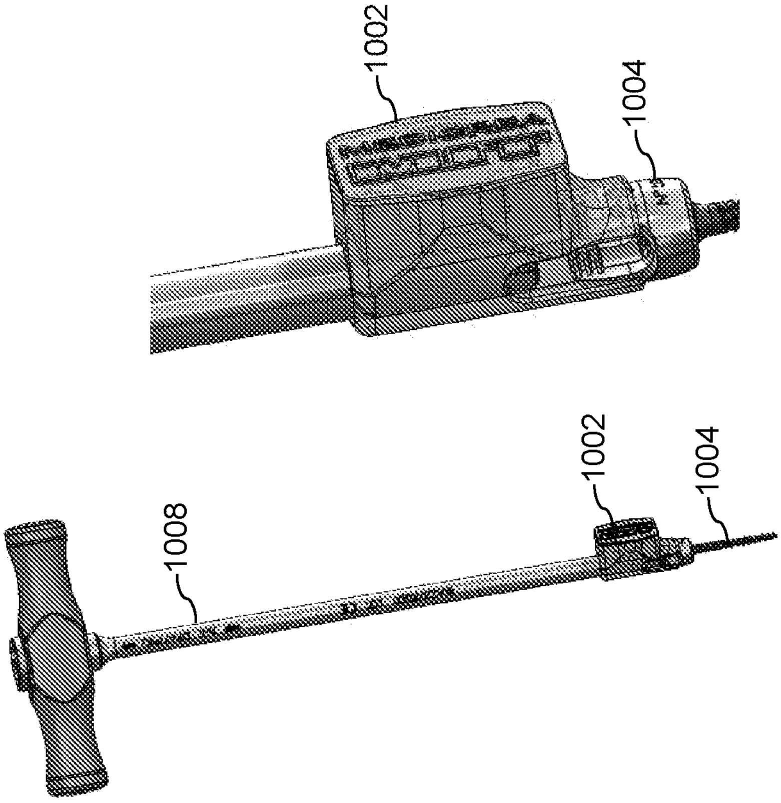
Figure 11B:
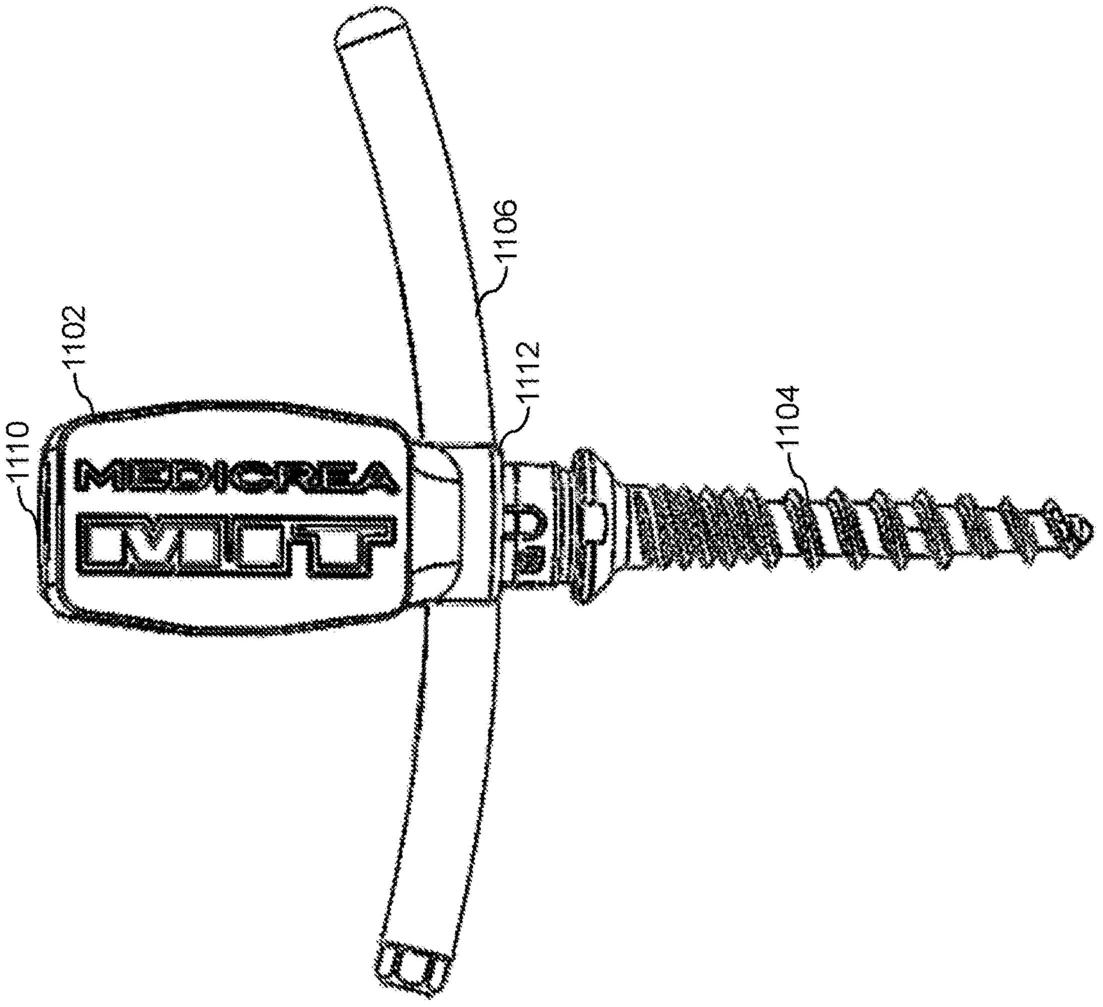
FIGS. 11A-11E illustrate an example embodiment(s) of an intraoperative tracking module and compatibility thereof.
Figure 11A:
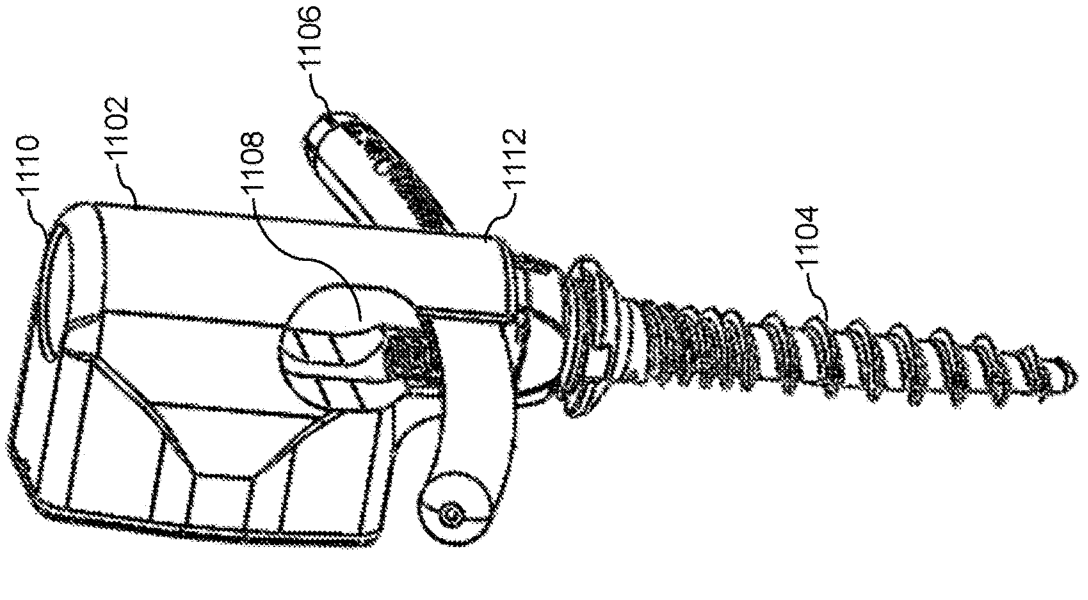
Figure 11E:
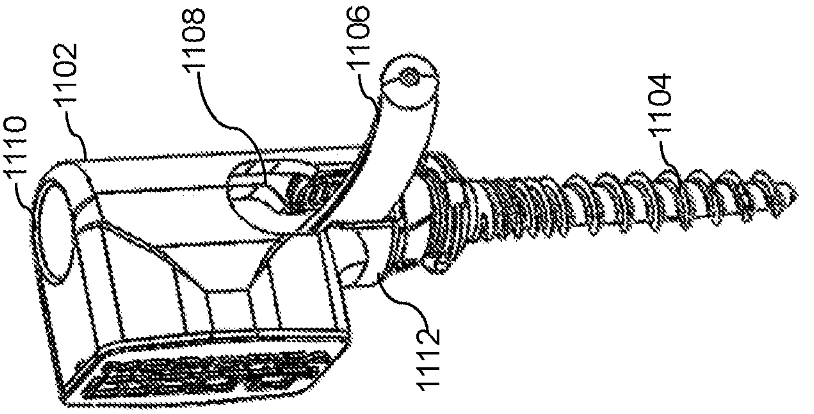
Figure 11D:
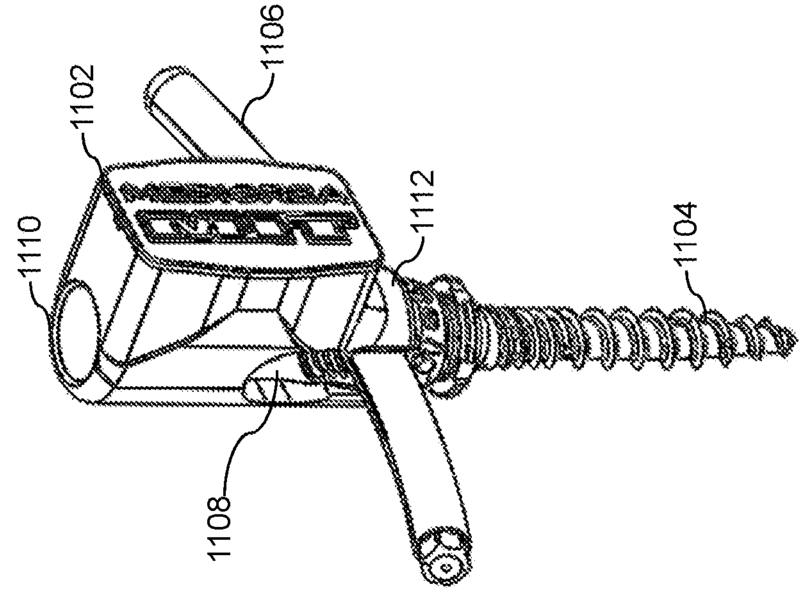
Figure 11C:
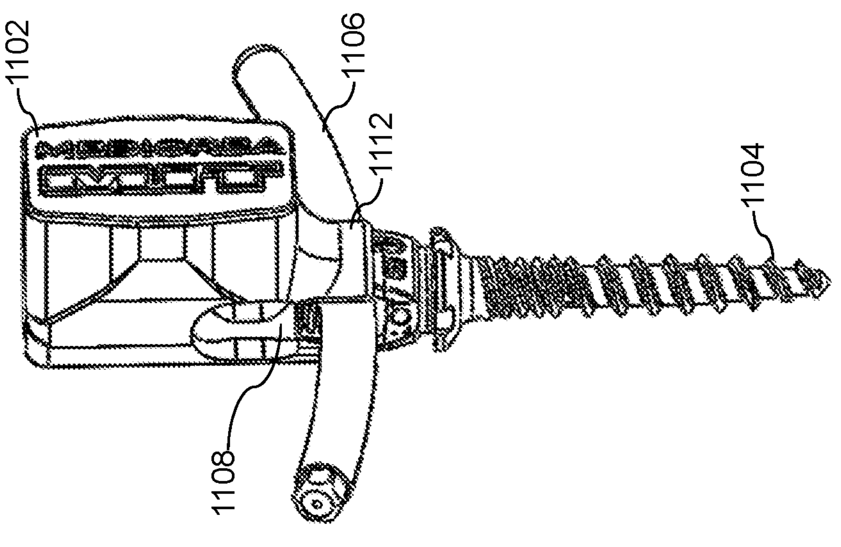
Figure 12A:
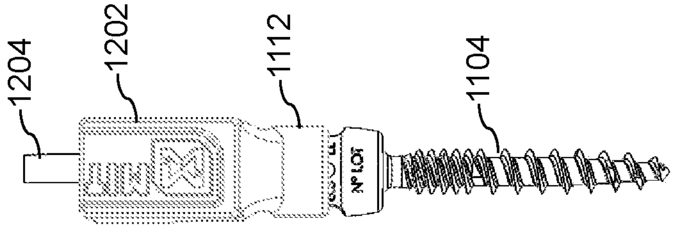
FIGS. 12A-12E illustrate an example embodiment(s) of an intraoperative tracking module and compatibility thereof.
Figure 12B:
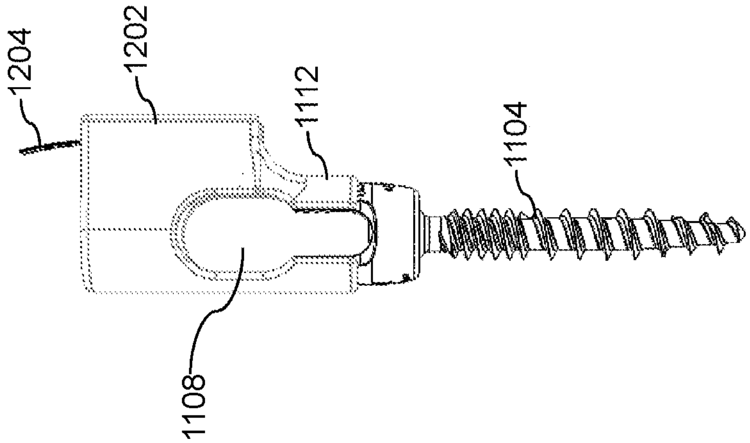
Figure 12C:
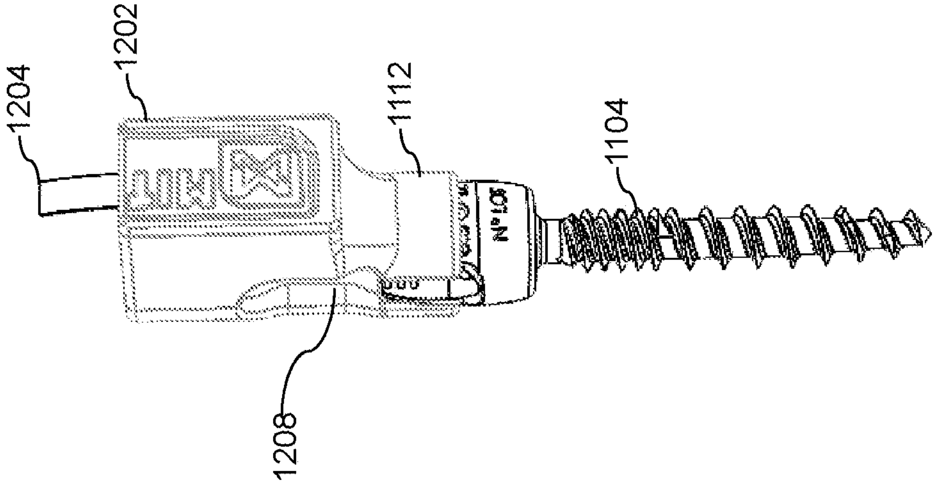
Figure 12E:
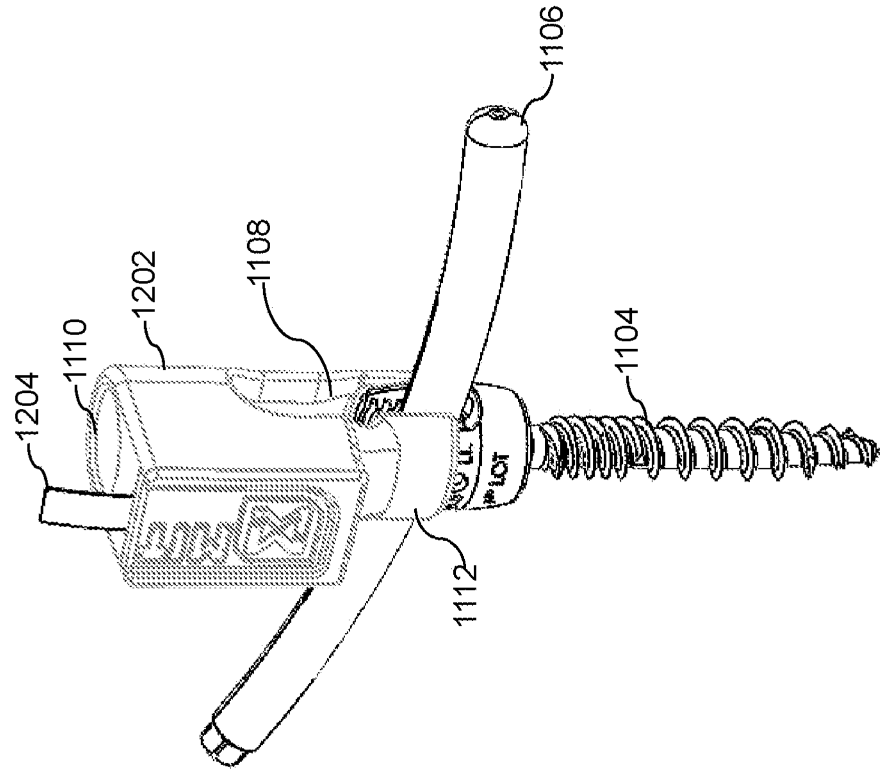
Figure 12D:
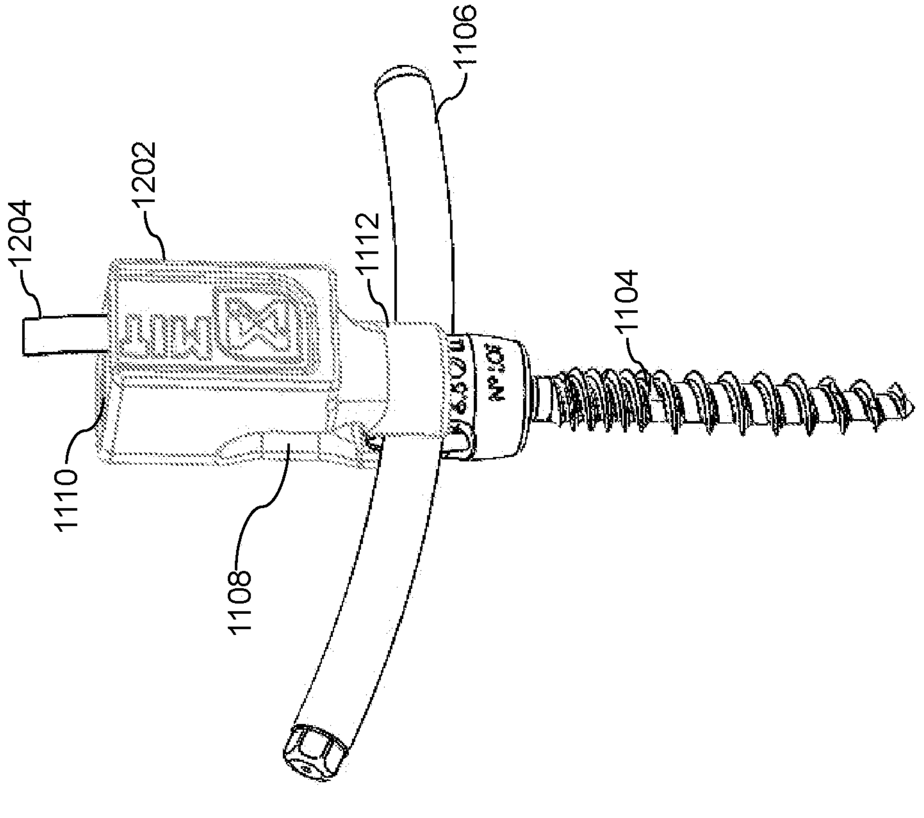
Figure 13D:
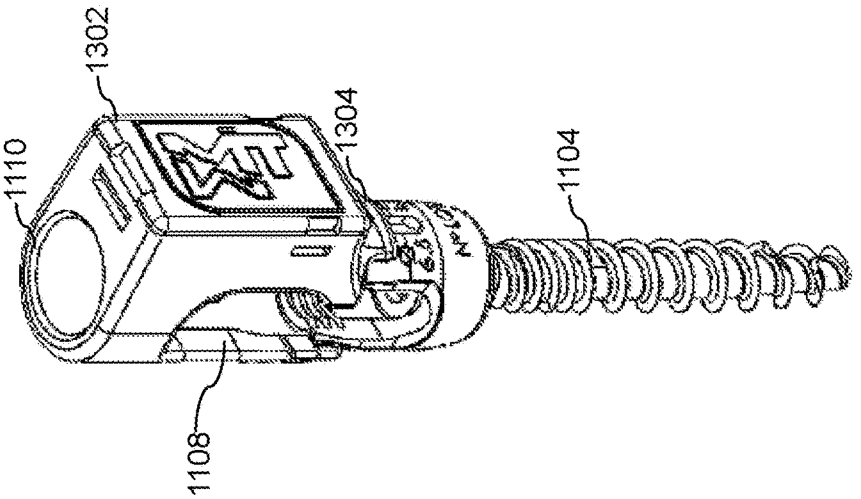
FIGS. 13A-13G illustrate an example embodiment(s) of an intraoperative tracking module and compatibility thereof.
Figure 13C:
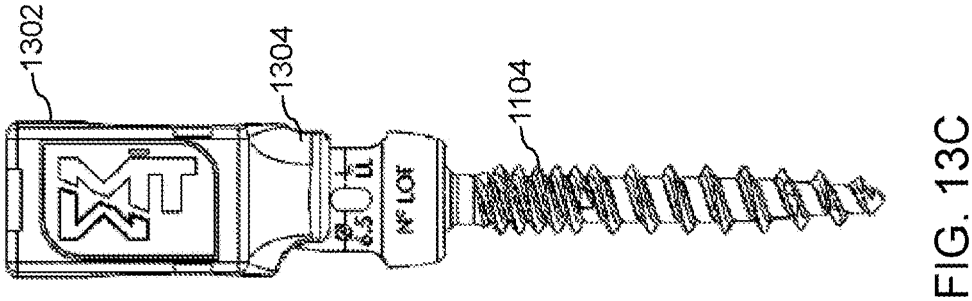
Figure 13B:
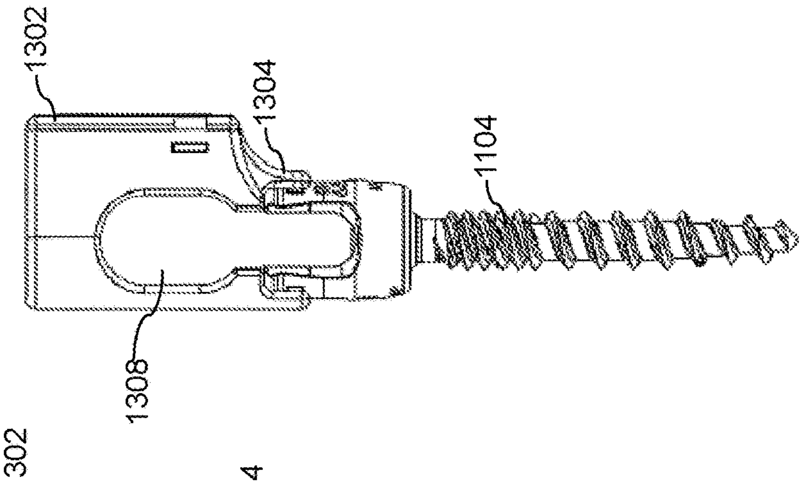
Figure 13A:
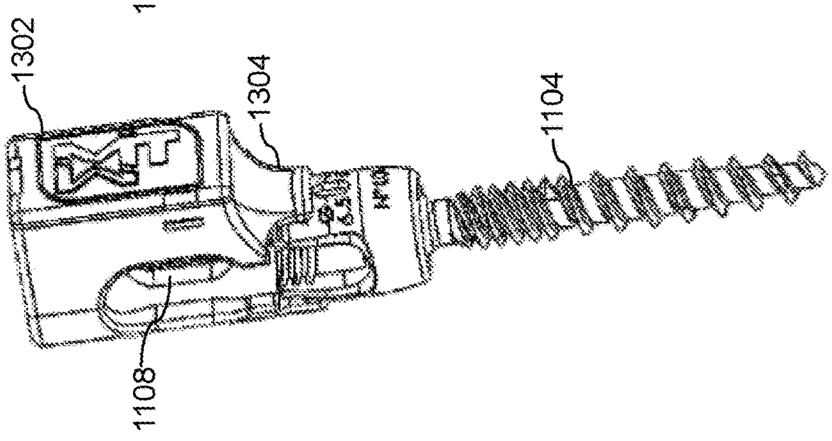
Figure 13G:
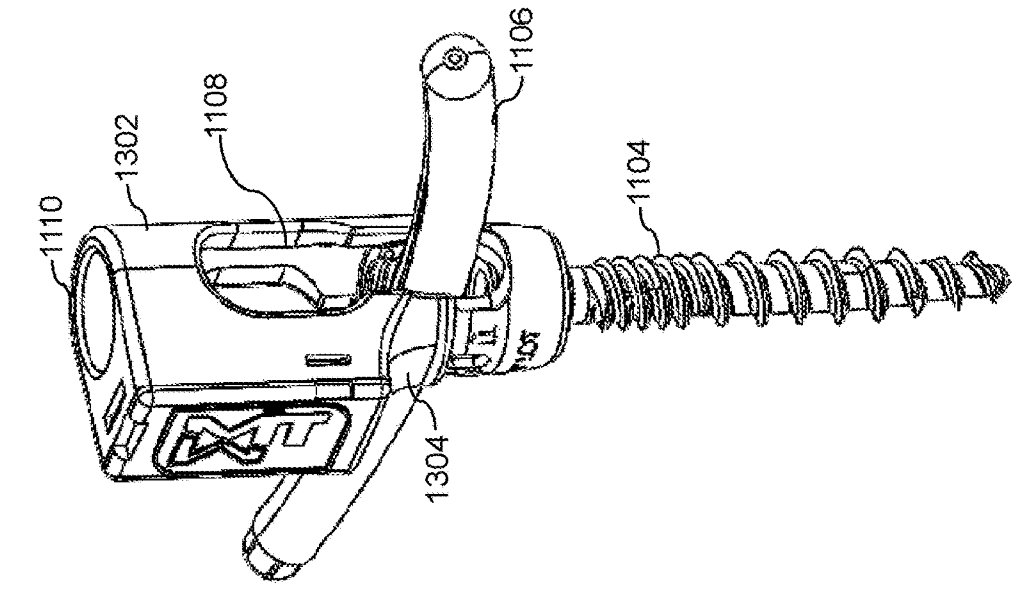
Figure 13F:
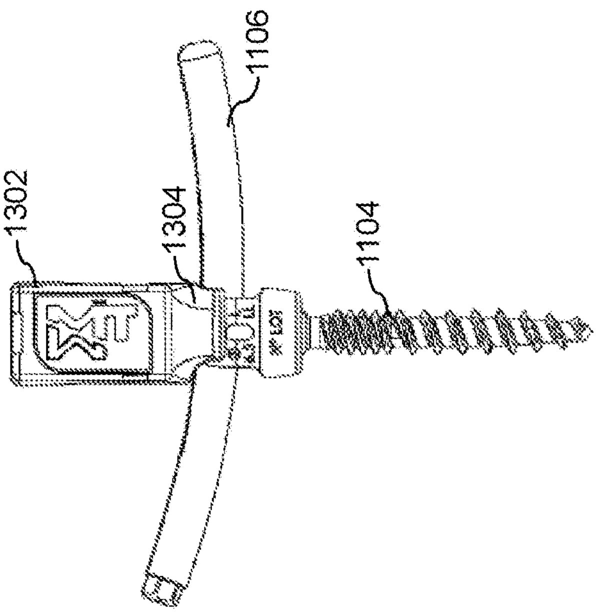
Figure 13E:
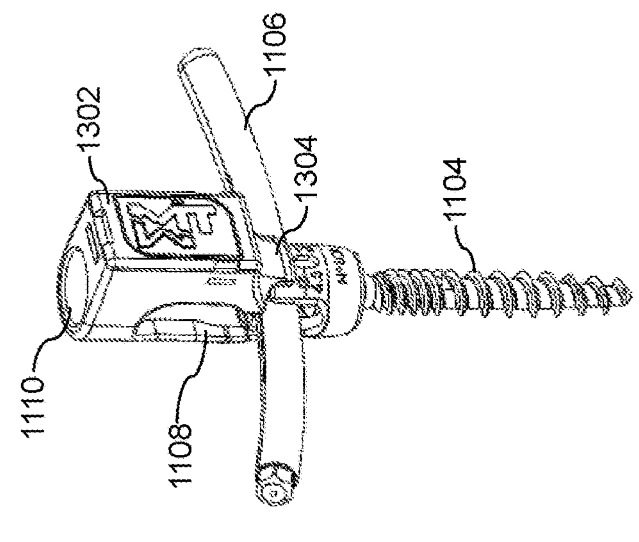
Figure 14A:
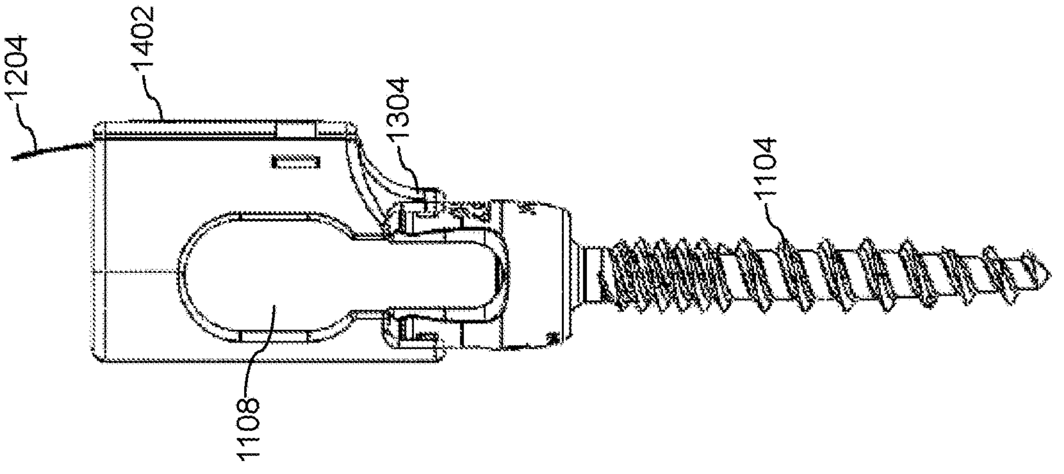
FIGS. 14A-14F illustrate an example embodiment(s) of an intraoperative tracking module and compatibility thereof.
Figure 14B:
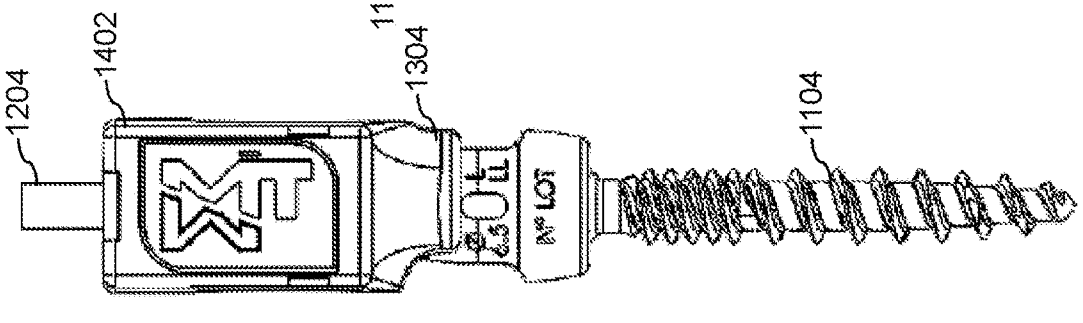
Figure 14C:
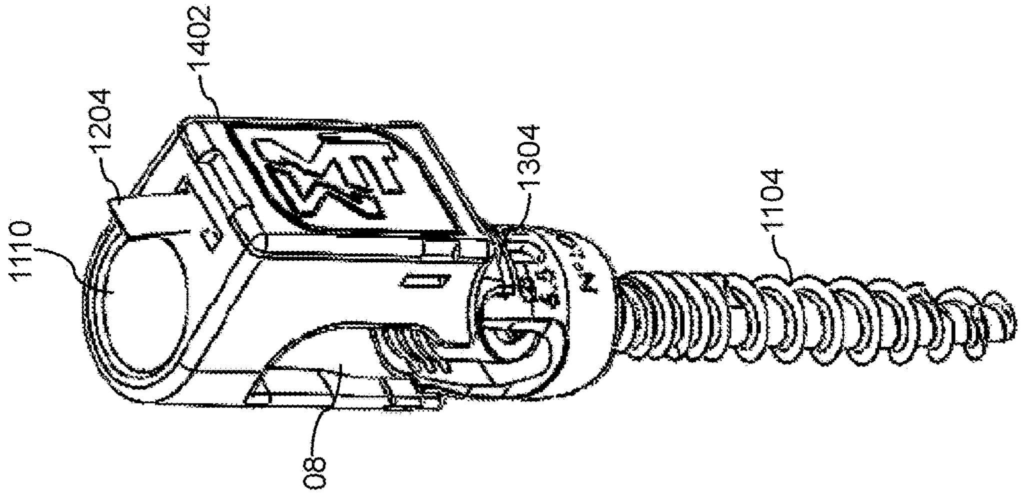
Figure 14D:
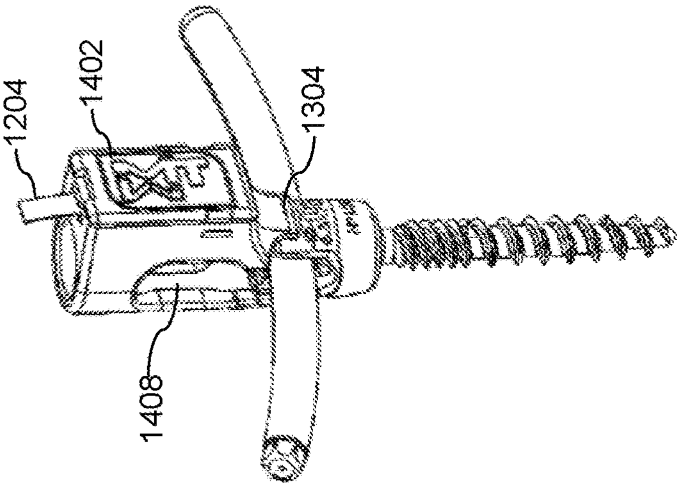
Figure 14E:
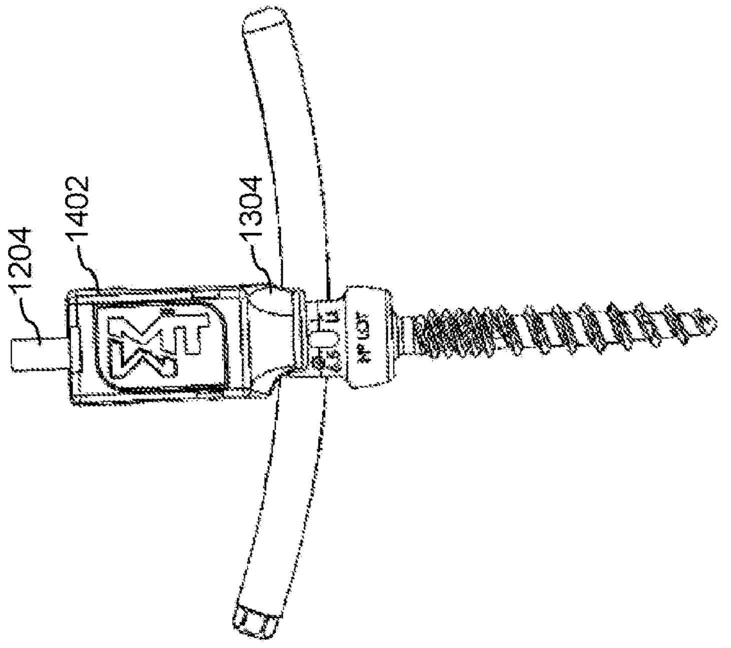
Figure 14F:
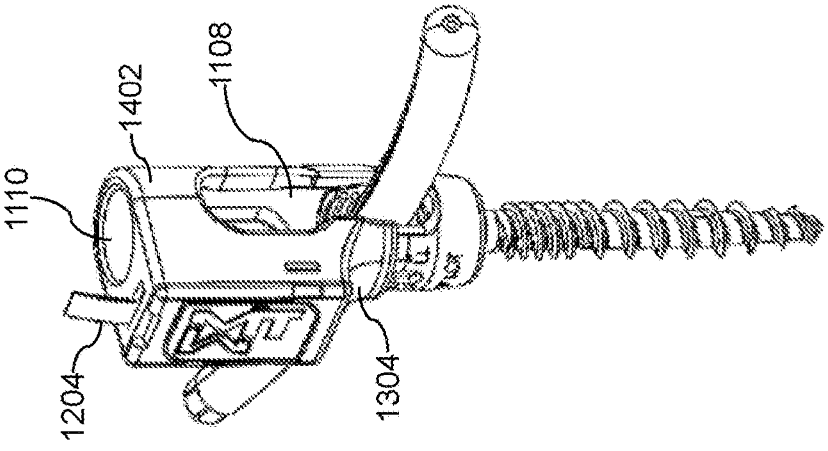

In some embodiments, as illustrated in FIGS. 10C and 10D, an intraoperative tracking module or device 1002 can be compatible with one or more instruments or surgical tools, such as a nut driver 1008 and/or a screw driver 1010. In particular, in some embodiments, an intraoperative tracking device and/or module 1002 can comprise an opening or hole along or substantially parallel to a vertical axis or longitudinal axis of the module or device 1002 to allow insertion, rotation, and/or removal of a nut driver 1008 and/or screw driver 1010, such that a nut driver 1008 and/or screw driver 1010 can access a vertebral screw 1004. In some embodiments, an intraoperative tracking device and/or module 1002 can comprise a first opening or hole along the vertical axis or longitudinal axis and a second opening or hole along the horizontal or latitudinal axis of the module or device 1002. In some embodiments, a longitudinal axis of the first opening or hole and a longitudinal axis of the second opening or hole can be substantially perpendicular.

Additional Features of Some Embodiments of Intraoperative Tracking Modules

FIGS. 11A-11E illustrate an example embodiment(s) of an intraoperative tracking module and compatibility thereof. In some embodiments, an intraoperative tracking module or device 1102 can comprise one or more electronic components and/or sensors, such as for example a gyroscope, accelerometer, power source, wireless transmitter, data filter, an electrical circuit, and/or the like.

As illustrated in FIGS. 11A-11E, in some embodiments, an intraoperative tracking module or device 1102 can comprise an opening, aperture, and/or access port 1110 at the top of the device that leads to a tunnel or hole or conduit along or substantially parallel to a vertical or longitudinal axis of the module or device 1102 throughout the whole vertical thickness or height of the module or device 1102, for example connecting a top end and a bottom end of the intraoperative tracking module or device 1102. In some embodiments, such opening, aperture, and/or access port 1110 at the top of the device and a vertical tunnel or conduit extending therefrom can allow insertion, rotation, and/or removal of one or more surgical tools, such as a nut driver and/or screwdriver, and access to a vertebral screw 1104.

In some embodiments, an intraoperative tracking module and/or device 1102 comprises an opening, aperture, tunnel, and/or hole 1108 along or substantially parallel to a horizontal or latitudinal axis of the device or module 1102 throughout the whole horizontal thickness or width of the module or device 1102. In some embodiments, such opening, aperture, and/or tunnel and/or hole 1108 can be located near the bottom of the module or device 1102, which can allow for insertion and/or placement of a spinal rod 1106 therethrough. In some embodiments, the opening, aperture, hole, and/or tunnel 1108 along a horizontal or latitudinal axis of the device or module 1102 can comprise a larger top section, comprising a larger cross-sectional area perpendicular to a horizontal or latitudinal axis of the device or module 1102, and a smaller bottom section, comprising a smaller cross-sectional area perpendicular to a horizontal or latitudinal axis of the device or module 1102. In some embodiments, the larger top section can facilitate and/or allow for easy initial insertion of a spinal rod 1106, which can then be lowered into the smaller bottom section to place the spinal rod 1106 within a tulip screw 1104.

In some embodiments, a width, along a horizontal or latitudinal axis, of the larger top section of the opening 1108 can be about 7 mm, about 7.5 mm, about 8 mm, about 8.5 mm, about 9 mm, about 9.5 mm, about 10 mm, about 10.5 mm, about 11 mm, about 11.5 mm, about 12 mm, and/or be within a range defined by two of the aforementioned values. In some embodiments, a width along a horizontal or latitudinal axis, of the smaller bottom section of the opening 1108 can be about 4 mm, about 4.5 mm, about 5 mm, about 5.5 mm, about 6 mm, about 6.5 mm, about 7 mm, about 7.5 mm, about 8 mm, about 8.5 mm, about 9 mm, and/or be within a range defined by two of the aforementioned values. In some embodiments, a width along a horizontal or latitudinal axis, of the smaller bottom section of the opening 1108 can be substantially equal to a diameter a spinal rod 1106.

In some embodiments, an intraoperative tracking module and/or device 1102 can comprise one or more protrusions or notches 1112, such as two in the illustrated embodiments in FIGS. 11A-11E, proximate to the bottom of the device or module 1102 for attaching the module or device 1102 to one or more protrusions or extensions or notches of a tulip screw 1104. In some embodiments, the one or more protrusions or notches 1112 can be spaced apart from each other, thereby creating a gap or opening through which a spinal rod 1106 can be placed. In some embodiments, the one or more protrusions or notches 1112 can comprise a width that substantially matches the width of one or more protrusions or notches of a tulip screw 1104. In addition, in some embodiments, the one or more protrusions or notches 1112 can be configured to attach to a circular notch of a tulip screw 1104, thereby providing stability when affixing the intraoperative tracking device or module 1102 to a tulip screw 1104.

In some embodiments, the one or more protrusions or notches 1112 can comprise one or more grooves on the internal surface thereof to facilitate attachment to a tulip screw. As such, in some embodiments, the bottom portion of an intraoperative tracking module or device 1102 can comprise a discontinuous circumference. In some embodiments, the one or more protrusions or notches 1112 can allow for each fixation and/or removal and/or breakage of an intraoperative tracking device or module 1102 from a tulip screw 1104. In some embodiments, the one or more protrusions or notches 1112 can comprise an arcuate shape or curvature to substantially match an arcuate shape or curvature of one or protrusions or notches of a tulip screw 1104.

FIGS. 12A-12E illustrate an example embodiment(s) of an intraoperative tracking module and compatibility thereof. The example embodiment(s) shown in FIGS. 12A-12E share some similar features with the example embodiment(s) shown in FIGS. 11A-11E. For example, some features in FIGS. 12A-12E with the same reference numbers as some features in FIGS. 11A-11E can comprise similar or the same characteristics.

As illustrated in FIGS. 12A-12E, in some embodiments, an intraoperative tracking module or device 1202 comprises a strip 1204. In some embodiments, the strip 1204 can be located proximate to a top edge of the intraoperative tracking device or module 1202, as illustrated in FIGS. 12A-12E, or can be located at or near another portion of the intraoperative tracking device or module 1202.

In some embodiments, the strip 1204 can be configured to act as a mechanism to turn on or power on the intraoperative tracking device or module 1204. For example, in some embodiments, a user or surgeon or medical personnel can pull on the strip 1204 to remove the strip, which can thereby complete a power circuit inside the intraoperative tracking device or module 1204, thereby initiating tracking and/or collection of data by the intraoperative tracking device. As such, in some embodiments, the surgeon or other medical personnel may pull and remove the strip 1204 after a screw 1104 has been secured to a vertebra and after an intraoperative tracking module or device 1202 is secured to the screw 1104.

In some embodiments, the strip 1204 can comprise non-conductive material, such as for example plastic or paper. As such, in some embodiments, the strip 1204 in its original position may interfere with the power circuit within the intraoperative tracking device or module 1202, thereby preventing tracking of data and/or undesired use of power, as the power source within the intraoperative tracking device or module 1202 may be limited. In some embodiments, once the strip 1204 is removed, the power circuit within the intraoperative tracking device or module 1202 can be completed, thereby powering on the intraoperative tracking device or module 1202.

FIGS. 13A-13G illustrate an example embodiment(s) of an intraoperative tracking module and compatibility thereof. The example embodiment(s) shown in FIGS. 13A-13G share some similar features with the example embodiment(s) shown in FIGS. 11A-11E and/or FIGS. 12A-12E. For example, some features in FIGS. 13A-13G with the same reference numbers as some features in FIGS. 11A-11E and/or FIGS. 12A-12E can comprise similar or the same characteristics.

As illustrated in FIGS. 13A-13G, in some embodiments, an intraoperative tracking module or device 1302 can comprise one or more protrusions or notches 1304, such as two in the illustrated embodiments in FIGS. 13A-13G, proximate to the bottom of the device or module 1302 for attaching the module or device 1302 to one or more protrusions or extensions or notches of a tulip screw 1104. In some embodiments, the one or more protrusions or notches 1304 can be spaced apart from each other, thereby creating a gap or opening through which a spinal rod 1106 can be placed.

In some embodiments, one or more of the one or more protrusions or notches 1304 can comprise a width that is narrower that the width of one or more protrusions or notches of a tulip screw. For example, in the example embodiment(s) illustrated in FIGS. 13A-13G, one edge of a protrusion or notch 1304 can substantially match or line up with an edge of a protrusion or notch of a tulip screw 1104, while another edge of a protrusion or notch 1304 can end before another edge of a protrusion or notch of a tulip screw 1104, thereby decreasing the area of overlap between a protrusion or notch 1304 and a protrusion or notch of a tulip screw 1104. In some embodiments, having a protrusion or notch 1304 of an intraoperative tracking module or device 1302 that is narrower that a protrusion or notch of a tulip screw 1104 can make it easier to break off or otherwise decouple the intraoperative tracking module or device 1302 from the tulip screw 1104 while maintaining sufficient stability to affix the intraoperative tracking module or device 1302 to the tulip screw 1104.

In addition, in some embodiments, the one or more protrusions or notches 1304 can be configured to attach to a horizontal notch of a tulip screw 1104 which can be located higher than a circular notch of a tulip screw 1104. In some embodiments, by allowing the one or more protrusions or notches 1304 to attach to a higher and/or horizontal notch of a tulip screw 1104, it can be easier to break off or otherwise decouple the intraoperative tracking module and/or device 1302 from a tulip screw 1104 and/or provide less stress thereto, while still providing sufficient stability when affixing the intraoperative tracking device or module 1302 to a tulip screw 1104.

Similar to the example embodiment(s) illustrated in FIGS. 11A-11E, in some embodiments, the one or more protrusions or notches 1304 can comprise one or more grooves on the internal surface thereof to facilitate attachment to a tulip screw. As such, in some embodiments, the bottom portion of an intraoperative tracking module or device 1302 can comprise a discontinuous circumference. In some embodiments, the one or more protrusions or notches 1304 can allow for each fixation and/or removal and/or breakage of an intraoperative tracking device or module 1302 from a tulip screw 1104. In some embodiments, the one or more protrusions or notches 1304 can comprise an overall arcuate shape or curvature to substantially match an arcuate shape or curvature of one or protrusions or notches of a tulip screw 1104.

FIGS. 14A-14F illustrate an example embodiment(s) of an intraoperative tracking module and compatibility thereof. The example embodiment(s) shown in FIGS. 14A-14F share some similar features with the example embodiment(s) shown in FIGS. 11A-11E and/or FIGS. 12A-12E and/or FIGS. 13A-13G. For example, some features in FIGS. 14A-14F with the same reference numbers as some features in FIGS. 11A-11E and/or FIGS. 12A-12E and/or FIGS. 13A-13G can comprise similar or the same characteristics.

As illustrated in FIGS. 14A-14F, in some embodiments with a narrower notch or protrusion 1304 proximate to the bottom end of an intraoperative tracking device or module 1402, the intraoperative tracking device or module 1402 can comprise a strip 1204, similar to the example embodiment(s) illustrated in FIGS. 12A-12E. One or more characteristics and/or features of a strip 1204 in some embodiments with a narrower notch or protrusion 1304 proximate to the bottom end of an intraoperative tracking device or module 1402 can be similar to a strip 1204 illustrated in the example embodiment(s) of FIGS. 12A-12E.

Additional Features of Some Embodiments of Intraoperative Tracking

Figure 15:
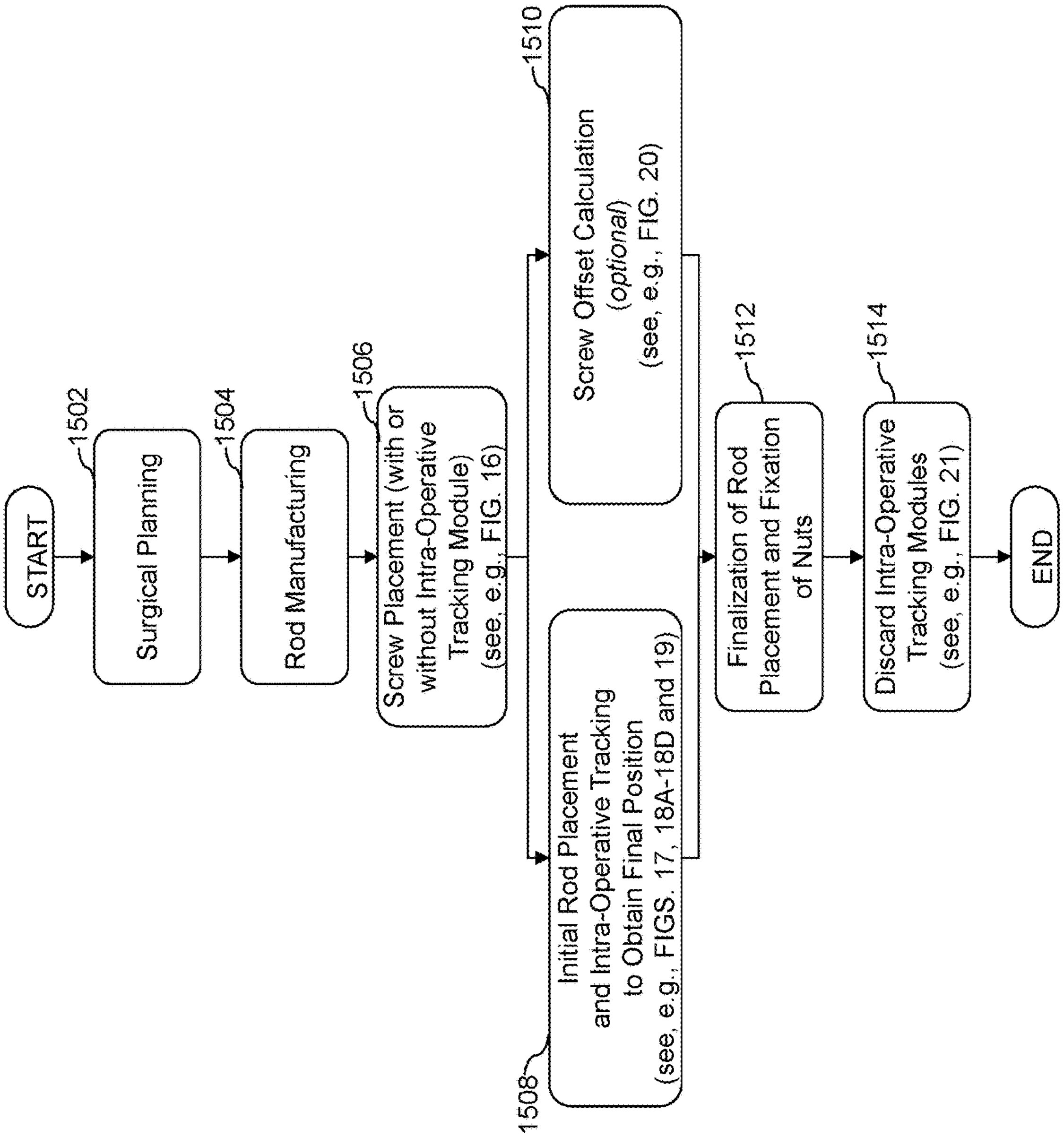
FIG. 15 is a flowchart illustrating an example embodiment(s) of intraoperative tracking and its role in developing patient-specific implants, treatments, operations, and/or procedures.

FIG. 15 is a flowchart illustrating an example embodiment(s) of intraoperative tracking and its role in developing patient-specific implants, treatments, operations, and/or procedures. In addition, FIG. 15 illustrates some embodiments of a surgical method and/or technique for applying intraoperative tracking.

As illustrated in FIG. 15, in some embodiments, the systems, devices, and methods described herein can be configured to generate a plan for spinal surgery at block 1502, utilizing one or more planning features and/or predictive modeling features described herein. In some embodiments, the systems, devices, and methods described herein can be configured to then develop and/or manufacture a patient-specific spinal rod at block 1504 according to the predetermined surgical plan.

In some embodiments, a surgeon or other medical personnel can place one or more screws, with or without an intraoperative tracking module attached to the screw, at block 1506. Additional details regarding screw placement are discussed further in connection with FIG. 16.

In some embodiments, a surgeon or other medical personnel can perform initial rod placement at block 1508. Further, in some embodiments, a surgeon or other medical personnel can initiate intraoperative tracking to assist in obtaining a final position of the rod at block 1508. Additional details regarding spinal rod insertion and/or finalization of a spinal rod position are discussed further in connection with FIGS. 17, 18A-18D, and 19.

In some embodiments, the systems, devices, and methods described herein can provide calculation of screw offset for one or more screws at block 1510 to account for any offset in tracking data from an intraoperative tracking module or device. Additional details regarding screw offset calculation are discussed further in connection with FIG. 20.

In some embodiments, a surgeon or other medical personnel can finalize the rod placement and fixate one or more nuts at block 1512. In some embodiments, once a spinal rod has been fixed on a spine of a patient, one or more intraoperative tracking modules or devices used for intraoperative tracking can be discarded at block 1514. Additional details regarding discarding one or more intraoperative tracking modules or devices are discussed further in connection with FIG. 21.

Figure 16:
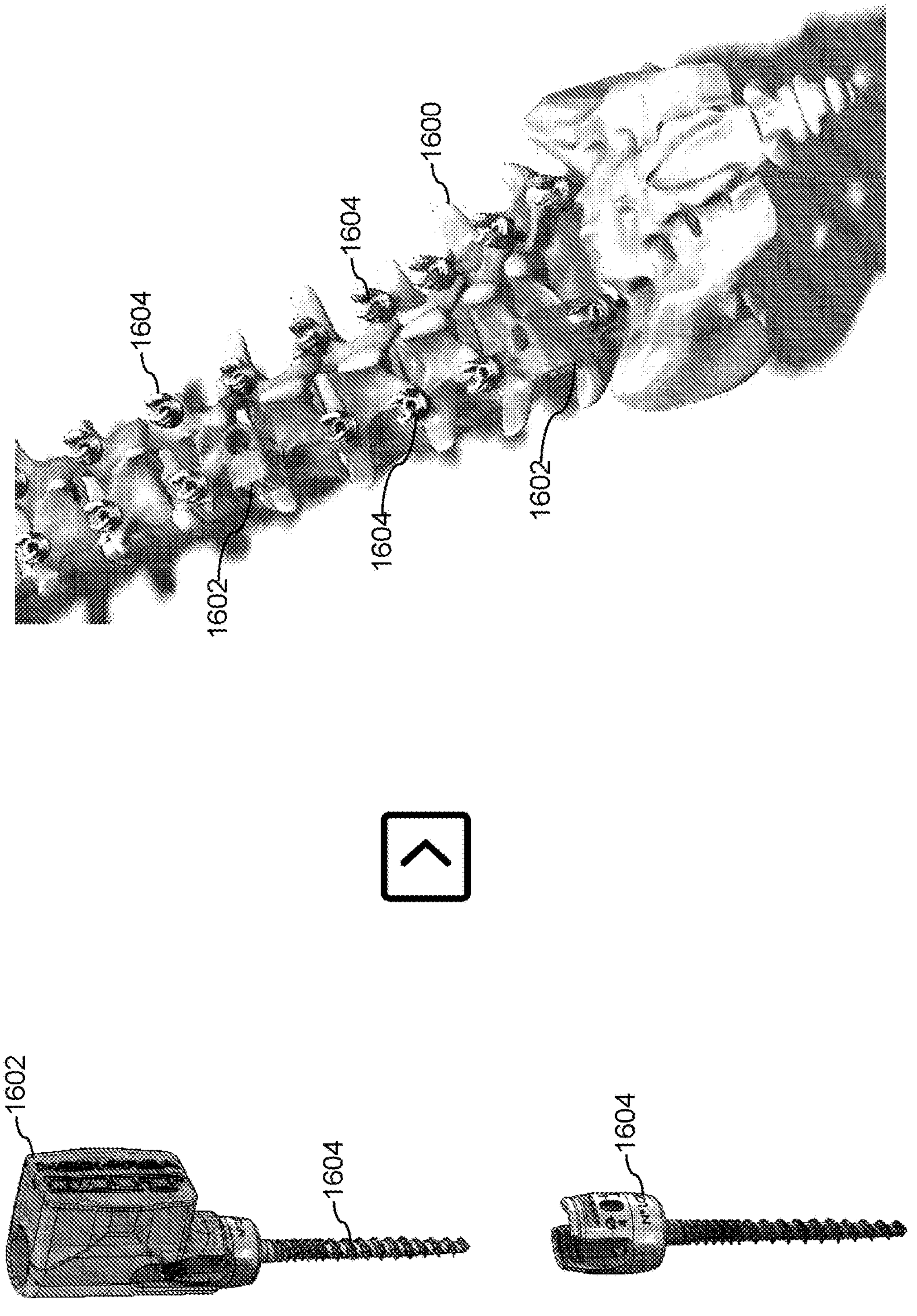
FIG. 16 is a schematic diagram illustrating an example embodiment(s) of positioning one or more spinal screws with an intraoperative tracking module and one or more spinal screws without an intraoperative tracking module on a spine during surgery.

FIG. 16 is a schematic diagram illustrating an example embodiment(s) of positioning one or more spinal screws with an intraoperative tracking module and one or more spinal screws without an intraoperative tracking module on a spine during surgery. As illustrated in FIG. 16, in some embodiments, one or more vertebral screws can be inserted into one or more vertebrae 1600 according to a preoperatively determined surgical plan. In particular, in some embodiments, one or more vertebral screws 1604 attached to an intraoperative tracking module or device 1602 can be affixed to one or more vertebrae 1600. For example, in some embodiments, one or more vertebral screws 1604 attached to an intraoperative tracking module or device 1602 can be affixed to one or more vertebrae 1600 of interest with extreme and/or substantial deformities. In addition, in some embodiments, one or more vertebral screws 1604 without an intraoperative tracking device or module 1602 attached thereto can be inserted and/or affixed to one or more other vertebrae 1600 and/or on instrumented levels. In some embodiments, a preoperatively determined surgical plan can comprise one or more suggested vertebrae for attaching one or more intraoperative tracking modules or devices 1602. In some embodiments, a surgeon can decide which vertebrae to attach one or more intraoperative tracking modules or devices 1602 either during or before surgery.

In some embodiments, the system can allow a surgeon to select via a user interface any subset of intraoperative tracking modules or devices 1602 attached to a vertebra for tracking purposes. For example, in some embodiments, a surgeon can request the system to track and/or provide an angle between two particular intraoperative tracking modules or devices 1602 attached to two different vertebrae. In some embodiments, the system can automatically provide angular tracking data between two particular intraoperative tracking modules or devices 1602 attached to two different vertebrae.

In some embodiments, an intraoperative tracking module or device 1602 can be provided to a surgeon or medical personnel as being affixed to a vertebral screw 1604. In some embodiments, a surgeon or medical personnel can attach an intraoperative tracking module or device 1602 to a vertebral screw 1604 in the operation room.

Figure 17:
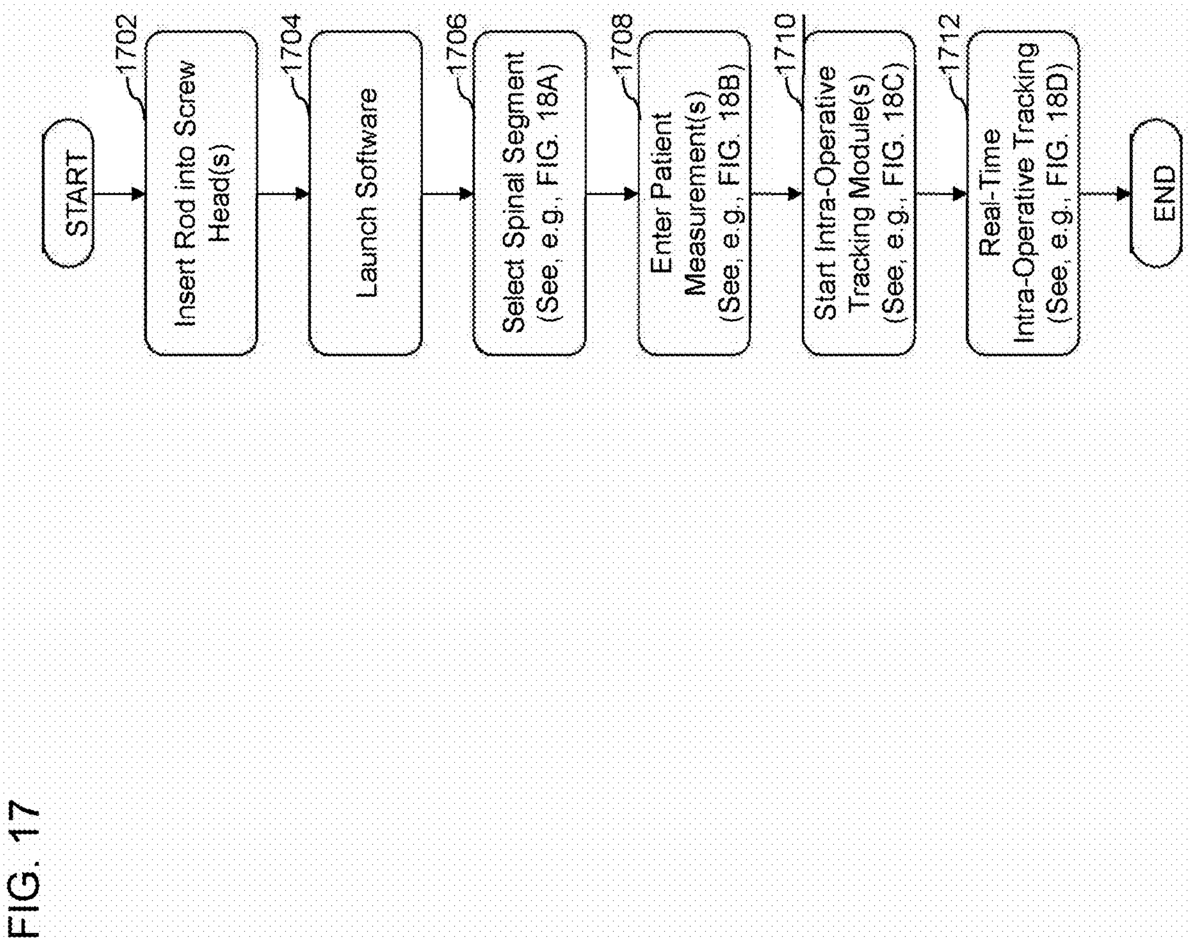
FIG. 17 is a flowchart illustrating an example embodiment(s) of rod placement and intraoperative tracking.

FIG. 17 is a flowchart illustrating an example embodiment(s) of rod placement and intraoperative tracking. As illustrated in FIG. 17, in some embodiments, a surgeon or other medical personnel can initially insert a spinal rod into one or more vertebral screw heads that are affixed to one or more vertebrae at block 1702. In some embodiments, a surgeon or other medical personnel can launch a software of the system at block 1704. In some embodiments, by launching the software, the system can generate and/or provide a user interface.

Figure 18A:
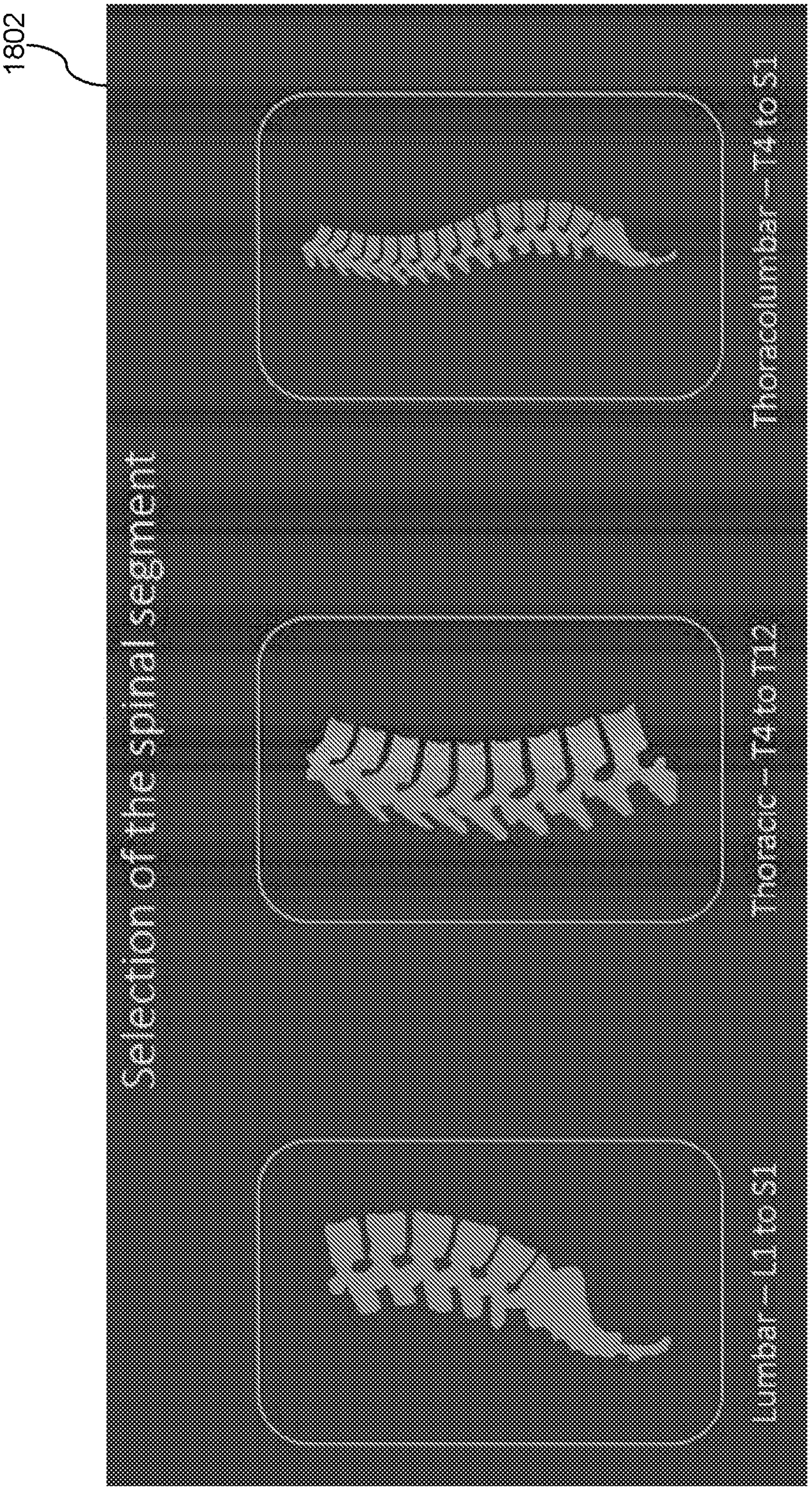
FIG. 18A-18D are screenshots of an example embodiment(s) of a software platform for assisting rod placement and intraoperative tracking.

In some embodiments, the user interface can comprise and/or provide a menu to select one or more spinal segments. FIG. 18A illustrates a screenshot 1802 of an example embodiment(s) of a user interface and/or software platform for selecting one or more spinal segments. As illustrated in FIG. 18A, in some embodiments, the user interface and/or software platform can allow a user to select one or more of a lumbar segment, which can comprise L1 to S1, a thoracic segment, which can comprise T4 to T12, and/or a thoracolumbar segment, which can comprise T4 to Si. Referring back to FIG. 17, in some embodiments, a user and/or surgeon and/or other medical personnel can select one or more spinal segments for performing intraoperative tracking at block 1706.

Figure 18B:
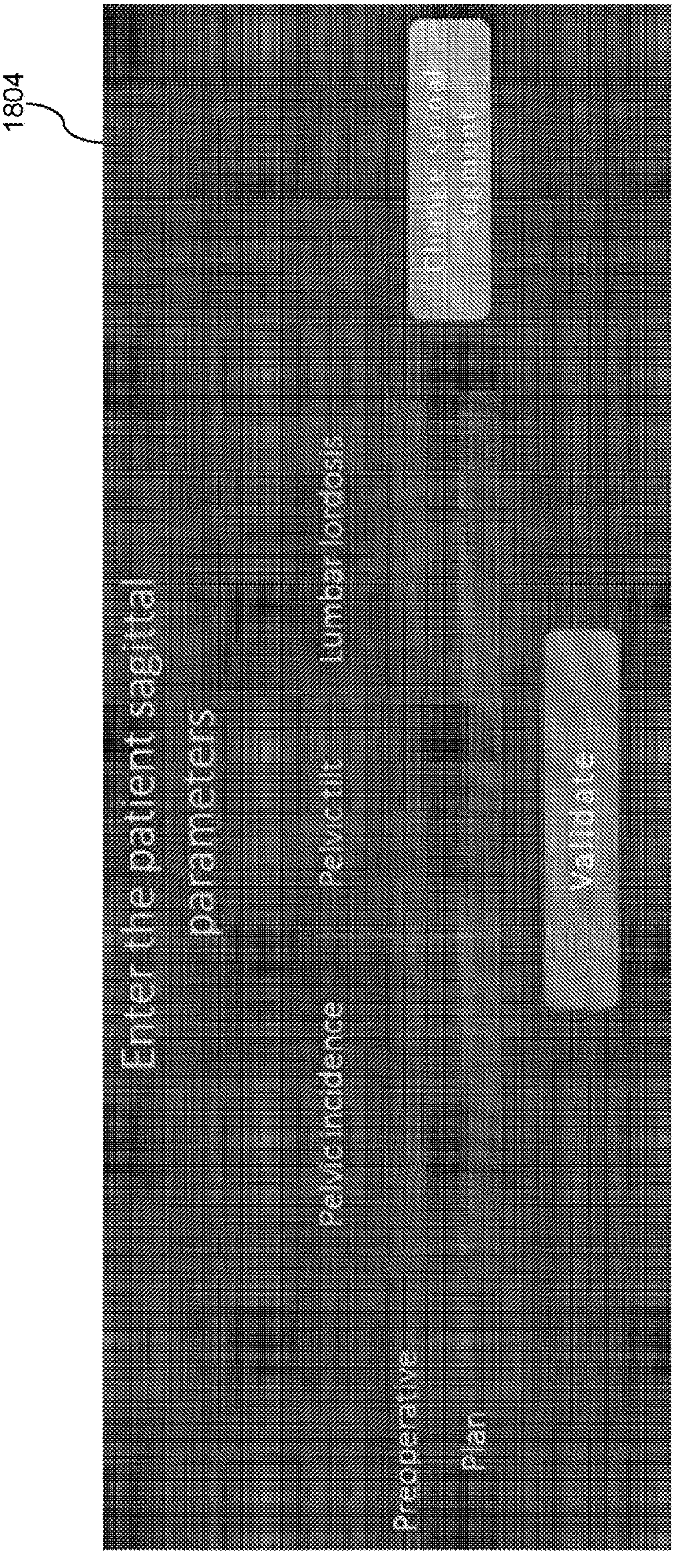

In some embodiments, the user interface can comprise and/or provide a menu to enter one or more patient measurements. FIG. 18B illustrates a screenshot 1804 of an example embodiment(s) of a user interface and/or software platform for entering one or more patient measurements. As illustrated in FIG. 18B, in some embodiments, the user interface and/or software platform can allow a user to enter one or more patient parameters. In some embodiments, the one or more patient parameters can comprise one or more patient sagittal parameters and/or other spinopelvic parameters, such as pelvic incidence (PI), pelvic tilt (PT), and/or lumbar lordosis (LL) of a preoperative state of the spine and/or of a preoperatively determined surgical plan. In some embodiments, the user interface and/or software platform can allow a user to enter one or more patient parameters and/or spinopelvic parameters of one or more spinal segments. Referring back to FIG. 17, in some embodiments, a user and/or surgeon and/or other medical personnel can enter one or more patient measurements and/or spinopelvic parameters at block 1708.

Figure 18C:
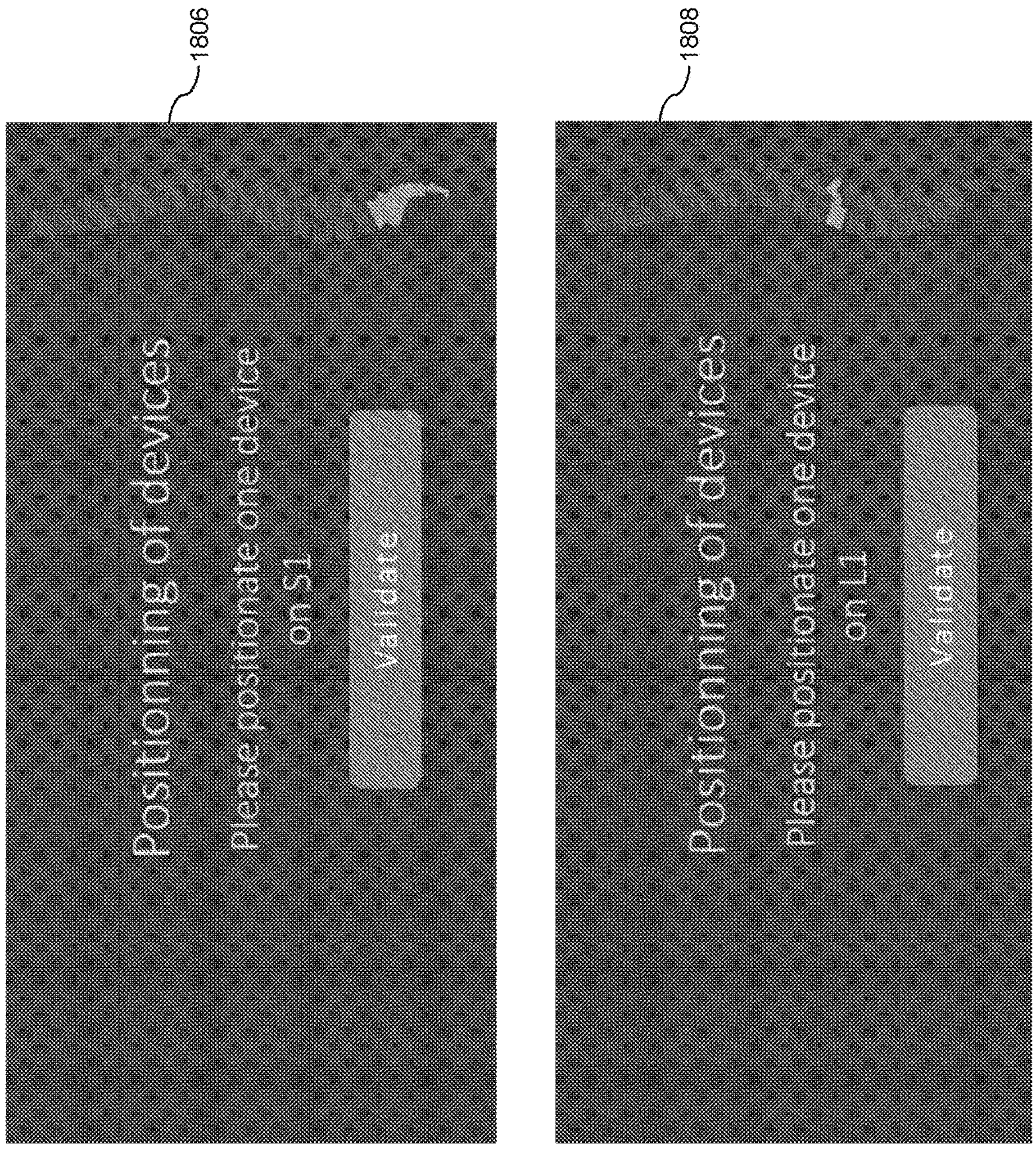

In some embodiments, the user interface can comprise and/or provide a menu to start or initiate one or more intraoperative tracking modules. FIG. 18C illustrates two screenshots 1806, 1808 of an example embodiment(s) of a user interface and/or software platform for initiating or starting one or more intraoperative tracking modules. As illustrated in FIG. 18C, in some embodiments, the user interface and/or software platform can prompt a user to position one or more intraoperative tracking modules or devices at one or more particular vertebrae, for example on S1 and/or L1. In some embodiments, the user interface and/or software platform can prompt validation of the positioning of the one or more intraoperative tracking modules or devices. Referring back to FIG. 17, in some embodiments, a user and/or surgeon and/or other medical personnel can start or initiate one or more intraoperative tracking modules at block 1710.

Figure 18D:
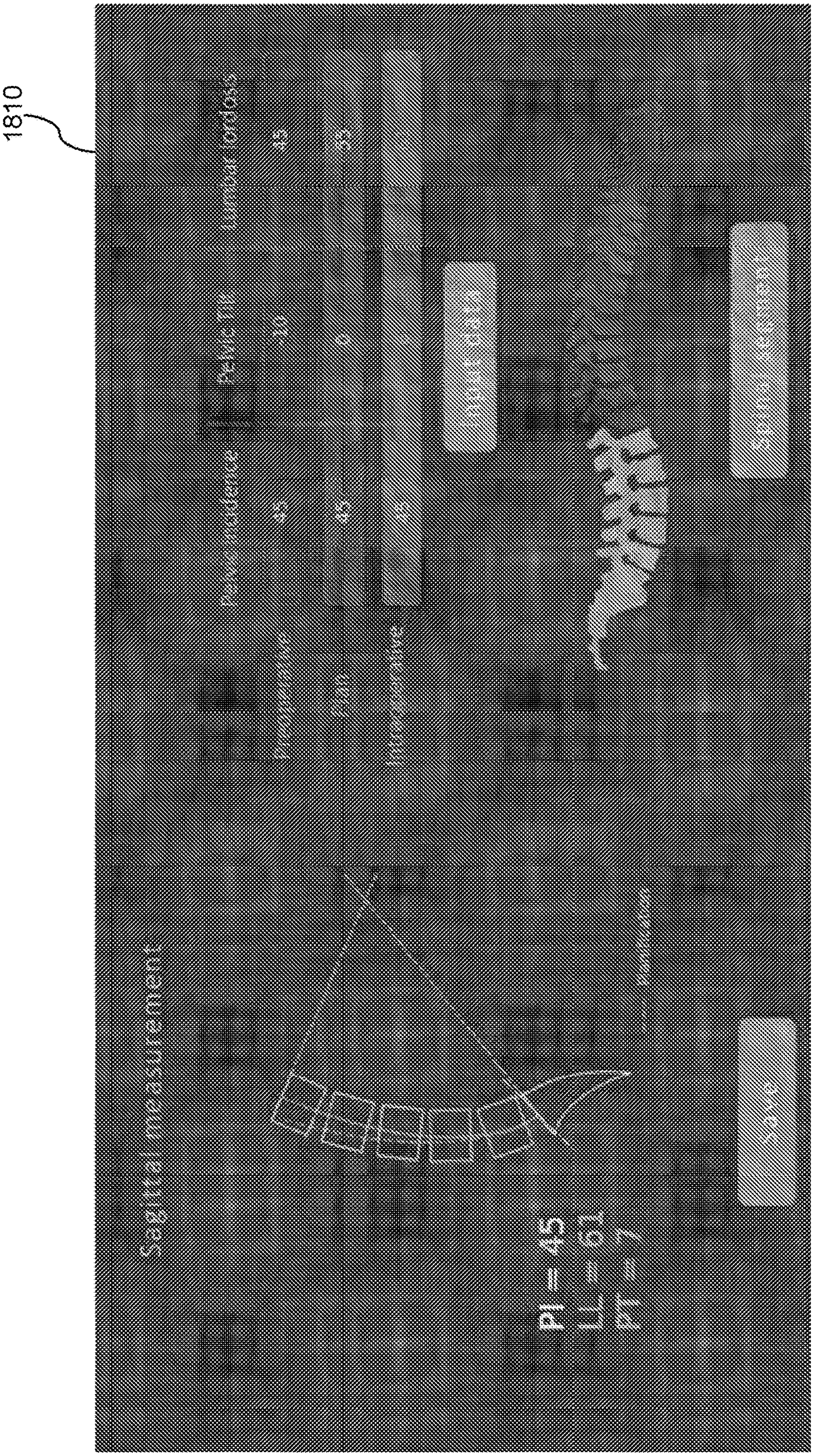

In some embodiments, the user interface can comprise and/or provide a menu for displaying intraoperative tracking in real-time, near real-time, and/or in substantially real-time. FIG. 18D illustrates a screenshot 1810 of an example embodiment(s) of a user interface and/or software platform for displaying intraoperative tracking. As illustrated in FIG. 18D, in some embodiments, the user interface and/or software platform can provide a graphical display of intraoperative tracking data, which can include one or more sagittal measurements, such as PI, LL, and/or PT during surgery. In some embodiments, the user interface and/or software platform can provide a graphical display of PI, LL, and/or PT taken from a preoperative state, from the preoperatively determined surgical plan, and/or current state as measured from one or more intraoperative tracking devices or modules. In some embodiments, the user interface and/or software platform can provide a graphical display of PI, LL, and/or PT for each spinal segment. As such, in some embodiments, a surgeon can be aware of the current state of spinal adjustment and/or surgery and modify the surgical procedure to better match the preoperatively determined surgical plan. Referring back to FIG. 17, in some embodiments, a user and/or surgeon and/or other medical personnel can be provided and/or follow intraoperative tracking data at block 1712.

Figure 19:
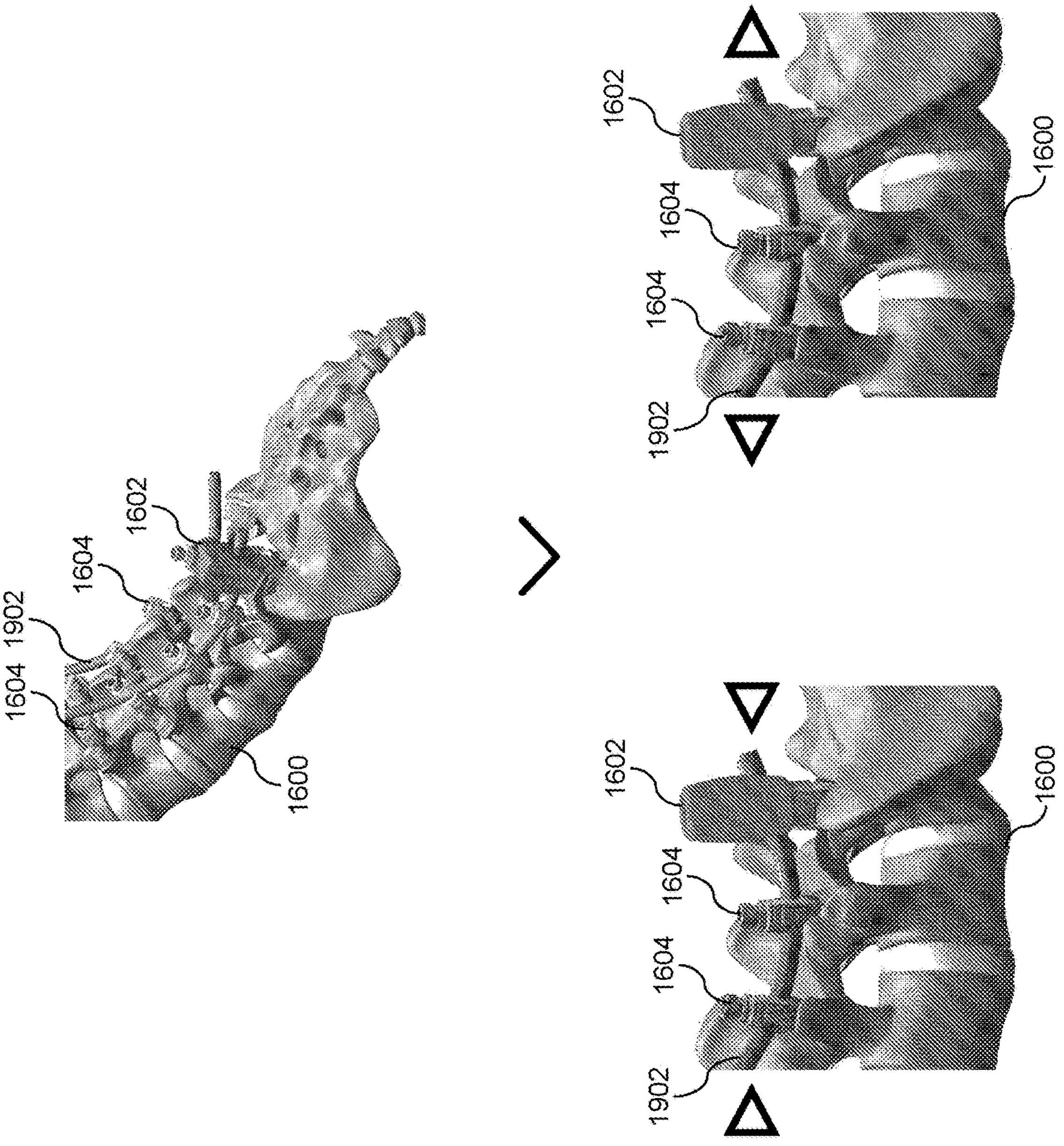
FIG. 19 is a schematic diagram illustrating an example embodiment(s) of positioning a rod during spinal surgery based on intraoperative tracking.

FIG. 19 is a schematic diagram illustrating an example embodiment(s) of positioning a rod during spinal surgery based on intraoperative tracking. As illustrated in FIG. 19, in some embodiments, a surgeon can utilize intraoperative tracking data to facilitate positioning of a spinal rod during surgery. In particular, in some embodiments, a surgeon can insert one or more nuts and compress and/or distract between one or more vertebral screws to obtain the preoperative planned value by referring to and/or with the assistance of intraoperative tracking.

Figure 20:
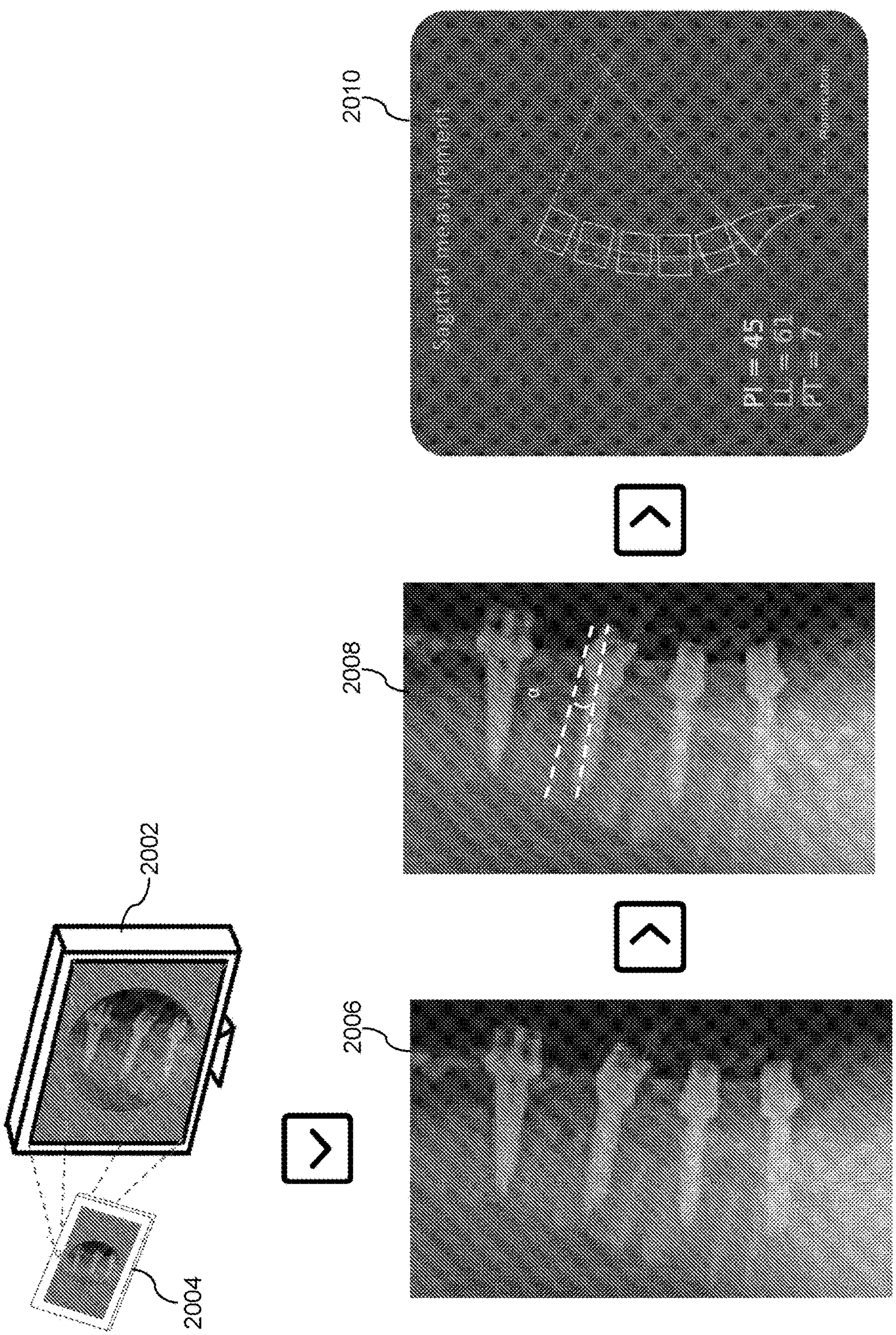
FIG. 20 is a flowchart and/or schematic diagram illustrating an example embodiment(s) of calculating screw offset for intraoperative tracking.

Referring back to FIG. 15, in some embodiments, the systems, devices, and methods described herein can provide calculation of screw offset for one or more screws at block 1510 to account for any offset in tracking data from an intraoperative tracking module or device. FIG. 20 is a flowchart and/or schematic diagram illustrating an example embodiment(s) of calculating screw offset for intraoperative tracking. In some embodiments, screw offset calculation and/or one or more features thereof can be optional. In some embodiments, screw offset calculation and/or one or more features thereof can be performed only if and when necessary.

In some embodiments, the systems, devices, and methods described herein can comprise and/or be configured to calculate the offset between an endplate vertebra and a screw. For example, in some embodiments, the offset between an endplate of a vertebra and a screw can be calculated on a sagittal fluoroscopy. In some embodiments, calculating an offset between an endplate vertebra and a screw can be advantageous, for example if a screw is not substantially perpendicular to an endplate of a vertebra. In some embodiments, such offset calculation can be advantageous because the system can be configured to measure an angle between two vertebrae based on one or more intraoperative tracking modules or devices attached to each of the two vertebrae.

In some embodiments, an offset calculation between an endplate vertebra and a screw may not be necessary for one or more vertebrae, for example if a screw is substantially perpendicular to an endplate of a vertebra and/or if it is assumed that a screw is substantially perpendicular to an endplate of a vertebra.

In some embodiments, as illustrated in FIG. 20, a surgeon and/or other medical personnel can take one or more medical images 2002 of a spine of the patient after attaching one or more intraoperative tracking devices or modules and/or one or more vertebral screws, for example in the operation room. In some embodiments, the one or more medical images 2002 can comprise one or more x-ray images, one or more CT images, one or more MRI images, and/or the like.

In some embodiments, the one or more medical images 2002 taken of a spine of the patient after attaching one or more intraoperative tracking devices or modules and/or one or more vertebral screws can be transmitted to the system for calculating an offset between an endplate vertebra and a screw. In some embodiments, the one or more medical images 2002 taken of a spine of the patient after attaching one or more intraoperative tracking devices or modules and/or one or more vertebral screws can be displayed on a computer display as illustrated in FIG. 20. In some embodiments, a surgeon or other medical personnel can take a photograph of the displayed one or more medical images 2002 by using a tablet computing device 2004 or other computing device, which can then act as an intermediary for transmitting the one or more medical images 2002 to the system for calculating an offset between an endplate vertebra and a screw. That way, in some embodiments, it can be possible to avoid any connectivity issues between the system and a medical imaging display system in the operation room that displays the one or more medical images 2002. In some embodiments, a software and/or user interface operating on the tablet computing device 2004 or other computing device can generate and/or display and/or provide guidance to a user for taking an accurate photograph of the one or more medical images 2002 to ensure a certain level of accuracy.

In some embodiments, once the system receives the one or medical images 2002, the system can be configured to focus on one or more regions and/or one or more vertebrae 2006 shown in the one or more medical images 2002 to calculate an offset between an endplate of a vertebra and a screw. In some embodiments, as illustrated in the example image of 2008, the system can be configured to identify a straight line at the center of a vertebral screw along and/or parallel to a longitudinal axis of the vertebral screw. In some embodiments, as illustrated in the example image of 2008, the system can be configured to identify a line extending from an edge or end of an endplate of a vertebra in which a vertebral screw has been inserted. In some embodiments, the system can be configured to automatically or semi-automatically determine or identify a straight line at the center of a vertebral screw along and/or parallel to a longitudinal axis of the vertebral screw and/or a line extending from an edge or end of an endplate of a vertebra in which a vertebral screw has been inserted. In some embodiments, the system can be configured to receive from a user a manual identification and/or determination of a straight line at the center of a vertebral screw along and/or parallel to a longitudinal axis of the vertebral screw and/or a line extending from an edge or end of an endplate of a vertebra in which a vertebral screw has been inserted. In some embodiments, the system can be configured to identify as an offset angle between an endplate of a vertebra and a screw inserted therein, an angle between a straight line at the center of a vertebral screw along or parallel to a longitudinal axis of the vertebral screw and a line extending from an edge or end of an endplate of a vertebra in which a vertebral screw has been inserted.

In some embodiments, based at least in part on the calculated offset angle between an endplate of a vertebra and a screw inserted therein, the system can be configured to update and/or generate one or more angle calculation taking into account the offset value. For example, in the illustrated example embodiment(s) 2010, the system can be configured to generate and/or update one or more sagittal measurements based at least in part on the calculated offset angle, such as for example PI, LL, PT, TK, and/or any other spinopelvic parameter.

Figure 21:
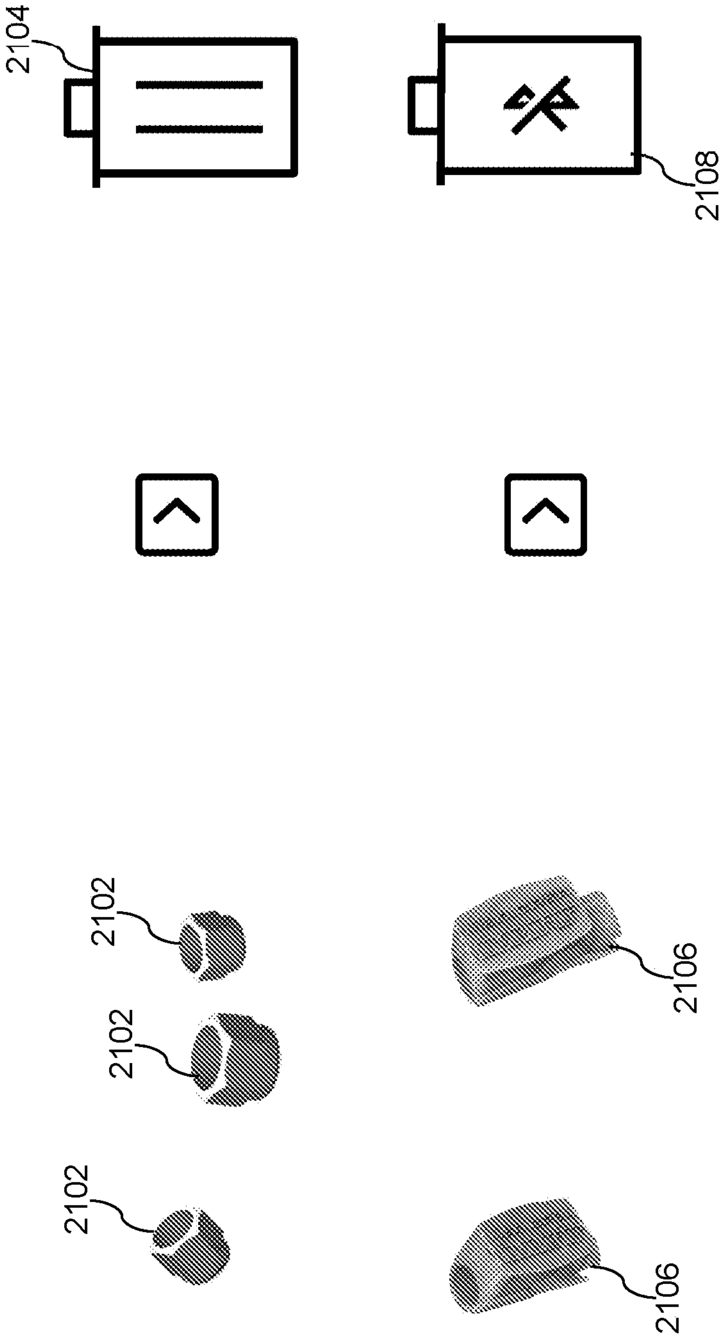
FIG. 21 is a flowchart and/or schematic diagram illustrating an example embodiment(s) of discarding intraoperative tracking modules and/or nuts after intraoperative tracking and/or finalization of rod placement.

Referring back to FIG. 15, in some embodiments, once a spinal rod has been finally fixated on a spine of a patient, whether or not an offset angle has been taken into account, one or more intraoperative tracking modules or devices used for intraoperative tracking can be discarded at block 1514. FIG. 21 is a flowchart and/or schematic diagram illustrating an example embodiment(s) of discarding intraoperative tracking modules and/or nuts after intraoperative tracking and/or finalization of rod placement.

In some embodiments, one or more intraoperative tracking modules or devices 2106 can be configured for single-use. In some embodiments, one or more intraoperative tracking modules or devices can be configured for multiple uses. In some embodiments, once intraoperative tracking is no longer needed, for example by obtaining a final position of a spinal rod and/or after completion of surgery, a surgeon or other medical personnel can break off one or more nuts 2102 and remove one or more intraoperative tracking modules or devices 2106 from the one or more vertebral screws.

In some embodiments, once intraoperative tracking is no longer needed, for example by obtaining a final position of a spinal rod and/or after completion of surgery, a software operating on the system can turn off or power off one or more intraoperative tracking devices or modules to stop tracking. In some embodiments, once intraoperative tracking is no longer needed, the surgeon or other medical personnel can remove one or more intraoperative tracking devices or modules 2106 from one or more vertebral screws and discard them in an anti-wave bag. In some embodiments, once intraoperative tracking is no longer needed, the surgeon or other medical personnel can break off one or more nuts 2102 and discard them.

Additional Features of Some Embodiments of Intraoperative Tracking

Figure 22:
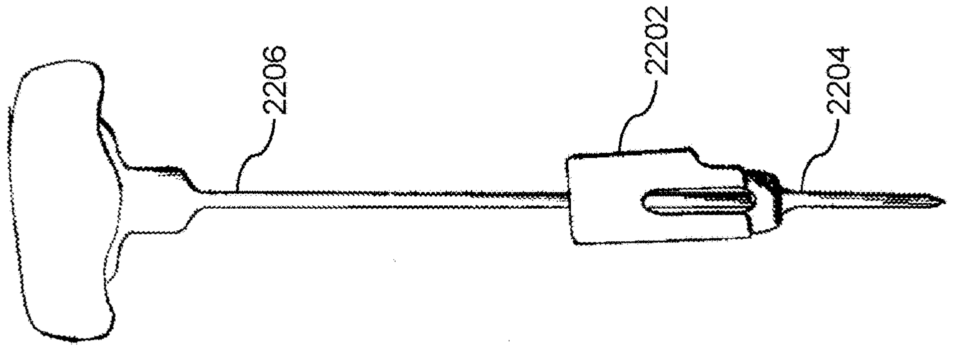
FIG. 22 illustrates an example embodiment(s) of intraoperative tracking that can be used in conjunction with PediGuard technology.

FIG. 22 illustrates an example embodiment(s) of intraoperative tracking that can be used in conjunction with PediGuard technology. As illustrated in FIG. 22, in some embodiments, an intraoperative tracking device or module 2202 can be configured to be attached to a screw 2204, such as a pedicle screw, and/or still allow use of a surgical tool 2206, such as a screwdriver, to be used while the intraoperative tracking device or module 2202 is attached to a screw 2204.

In some embodiments, systems, methods, and devices described herein can be used in conjunction and/or in combination with PediGuard technology. In some embodiments, an intraoperative tracking device or module 2202 can be configured to be used in conjunction with and/or in combination with PediGuard technology. In particular, in some embodiments, the systems, devices, and methods described herein can provide an intelligent screw, which can measure, for example, angulation of the screw, impedance measures, and/or the like. In some embodiments, a measured angulation of the screw by the system can allow and/or facilitate control of the correction. In some embodiments, an impedance measure determined by the system can allow and/or facilitate control of the screw positioning. In some embodiments, the system can comprise a cannulated screw equipped with one or more intra-operative tracking devices or systems. In some embodiments, one or more intra-operative tracking devices or systems can be assembled with a PediGuard device or system.

In some embodiments, an example method of using an intra-operative tracking system, device or module 2202 in conjunction with PediGuard technology can include one or more of the following processes: insert screw with PediGuard to guide the screw; implement rod passing the intra-operative tracking device housing; and/or measure angulation by an inertial sensor(s) of the intra-operative tracking device, system, and/or technology.

Figure 23A:
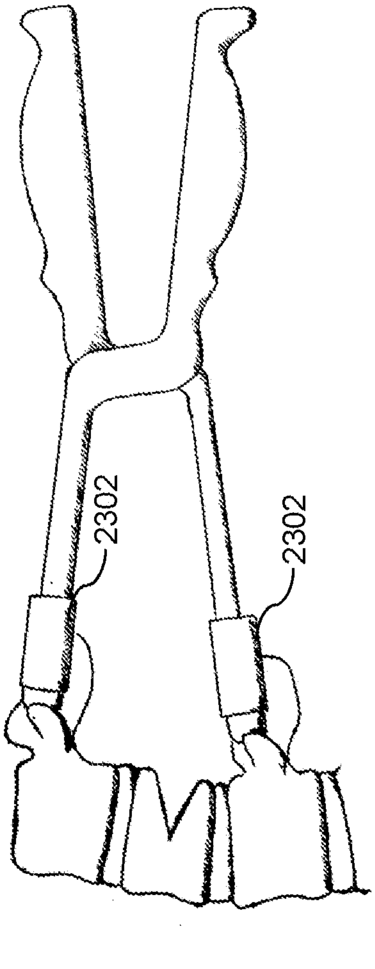
FIGS. 23A-23B illustrates an example embodiment(s) of intra-operative tracking that can be used in conjunction with Choker technology.
Figure 23B:
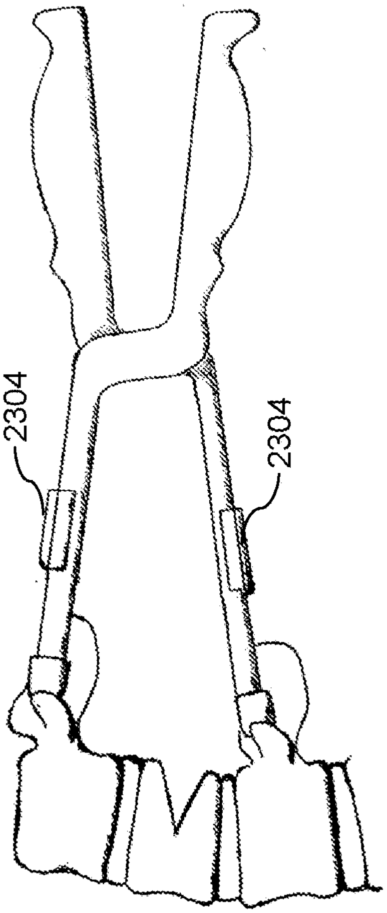

FIGS. 23A-23B illustrates an example embodiment(s) of intra-operative tracking that can be used in conjunction with Choker technology. In some embodiments, Choker technology can be defined as the combination of instruments allowing the precise and controlled 3D correction of the spine applicable to all or some spinal conditions, including for example, osteotomies, scoliosis, spondylolisthesis, trauma and/or associated implants (monoaxial screws, connectors, transverse and longitudinal bars specific to the Choker system) that can first serve as connection point for the instruments during the correction manoeuvres and/or remain as internal stabilizers.

As illustrated in FIG. 23A, in some embodiments, Choker technology can be used with an intra-operative tracking equipped screw(s) 2302 via the device and/or system housing, which can allow the system or measure angulation of osteotomy and reduction thereof. As illustrated in FIG. 23B, in some embodiments, Choker technology can be used in conjunction with intra-operative tracking systems, devices, 2304 and methods herein directly, without screws with sensors in them, to measure angulation of osteotomy and reduction thereof.

Figure 24:
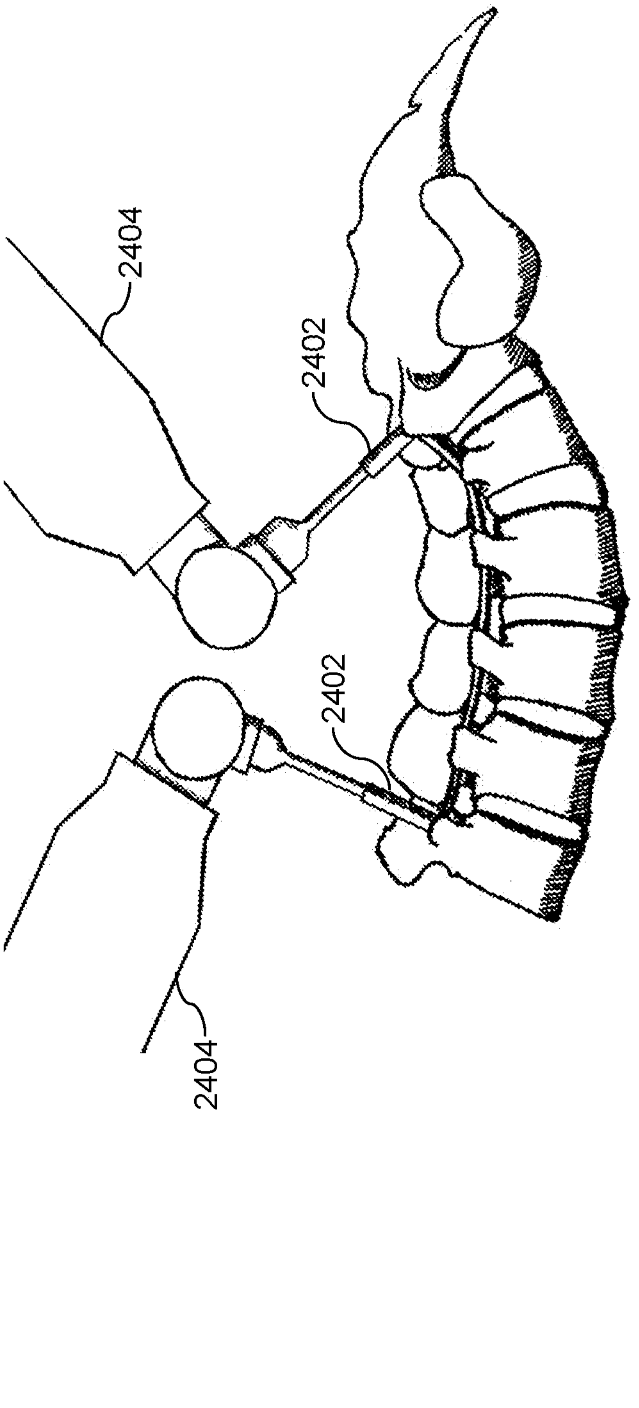
FIG. 24 illustrates an example embodiment(s) of intraoperative tracking that can be used in conjunction with a surgical robot(s)

FIG. 24 illustrates an example embodiment(s) of intra-operative tracking that can be used in conjunction with a surgical robot(s). As illustrated in FIG. 24, in some embodiments, systems, devices, and methods for intra-operative tracking 2402 described herein can be used in conjunction with a surgical robot 2404. For example, in some embodiments, a surgical robot 2404 can be used in conjunction with a screw(s) that comprises one or more intra-operative tracking sensors, devices, and/or systems 2402. In some embodiments, a surgical robot(s) 2404 can be configured to place a screw comprising intra-operative tracking technology 2402 parallel to one or more endplates to avoid and/or minimize error of placement.

Figure 25:
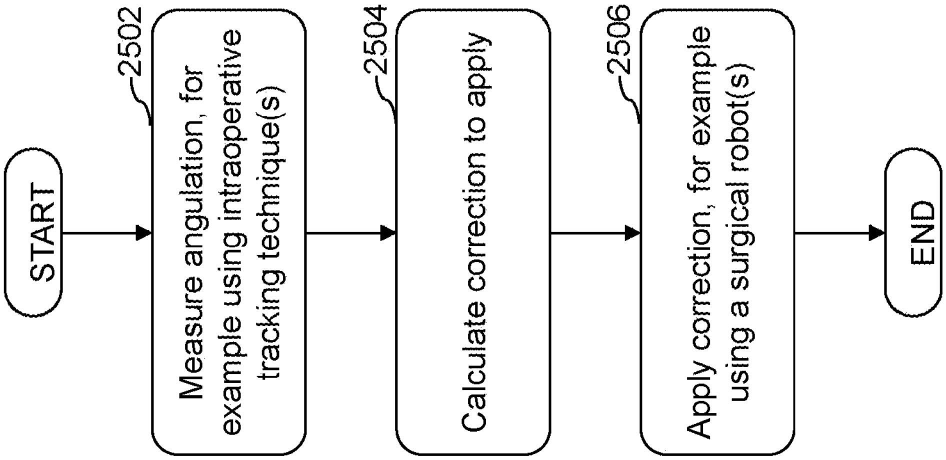
FIG. 25 illustrates an example embodiment(s) of intraoperative tracking that can be used in conjunction with a surgical robot(s)

FIG. 25 illustrates an example embodiment(s) of intra-operative tracking that can be used in conjunction with a surgical robot(s). As illustrated in FIG. 25, in some embodiments, a surgical robot can be configured to utilize intra-operative tracking technology to perform one or more gestures and/or processes to finalize spinal correction application, such as compression and/or distraction of one or more screws. In some embodiments, the system can be configured to measure angulation, for example using intra-operative tracking systems, devices, and/or methods described herein at block 2502. In some embodiments, the system can be configured to calculate a correction to apply at block 2504. In some embodiments, the system can be configured to apply the correction, for example using a surgical robot(s) at block 2506.

In some embodiments, a surgical robot(s) operating in conjunction with intra-operative tracking systems, devices, and methods herein can be used for one or more of the following surgical steps: screw insertion to ensure optimal positioning of a screw(s) with a vertebral endplate(s); insertion of rod, for example once screws are implanted; measuring one or more spine angles; and/or applying a correction as needed. In some embodiments, a surgical robot(s) operating in conjunction with intra-operative tracking systems, devices, and methods herein can comprise one or more sensors, such as for example inertial and/or pressure sensors.

Screw Planning

In some embodiments, systems, devices, and methods described herein are configured to develop, design, and/or plan patient-specific and/or surgeon-specific spinal screws and/or other implants prior to surgery. In particular, in some embodiments, the systems, methods, and devices described herein can be configured to plan and/or design patient-specific and/or surgeon-specific spinal screws, based on analyzing one or more medical images of a patient for example, prior to surgery, thereby decreasing the number of spinal screws that need to prepared for and be available during spinal surgery, for example in a screw kit.

In some embodiments, the systems, methods, and devices described herein can be configured to collect data, such as pre-operative data of a spine of a patient. For example, in some embodiments, the systems, methods, and devices can be configured to utilize a data collection protocol for screw planning by analyzing one or more x-ray images, CT-scan images, and/or any other medical images of a patient. In some embodiments, based on such data collected from one or more x-ray images, CT-scan images, and/or other medical images, the system can be configured to dynamically and/or automatically determine one or more desired lengths, diameters, and/or ranges thereof, of one or more screws for implantation in a specific vertebra of a specific patient. In some embodiments, based on data collected from one or more x-ray images, CT-scan images, and/or other medical images, the system can be configured to allow a user to determine one or more desired lengths, diameters, and/or ranges thereof, of one or more screws for implantation in a specific vertebra of a specific patient.

In some embodiments, based on such one or more desired lengths, diameters, and/or ranges thereof, whether determined automatically by the system and/or with user input, the system can be configured to allow picking out beforehand, prior to surgery, a patient-specific screw kit that is tailored for that particular patient, which can includes one or more screws that are determined to fit or likely fit the patient. As such, in some embodiments, the system can reduce the range of possible screws used by the surgeon during surgery and the size of the necessary stock to be maintained.

In some embodiments, the systems, methods, and/or devices described herein can be configured to plan and/or design one or more patient-specific and/or surgeon-specific vertebral screws for implantation prior to spinal surgery based on one or more preoperative x-ray images, such as for example sagittal and/or coronal images, and/or one or more axial slices from one or more postoperative and/or intraoperative CT images of a spine of a patient. In some embodiments, the systems, devices, and/or methods described herein can be configured to utilize one or more data collected from a data collection protocol and/or one or more patient information, such as for example gender and/or age, for planning and/or designing one or more patient-specific and/or surgeon-specific vertebral screws for implantation prior to spinal surgery.

In some embodiments, the systems, devices, and methods described herein can be configured to collect and/or obtain data from one or more preoperative and/or postoperative x-ray images by using one or more sagittal wizards to determine, for example, one or more of a height and/or length of a vertebra, a diameter of an implanted screw, and/or a distance between a screw and a vertebra. In some embodiments, the systems, devices, and methods described herein can be configured to collect and/or obtain data from one or more preoperative and/or postoperative x-ray images by using one or more coronal wizards to determine, for example, one or more Cobb angles, slope of a vertebra, and/or distance between one or more parts of screws. In some embodiments, the systems, devices, and methods described herein can be configured to collect and/or obtain one or more other anatomical measurements from one or more sagittal and/or coronal x-ray images.

In some embodiments, the systems, methods, and/or devices described herein that utilize one or more axial slices from one or more postoperative and/or intraoperative CT images can be configured to determine an angle between the axis of a vertebral screw and an axis of a vertebra to which a screw is attached to. In some embodiments, the systems, methods, and/or devices described herein can be configured to analyze one or more preoperative CT scans and/or one or more axial slices thereof to determine the length and/or a diameter of a screw for surgical planning purposes prior to surgery. In some embodiments utilizing one or more CT scans, the systems, devices, and methods described herein can be configured to utilize 3D reconstruction.

In some embodiments, the systems, devices, and methods described herein, whether utilizing one or more sagittal and/or coronal and/or frontal x-ray images and/or CT images, can be configured to utilize one or more data collected from one or more medical images for screw planning purposes.

In some embodiments, the systems, devices, and/or methods described herein are configured to generate and/or develop a screw planning memo for a surgeon prior to spinal surgery. In particular, in some embodiments, the systems, devices, and/or methods described herein can be configured to gather information obtained during the analysis to generate a screw planning memo. In some embodiments, the systems, devices, and/or methods described herein can be configured to assist with selecting and/or developing one or more vertebral screws in advance of spinal surgery and/or allow reducing an inventory thereof prior to spinal surgery. In some embodiments, the systems, devices, and/or methods described herein can be configured to be implemented using one or more computer systems, which can be coupled to a network and/or include one or more internal and/or external data sources.

Figure 26B:
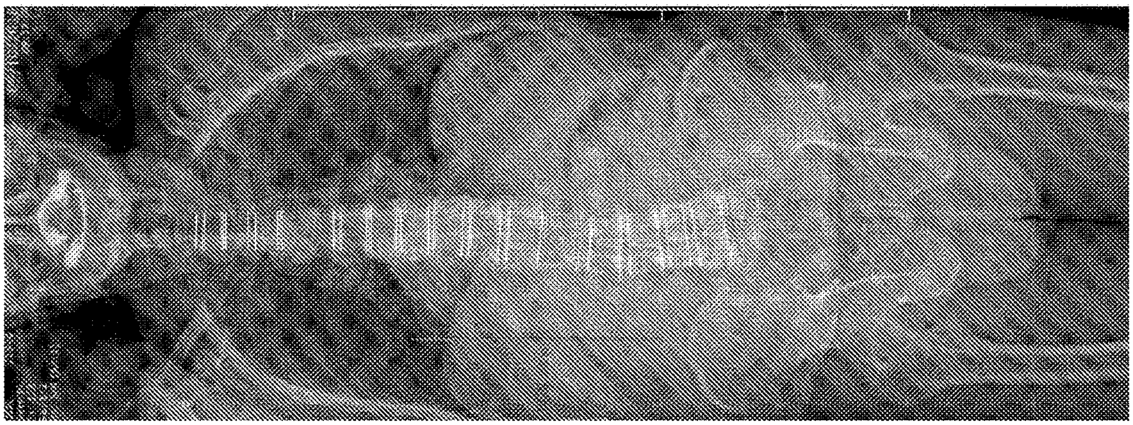
FIGS. 26A-26B illustrate an example(s) of a preoperative spinal x-ray image(s) that can be used for one or more embodiments described herein.
Figure 26A:
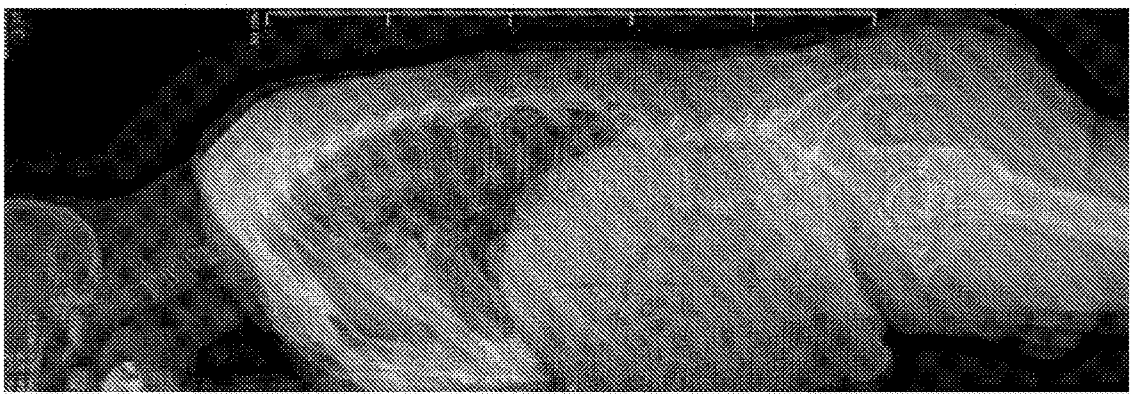

In particular, in some embodiments, the systems, methods, and devices can be configured to obtain necessary data, such as one or more anatomical measurements, from or more pre-operative x-ray images of the spine of a patient. For example, in some embodiments, the system can be configured to use one or more sagittal and/or coronal and/or frontal x-ray images and/or wizards as illustrated in FIGS. 26A-26B. FIGS. 26A-26B illustrate an example(s) of a preoperative spinal x-ray image(s) that can be used for one or more embodiments described herein, such as for example relating to screw planning, predictive modeling, and/or intraoperative tracking.

In some embodiments, the system can utilize a "screw wizard," that can allow a user to perform one or more screw planning processes and/or measurements, such as any of those described herein, without necessarily going through any three-dimensional reconstruction. In some embodiments, one or more or all measurements can be taken on every instrumented vertebra pre-operatively and/or post-operatively.

Figure 27C:
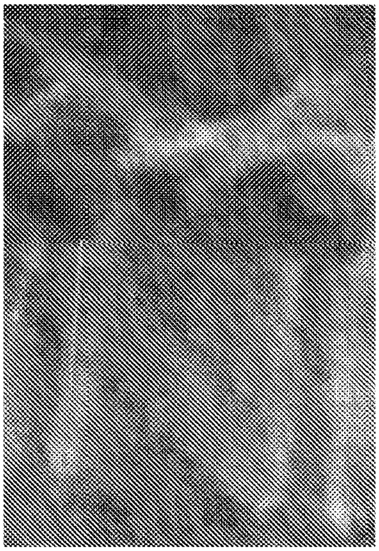
FIGS. 27A-27C illustrate an example(s) of a preoperative sagittal spinal x-ray image(s) that can be used for one or more embodiments described herein.
Figure 27B:
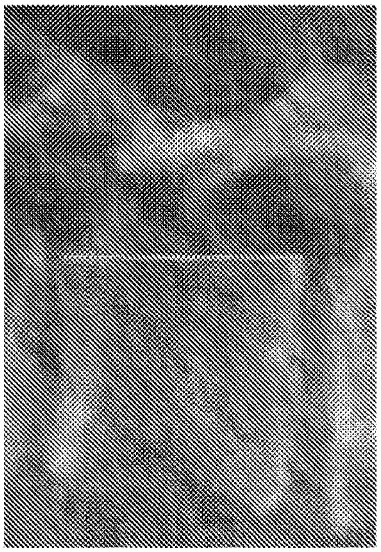
Figure 27A:

FIGS. 27A-27C illustrate an example(s) of a preoperative sagittal spinal x-ray image(s) that can be used for one or more embodiments described herein. FIGS. 27A-27C illustrate an example(s) of a preoperative sagittal spinal x-ray image(s) that can be used for one or more embodiments described herein, such as for example relating to screw planning, predictive modeling, and/or intraoperative tracking.

In particular, in some embodiments, by analyzing one or more pre-operative sagittal x-ray images, the system can be configured to and/or utilized to determine an anterior height of a vertebra as illustrated in the example in FIG. 27A. In some embodiments, by analyzing one or more pre-operative sagittal x-ray images, the system can be configured to and/or be utilized to determine a posterior height of the vertebra as illustrated in the example in FIG. 27B. In some embodiments, by analyzing one or more pre-operative sagittal x-ray images, the system can be configured to and/or be utilized to determine an upper length of the vertebra as illustrated in the example of FIG. 27C.

FIGS. 28A-28D illustrate an example(s) of a preoperative coronal spinal x-ray image(s) that can be used for one or more embodiments described herein. FIGS. 28A-28D illustrate an example(s) of a preoperative coronal spinal x-ray image(s) that can be used for one or more embodiments described herein, such as for example relating to screw planning, predictive modeling, and/or intraoperative tracking.

Figure 28B:
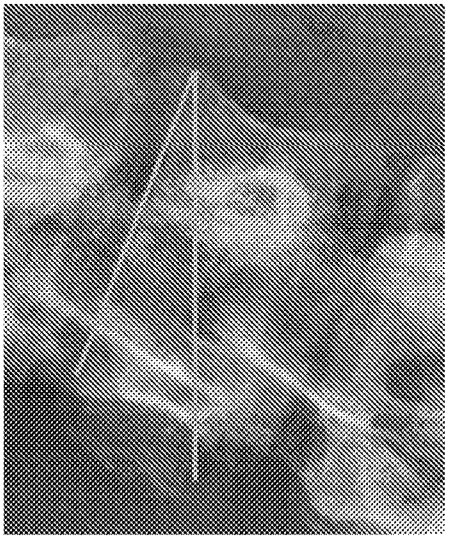
FIGS. 28A-28D illustrate an example(s) of a preoperative coronal spinal x-ray image(s) that can be used for one or more embodiments described herein.
Figure 28D:
Figure 28A:
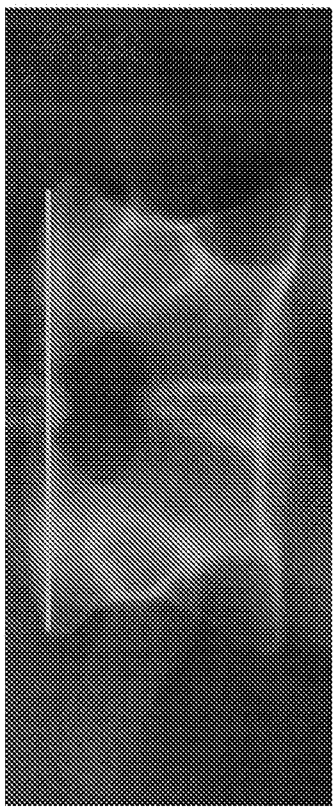
Figure 28C:
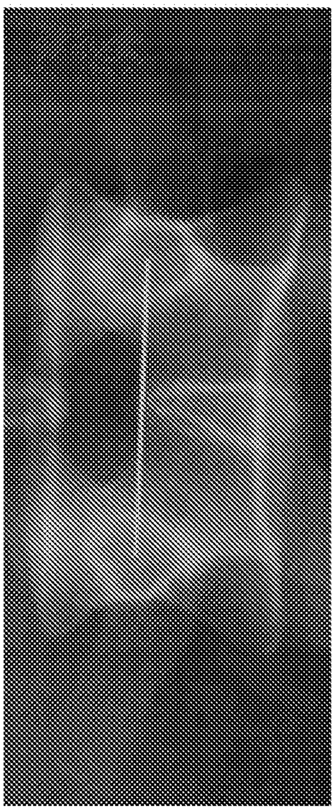

In particular, in some embodiments, by analyzing one or more pre-operative coronal x-ray images, the system can be configured to and/or utilized to determine one or more Cobb angles, such as for example levels, angles, and/or side of a deformity. In some embodiments, by analyzing one or more pre-operative coronal x-ray images, the system can be configured to and/or be utilized to determine an upper width of the vertebra as illustrated in the example of FIG. 28A. In some embodiments, by analyzing one or more pre-operative coronal x-ray images, the system can be configured to and/or be utilized to determine a slope of the vertebra, such as for example an angle between the upper endplate of the vertebra and a horizontal line, as illustrated in the example of FIG. 28B. In some embodiments, by analyzing one or more pre-operative coronal x-ray images, the system can be configured to and/or be utilized to determine a distance between two pedicles, such as for example as measured from the center, as illustrated in the example of FIG. 28C. In some embodiments, by analyzing one or more pre-operative coronal x-ray images, the system can be configured to and/or be utilized to determine a distance between a pedicle and a right and/or left edge of a vertebra as illustrated in the example of FIG. 28D.

In some embodiments, the systems, methods, and devices can be configured to collect a list of screws that were previously used in prior cases, for example by a particular surgeon(s) for use in screw planning for future cases. In some embodiments, the systems, methods, and devices can be configured to identify which screw(s) was used at which level by analyzing and/or taking additional measurements on one or more post-operative x-ray images of the spine of a patient from previous cases.

FIGS. 29A-29E illustrate an example(s) of a postoperative sagittal spinal x-ray image(s) that can be used for one or more embodiments described herein. FIGS. 29A-29E illustrate an example(s) of a postoperative sagittal spinal x-ray image(s) that can be used for one or more embodiments described herein, such as for example relating to screw planning, predictive modeling, and/or intraoperative tracking.

Figure 29A:
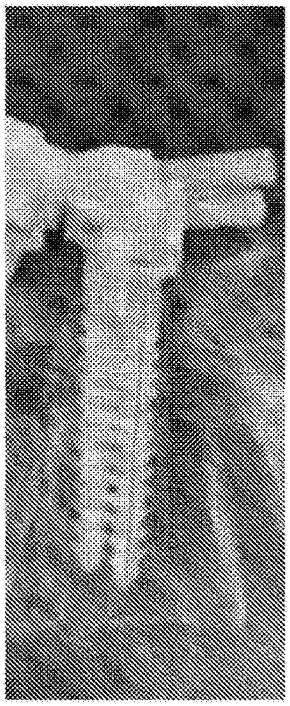
FIGS. 29A-29E illustrate an example(s) of a postoperative sagittal spinal x-ray image(s) that can be used for one or more embodiments described herein.
Figure 29B:
Figure 29C:
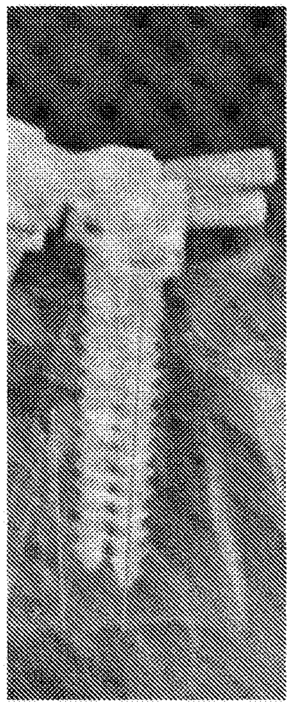
Figure 29D:
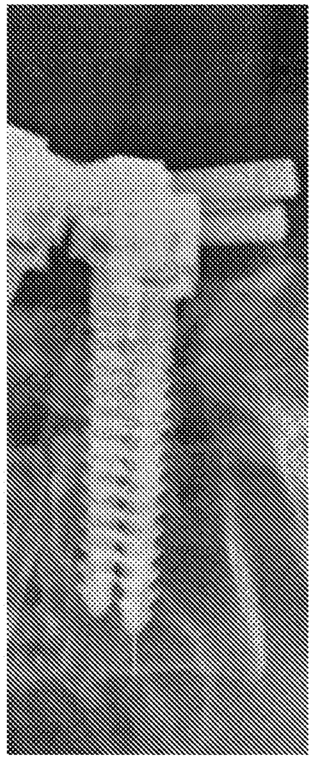
Figure 29E:
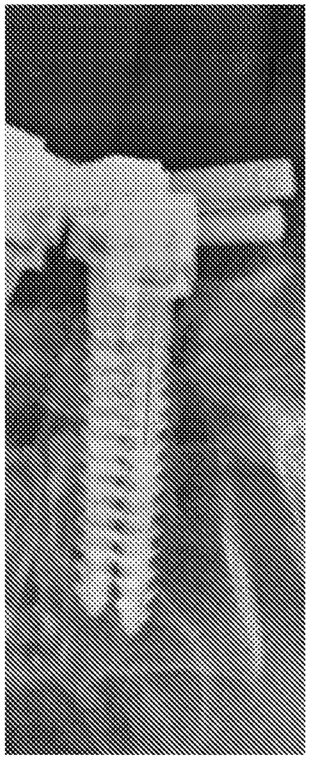

In some embodiments, by analyzing one or more post-operative sagittal x-ray images, the system can be configured to and/or be utilized to determine a length(s) of an implanted screw(s) as illustrated in the example of FIG. 29A. In some embodiments, by analyzing one or more post-operative sagittal x-ray images, the system can be configured to and/or be utilized to determine a diameter(s) of an implanted screw(s) as illustrated in the example of FIG. 29B. In some embodiments, by analyzing one or more post-operative sagittal x-ray images, the system can be configured to and/or be utilized to determine an angle(s) between an implanted screw(s) and an upper endplate of a vertebra as illustrated in the example of FIG. 29C. In some embodiments, by analyzing one or more post-operative sagittal x-ray images, the system can be configured to and/or be utilized to determine a distance between the anterior extremity of a screw(s) and an anterior wall of a vertebra as illustrated in the example of FIG. 29D. In some embodiments, by analyzing one or more post-operative sagittal x-ray images, the system can be configured to and/or be utilized to determine a distance between a posterior wall of the vertebra and a posterior extremity of a screw(s), such as for example the body of the screw without the head, as illustrated in the example of FIG. 29E.

Figure 30B:
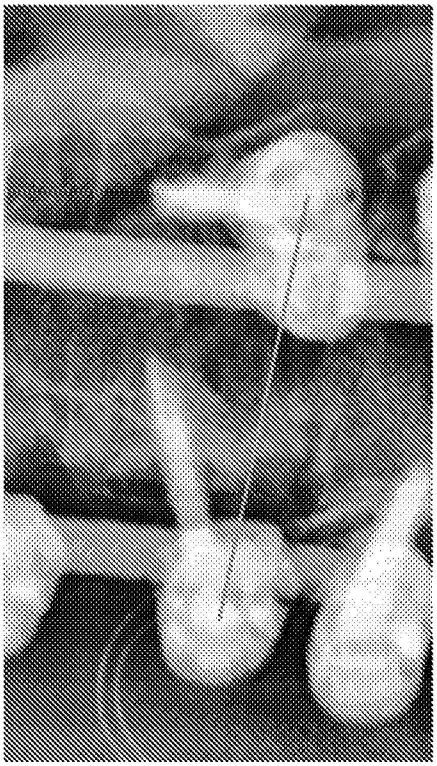
FIGS. 30A-30B illustrate an example(s) of a postoperative coronal spinal x-ray image(s) that can be used for one or more embodiments described herein.
Figure 30A:
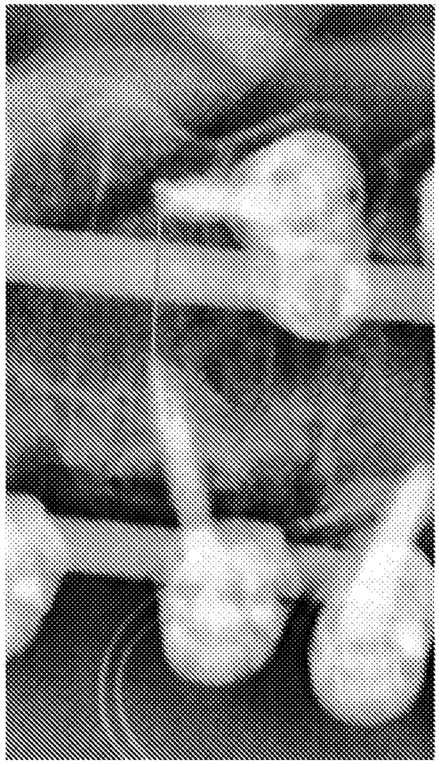

FIGS. 30A-30B illustrate an example(s) of a postoperative coronal spinal x-ray image(s) that can be used for one or more embodiments described herein. FIGS. 30A-30B illustrate an example(s) of a postoperative coronal spinal x-ray image(s) that can be used for one or more embodiments described herein, such as for example relating to screw planning, predictive modeling, and/or intraoperative tracking.

In some embodiments, by analyzing one or more post-operative coronal x-ray images, the system can be configured to and/or utilized to determine a distance between both anterior extremities of a screw(s) as illustrated in the example of FIG. 30A. In some embodiments, by analyzing one or more post-operative coronal x-ray images, the system can be configured to and/or utilized to determine a distance between two connectors or head of a screw(s) as illustrated in the example of FIG. 30B.

Figure 31:
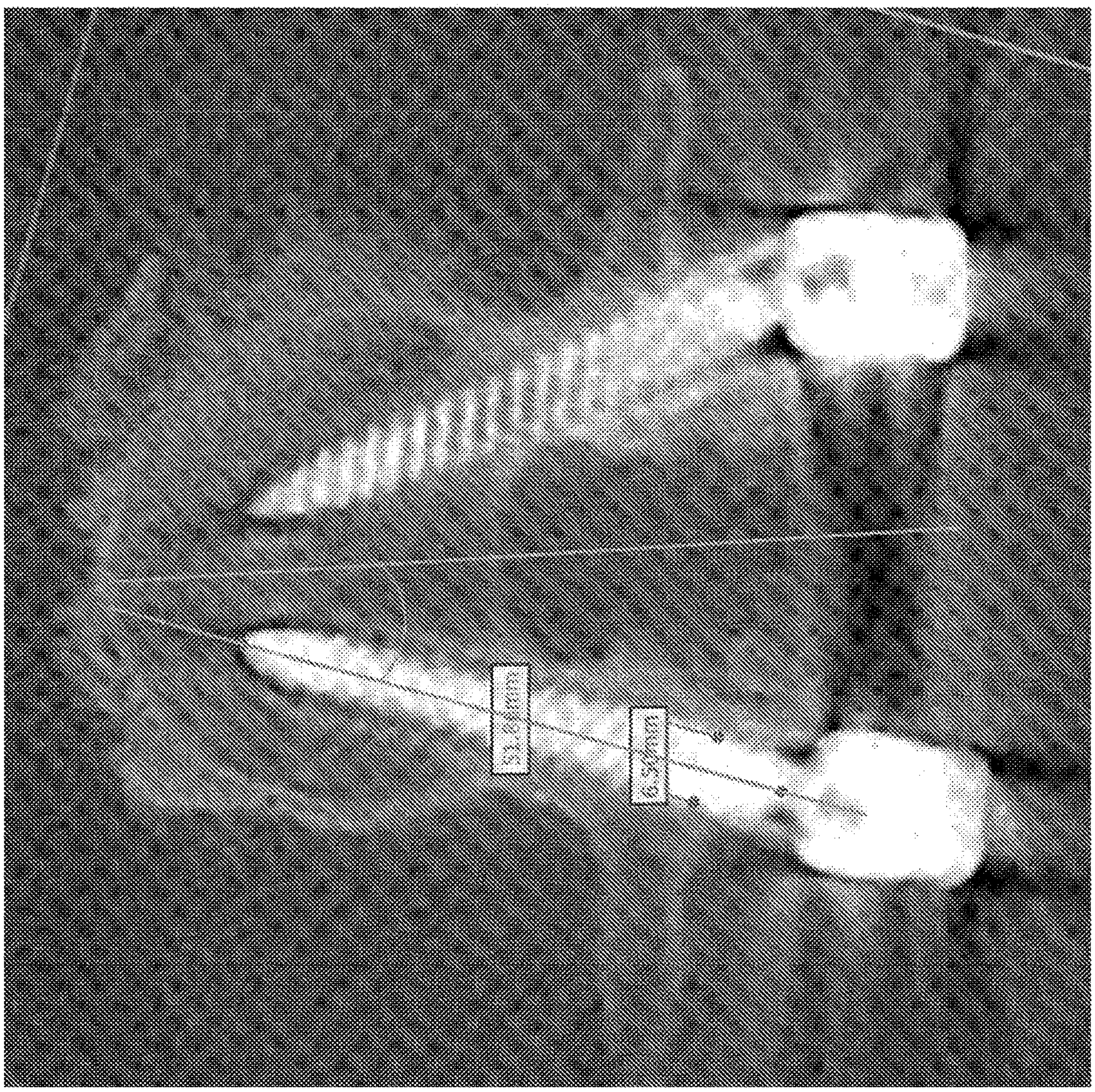
FIG. 31 illustrates an example(s) of a postoperative and/or intraoperative CT scan that can be used for one or more embodiments described herein.

FIG. 31 illustrates an example(s) of a postoperative and/or intraoperative CT scan that can be used for one or more embodiments described herein. FIG. 31 illustrates an example(s) of a postoperative and/or intraoperative CT image that can be used for one or more embodiments described herein, such as for example relating to screw planning, predictive modeling, and/or intraoperative tracking.

In particular, in some embodiments, the systems, methods, and devices can be configured to utilize one or more post-operative or intra-operative CT scans when available in screw planning. In particular, in some embodiments, the system can be configured to utilize one or more slices from a CT scan, such as for example axial slices, taken pre-operatively, post-operatively, and/or intra-operatively to determine and/or use to determine an angle between the axis of a screw(s) and the vertebra axis as illustrated in the example of FIG. 31.

As noted above, in some embodiments, the system can be configured to utilize one or more slices from a pre-operative CT scan. Further, in some embodiments, the system can be configured to render a three-dimensional model or rendering of the vertebra, which may or may not include an implanted screw, for example by performing three-dimensional reconstruction based on the CT-scan images. Furthermore, in some embodiments, screw planning can be useful and/or advantageous for assessing the angle between the screw and vertebra, as well as for determining the screw length and/or diameter. For example, in some embodiments, the system can be configured to determine and/or predict a desired length and/or diameter, and/or one or more ranges thereof, of a screw for a particular vertebra, based on analysis of one or more CT-scan images.

In some embodiments, the systems, methods, and devices can be configured to utilize one or more patient information in screw planning. For example, in some embodiments, the system can be configured to analyze one or more previous cases based on certain patient information to use in developing screw planning for a particular patient. In some embodiments, patient information can comprise sex, age, and/or height of a patient.

In some embodiments, the systems, methods, and devices can be configured to generate a screw planning memo for a surgeon based in part on the information and analysis conducted by the system as described herein.

Figure 32A:
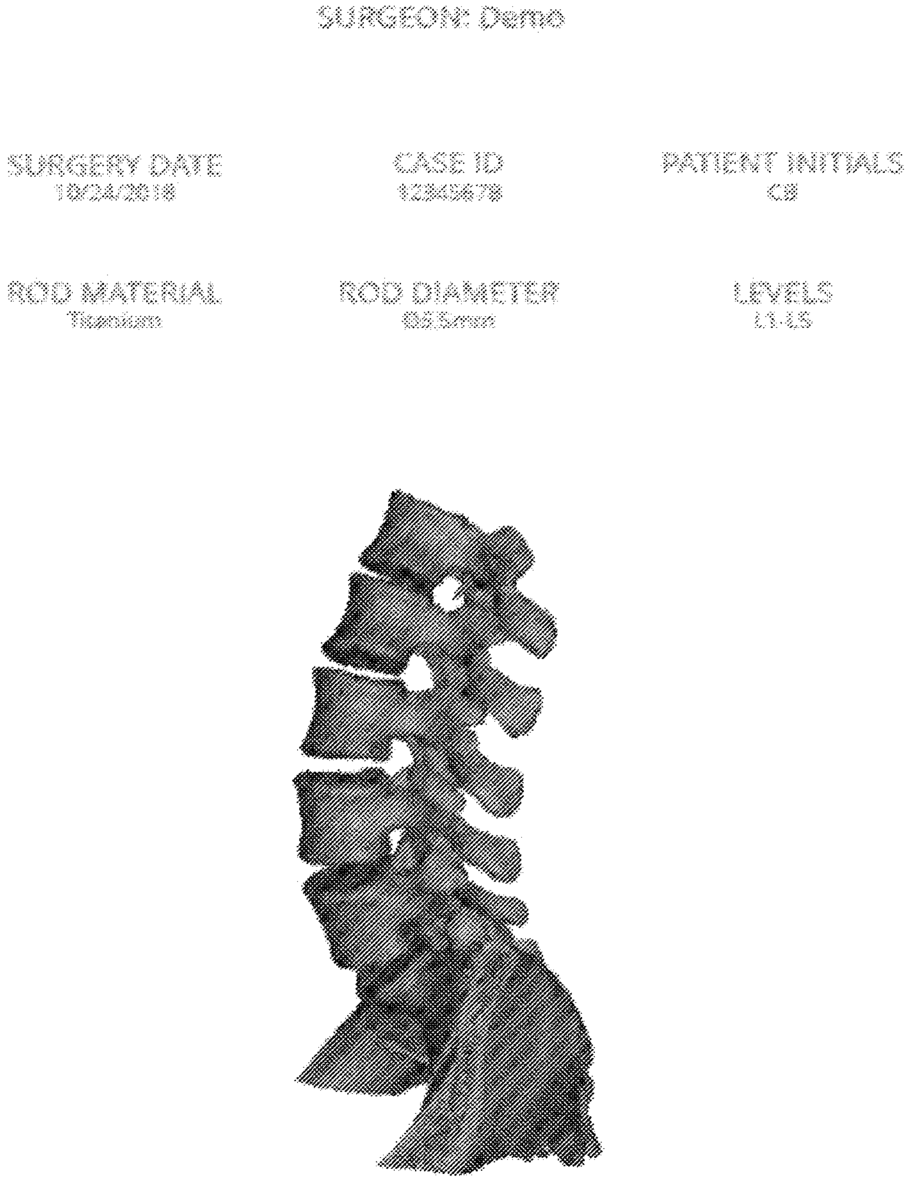
Figure 32B:
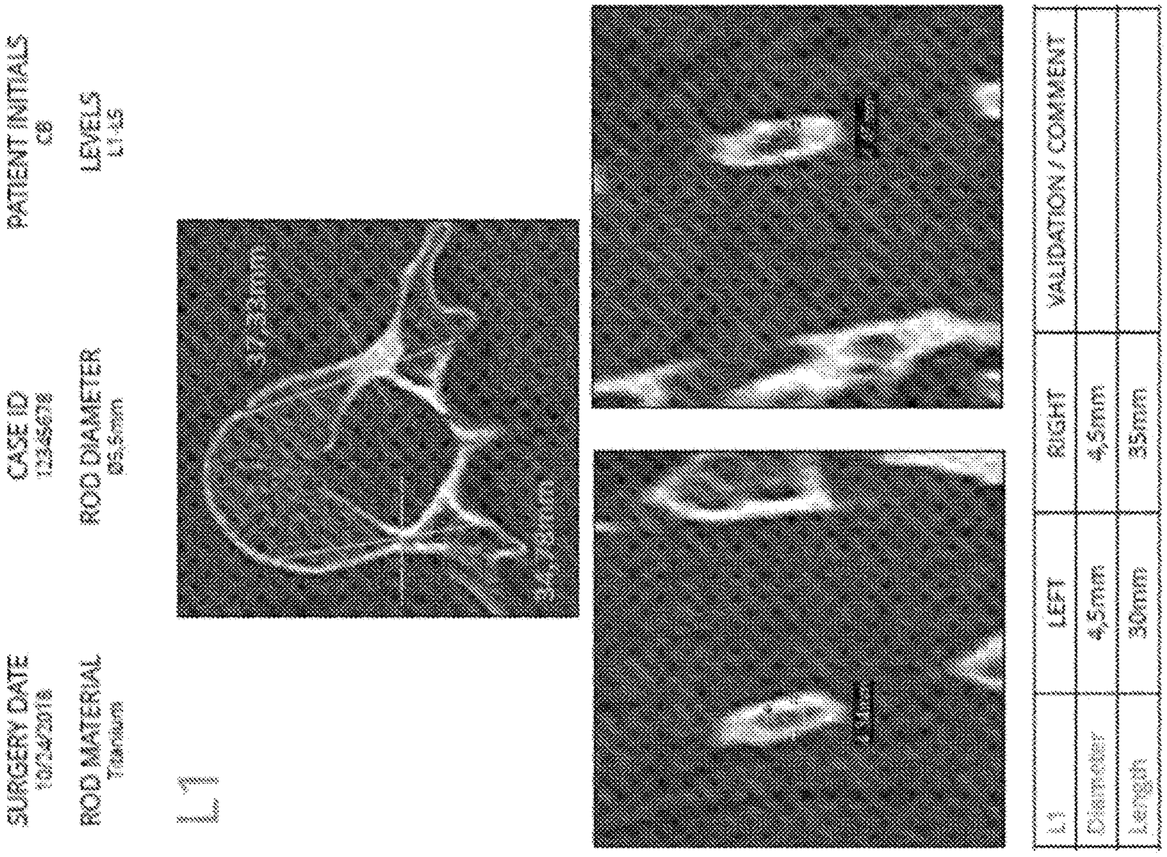
Figure 32C:
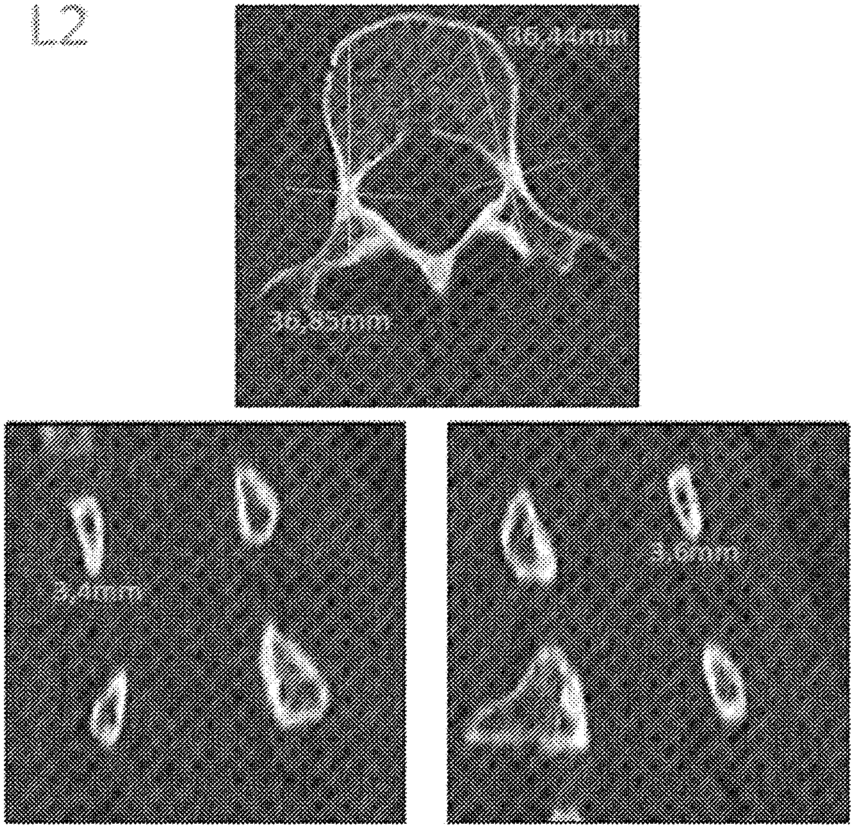
Figure 32D:
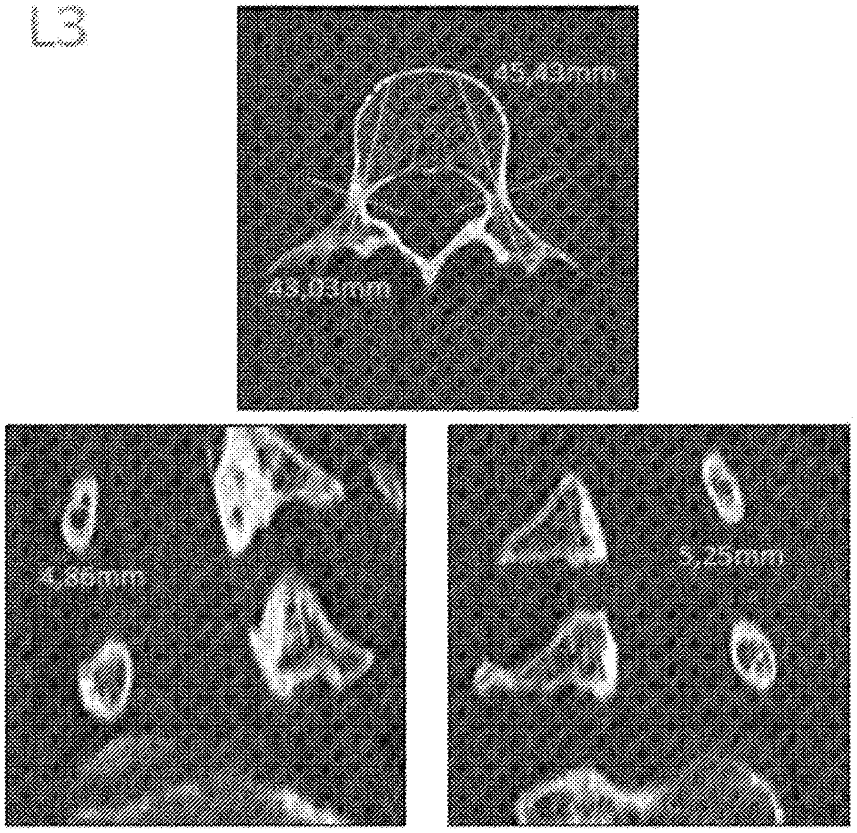
Figure 32E:
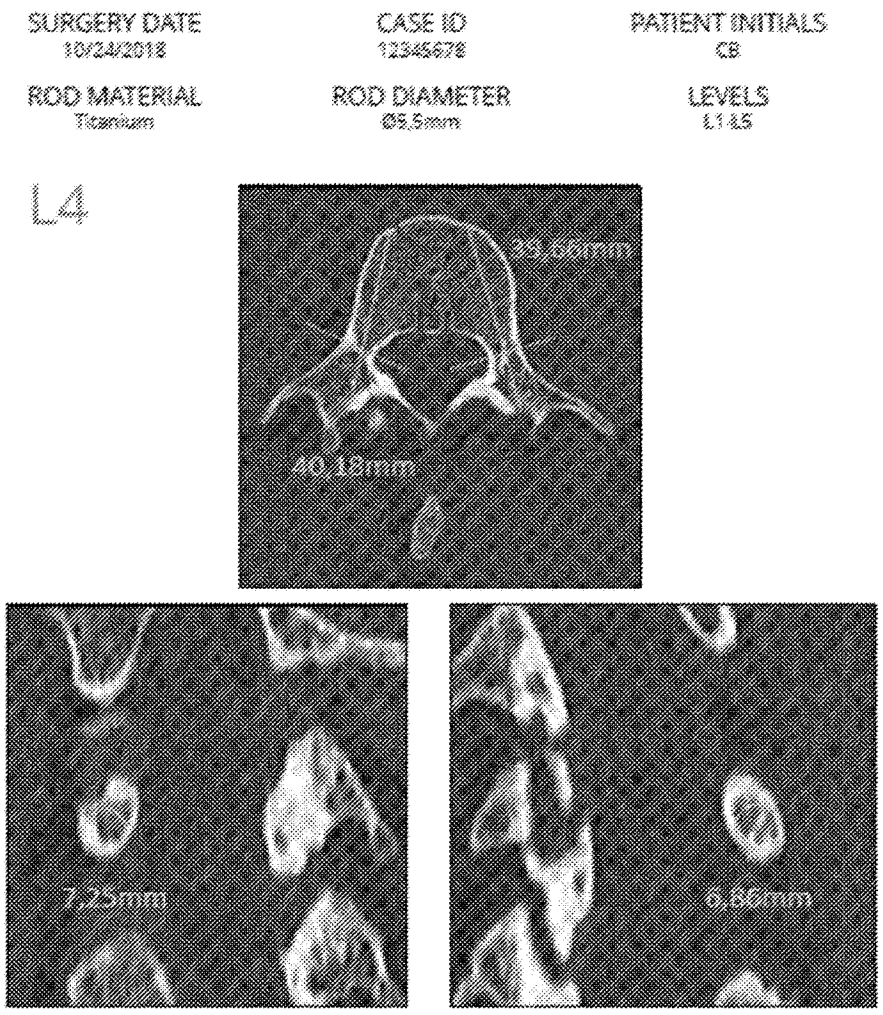
Figure 32G:
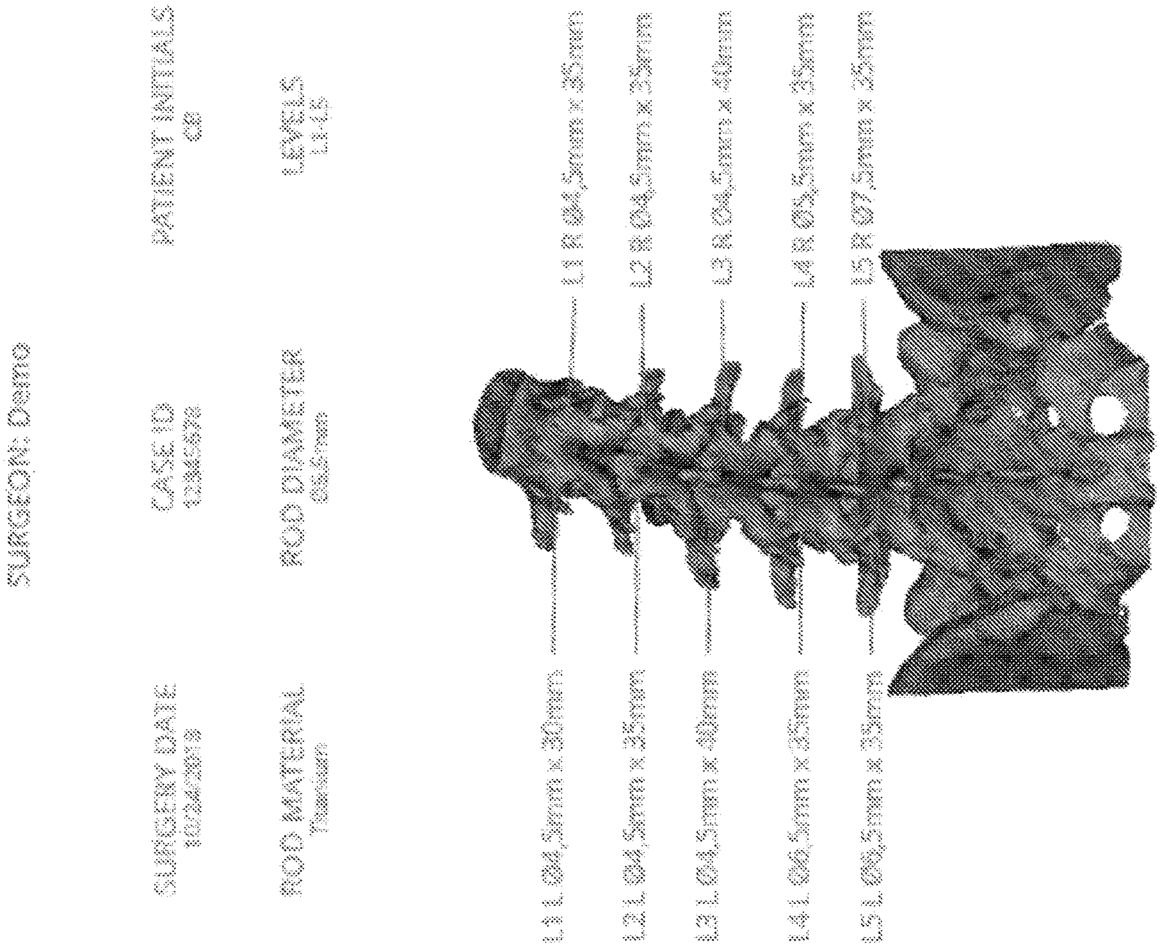

FIGS. 32A-32G illustrate an example embodiment(s) of a screw planning memo(s), such as for example based on one or more CT scans and/or x-ray images of a patient. As illustrated in FIGS. 32A-32G, in some embodiments, the system can be configured to generate a screw planning memo for a surgeon. In some embodiments, the screw planning memo can be for a particular segment of a spine of patient, such as for L1-L5 in FIGS. 32A-32G. In some embodiments, the screw planning memo can comprise one or more sectional images for each vertebra, such as for example L1-L5 in FIGS. 32A-32G, and can provide information relating to the maximum diameter and/or length of a left and/or right screw that can be inserted into each vertebral level. As illustrated in FIG. 32G, in some embodiments, the system can be configured to generate a summary of the diameter and/or length of one or more vertebral screws for inserting into one or more vertebrae of the spinal section of interest, such as for example L1-L5. In some embodiments, based on the screw planning memo, the surgeon and/or other medical personnel can be provided a kit comprising screws with a diameter and/or length that is within about 1%, about 2%, about 3% about 4%, about 5%, about 6%, about 7%, about 8%, about 9%, and/or about 10% of the determined diameter and/or length of one or more vertebral screws for inserting into one or more vertebrae of the spinal section of interest, such as for example L1-L5. In some embodiments, based on the screw planning memo, the surgeon and/or other medical personnel can be provided a kit comprising screws with a diameter and/or length that is within a range defined by two of the aforementioned values.

Figure 33A:
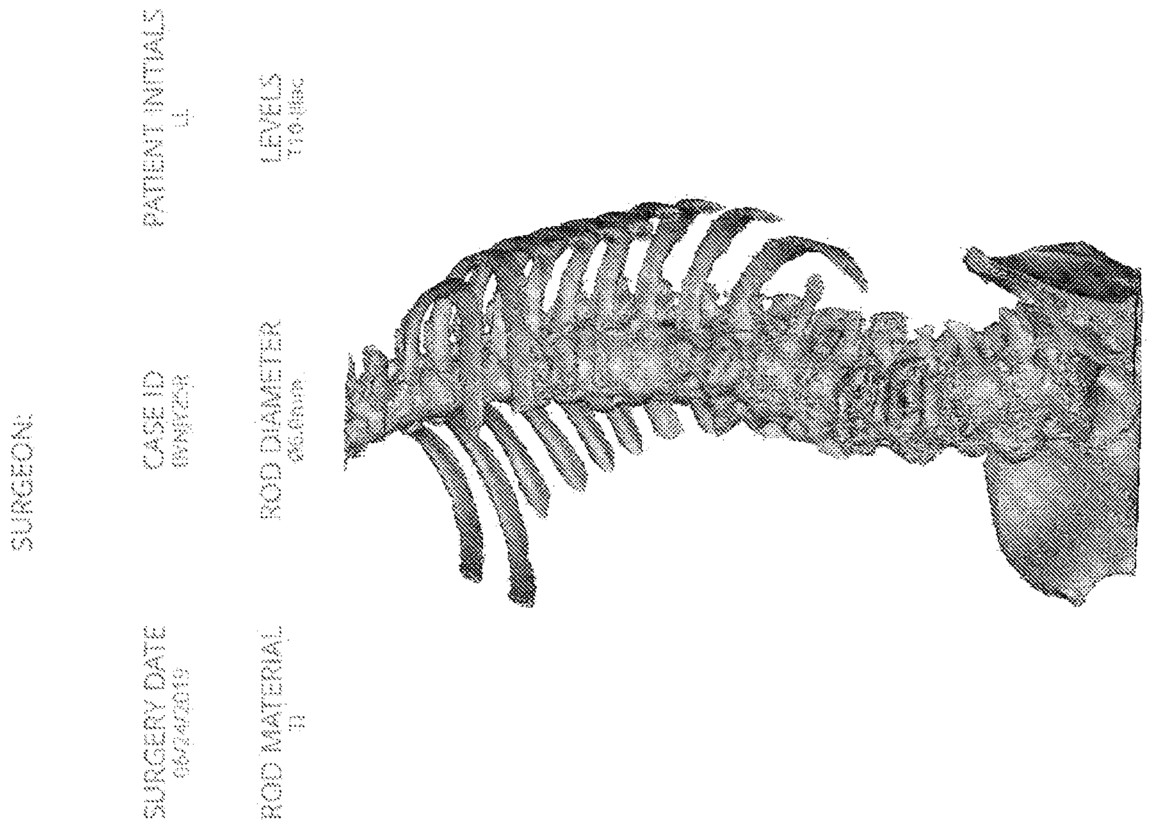
Figure 33C:
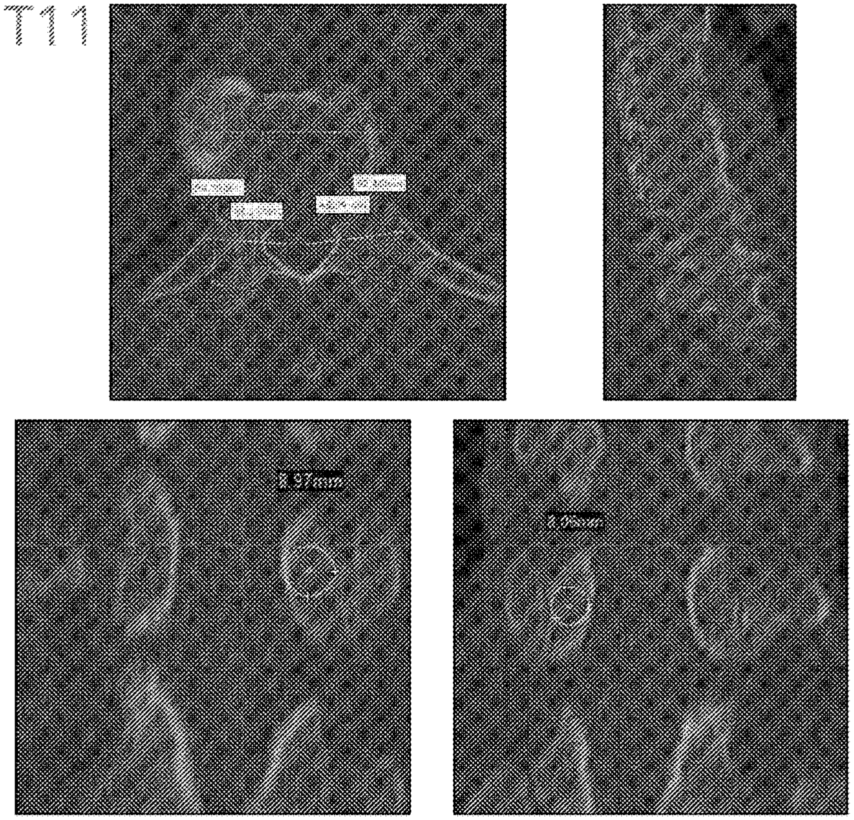
Figure 33D:
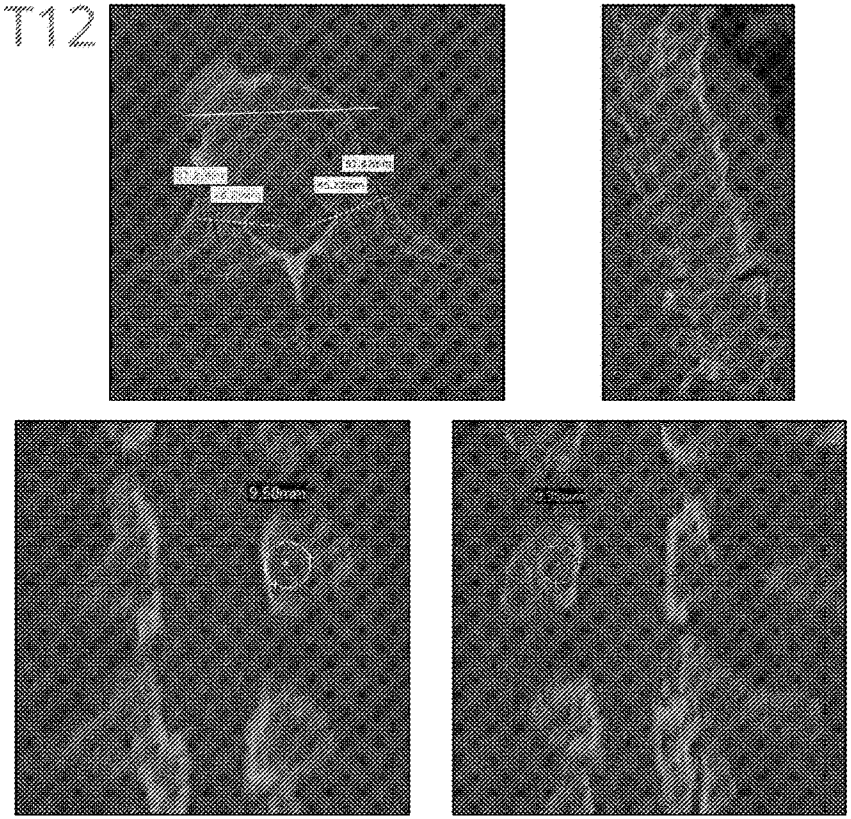
Figure 33F:
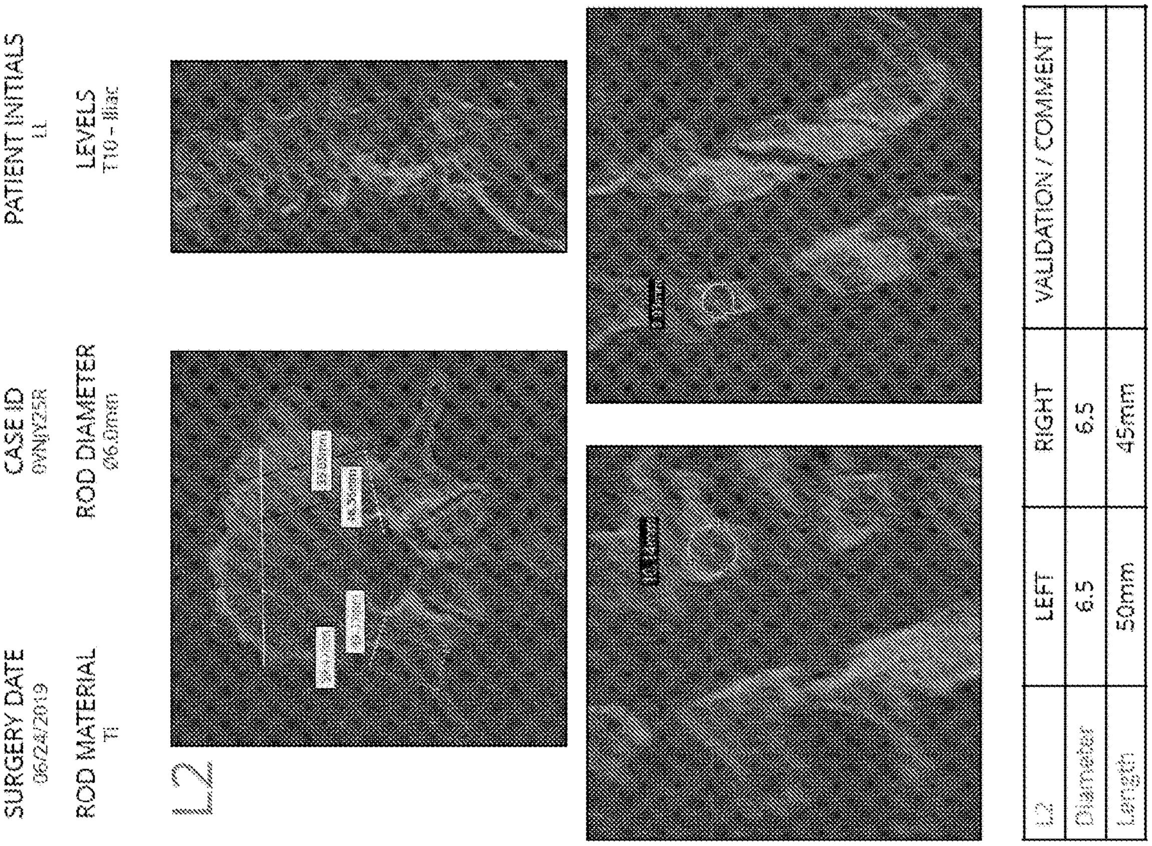
Figure 33G:
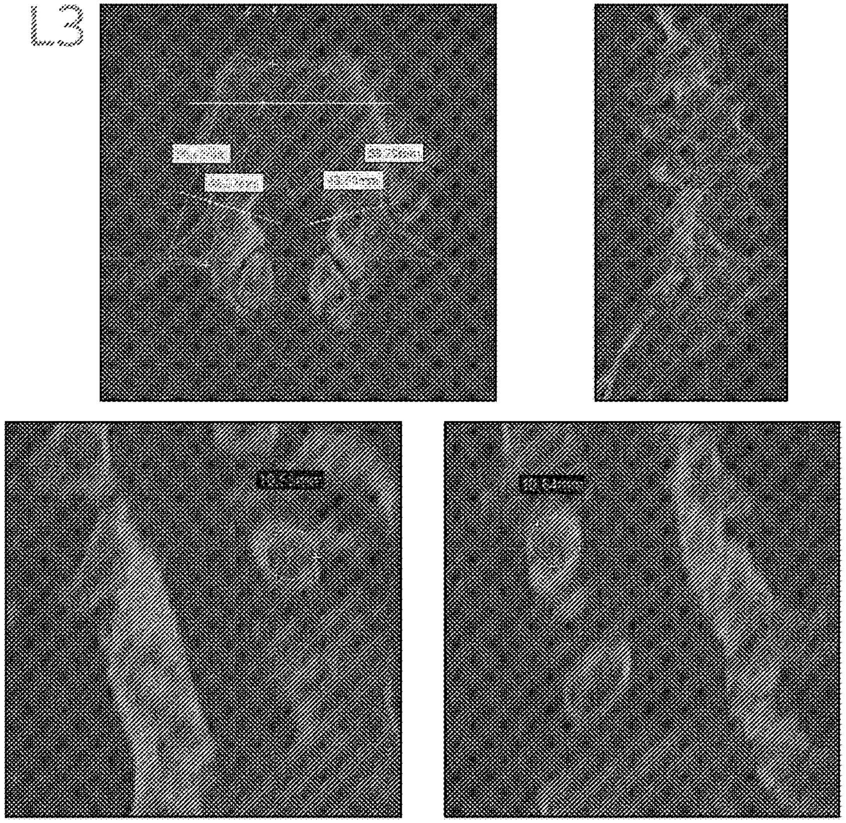
Figure 33H:
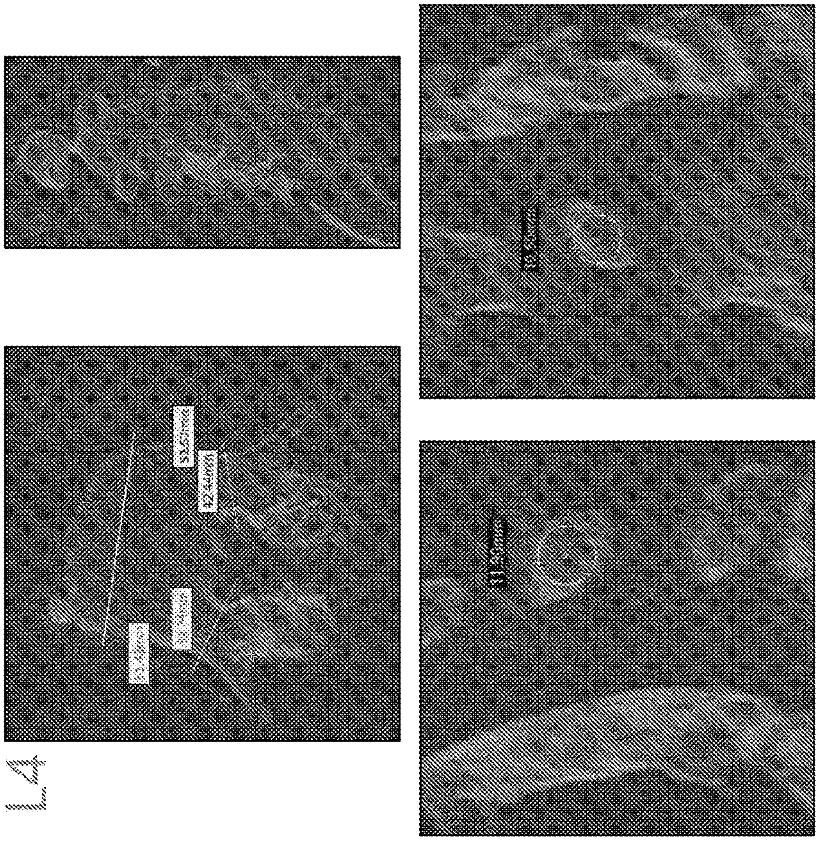
Figure 33I:
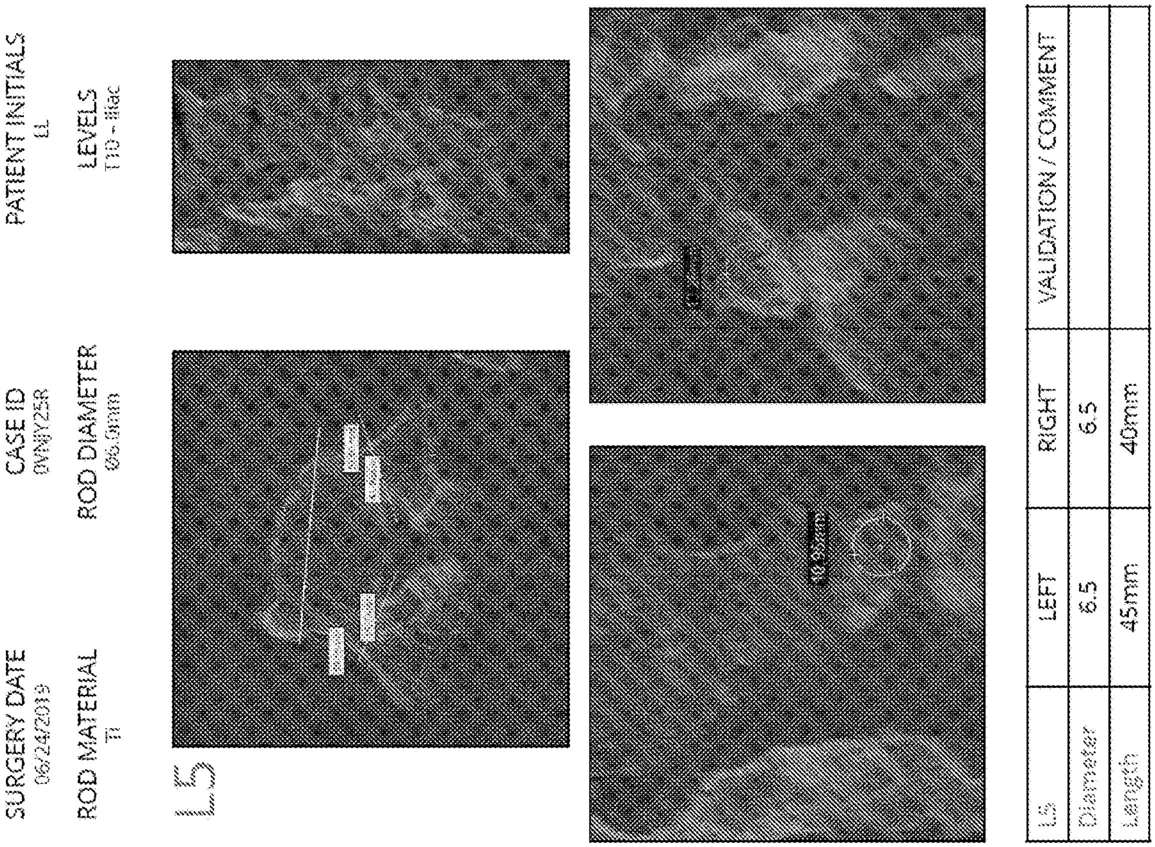
Figure 33K:
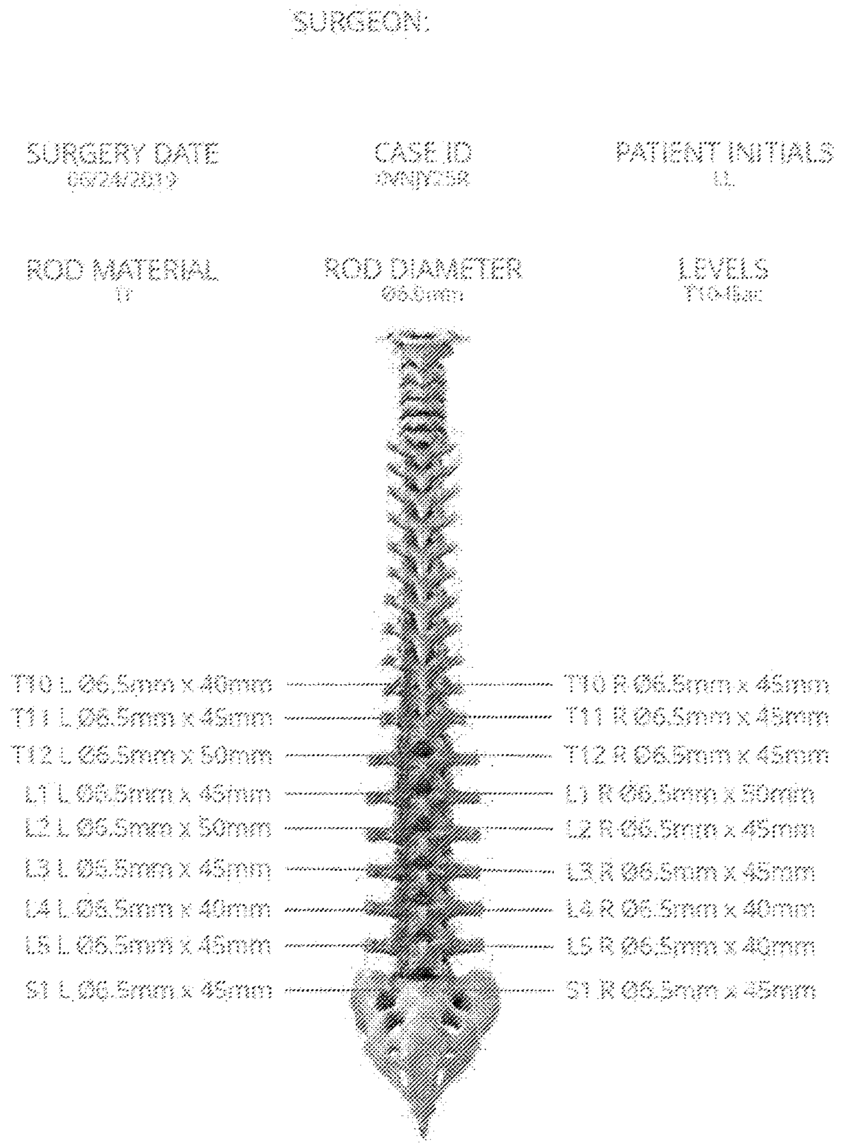

FIGS. 33A-33K illustrate an example embodiment(s) of a screw planning memo(s), such as for example based on one or more CT scans for a particular surgeon and/or patient. As illustrated in FIGS. 33A-33K, in some embodiments, the system can be configured to generate a screw planning memo for a surgeon. In some embodiments, the screw planning memo can be for a particular segment of a spine of patient, such as for T10-Iliac or T10 to S1 in FIGS. 33A-33K. In some embodiments, the screw planning memo can comprise one or more sectional images for each vertebra, such as for example T10 to S1 in FIGS. 33A-33K, and can provide information relating to the maximum diameter and/ or length of a left and/or right screw that can be inserted into each vertebral level. As illustrated in FIG. 33K, in some embodiments, the system can be configured to generate a summary of the diameter and/or length of one or more vertebral screws for inserting into one or more vertebrae of the spinal section of interest, such as for example T10 to Si. In some embodiments, based on the screw planning memo, the surgeon and/or other medical personnel can be provided a kit comprising screws with a diameter and/or length that is within about 1%, about 2%, about 3% about 4%, about 5%, about 6%, about 7%, about 8%, about 9%, and/or about 10% of the determined diameter and/or length of one or more vertebral screws for inserting into one or more vertebrae of the spinal section of interest, such as for example T10 to S1. In some embodiments, based on the screw planning memo, the surgeon and/or other medical personnel can be provided a kit comprising screws with a diameter and/or length that is within a range defined by two of the aforementioned values.

System

Figure 34:
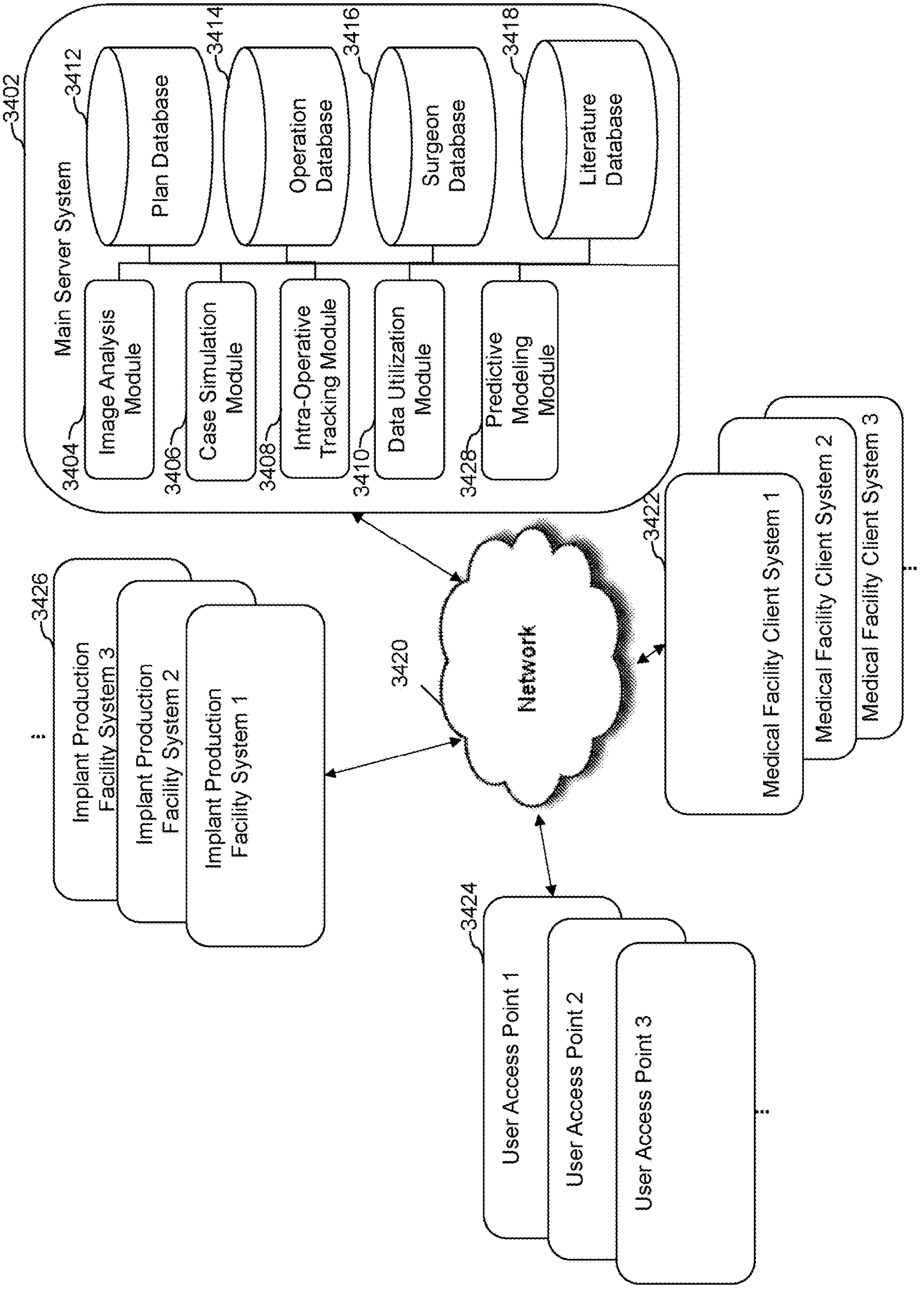
FIG. 34 is a schematic diagram illustrating an embodiment(s) of a system for developing patient-specific spinal implants, treatments, operations, and/or procedures.

FIG. 34 is a schematic diagram illustrating an embodiment of a system for developing patient-specific spinal treatments, operations, and procedures. In some embodiments, a main server system 3402 may comprise an image analysis module 3404, a case simulation module 3406, an intra-operative tracking module 3408, a data utilization module 3410, a predictive modeling module 3428, a plan database 3412, an operation database 3414, a surgeon database 3416, and/or a literature database 3418. The main server system can be connected to a network 3420. The network can be configured to connect the main server to one or more implant production facility systems 3426, one or more medical facility client systems 3422, and/or one or more user access point systems 3424.

The image analysis module 3404 may function by providing image analysis and/or related functions as described herein. The case simulation module 3406 may function by performing surgical planning, case simulation, and/or related functions as described herein. The intra-operative tracking module 3408 may function by performing intra-operative tracking and/or related functions as described herein. The data utilization module 3410 may function by retrieving and/or storing data from and to one or more databases and/or related functions as described herein. The predictive modeling module 3428 may function by performing one or more predictive modeling processes as described herein.

The plan database 3412 may provide a collection of all plans that have been generated by the system and/or related data. The operation database 3414 may provide a collection of all surgical operations that have been performed utilizing the system and/or related data. The surgeon database 3416 may provide a collection of all surgeons who have utilized the system and/or related data, such as surgeon preferences, skill levels, or the like. The literature database 3418 may provide a collection of scientific literature related to spinal surgery.

Computer System

Figure 35:
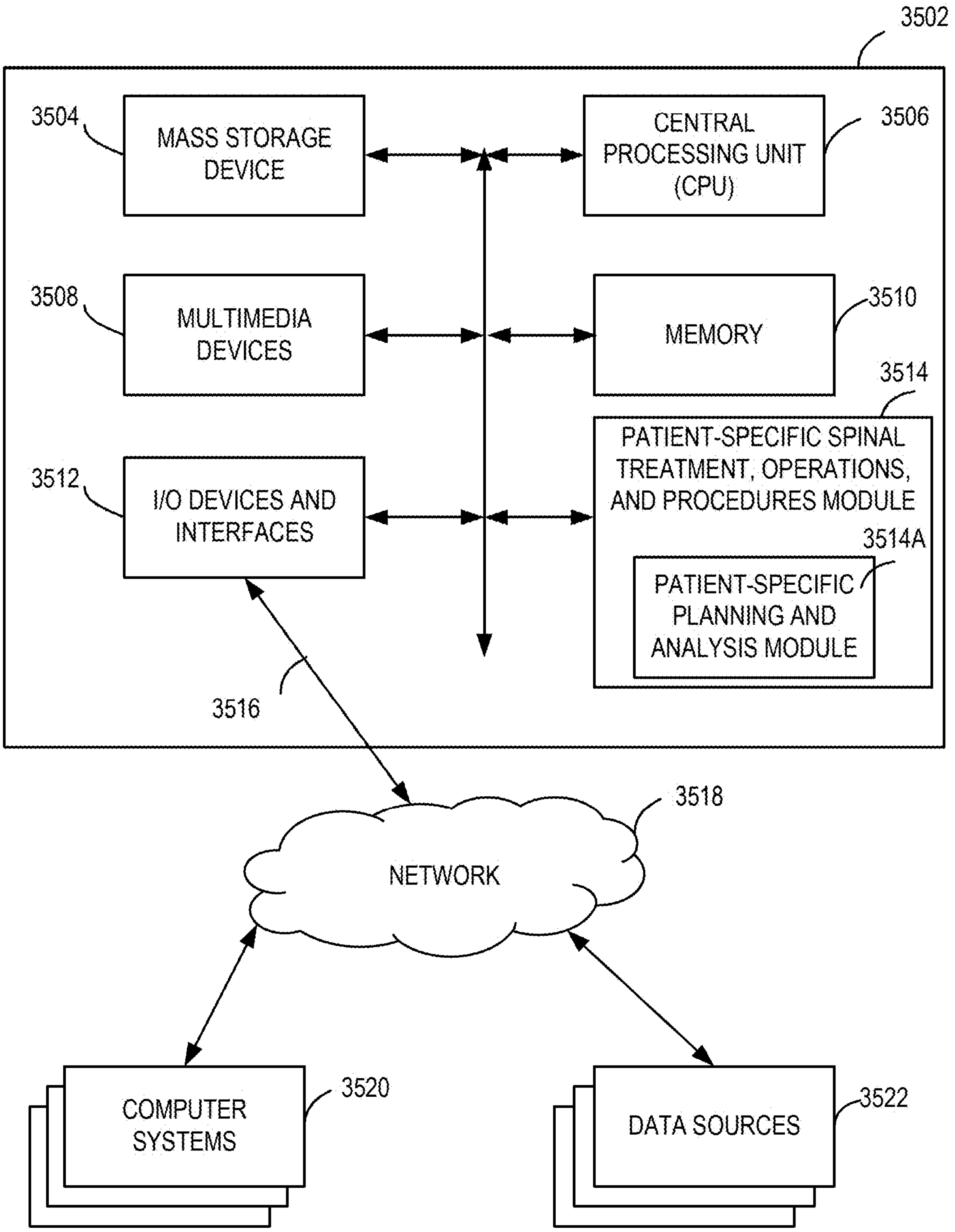
FIG. 35 is a block diagram depicting an embodiment(s) of a computer hardware system configured to run software for implementing one or more embodiments of a system for developing patient-specific spinal implants, treatments, operations, and/or procedures.

In some embodiments, the systems, processes, and methods described herein are implemented using a computing system, such as the one illustrated in FIG. 35. The example computer system 3502 is in communication with one or more computing systems 3520 and/or one or more data sources 3522 via one or more networks 3518. While FIG. 35 illustrates an embodiment of a computing system 3502, it is recognized that the functionality provided for in the components and modules of computer system 3502 may be combined into fewer components and modules, or further separated into additional components and modules.

The computer system 3502 can comprise a patient-specific spinal treatment, operations, and procedures module 3514 that carries out the functions, methods, acts, and/or processes described herein. The patient-specific spinal treatment, operations, and procedures module 3514 is executed on the computer system 3502 by a central processing unit 3506 discussed further below.

In general the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 3502 includes one or more processing units (CPU) 3506, which may comprise a microprocessor. The computer system 3502 further includes a physical memory 3510, such as random access memory (RAM) for temporary storage of information, a read only memory (ROM) for permanent storage of information, and a mass storage device 3504, such as a backing store, hard drive, rotating magnetic disks, solid state disks (SSD), flash memory, phase-change memory (PCM), (Point memory, diskette, or optical media storage device). Alternatively, the mass storage device may be implemented in an array of servers. Typically, the components of the computer system 3502 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 3502 includes one or more input/output (I/O) devices and interfaces 3512, such as a keyboard, mouse, touch pad, and printer. The I/O devices and interfaces 3512 can include one or more display devices, such as a monitor, that allows the visual presentation of data to a user. More particularly, a display device provides for the presentation of GUIs as application software data, and multi-media presentations, for example. The I/O devices and interfaces 3512 can also provide a communications interface to various external devices. The computer system 3502 may comprise one or more multi-media devices 3508, such as speakers, video cards, graphics accelerators, and microphones, for example.

The computer system 3502 may run on a variety of computing devices, such as a server, a Windows server, a Structure Query Language server, a Unix Server, a personal computer, a laptop computer, and so forth. In other embodiments, the computer system 3502 may run on a cluster computer system, a mainframe computer system and/or other computing system suitable for controlling and/or communicating with large databases, performing high volume transaction processing, and generating reports from large databases. The computing system 3502 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 3502 illustrated in FIG. 35 is coupled to a network 3518, such as a LAN, WAN, or the Internet via a communication link 3516 (wired, wireless, or a combination thereof). Network 3518 communicates with various computing devices and/or other electronic devices. Network 3518 is communicating with one or more computing systems 3520 and one or more data sources 3522. The patient-specific spinal treatment, operations, and procedures module 3514 may access or may be accessed by computing systems 3520 and/or data sources 3522 through a web-enabled user access point. Connections may be a direct physical connection, a virtual connection, and other connection type. The web-enabled user access point may comprise a browser module that uses text, graphics, audio, video, and other media to present data and to allow interaction with data via the network 3518.

Access to the patient-specific spinal treatment, operations, and procedures module 3514 of the computer system 3502 by computing systems 3520 and/or by data sources 3522 may be through a web-enabled user access point such as the computing systems' 3520 or data source's 3522 personal computer, cellular phone, smartphone, laptop, tablet computer, e-reader device, audio player, or other device capable of connecting to the network 3518. Such a device may have a browser module that is implemented as a module that uses text, graphics, audio, video, and other media to present data and to allow interaction with data via the network 3518.

The output module may be implemented as a combination of an all-points addressable display such as a cathode ray tube (CRT), a liquid crystal display (LCD), a plasma display, or other types and/or combinations of displays. The output module may be implemented to communicate with input devices 3512 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 3502 may comprise a physical or logical connection established between a remote microprocessor and a mainframe host computer for the express purpose of uploading, downloading, or viewing interactive data and databases on-line in real time. The remote microprocessor may be operated by an entity operating the computer system 3502, including the client server systems or the main server system, and/or may be operated by one or more of the data sources 3522 and/or one or more of the computing systems 3520. In some embodiments, terminal emulation software may be used on the microprocessor for participating in the micro-mainframe link.

In some embodiments, computing systems 3520 who are internal to an entity operating the computer system 3502 may access the patient-specific spinal treatment, operations, and procedures module 3514 internally as an application or process run by the CPU 3506.

The computing system 3502 may include one or more internal and/or external data sources (for example, data sources 3522). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 3502 may also access one or more databases 3522. The databases 3522 may be stored in a database or data repository. The computer system 3502 may access the one or more databases 3522 through a network 3518 or may directly access the database or data repository through I/O devices and interfaces 3512. The data repository storing the one or more databases 3522 may reside within the computer system 3502.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Figure 36:
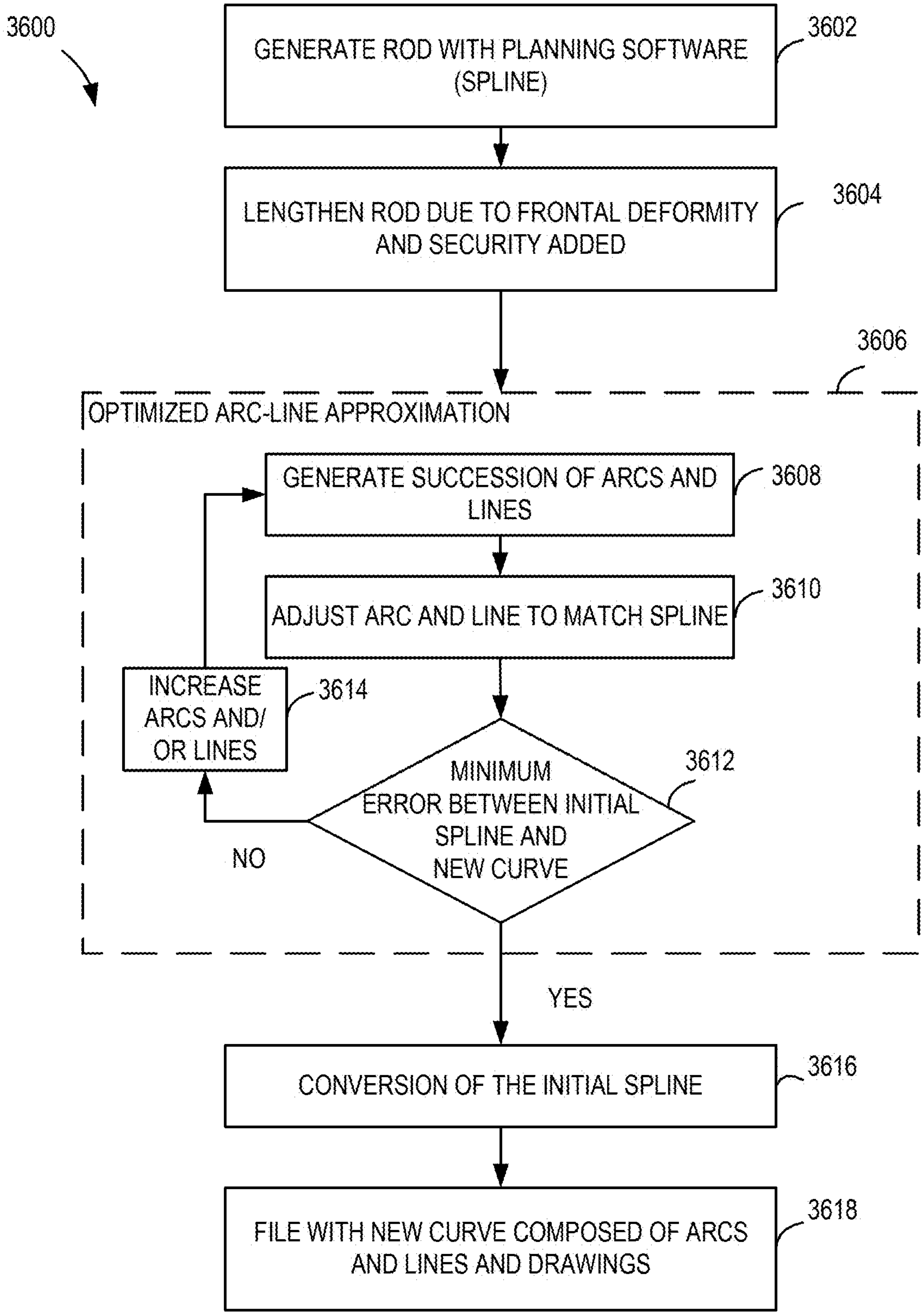
FIG. 36 is a flow chart that illustrates an example method for developing patient-specific spinal implant such as a spinal rod.
Figure 37:
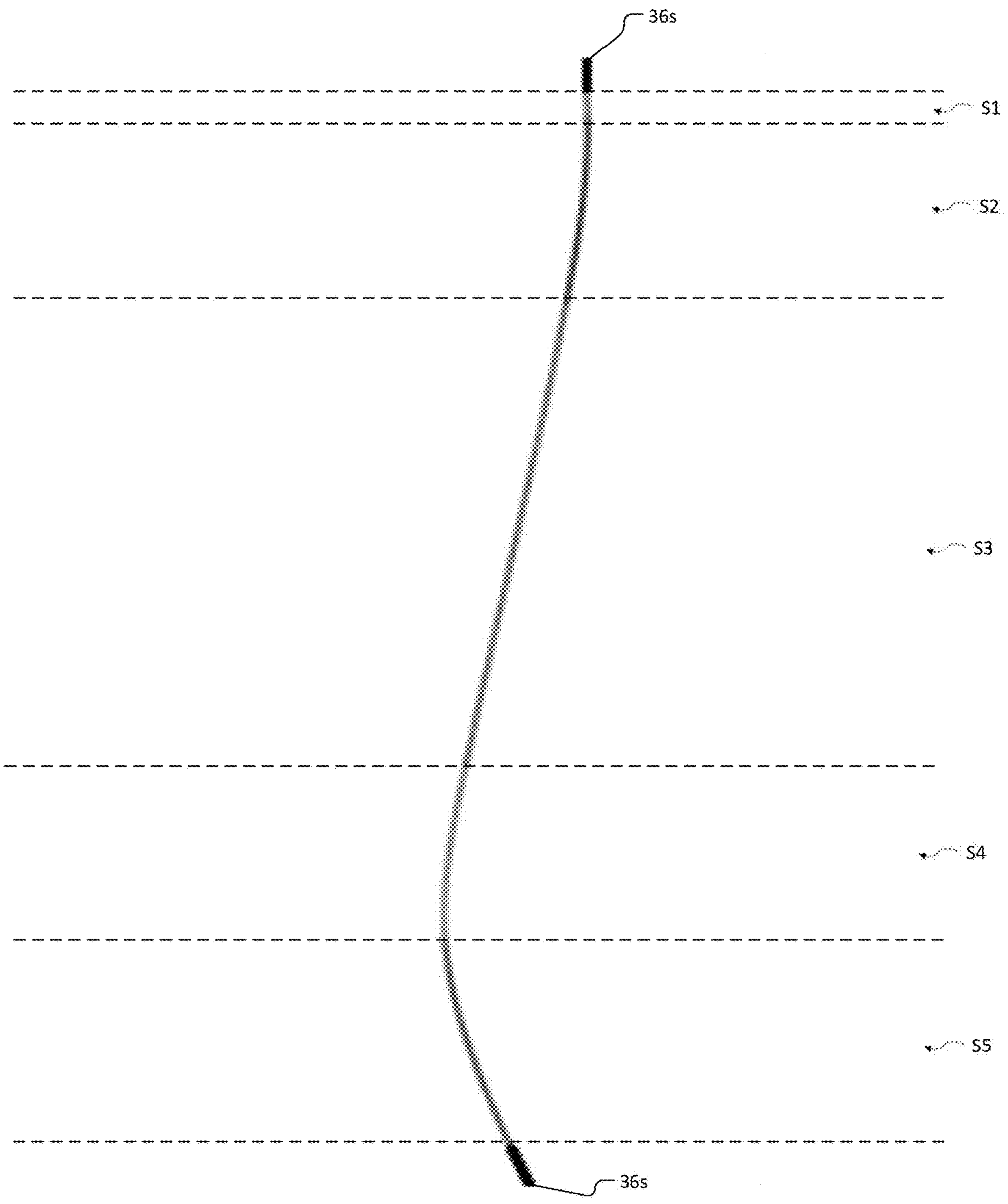
FIG. 37 is a graphical representation that illustrates an example spline curve of a rod for a patient' anatomy.

FIG. 36 illustrates an example flow chart of an example method 3600 for developing a patient-specific spinal implant, such as a rod derived from a spline 100 shown in FIG. 37. The method will be discussed concurrently with reference to FIGS. 38A-38D and FIG. 39. At step 3602, a plan for a patient-specific spinal rod, may be developed, for example based on spline 100 of FIG. 37. In practice, a rod may be created with geometrical properties based on the spline 100 that is developed according to method 3600. The rod and spline 100 may principally comprise five segments with each having a different curvature based on, for example, a Bezier Curve. For example, as illustrated in FIG. 37 the spline illustrated includes five segments S1, S2, S3, S4, and S5. At step, 3604 lengthening of the initially designed spinal rod due to frontal deformity of the spine and/or an additional security 36*s* may be added (see FIG. 37). By way of non-limiting example, the security 36*s* may include an extension of the spline curve by about 5-10 millimeters (mm). In other embodiments, the extension of the spline may be between a range of about 0 mm-15 mm, for example. The additional security may be added based on a surgeon's preference. Accordingly, if the surgeon prefers there to be no extension, then the additional extension may be 0 mm, for example. It should be understood, that the extension is not limited to the ranges described herein and the system will allow a surgeon to set a security length of a particular length.

Figure 38A:
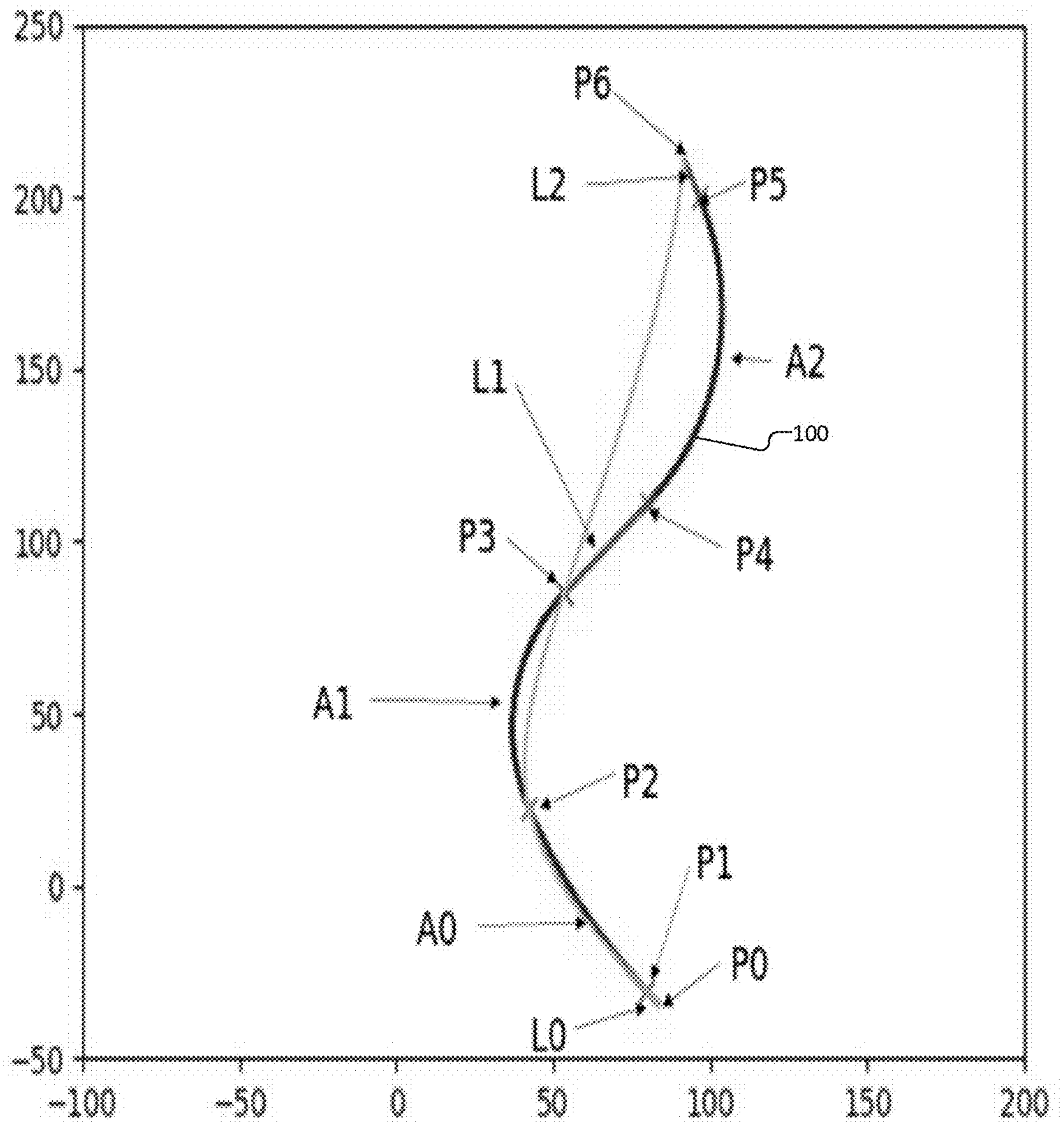
FIGS. 38A-38D are graphical representations that illustrate example successive iterations of approximating the spline curve of the rod with arcs and lines.

At 3606, the system may be configured to perform a process for optimized arc-line approximation of the lengthened spline curve. The optimized arc-line approximation may comprise various sub-routines, looped sub-steps, and/or mathematical calculations such as interpolation and calculation of a plurality of arc line segments as would be understood by a person having ordinary skill in the art, for example. At step 3608, the system may first generate a succession of arcs and lines between a plurality of reference points. For example, as shown in FIG. 38A, reference points are shown as P0, P1, P2, P3, P4, P5, and P6; reference arcs are shown as A0, A1, and A2, and reference lines are shown as L0, L1, and L2. With respect to the reference arcs, A0 is approximated between point P1 and P2, A1 is approximated between points P2 and P3, A2 is approximated between points P4 and P5. With respect to the reference lines, L0 is drawn between P0 and P1, L1 is drawn between P3 and P4, and L2 is drawn between P5 and P6. In this way, three reference lines and three reference arcs are illustrated and the generation thereof will be explained in further detail below.

FIGS. 38A-38D are graphical representations 3800A-3800D that illustrate successive iterations of approximating the spline curve 3800 of the rod with arcs and lines. For example, the system may generate a first graphical representation 3800A, a second graphical representation 3800B based on the first graphical representation 3800A, a third graphical representation 3800C based on the second graphical representation 3800B, and a fourth graphical representation 3800D based on the third graphical representation. However, it should be understood the system may generate more or less graphical representations until the graphical representation obtained closely or nearly identically approximates the desired curvature of the rod.

In general, the optimized arc-line approximation may begin with a least number of arcs to estimate the spline. In some embodiments, based on the manufacturer, there may be a maximum number of arcs that can be used in the process. However, for the sake of illustration and understanding, the spline curve 300 is first approximated by three (3) arcs A0, A1 and A2 and three lines in FIG. 38A. The arcs A1 and A2 are linked and separated by line L2, for example. The line L1 of FIG. 38A, extends from the top of spline segment S1 to the beginning of arc A1. The line L2 extends from point P3, which is the last point on arc A1 to point P4, which lies on spline segment S1. Lines L1 and L2 each have a corresponding length and slope relative to the spline curve 300. The length and slope of a line (i.e., lines L1 and L2) are adjustable parameters that may be incrementally adjusted until approximation can be achieved.

For example, the first approximation may be made by a line L0 from point P0 to P1, an arc A0 starting at P1 and ending at P2, an arc A1 starting at P2 ending at P3, a line P1 from P3 to P4, an arc starting at P4 ending at P5 and a line between P5 and P6. Now, the system may fix points P0 and P6 and match the P0 as the first point for an arc and P6 as the last point of an arc with an object to calculate a final position for points P1, P2, P3, P4, and P5. In some embodiments, a purpose of the optimized arc-line approximation 3606 is to determine and locate the appropriate points P1, P2, P3, P4, and P5 so that the curvature and/or geometry of spline segments S1, S2, S3, S4, and S5 may be designed with a predetermined tolerance. In some example embodiments, the predetermined tolerance may be about 1.5 mm although the disclosed system may establish a different tolerance dependent solely on user preferences.

Arc A2 extends from point P4 to point P6. Furthermore, arc A2 intersects the spline at point P5. The arc A2 has an arc portion from points P5 to point P6, which approximates the curvature of the spline segment S3. FIG. 4B is an intermediate arc-line curve that approximates the spline curve 300. FIG. 4C is a final arc-line curve that approximates the spline curve 300 and meets the minimum error criteria. In some embodiments, in order to meet manufacturing specifications, the system may need to generate a succession of arcs and/or lines to approximate the spline curve 300.

At 3610, the system may adjust the arc's curvature and the line slope in a direction to approximate the spline curve 300. For example, a first iteration is shown FIG. 38B. The system may obtain the first iteration shown in FIG. 38B by adjusting the position of the starting point of the arc, the ending point of the arc and the center of the arc of FIG. 38A to that shown in FIG. 38B. Similarly, the system may adjust the starting point and endpoint point of each line. Additionally, the system may adjust the arc's center position and curvature of the arc's angle and the line slope and length to approximate the spline curve 300 within a pre-determined tolerance. An iterative step of this process may begin with FIG. 38A and a first iteration may be shown as curve C1 in FIG. 38B.

Figure 38B:
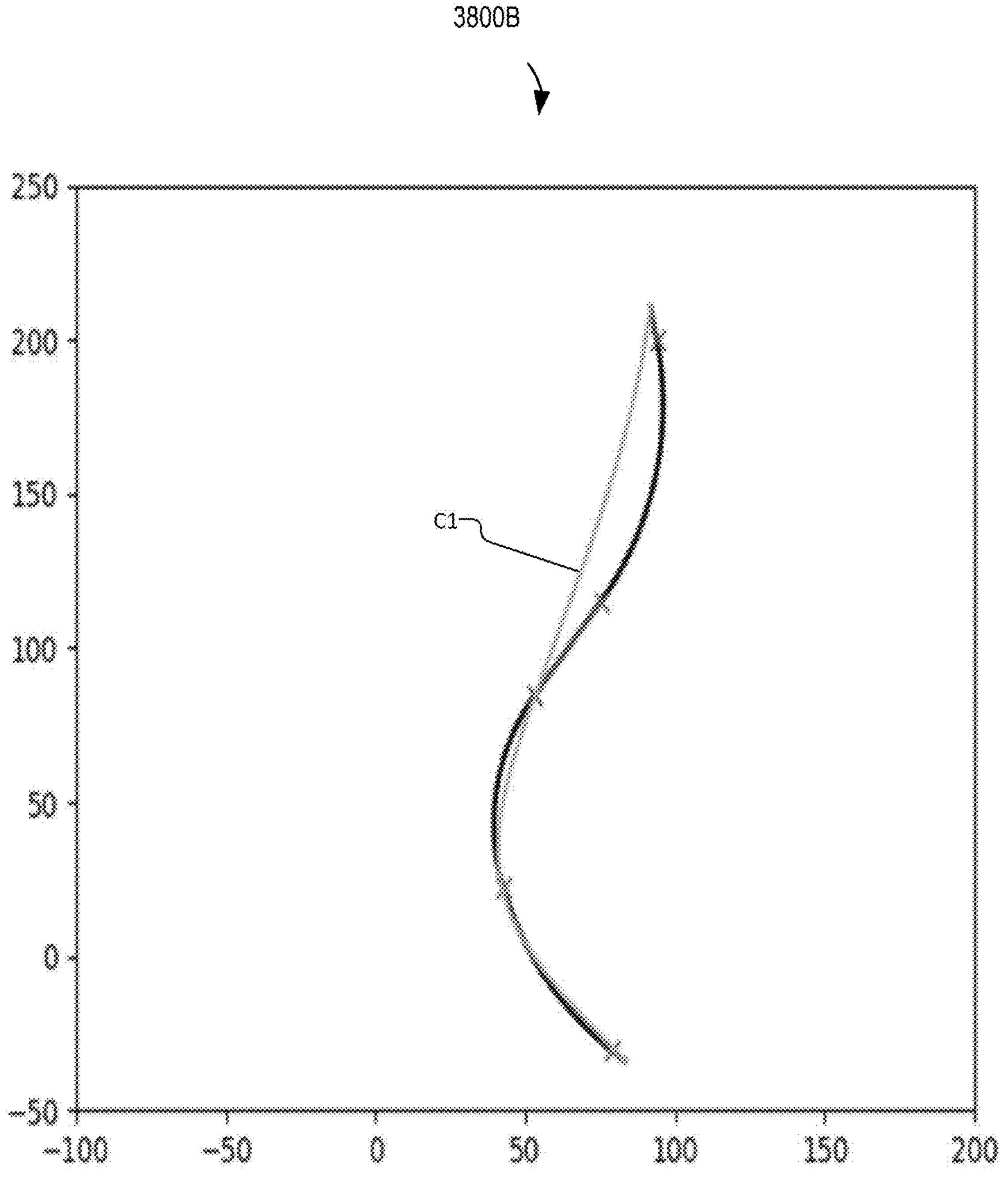
Figure 38C:
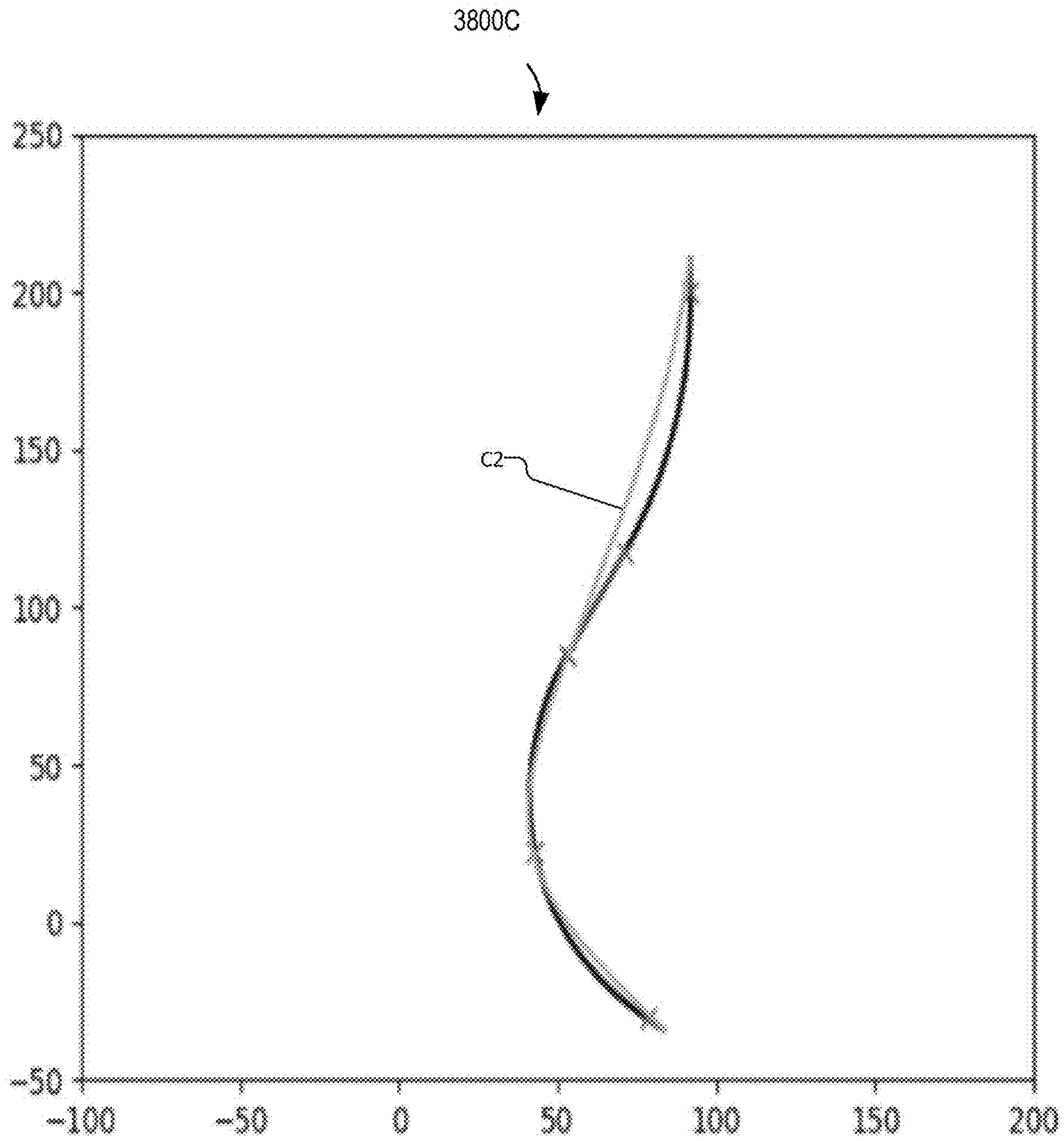

At step 3612, a determination may be made whether a minimum level of error has been achieved between the initial spline curve 300 and the arc-line approximation of the new curve C1. If the determination is "NO," the arcs and/or lines may be adjusted at 3614 and the process returns to generate a new succession of arcs and lines, at 3608, with the revised set of arcs and lines. In FIG. 38B, the system has determined "NO" because new curve C1 does not accurately reflect an approximation of the spine curve 300 that is within the pre-determined tolerance. Therefore, the system returns to step 3608 and does a second iteration shown in FIG. 38C as curve C2. In FIG. 38C, the system once again performs step 3612 to determine whether curve C2 is within the pre-determined tolerance and once again the system determines "NO" curve C2 is not within the pre-determined tolerance. Accordingly, the system returns to step 3608 and does a third iteration shown in FIG. 38D as curve C3. Similarly as before, the system once again performs step 3612 to determine whether curve C3 is within the pre-determined tolerance and as shown in FIG. 38D curve C3 approximates the spine curve 300 very closely and there are no sections of the curve C3 that fall outside of the pre-determined tolerance.

Figure 38D:
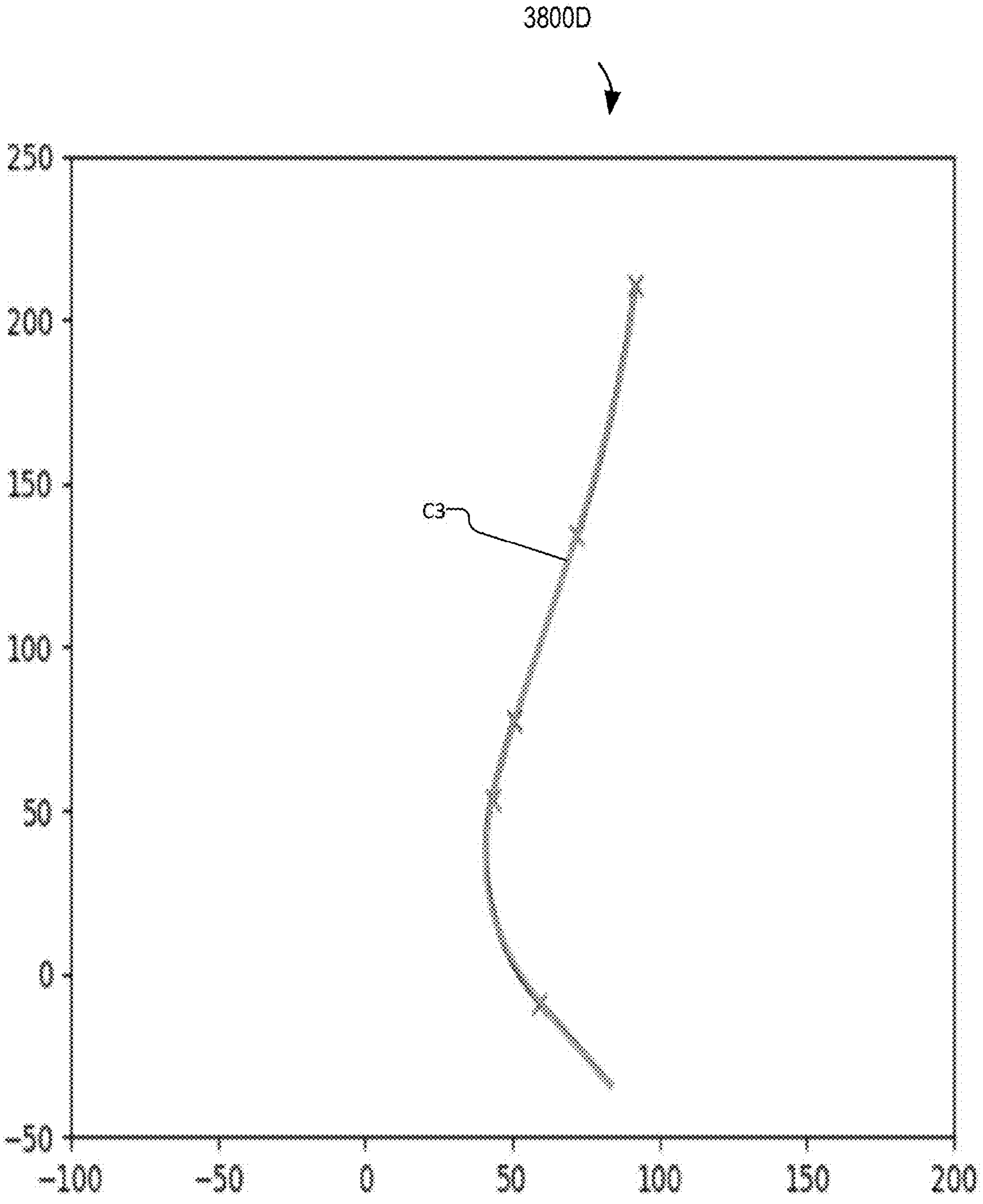

Accordingly, in FIG. 38D the system has performed at step 3612, with a determination of "YES" and can therefore move on to step 3616. At step 3616, the system can be configured to perform automatic and/or dynamic conversion of the initial spline, for example. Next, at step 3618, the system can be configured to produce and/or generate an Initial Graphics Exchange Specification (IGES) file comprising curve C3 composed of one or more arcs and/or lines and/or drawing specifications for manufacturing. In some embodiments, the IGES file can be transferred to a manufacturing system and/or an apparatus for manufacturing the patient-specific spinal rod, for example a 3D printer. In some embodiments, instead of an IGES file another type of Computer-aided Design (CAD) file may be generated for import into an AutoCAD programming application of a manufacturer. In various embodiments, other types of computer-aided design programming applications may be used. The particular type of drawing software utilized is not dependent on the system as the system can, irrespective of the particular platform or software utilized, generate manufacture or machine drawings to manufacture a rod with the attributes determined by method 3600. For example, machine drawings may be generated for a machinist to manufacture a rod conforming to the curve C3. For example, such drawings may include reference points and radius of curvature or bending directions of each particular segment of curve C3. For example still, the system may generate manufacturing instructions informing a machinist how to bend a rod to conform to curve C3 in a format that would be understood by a person having ordinary skill in the art of machining, engineering, and computer aided design software, for example.

Figure 39:
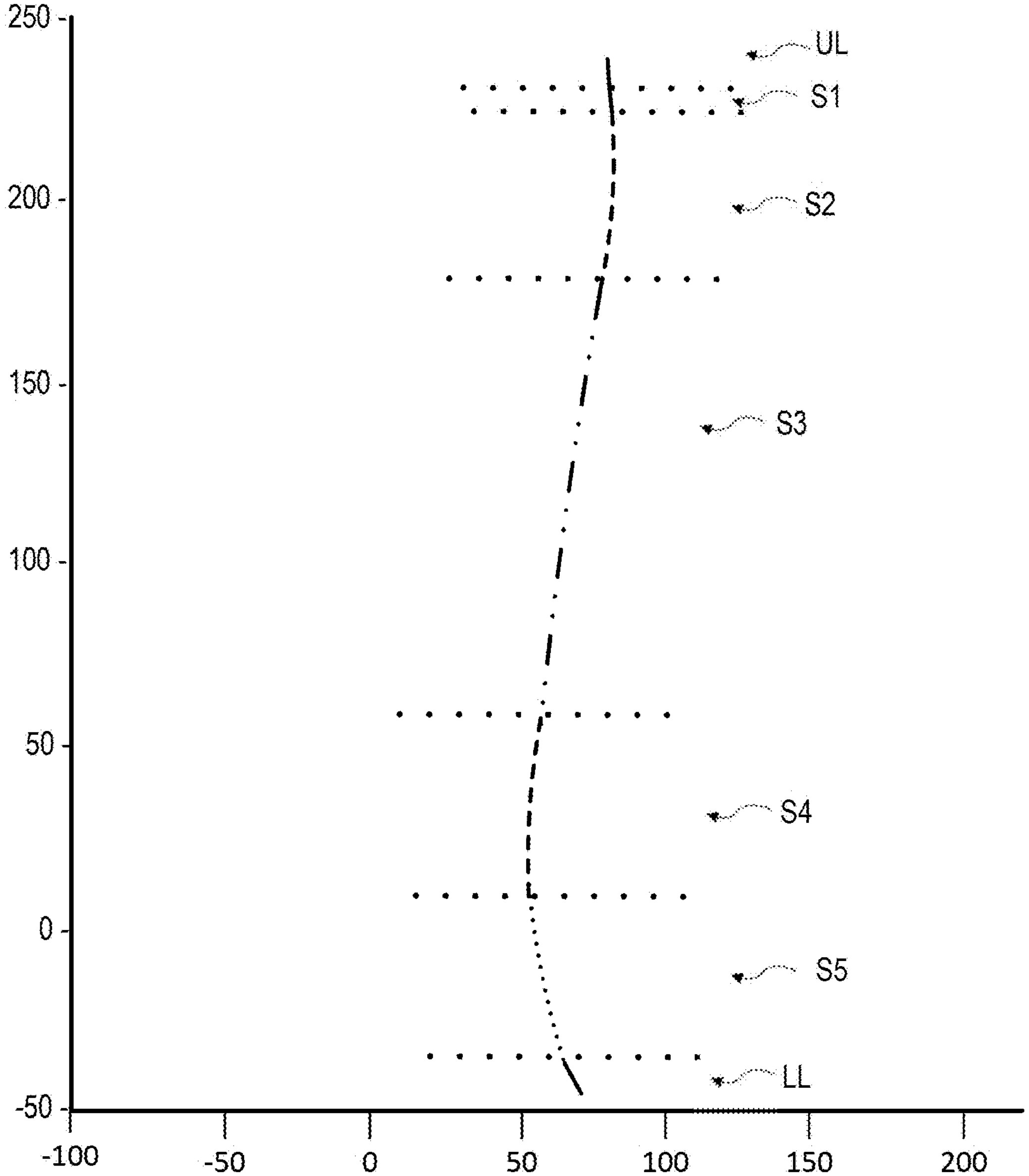
FIG. 39 is a graphical representation that illustrates an example spline curve of a rod for a patient' anatomy.

FIG. 39 is a graphical representation that illustrates an example spline curve of a rod for a patient' anatomy. In FIG. 39, the spline curve 3900 has a plurality of spline segments S1, S2, S3, S4 and S5. As illustrated, the spline segments S1, S2, S3, S4 and S5 represent a portion of the spline where the curvature changes as represented in the curve 3900. As explained above, each segment S1, S2, S3, S4 and S5 may be manufactured into shape by a machinist with directions provided by the system. For example still, each segment may comprise a start point, an end point, a center point, and such curvature of the segment may be defined by an arc of a circle having a radius of curvature determined by the system at method 3600.

Additional Embodiments

Although the embodiments discussed herein generally relate to patient-specific spinal treatment, operations, and procedures, the systems, methods, and devices disclosed herein can be used for any non-spinal patient-specific treatment, operations, and procedure as well. In addition, the systems, methods, and devices disclosed herein can be used with x-ray, MRI, CT, or any other imaging systems or devices that produce two-dimensional and/or three-dimensional medical image or video data.

Various embodiments described herein relate to systems, methods, and devices for developing patient-specific spinal implants, treatments, operations, and/or procedures. In particular, some embodiments described herein are directed to the design and/or manufacture of patient-specific spinal rods, cages, screws, and/or the like. In some embodiments, the systems, methods, and devices described herein are configured to design and/or produce a patient-specific spinal rod based at least in part on a mathematical curve. In some embodiments, the systems, methods, and devices described herein are configured to design and/or produce a patient-specific spinal rod based at least in part on using an Initial Graphics Exchange Specification (IGES) file format.

In some embodiments, the systems, devices, and methods described herein can be configured to create and/or generate one or more arcs from a mathematical curve. In particular, to entrust the manufacture of a patient-specific spinal rod by a third party, such as a subcontractor, there is a need to provide a technically accurate and/or precise surgical plan for manufacturing the patient-specific spinal rod. In order to do so, in some embodiments, the system is configured to define specifications for a patient-specific spinal rod based at least in part on a succession of one or more circular arcs and/or one or more radii of curvature of given lengths and/or one or more straight lines.

In some embodiments, such specifications for a patient-specific spinal rod, such as for example one or more circular arcs, one or more radii of curvature of given lengths, one or more straight lines, and/or a combination of the same, can be generated and/or determined manually, for example using a mathematical curve as input data which can be time consuming.

In some embodiments, specifications for a patient-specific spinal rod, such as for example one or more circular arcs, one or more radii of curvature of given lengths, one or more straight lines, and/or a combination of the same, can be generated and/or determined automatically and/or dynamically, for example. The patient-specific spinal rod may be generated or determined based on one or more inputs, such as medical images, spinal measurements, spinal parameters, mathematical model representing the spine, spline, and/or the like. In some embodiments, the system can be configured to perform one or more successive iterations to automatically and/or dynamically transform a mathematical curve representative a spine of a patient into a succession of arcs of circles and/or straight lines.

In some embodiments, the system can be configured to utilize an Initial Graphics Exchange Specification (IGES) file format in developing specifications of a patient-specific spinal implant, such as a spinal rod. Use of IGES file format can overcome the arcs of circles in some embodiments. In some embodiments, the system can be configured to automate the generation of output files in IGES format, a graphics data exploitation format, which can be used directly for the manufacturing and/or industrialization phases, which can in turn provide automation of IGES file generation and/or planning.

The method steps may be performed in the order shown or a different order. One or more of the steps may be performs contemporaneously. Furthermore, one or more steps may be added or omitted in an iteration.

Although this disclosure has been disclosed in the context of certain embodiments and examples, it will be understood by those skilled in the art that the disclosure extends beyond the specifically disclosed embodiments to other alternative embodiments and/or uses of the disclosure and obvious modifications and equivalents thereof In addition, while several variations of the embodiments of the disclosure have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosed disclosure. Any methods disclosed herein need not be performed in the order recited. Thus, it is intended that the scope of the disclosure herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the disclosures or claims.

Further, while the methods and devices described herein may be susceptible to various modifications and alternative forms, specific examples thereof have been shown in the drawings and are herein described in detail. It should be understood, however, that the disclosure is not to be limited to the particular forms or methods disclosed, but, to the contrary, the disclosure is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed:

1. A computer-implemented method, comprising:

providing a computing system comprising a processor;

receiving a digital representation of a target geometry for a spinal rod, the digital representation comprising a curved line;

generating a spline data set comprising a plurality of spline segments, each spline segment being sequentially linked to an adjacent spline segment;

adjusting, iteratively, each spline segment until the plurality of spline segments approximate the curved line;

after the plurality of spline segments approximate the curved line, generating manufacturing instructions informing how to bend a rod to conform to the approximation of the curved line; and providing, to a user, the manufacturing instructions on a user interface of the computing system.

2. The method of claim 1, wherein providing the manufacturing instructions comprises providing reference points and bending directions of each particular spline segment.

3. The method of claim 1, wherein the user interface comprises a display screen.

4. The method of claim 1, wherein generating the spline data set comprises defining each spline segment by a corresponding arc or a corresponding line extending between a corresponding starting point and a corresponding ending point.

5. The method of claim 1, wherein adjusting each spline segment comprises adjusting at least one spline segment of the plurality of spline segments by adjusting a curvature of an arc between a corresponding starting point and a corresponding ending point.

6. The method of claim 1, wherein adjusting each spline segment comprises:

adjusting each spline segment of the plurality of spline segments by adjusting a location of a corresponding starting point and a corresponding ending point of each spline segment; and adjusting, after adjusting the location the corresponding starting point and the corresponding ending point, each spline segment of the plurality of spline segments by adjusting a curvature of an arc between the corresponding starting point and the corresponding ending point of each spline segment.

7. The method of claim 1, wherein adjusting each spline segment comprises:

adjusting each spline segment of the plurality of spline segments by adjusting at least one starting point and/or at least one ending point; and adjusting a curvature of an arc of each spline segment defined by the arc.

8. The method of claim 1, further comprising lengthening the spline data set to include a security comprising an extension of at least one spline curve prior to the adjusting each spline segment.

9. The method of claim 1, wherein adjusting each spline segment comprises adjusting each spline segment of the plurality of spline segments by adjusting a curvature of an arc between a corresponding starting point and a corresponding ending point or by adjusting a location of the corresponding starting point and the corresponding ending point.

10. The method of claim 9, wherein adjusting each spline segment comprises adjusting each spline segment iteratively until each spline segment of the plurality of spline segments is within a predefined tolerance relative to the curved line corresponding to the target geometry.

11. A surgical planning and assessment system, the system comprising:

a computing system comprising a processor, wherein the computing system comprises computer executable code that, when executed by the processor, is configured to:

receive a digital representation of a target geometry of a spinal rod, the digital representation comprising a curved line;

generate a spline data set comprising a plurality of spline segments, each spline segment being sequentially linked to an adjacent spline segment;

adjust, iteratively, each spline segment until the plurality of spline segments approximate the curved line;

after the plurality of spline segments approximate the curved line, generate manufacturing instructions informing how to bend a rod to conform to the approximation of the curved line; and provide, to a user, the manufacturing instructions on a user interface of the computing system.

12. The surgical planning and assessment system of claim 11, wherein providing the manufacturing instructions comprises providing reference points and bending directions of each particular spline segment.

13. The surgical planning and assessment system of claim 11, wherein the user interface comprises a display screen.

14. The surgical planning and assessment system of claim 11, wherein generating the spline data set comprises defining each spline segment by a corresponding arc or a corresponding line extending between a corresponding starting point and a corresponding ending point.

15. The surgical planning and assessment system of claim 11, wherein adjusting each spline segment comprises adjusting at least one spline segment of the plurality of spline segments by adjusting a curvature of an arc between a corresponding starting point and a corresponding ending point.

16. The surgical planning and assessment system of claim 11, wherein adjusting each spline segment comprises:

adjusting each spline segment of the plurality of spline segments by adjusting a location of a corresponding starting point and a corresponding ending point of each spline segment; and adjusting, after adjusting the location the corresponding starting point and the corresponding ending point, each spline segment of the plurality of spline segments by adjusting a curvature of an arc between the corresponding starting point and the corresponding ending point of each spline segment.

17. The surgical planning and assessment system of claim 11, wherein adjusting each spline segment comprises:

adjusting each spline segment of the plurality of spline segments by adjusting at least one starting point and/or at least one ending point; and adjusting a curvature of an arc of each spline segment defined by the arc.

18. The surgical planning and assessment system of claim 11, wherein adjusting each spline segment comprises adjusting each spline segment of the plurality of spline segments by adjusting a curvature of an arc between a corresponding starting point and a corresponding ending point or by adjusting a location of the corresponding starting point and the corresponding ending point.

19. The surgical planning and assessment system of claim 11, further comprising lengthening the spline data set to include a security comprising an extension of at least one spline curve prior to the adjusting each spline segment.

20. The surgical planning and assessment system of claim 19, wherein adjusting each spline segment comprises adjusting each spline segment iteratively until each spline segment of the plurality of spline segments is within a predefined tolerance relative to the curved line corresponding to the target geometry.

* * * * *